(12) United States Patent
Hood et al.

(10) Patent No.: US 11,560,378 B2
(45) Date of Patent: Jan. 24, 2023

(54) TREATMENT OF OSTEOARTHRITIS

(71) Applicant: BioSplice Therapeutics, Inc., San Diego, CA (US)

(72) Inventors: John Hood, San Diego, CA (US); David Mark Wallace, San Diego, CA (US); Sunil Kumar KC, San Diego, CA (US); Yusuf Yazici, La Jolla, CA (US); Christopher Swearingen, San Marcos, CA (US); Luis A Dellamary, San Marcos, CA (US)

(73) Assignee: BioSplice Therapeutics, Inc., San Diego, CA (US)

( * ) Notice: Subject to any disclaimer, the term of this patent is extended or adjusted under 35 U.S.C. 154(b) by 142 days.

(21) Appl. No.: 17/108,544

(22) Filed: Dec. 1, 2020

(65) Prior Publication Data

US 2021/0292318 A1    Sep. 23, 2021

Related U.S. Application Data

(60) Division of application No. 16/710,099, filed on Dec. 11, 2019, now Pat. No. 10,882,860, which is a continuation of application No. 15/773,951, filed as application No. PCT/US2016/060868 on Nov. 7, 2016, now Pat. No. 10,544,139.

(60) Provisional application No. 62/303,168, filed on Mar. 3, 2016, provisional application No. 62/252,332, filed on Nov. 6, 2015.

(51) Int. Cl.
| | |
|---|---|
| *C07D 513/02* | (2006.01) |
| *C07D 515/02* | (2006.01) |
| *A61K 31/44* | (2006.01) |
| *C07D 471/04* | (2006.01) |
| *A61K 31/444* | (2006.01) |
| *A61P 19/02* | (2006.01) |
| *A61P 29/00* | (2006.01) |
| *A61K 31/4545* | (2006.01) |
| *A61K 31/496* | (2006.01) |
| *A61K 31/5377* | (2006.01) |
| *A61K 9/00* | (2006.01) |

(52) U.S. Cl.
CPC .......... *C07D 471/04* (2013.01); *A61K 9/0019* (2013.01); *A61K 31/444* (2013.01); *A61K 31/4545* (2013.01); *A61K 31/496* (2013.01); *A61K 31/5377* (2013.01); *A61P 19/02* (2018.01); *A61P 29/00* (2018.01); *C07B 2200/13* (2013.01)

(58) Field of Classification Search
CPC ............................ C07D 513/02; C07D 515/02
USPC ......................................................... 514/303
See application file for complete search history.

(56) References Cited

U.S. PATENT DOCUMENTS

| | | | |
|---|---|---|---|
| 4,164,559 A | 8/1979 | Miyata et al. |
| 4,474,752 A | 10/1984 | Haslam et al. |
| 4,603,139 A | 7/1986 | King |
| 5,037,844 A | 8/1991 | Hamminga et al. |
| 5,922,733 A | 7/1999 | Forbes et al. |
| 6,120,484 A | 9/2000 | Silverstein |
| 6,358,978 B1 | 3/2002 | Ritzeler et al. |
| 6,377,849 B1 | 4/2002 | Lenarz et al. |
| 6,440,102 B1 | 8/2002 | Arenberg et al. |
| 6,555,539 B2 | 4/2003 | Reich et al. |
| 6,648,873 B2 | 11/2003 | Arenberg et al. |
| 6,831,175 B2 | 12/2004 | Li et al. |
| 6,884,890 B2 | 4/2005 | Kania et al. |
| 6,897,208 B2 | 5/2005 | Edwards et al. |
| 6,911,211 B2 | 6/2005 | Eini et al. |
| 6,919,461 B2 | 7/2005 | Reich et al. |
| 7,008,953 B2 | 3/2006 | Kephart et al. |
| 7,064,215 B2 | 6/2006 | Renhowe et al. |
| 7,232,912 B2 | 6/2007 | Reich et al. |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

Pharmacology, 10th ed., Kharkevich (ed)., 2010, pp. 73-74 (English Translation).
Pharmacology, Zhulenko (ed)., 2008, pp. 34-35 (English Translation).

(Continued)

*Primary Examiner* — Niloofar Rahmani
(74) *Attorney, Agent, or Firm* — Fish & Richardson P.C.

(57) ABSTRACT

Provided are compositions and methods for treating osteoarthritis including intra-articular administration of a compound of Formula (I)

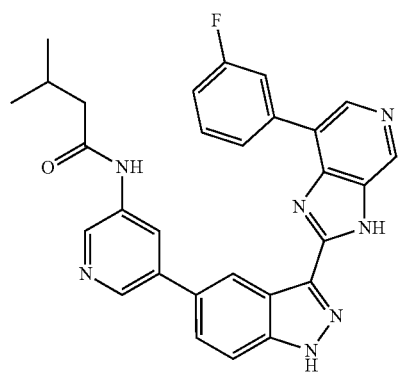

including amorphous and polymorph forms thereof.

8 Claims, 41 Drawing Sheets

(56) References Cited

U.S. PATENT DOCUMENTS

| | | |
|---|---|---|
| 7,285,565 B2 | 10/2007 | Zhu et al. |
| 7,390,815 B2 | 6/2008 | Davies et al. |
| 7,429,609 B2 | 9/2008 | Ohi et al. |
| 7,452,993 B2 | 11/2008 | Arnold et al. |
| 7,468,376 B2 | 12/2008 | Rosales et al. |
| 7,482,342 B2 | 1/2009 | D'Orchymont et al. |
| 7,488,737 B2 | 2/2009 | Xie et al. |
| 7,491,710 B2 | 2/2009 | Cherrier et al. |
| 7,541,367 B2 | 6/2009 | Chiu et al. |
| 7,626,021 B2 | 12/2009 | Arnold et al. |
| 7,642,278 B2 | 1/2010 | Jansen et al. |
| 7,666,867 B2 | 2/2010 | Makriyannis et al. |
| 7,812,043 B2 | 10/2010 | Lau et al. |
| 7,829,558 B2 | 11/2010 | Arnold et al. |
| 7,842,711 B2 | 11/2010 | D'Orchymont et al. |
| 7,902,217 B2 | 3/2011 | Xie et al. |
| 7,943,616 B2 | 5/2011 | Cox et al. |
| 8,008,481 B2 | 8/2011 | Ericsson et al. |
| 8,088,772 B2 | 1/2012 | Garcia et al. |
| 8,129,519 B2 | 3/2012 | Cholody et al. |
| 8,158,647 B2 | 4/2012 | Blaney et al. |
| 8,252,812 B2 | 8/2012 | Hood et al. |
| 8,288,425 B2 | 10/2012 | Edwards et al. |
| 8,304,408 B2 | 11/2012 | Wrasidlo et al. |
| 8,450,340 B2 | 5/2013 | Hood et al. |
| 8,604,052 B2 | 12/2013 | Hood et al. |
| 8,618,128 B1 | 12/2013 | Hood et al. |
| 8,637,508 B2 | 1/2014 | Badiger et al. |
| 8,664,241 B2 | 3/2014 | Hood et al. |
| 8,673,936 B2 | 3/2014 | Hood et al. |
| 8,697,887 B2 | 4/2014 | Hood et al. |
| 8,703,794 B2 | 4/2014 | Hood et al. |
| 8,815,897 B2 | 8/2014 | Hood et al. |
| 8,822,478 B2 | 9/2014 | Hood et al. |
| 8,846,714 B2 | 9/2014 | Hood et al. |
| 8,883,822 B2 | 11/2014 | Hood et al. |
| 8,901,150 B2 | 12/2014 | Hood et al. |
| 8,987,298 B2 * | 3/2015 | Hood .............. A61P 43/00 514/303 |
| 9,012,472 B2 | 4/2015 | Hood et al. |
| 9,056,874 B2 | 6/2015 | Adams et al. |
| 9,067,939 B2 | 6/2015 | Hood et al. |
| 9,090,613 B2 | 7/2015 | Hood et al. |
| 9,174,967 B2 | 11/2015 | Körber et al. |
| 9,199,991 B2 | 12/2015 | Hood et al. |
| 9,221,793 B2 | 12/2015 | Hood et al. |
| 9,233,104 B2 | 1/2016 | Hood et al. |
| 9,260,425 B2 | 2/2016 | Do et al. |
| 9,381,192 B2 | 7/2016 | Hood et al. |
| 9,446,035 B2 | 9/2016 | Hood et al. |
| 9,475,807 B2 | 10/2016 | KC et al. |
| 9,475,825 B2 | 10/2016 | KC et al. |
| 9,493,487 B2 | 11/2016 | KC et al. |
| 9,538,272 B2 | 1/2017 | Auclair et al. |
| 9,540,398 B2 | 1/2017 | KC et al. |
| 9,546,185 B2 | 1/2017 | KC et al. |
| 9,586,977 B2 | 3/2017 | Hood et al. |
| 9,657,016 B2 | 5/2017 | KC et al. |
| 9,738,638 B2 | 8/2017 | KC et al. |
| 9,745,271 B2 | 8/2017 | Hood et al. |
| 9,758,531 B2 | 9/2017 | KC et al. |
| 9,763,927 B2 | 9/2017 | Hood et al. |
| 9,763,951 B2 | 9/2017 | KC et al. |
| 9,802,916 B2 | 10/2017 | Hood et al. |
| 9,815,854 B2 | 11/2017 | KC et al. |
| 9,828,372 B2 | 11/2017 | KC et al. |
| 9,844,536 B2 | 12/2017 | KC et al. |
| 9,855,272 B2 | 1/2018 | Hood et al. |
| 9,889,140 B2 | 2/2018 | KC et al. |
| 9,908,867 B2 | 3/2018 | KC et al. |
| 9,994,563 B2 | 6/2018 | Hood et al. |
| 10,016,406 B2 | 7/2018 | Hood et al. |
| 10,023,572 B2 | 7/2018 | KC et al. |
| 10,052,331 B2 | 8/2018 | KC et al. |
| 10,071,086 B2 | 9/2018 | Hood et al. |
| 10,072,004 B2 | 9/2018 | KC |
| 10,081,631 B2 | 9/2018 | KC et al. |
| 10,131,677 B2 | 11/2018 | Sunil et al. |
| 10,195,185 B2 | 2/2019 | KC et al. |
| 10,329,309 B2 | 6/2019 | KC et al. |
| 10,342,788 B2 | 7/2019 | Hood et al. |
| 10,350,199 B2 | 7/2019 | KC et al. |
| 10,383,861 B2 | 8/2019 | KC et al. |
| 10,392,383 B2 | 8/2019 | KC et al. |
| 10,407,425 B2 | 9/2019 | Hood et al. |
| 10,464,924 B2 | 11/2019 | Hood et al. |
| 10,526,347 B2 | 1/2020 | KC et al. |
| 10,533,020 B2 | 1/2020 | KC et al. |
| 10,544,139 B2 | 1/2020 | Hood et al. |
| 10,596,154 B2 | 3/2020 | Hood et al. |
| 10,604,512 B2 | 3/2020 | Hood et al. |
| 10,633,380 B2 | 4/2020 | KC et al. |
| 10,654,832 B2 | 5/2020 | Hood |
| 10,758,523 B2 | 9/2020 | Dellamary |
| 10,806,726 B2 | 10/2020 | Deshmukh et al. |
| 10,899,757 B2 | 1/2021 | Hood et al. |
| 10,947,228 B2 | 3/2021 | Hood et al. |
| 10,981,909 B2 | 4/2021 | KC |
| 11,066,388 B2 | 7/2021 | Hood et al. |
| 2002/0103229 A1 | 8/2002 | Bhagwat et al. |
| 2002/0161022 A1 | 10/2002 | Reich et al. |
| 2003/0139463 A1 | 7/2003 | Reich et al. |
| 2003/0199516 A1 | 10/2003 | Moser et al. |
| 2004/0048868 A1 | 3/2004 | Edwards et al. |
| 2004/0077681 A1 | 4/2004 | Rawlings et al. |
| 2004/0176325 A1 | 9/2004 | Munson et al. |
| 2004/0236101 A1 | 11/2004 | Makriyannis et al. |
| 2005/0009894 A1 | 1/2005 | Babin et al. |
| 2005/0026960 A1 | 2/2005 | Kephart et al. |
| 2005/0070546 A1 | 3/2005 | Arrington et al. |
| 2005/0090529 A1 | 4/2005 | McAlpine et al. |
| 2005/0192262 A1 | 9/2005 | Hagstrom et al. |
| 2005/0208582 A1 | 9/2005 | Ohi et al. |
| 2005/0250808 A1 | 11/2005 | Xie et al. |
| 2005/0261339 A1 | 11/2005 | Ohi et al. |
| 2006/0004000 A1 | 1/2006 | D'Orchymont et al. |
| 2006/0014756 A1 | 1/2006 | Edwards et al. |
| 2006/0079564 A1 | 4/2006 | Jansen et al. |
| 2006/0094706 A1 | 5/2006 | Panich et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lau et al. |
| 2007/0049598 A1 | 3/2007 | Billedeau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0132495 A1 | 6/2008 | Berdini et al. |
| 2008/0255085 A1 | 10/2008 | Arvidsson et al. |
| 2008/0262205 A1 | 10/2008 | Haar et al. |
| 2008/0287452 A1 | 11/2008 | Bursavich et al. |
| 2009/0005356 A1 | 1/2009 | Blaney et al. |
| 2009/0005377 A1 | 1/2009 | Almansa Rosales et al. |
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0118232 A1 | 5/2009 | Xie et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0280063 A1 | 11/2010 | Price et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0034491 A1 | 2/2011 | Hood et al. |
| 2011/0034497 A1 | 2/2011 | Hood et al. |

(56) References Cited

U.S. PATENT DOCUMENTS

| | | |
|---|---|---|
| 2011/0082144 A1 | 4/2011 | Lau et al. |
| 2011/0178075 A1 | 7/2011 | Xie et al. |
| 2011/0190290 A1 | 8/2011 | Hood et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0040976 A1 | 2/2013 | Hood et al. |
| 2013/0079329 A1 | 3/2013 | Hood et al. |
| 2013/0225576 A1 | 8/2013 | Hood et al. |
| 2013/0267495 A1 | 10/2013 | Hood et al. |
| 2013/0267548 A1 | 10/2013 | Follmann et al. |
| 2013/0296302 A1 | 11/2013 | Hood et al. |
| 2013/0296307 A1 | 11/2013 | Hood et al. |
| 2013/0296341 A1 | 11/2013 | Hood et al. |
| 2014/0005170 A1 | 1/2014 | Hood et al. |
| 2014/0005206 A1 | 1/2014 | Hood et al. |
| 2014/0005383 A1 | 1/2014 | Hood et al. |
| 2014/0045815 A1 | 2/2014 | Hood et al. |
| 2014/0179696 A1 | 6/2014 | Hood et al. |
| 2014/0194441 A1 | 7/2014 | KC et al. |
| 2014/0263319 A1 | 9/2014 | Fazi et al. |
| 2014/0323479 A1 | 10/2014 | Hood et al. |
| 2014/0364451 A1 | 12/2014 | John et al. |
| 2015/0045360 A1 | 2/2015 | Hood et al. |
| 2015/0045379 A1 | 2/2015 | Hood et al. |
| 2015/0072981 A1 | 3/2015 | Hood et al. |
| 2015/0087687 A1 | 3/2015 | Brown et al. |
| 2015/0111872 A1 | 4/2015 | Desroy et al. |
| 2015/0150862 A1 | 6/2015 | Hood et al. |
| 2015/0152105 A1 | 6/2015 | Hood et al. |
| 2016/0068529 A1 | 3/2016 | Hood et al. |
| 2016/0068547 A1 | 3/2016 | KC et al. |
| 2016/0068548 A1 | 3/2016 | KC et al. |
| 2016/0068549 A1 | 3/2016 | KC et al. |
| 2016/0068550 A1 | 3/2016 | KC et al. |
| 2016/0068551 A1 | 3/2016 | KC et al. |
| 2016/0075701 A1 | 3/2016 | KC et al. |
| 2016/0090380 A1 | 3/2016 | KC |
| 2016/0101092 A1 | 3/2016 | KC |
| 2016/0128991 A1 | 4/2016 | Hood et al. |
| 2016/0297812 A1 | 5/2016 | Hood et al. |
| 2016/0304488 A1 | 10/2016 | Hood et al. |
| 2016/0318954 A1 | 10/2016 | Hood et al. |
| 2017/0065574 A1 | 3/2017 | Hood et al. |
| 2017/0202846 A1 | 3/2017 | Hood et al. |
| 2017/0216299 A1 | 7/2017 | Hood et al. |
| 2017/0224697 A1 | 8/2017 | KC et al. |
| 2017/0260179 A1 | 8/2017 | KC et al. |
| 2017/0260209 A1 | 9/2017 | KC et al. |
| 2017/0267697 A1 | 9/2017 | KC et al. |
| 2017/0333409 A1 | 9/2017 | KC et al. |
| 2017/0349584 A1 | 11/2017 | Hood et al. |
| 2018/0086754 A1 | 3/2018 | KC et al. |
| 2018/0133199 A1 | 3/2018 | KC et al. |
| 2018/0141963 A1 | 5/2018 | Dellamary |
| 2018/0148444 A1 | 5/2018 | KC et al. |
| 2018/0153873 A1 | 5/2018 | KC et al. |
| 2018/0162840 A1 | 6/2018 | Hood et al. |
| 2018/0177787 A1 | 6/2018 | KC et al. |
| 2018/0185343 A1 | 6/2018 | KC et al. |
| 2018/0201624 A1 | 7/2018 | Deshmukh et al. |
| 2018/0207141 A1 | 7/2018 | KC et al. |
| 2018/0214427 A1 | 7/2018 | KC et al. |
| 2018/0214428 A1 | 8/2018 | KC et al. |
| 2018/0214429 A1 | 8/2018 | KC et al. |
| 2018/0215753 A1 | 8/2018 | KC et al. |
| 2018/0221341 A1 | 8/2018 | KC et al. |
| 2018/0221350 A1 | 8/2018 | KC et al. |
| 2018/0221351 A1 | 8/2018 | KC et al. |
| 2018/0221352 A1 | 8/2018 | KC et al. |
| 2018/0221353 A1 | 8/2018 | KC et al. |
| 2018/0221354 A1 | 8/2018 | KC et al. |
| 2018/0222891 A1 | 8/2018 | KC et al. |
| 2018/0222923 A1 | 8/2018 | KC et al. |
| 2018/0228780 A1 | 8/2018 | KC et al. |
| 2018/0228781 A1 | 8/2018 | KC et al. |
| 2018/0228782 A1 | 8/2018 | KC et al. |
| 2018/0228783 A1 | 8/2018 | KC et al. |
| 2018/0228784 A1 | 8/2018 | KC et al. |
| 2018/0228785 A1 | 8/2018 | KC et al. |
| 2018/0230142 A1 | 8/2018 | KC et al. |
| 2018/0237416 A1 | 8/2018 | KC et al. |
| 2018/0250269 A1 | 8/2018 | Hood et al. |
| 2018/0256588 A1 | 9/2018 | KC et al. |
| 2018/0318292 A1 | 9/2018 | Hood et al. |
| 2019/0071440 A1 | 3/2019 | Hood et al. |
| 2019/0112304 A1 | 3/2019 | Hood et al. |
| 2019/0119276 A1 | 4/2019 | Hood et al. |
| 2019/0119303 A1 | 4/2019 | KC et al. |
| 2019/0134013 A1 | 4/2019 | KC et al. |
| 2019/0194187 A1 | 5/2019 | Hood et al. |
| 2019/0352279 A1 | 6/2019 | KC |
| 2020/0155525 A1 | 5/2020 | KC et al. |
| 2020/0190082 A1 | 5/2020 | Hood et al. |
| 2020/0239436 A1 | 6/2020 | Hood et al. |
| 2020/0325133 A1 | 7/2020 | Hood |
| 2021/0002273 A1 | 1/2021 | KC |
| 2021/0121448 A1 | 1/2021 | Deshmukh et al. |
| 2021/0145807 A1 | 4/2021 | Dellamary |
| 2021/0292319 A1 | 9/2021 | Hood et al. |
| 2022/0024914 A1 | 1/2022 | KC |

FOREIGN PATENT DOCUMENTS

| | | |
|---|---|---|
| CN | 1829713 | 9/2006 |
| CN | 101440092 | 5/2009 |
| CN | 102105464 | 6/2011 |
| CN | 103929963 | 7/2014 |
| EA | 200200768 | 2/2003 |
| FR | 3011239 | 4/2015 |
| KR | 20140143796 | 12/2014 |
| KZ | 20122 | 1/2010 |
| RU | 2331640 | 8/2008 |
| RU | 2350271 | 3/2009 |
| RU | 2416610 | 4/2011 |
| RU | 2472508 | 1/2013 |
| RU | 2018120728 | 12/2019 |
| WO | WO1987005297 | 9/1987 |
| WO | WO1996002537 | 2/1996 |
| WO | WO2001002369 | 1/2001 |
| WO | WO2001053268 | 7/2001 |
| WO | WO2003004488 | 1/2003 |
| WO | WO2003035005 | 5/2003 |
| WO | WO2003035065 | 5/2003 |
| WO | WO2003035644 | 5/2003 |
| WO | WO2003051366 | 6/2003 |
| WO | WO2003070236 | 8/2003 |
| WO | WO2003070706 | 8/2003 |
| WO | WO2003097610 | 11/2003 |
| WO | WO2003101968 | 12/2003 |
| WO | WO2003101993 | 12/2003 |
| WO | WO2004014864 | 2/2004 |
| WO | WO2004031158 | 4/2004 |
| WO | WO2004076450 | 9/2004 |
| WO | WO 2005/002552 | 1/2005 |
| WO | WO 2005/012256 | 2/2005 |
| WO | WO2005009997 | 2/2005 |
| WO | WO2005012301 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006001894 | 1/2006 |
| WO | WO2006015124 | 2/2006 |
| WO | WO2006024945 | 3/2006 |
| WO | WO2006054143 | 5/2006 |
| WO | WO2006054151 | 5/2006 |
| WO | WO2006063302 | 6/2006 |
| WO | WO2006063841 | 6/2006 |
| WO | WO2006130673 | 12/2006 |

(56) References Cited

FOREIGN PATENT DOCUMENTS

| | | |
|---|---|---|
| WO | WO2007061360 | 5/2007 |
| WO | WO 2007/077435 | 7/2007 |
| WO | WO2007107346 | 9/2007 |
| WO | WO2007117465 | 10/2007 |
| WO | WO2007147874 | 12/2007 |
| WO | WO 2008/007113 | 1/2008 |
| WO | WO 2008/048502 | 4/2008 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |
| WO | WO2009011850 | 1/2009 |
| WO | WO2009016072 | 2/2009 |
| WO | WO2009029609 | 3/2009 |
| WO | WO2009061345 | 5/2009 |
| WO | WO 2009152868 | 12/2009 |
| WO | WO2010064875 | 6/2010 |
| WO | WO2010107765 | 9/2010 |
| WO | WO2010111060 | 9/2010 |
| WO | WO2010132725 | 11/2010 |
| WO | WO 2011/003065 | 1/2011 |
| WO | WO2011011722 | 1/2011 |
| WO | WO2011019648 | 2/2011 |
| WO | WO2011019651 | 2/2011 |
| WO | WO2011050245 | 4/2011 |
| WO | WO2011079076 | 6/2011 |
| WO | WO2011084486 | 7/2011 |
| WO | WO2011123890 | 10/2011 |
| WO | WO2012068589 | 5/2012 |
| WO | WO2012104388 | 8/2012 |
| WO | WO2012129562 | 9/2012 |
| WO | WO2013024011 | 2/2013 |
| WO | WO2013030138 | 3/2013 |
| WO | WO2013113722 | 8/2013 |
| WO | WO2013166396 | 11/2013 |
| WO | WO2015143380 | 9/2015 |
| WO | WO 2016/040193 | 3/2016 |
| WO | WO 2016040185 | 3/2016 |
| WO | WO2017079765 | 5/2017 |
| WO | WO 2020/006115 | 1/2020 |

OTHER PUBLICATIONS

Ator et al., "Overview of Drug Discovery and Development," Current Protocols in Pharmacology, 2006, Unit 9.9, 26 pages.
Deep et al., "New Combination Therapies with Cell Cycle Agents," Curr. Opin. Investig. Drugs, Jun. 2008, 9(6):591-604.
Guo et al., "Wnt/β-catenin signaling is sufficient and necessary for synovial joint formation," Genes & Development, Oct. 1, 2004, 18(19):2404-2417.
Hengstschlager et al., "Cyclin-dependent kinases at the G1-S transition of the mammalian cell cycle," Mutation Research, 1999, 436:1-9.
International Preliminary Report on Patentability in International Appln. No. PCT/US2020/013995, dated Jul. 29, 2021, 18 pages.
International Search Report and Written Opinion in International Application No. PCT/US2020/013995, dated Sep. 7, 2020, 16 pages.
Iwai et al., "Anti-tumor efficacy of a novel CLK inhibitor via targeting RNA splicing and MYC-dependent vulnerability," EMBO Molecular Medicine, Jun. 2018, 10(6):e8289, 15 pages.
Kharkevich, Pharmacology, 10th ed., GEOTAR-Media, 2010, Summary only, 1 page.
Kojima et al., "Optimization of development form in drug development," Pharmacia, 2016, 52(5):387-391.
Lapenna et al., "Cell cycle kinases as therapeutic targets for cancer," Nature Review—Drug Discovery, Jul. 2009, 8:547-566.
Lui et al., "Expression of Wnt pathway mediators in metaplasic tissue in animal model and clinical samples of tendinopathy," Rheumatology, Sep. 1, 2013, 52(9):1609-1618.
Majithia et al., "Rheumatoid arthritis: diagnosis and management," The American Journal of Medicine, Nov. 1, 2007, 120(11):936-939.
Malumbres et al., "CDK inhibitors in cancer therapy: what is next?" Trends in Pharmacological Sciences, Dec. 2007, 29(1):16-21.
Moon et al., "WNT and β-catenin signalling: diseases and therapies," Nature Reviews Genetics, Sep. 2004, 5(9):691-701.
Nakagami, "Preformation and Drug Development," Pharmacia, Mar. 1, 2003, 39 (3):204-208.
Nigg, "Mitotic Kinases as Regulators of Cell Division and its Checkpoints," Nature Reviews—Molecular Cell Biology, Jan. 2001, 2:21-32.
Nusse et al., "Three decades of Wnts: a personal perspective on how a scientific field developed," The EMBO Journal, Jun. 13, 2012, 31(12):2670-2684.
Olsen et al., "Bone development," Annual Review of Cell and Developmental Biology, Nov. 2000, 16(1):191-220.
Riggs et al., "The discovery of a dual TTK protein kinase/CDC2-like kinase (CLK2) inhibitor for the treatment of triple negative breast cancer initiated from a phenotypic screen," Journal of Medicinal Chemistry, Nov. 9, 2017, 60(21):8989-9002.
Santamaria et al., "Cdk1 is sufficient to drive the mammalian cell cycle," Nature, Aug. 16, 2007, 448:811-815.
Sharma et al., "Inhibitors of Cyclin Dependent Kinases: Useful Targets for Cancer Treatment," Current Cancer Drug Targets, 2008, 8(1):53-75.
Shi et al., "Uniaxial mechanical tension promoted osteogenic differentiation of rat tendon-derived stem cells (rTDSCs) via the Wnt5a-RhoA pathway," Journal of Cellular Biochemistry, Oct. 2012, 113(10):3133-3142.
Stahly, "The Importance of Salt Selection and Polymorph Screening for the Drug Product," Journal of Pharmaceutical Science and Technology Japan, 2006, 66(6):435-439.
Tchetina et al., "Increased type II collagen degradation and very early focal cartilage degeneration is associated with upregulation of chondrocyte differentiation related genes in early human articular cartilage lesions," The Journal of Rheumatology, May 1, 2005, 32(5):876-886.
Thomas et al., "Identification of a novel 3, 5-disubstituted pyridine as a potent, selective, and orally active inhibitor of Akt1 kinase," Bioorganic & Medicinal Chemistry Letters, Jul. 15, 2006, 16(14):3740-3744.
Zhulenko et al., Pharmacology, Colossus, 2008, Summary only, 1 page.
med.unc.edu [online], "Buffers," 2006, retrieved on Oct. 12, 2021, retrieved from URL<https://www.med.unc.edu/pharm/sondeklab/wp-content/uploads/sites/868/2018/10/buffers_calbiochem.pdf>, 38 pages.
"Application +A2:A31 of Hamish Christopher Swan Wood, Norman Whittaker, Irene Stirling and Kyuji Ohta," 582 F.2d 638 (Fed. Cir. 1978), 2 pages.
Adaimy et al., "Mutation in WNT10A Is Associated with an Autosomal Recessive Ectodermal Dysplasia: The Odonto-onychodermal Dysplasia," Am. J. Hum. Genet., (Oct. 2007), 81(4), 821-828.
Adult Brain Tumors Treatment, National Cancer Institute, pp. 1-21 (Jan. 24, 2013), 21 pages.
Ai et al., "Optimal Method to Stimulate Cytokine Production and Its Use in Immunotoxicity Assessment," Int J Environ Res Public Health, Sep. 2013, 10(9):3834-3842.
Anastas and Moon, "WNT signaling pathways as therapeutic targets in cancer," Nat Rev Cancer, 13(1):11-26, Jan. 2013.
Anastassiadis et al., "Comprehensive assay of kinase catalytic activity reveals features of kinase inhibitor selectivity," Nat. Biotechnol., Oct. 2011, 29(11):1039-1045.
Andres, "Molecular genetics and animal models in autistic disorder," Brain Research Bulletin, (2002), 57(1), 109-119.
Barker and Clevers, "Mining the Wnt pathway for cancer therapeutics," Nat Rev Drug Discov., 5(12):997-1014, Dec. 2006.

(56) References Cited

OTHER PUBLICATIONS

Barroga et al., "Discovery of an Intra-Articular Injection Small Molecule Inhibitor of the Wnt Pathway (SM04690) As a Potential Disease Modifying Treatment for Knee Osteoarthritis," 2015 ACR/ARHP Annual Meeting, Abst. No. 2007, Sep. 29, 2015, retrieved on Sep. 27, 2018, URL <https://acrabstracts.org/abstract/discovery-of-an-intra-articular-injection-small-molecule-inhibitor-of-the-wnt-pathway-sm04690-as-a-potential-disease-modifying-treatment-for-knee-osteoarthritis/>, 3 pages.

Bass, "Why the difference between tendinitis and tendinosis matters," International Journal of Therapeutic Massage and Bodywork, vol. 5, No. 1, Mar. 2012.

Bed "Chemistry", edited by I. L. Knunyants, scientific publishing house "Big Russian Encyclopedia," M., 2000, 5 pages.

Bendele, "Animal Models of Arthritis: Relevance to Human Disease," Toxicol Pathol 1999 27:134-142.

Bernstein, "Polymorphism in Molecular Crystals," Analytical Techniques for Polymorphs, 2002, 115-118, 272.

Beyer et al., "Extended report: β-catenin is a central mediator of pro-fibrotic Wnt signaling in systemic sclerosis," Ann Rheum Dis, 71:761-767, online Feb. 2012.

Bharath et al., "Evaluation of Myofibroblasts by Expression of Alpha Smooth Muscle Actin: A Marker in Fibrosis, Dysplasia and Carcinoma," Journal of Clinical and Diagnostic Research, 2014, 8(4):ZC14-ZC17.

Biason-Lauber et al., "A WNT4 Mutation Associated with Müllerian-Duct Regression and Virilization in a 46,XX Woman," N. Engl. J. Med., (Aug. 2004), 351(8), 792-798.

Blaydon et al., "The gene encoding R-spondin 4 (RSPO4), a secreted protein implicated in Wnt signaling, is mutated in inherited anonychia," Nat. Genet, (Nov. 2006), 38(11), 1245-1247.

Blom et al., "Involvement of the Wnt signaling pathway in experimental and human osteoarthritis: prominent role of Wnt-induced signaling protein 1," Arthritis Rheum., 60(2):501-512, Feb. 2009.

Bollong et al., "Small molecule-mediated inhibition of myofibroblast transdifferentiation for the treatment of fibrosis," PNAS, 2017, 114:18:4679-4684.

Bone fractures—https://my.clevelandclinic.org/health/diseases/15241—bone-fractures—Jun. 2018, 5 pages.

Boyden et al., "High Bone Density Due to a Mutation in LDL-Receptor-Related Protein 5," N. Engl. J. Med., (May 2002), 346(20):1513-1521.

Brack et al., "Increased Wnt signaling during aging alters muscle stem cell fate and increases fibrosis," Science., 317(5839):807-810, Aug. 2007.

Braga et al., "Making crystals from crystals: a green route to crystal engineering and polymorphism," J. Royal Soc. Chem. Commun., 2005, 3635-3645.

Brown et al., "Toxicity and toxicokinetics of the cyclin-dependent kinase inhibitor AG-024322 in cynomolgus monkeys following intravenous infusion," Cancer Chemother Pharmacol., 62(6):1091-1101, Epub May 2008.

Byrn et al., "Pharmaceutical solids: a strategic approach to regulatory considerations," Pharmaceutical Research, Jul. 1995, 12(7):945-954.

Caira, "Crystalline Polymorphism of Organic Compounds," Topics in Current Chemistry, Jan. 1998, 198:163-208.

Cancer definition in MedicineNet.com-2005, 1 page.

"Cancer Drug Design and Discovery," Neidle, Stephen, ed. (Elsevier/Academic Press, 2008), 5 pages.

Carpino et al., "Alpha-SMA expression in hepatic stellate cells and quantitative analysis of hepatic fibrosis in cirrhosis and in recurrent chronic hepatitis after liver transplantation," Digestive and Liver Disease, 2005, 37:349-356.

Cecil Textbook of Medicine, edited by Bennet, J.C., and Plum F., 20th edition, vol. 1, 1004-1010, 1996.

Chanput et al., "Transcription profiles of LPS-stimulated THP-1 monocytes and macrophages: a tool to study inflammation modulating effects of food-derived compounds," Food Funct, Dec. 2010, 1(3):254-61.

Chilosi et al., "The pathogenesis of COPD and IPF: Distinct horns of the same devil?" Respiratory Research, 13:3, 2012.

Chinese Search Report for application No. 201080044979.2, dated Mar. 14, 2013, 4 pages.

Chinese Search Report for application No. 201080061866.3, dated Aug. 28, 2013, 4 pages.

Chockalingam et al., "Elevated aggrecanase activity in a rat model of joint injury is attenuated by an aggrecanase specific inhibitor," Osteoarthritis Cartilage, Mar. 2011, 19(3): 315-323.

Chou and Talalay, "Quantitative analysis of dose-effect relationships: the combined effects of multiple drugs or enzyme inhibitors," Advances in Enzyme Regulation (1984), 22, 27-55.

Chou, "Drug combination studies and their synergy quantification using the Chou-Talalay method," Cancer Res., 70(2):440-446, Jan. 2010.

Chou, "Graphic rule for drug metabolism systems," Current Drug Metabolism, (May 2010) 11(4):369-378.

Christodoulides et al., "WNT10B mutations in human obesity," Diabetologia, (2006) 49(4):678-684.

Clevers and Nusse, "Wnt/β-catenin signaling and disease," Cell, (Jun. 2012), 149(6):1192-1205.

Clevers, "Wnt/beta-catenin signaling in development and disease," Cell, (Nov. 2006), 127(3), 469-480.

clinicaltrials.gov [online]. ClinicalTrials.gov Identifier: NCT02095548, "Phase 1, Dose Escalation Study Evaluating the Safety, Tolerability, Pharmacokinetics and Pharmacodynamics of SM04690 in Moderate to Severe Knee Osteoarthritis (OA)," Mar. 26, 2014, [retrieved on Aug. 1, 2018]. Retrieved from the Internet: URL<https://clinicaltrials.gov/ct2/show/NCT02095548?term=NCT02095548&rank=1>, 7 pages.

clinicaltrials.gov [online]. ClinicalTrials.gov Identifier: NCT02536833, "A Study Evaluating the Safety, Tolerability, and Efficacy of SM04690 Injected in the Target Knee Joint of Moderately to Severely Symptomatic Osteoarthritis Subjects," Sep. 1, 2015, [retrieved on Aug. 1, 2018], Retrieved from the Internet: URL<https://clinicaltrials.gov/ct2/show/NCT02536833?term=NCT02536833&rank=1>, X pages.

Corr, "Wnt-beta-catenin signaling in the pathogenesis of osteoarthritis," Nat Clin Pract Rheumatol., 4(10):550-556, Oct. 2008.

D'Alessio et al., "Benzodipyrazoles: a new class of potent CDK2 inhibitors," Bioorganic & Medicinal Chemistry Letters (2005), 15(5), 1315-1319.

Damia "Contemporary pre-clinical development of anticancer agents—What are the optimal preclinical models?" European Journal of Cancer 2009, 45, 2768-2781 p. 2778.

Dann et al., "Insights into Wnt binding and signaling from the structures of two Frizzled cysteine-rich domains," Nature, (Jul. 2001), 412, pp. 86-90.

Datta et al., "Novel therapeutic approaches for pulmonary fibrosis," Br J Pharmacol., 163(1):141-172, May 2011.

Davidovich et al., "Detection of Polymorphism by Powder X-Ray Diffraction: Interferences by Preferred Orientation," American Pharmaceutical Review, 2004, 7:(1):10, 12, 14, 16, and 100.

Davidson et al., "Emerging links between CDK cell cycle regulators and Wnt signaling," Trends Cell Biol., Aug. 2010, 20(8):453-460.

De Ferrari and Inestrosa, "Wnt signaling function in Alzheimer's disease," Brain Research Reviews, (2000), 33(1): 1-12.

De Ferrari and Moon, "The ups and downs of Wnt signaling in prevalent neurological disorders," Oncogene, (2006) 25(57): 7545-7553.

De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.

Dean "Analytical Chemistry Handbook," 1995, 10.24-10.26.

Dermer et al., "Another Anniversary for the War on Cancer," Bio/Technology, Mar. 1994, 12:320.

Deshmkukh et al., "Abstract: A Small Molecule Inhibitor of the Wnt Pathway (SM04755) as a Potential Topical Treatment for Tendinopathy," Abstract from the Orthobiologic Institute (TOBI) Annual Symposium, Las Vegas, Nevada, Jun. 7, 2018, 1 page.

Deshmkukh et al., "Abstract: Discovery of a Small Molecule Inhibitor of the Wnt Pathway (SM04755) as a Potential Topical

(56) References Cited

OTHER PUBLICATIONS

Treatment for Tendinopathy," Abstract from Osteoarthritis Research Society International (OARSI), Las Vegas, Nevada, Apr. 27, 2017, 2 pages.

Deshmkukh et al., "Abstract: Discovery of a Small Molecule Inhibitor of the Wnt Pathway (SM04755) as a Potential Topical Treatment for Tendinopathy," Abstract from the World Congress on Osteoporosis Osteoarthritis and Musculoskeletal Disease, Florence, Italy, Mar. 23, 2017, 2 pages.

Deshmkukh et al., "Abstract: Experimental Tendinopathy Treatment with SM04755, a Topical Small Molecule Inhibitor of the Wnt Pathway," Abstract from Osteoarthritis Research Society International (OARSI), Liverpool, England, Apr. 26, 2018, 3 pages.

Deshmkukh et al., "Abstract: Experimental Tendinopathy Treatment with SM04755, a Topical Small Molecule Wnt Pathway Inhibitor," Abstract from the Orthobiologic Institute (TOBI) Annual Symposium, Las Vegas, Nevada, Jun. 7, 2018, 2 pages.

Deshmkukh et al., "Poster: A Small Molecule Inhibitor of the Wnt Pathway (SM04755) as a Potential Topical Treatment for Tendinopathy," Poster from the Orthobiologic Institute (TOBI) Annual Symposium, Las Vegas, Nevada, Jun. 7, 2018, 1 page.

Deshmkukh et al., "Poster: Discovery of a Small Molecule Inhibitor of the Wnt Pathway (SM04755) as a Potential Topical Treatment for Tendinopathy," Poster from the World Congress on Osteoporosis Osteoarthritis and Musculoskeletal Disease, Florence, Italy, Mar. 23, 2017, 1 page.

Deshmkukh et al., "Poster: Experimental Tendinopathy Treatment with SM04755, a Topical Small Molecule Wnt Pathway Inhibitor," Poster from the Orthobiologic Institute (TOBI) Annual Symposium, Las Vegas, Nevada, Jun. 7, 2018, 2 pages.

Deshmkukh et al., "Presentation: Experimental Tendinopathy Treatment with SM04755, a Topical Small Molecule Inhibitor of the Wnt Pathway," Presentation from Osteoarthritis Research Society International (OARSI), Liverpool, England, Apr. 26, 2018, 17 pages.

Deshmukh et al., "Abstract #EULAR-6427: Discovery of a Small Molecule Inhibitor of the Wnt Pathway (SM04755) as a Potential Topical Treatment for Tendinopathy," Abstract from Annual European Congress of Rheumatology (EULAR), Madrid, Spain, Jun. 14, 2017, 2 pages.

Deshmukh et al., "Abstract #THU0522: Experimental Tendinopathy Treatment with SM04755, a Topical Small Molecule Inhibitor of the Wnt Pathway," Abstract from Annual European Congress of Rheumatology (EULAR), Amsterdam, Netherlands, Jun. 13-16, 2018, 2 pages.

Deshmukh et al., "Abstract: Discovery of a Small Molecule Inhibitor of the Wnt Pathway (SM04755) as a Potential Topical Treatment for Tendinopathy," Abstract from Orthopaedic Research Society Annual Meeting, New Orleans, Louisiana, Mar. 19, 2017, 1 page.

Deshmukh et al., "Abstract: Discovery of a Small Molecule Inhibitor of the Wnt Pathway (SM04755) as a Potential Topical Treatment for Tendinopathy," Abstract from Regenerative Medicine and Biology From Development to Regeneration, St. Louis, Missouri, May 4, 2017, 2 pages.

Deshmukh et al., "Abstract: Experimental tendinopathy treatment with SM04755, a topical small molecule inhibitor of the Wnt pathway," Abstract from Orthopaedic Research Society Annual Meeting, New Orleans, Louisiana, Mar. 10, 2018, 2 pages.

Deshmukh et al., "Poster # 1459: Experimental tendinopathy treatment with SM04755, a topical small molecule inhibitor of the Wnt pathway," Poster from Orthopaedic Research Society Annual Meeting, New Orleans, Louisiana, Mar. 19, 2018, 1 page.

Deshmukh et al., "Poster #443: Discovery of a Small Molecule Inhibitor of the Wnt Pathway (SM04755) as a Potential Topical Treatment for Tendinopathy," Poster from Osteoarthritis Research Society International (OARSI), Las Vegas, Nevada, Apr. 27, 2017, 1 page.

Deshmukh et al., "Poster #SAT067: Discovery of a Small Molecule Inhibitor of the Wnt Pathway (SM04755) as a Potential Topical Treatment for Tendinopathy," Poster from Annual European Congress of Rheumatology (EULAR), Madrid, Spain, Jun. 14, 2017, 1 page.

Deshmukh et al., "Poster #THU0522: Experimental Tendinopathy Treatment with SM04755, a Topical Small Molecule Inhibitor of the Wnt Pathway," Poster from Annual European Congress of Rheumatology (EULAR), Amsterdam, Netherlands, Jun. 13-16, 2018, 1 page.

Deshmukh et al., "Poster: Discovery of a Small Molecule Inhibitor of the Wnt Pathway (SM04755) as a Potential Topical Treatment for Tendinopathy," Poster from Regenerative Medicine and Biology From Development to Regeneration, St. Louis, Missouri, May 4, 2017, 2 pages.

Deshmukh et al., "Presentation: Discovery of a Small Molecule Inhibitor of the Wnt Pathway (SM04755) as a Potential Topical Treatment for Tendinopathy," Presentation from Orthopaedic Research Society Annual Meeting, New Orleans, Louisiana, Mar. 19, 2017, 19 pages.

Deshmukh et al., A Small Molecule, SM04690, Has Inhibitory Effects on the Wnt Pathway and Inflammation in Vitro, with Potential Implications for the Treatment of Osteoarthritis [abstract]. Arthritis Rheumatol. 2016; 68 (suppl 10). https://acrabstracts.org/abstract/a-small-molecule-sm04690-has-inhibitory-effects-on-the-wnt-pathway-and-inflammation-in-vitro-with-potential-implications-for-the-treatment-of-osteoarthritis/. Accessed Dec. 28, 2020.

Deshmukh et al., "A small-molecule inhibitor of the Wnt pathway (SM04690) as a potential disease modifying agent for the treatment of osteoarthritis of the knee," Osteoarthritis and Cartilage, Jan. 2018, 26(1):18-27.

Deshmukh et al., "Abstract #1104: Discovery of a Small Molecule Inhibitor of the Wnt Pathway(SM04755) As a Potential Topical Treatment for Chronic Tendinopathy," Abstract from 2016 ACR/ARHP Annual Meeting, Nov. 14, 2016, 3 pages.

Deshmukh et al., "Experimental Tendinopathy Treatment with SM04755, a Topical., Small Molecule Inhibitor of the Wnt Pathway," Abstract of Oral Presentation at #1952 at the American College of Rheumatology (ACR) Conference 2018, Chicago, Illinois, Oct. 19-24, 2018, 2 pages.

Deshmukh et al., "Experimental Tendinopathy Treatment with SM04755, a Topical., Small Molecule Inhibitor of the Wnt Pathway," Slides Present at #1952 at the American College of Rheumatology (ACR) Conference 2018, Chicago, Illinois, Oct. 19-24, 2018, 22 pages.

Deshmukh et al., "Poster #1104: Discovery of a Small Molecule Inhibitor of the Wnt Pathway(SM04755) As a Potential Topical Treatment for Chronic Tendinopathy," Poster from 2016 ACR/ARHP Annual Meeting, Nov. 14, 2016, 3 pages.

Dessalew et al., "3D-QSAR CoMFA and CoMSIA study on benzodipyrazoles as cyclin dependent kinase 2 inhibitors," Medicinal Chemistry, (2008), 4(4), 313-321.

Dong et al., "QSAR study of Akt/protein kinase B (PKB) inhibitors using support vector machine," European Journal of Medicinal Chemistry, (Oct. 2009), pp. 44(10): 4090-4097.

Doumpas et al., "TCF/LEF dependent and independent transcriptional regulation of Wnt/b-catenin target genes," The EMBO Journal, Nov. 13, 2018 1-14.

Du Bois, "Strategies for treating idiopathic pulmonary fibrosis," Nature Reviews Drug Discovery, 9(2): 129-140 (Feb. 2010).

Edamoto et al., "Alterations of RB1, p53 and Wnt pathways in hepatocellular carcinomas associated with hepatitis C, hepatitis B and alcoholic liver cirrhosis," Int J Cancer., 106(3):334-341, Sep. 1, 2003.

Egloff et al., "Gastrin-releasing peptide receptor expression in non-cancerous bronchial epithelia is associated with lung cancer: a case-control study," Respiratory Research, 13:9, Feb. 2012.

Enzo et al., "The Wnt/β-catenin pathway in human fibrotic-like diseases and its eligibility as a therapeutic target," Molecular and Cellular Therapies, 2015, 3(1), 13 pages.

Espada et al., "Wnt signalling and cancer stem cells," Clin. Transl. Oncol., (2009), 11(7), 411-27.

European Search Report for Application No. 13772420.9 dated Mar. 19, 2015, 4 pages.

European Search Report for Application No. 15174246.7, dated Jan. 4, 2016, 9 pages.

European Search Report for Application No. 15177852.9 dated Jan. 8. 2016, 10 pages.

(56) References Cited

OTHER PUBLICATIONS

European Search Report for Application No. 12830938.2 dated Mar. 3, 2015, 6 pages.
European Search Report in Application No. 10808586.1, dated Jan. 8, 2013, 9 pages.
European Search Report in Application No. 10808589.5, dated Jan. 8, 2013, 4 pages.
European Search Report in Application No. 10842538, dated Apr. 25, 2013, 6 pages.
Ewan et al., "A useful approach to identify novel small-molecule inhibitors of Wnt-dependent transcription," Cancer Res. (2010), 70(14), 5963-5973.
Exhibit A: *Otsuka Pharmaceutical Co., Ltd., v. Sandoz, Inc., Sun Pharmaceutical Industries, Ltd., Synton BV, Synthon Holding BV, Synthon Laboratories, Inc., and Synton Pharmaceuticals, Inc., and Apotex Inc. and Apotex Corp., and Teva Pharmaceuticals USA, Inc., Barr Laboratories, Inc., and Barr Pharmaceuticals, Inc.*, Decision on Appeal., 2011-1126, -1127, May 7, 2012, 33 pages.
Extended European Search Report for Application No. 14737972.1, dated Jul. 6, 2016, 7 pages.
Extended European Search Report for Application No. 17169783.2, dated Jan. 19, 2018, 6 pages.
Extended European Search Report for Application No. 17187452.2, dated Jan. 24, 2018, 6 pages.
Florez et al., "TCF7L2 Polymorphisms and Progression to Diabetes in the Diabetes Prevention Program," N. Engl. J. Med., (Jul. 2006), 355(3):241-250.
Forestier et al., "Prevalence of generalized osteoarthritis in a population with knee osteoarthritis," Joint Bone Spine, May 2011, 78(3):275-278.
Freese et al., "Wnt signaling in development and disease," Neurobiology of Disease, (2010) 38(2):148-153.
Freshney et al., "Culture of Animal Cells, A Manual of Basic Technique," Alan R. Liss, Inc., 1983, New York, p. 1-6.
Friedman et al., "Therapy for fibrotic diseases: nearing the starting line," Science Translational Medicine, Jan. 2013, 5(167):167sr1, 17 pages.
Fujii et al., "An antagonist of disheveled protein-protein interaction suppresses beta-catenin-dependent tumor cell growth," Cancer Res., 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," Pediatric and Developmental Pathology (2003), 6(4): 299-306.
GastricMALTLynnphonna—LynnphonnaAssociation—2011, 10 pages.
Giles et al., "Caught up in a Wnt storm: Wnt signaling in cancer," Biochim Biophys Acta., Jun. 2003, 1653(1):1-24.
Gitter et al., "Characteristics of human synovial fibroblast activation by IL-1 beta and TNF alpha," Immunology, Feb. 1989, 66(2):196-200.
Golub et al., "Molecular Classification of Cancer: Class Discovery and Class Prediction by Gene Expression Monitoring," Science, Oct. 1999, 286(5439):531-537.
Gudjonsson et al., "Mouse models of psoriasis. Journal of Investigative Dermatology," Jun. 1, 2007, 127(6):1292-1308.
Guillory (in Brittain ed.), "Polymorphism in Pharmaceutical Solids," NY: Marcel Dekker, Inc., 1999, 1-2, 125-181, 183-226.
Gunther et al., "Prevalence of generalised osteoarthritis in patients with advanced hip and knee osteoarthritis: the Ulm Osteoarthritis Study," Ann. Rheum. Dis., Dec. 1998, 57(12):717-723.
Guo et al., "Wnt/β-Catenin Signaling: a Promising New Target for Fibrosis Diseases," Physiol. Res., 2012, 61:337-346.
Handeli and Simon, "A small-molecule inhibitor of Tcf/beta-catenin signaling down-regulates PPARgamma and PPARdelta activities," Mol Cancer Ther., 7(3):521-529, Mar. 2008.
Hayami et al., "Characterization of articular cartilage and subchondral bone changes in the rat anterior cruciate ligament transection and meniscectomized models of osteoarthritis," Bone, Feb. 2006, 38(2):234-243.

Henderson Jr. et al., "Inhibition of Wnt/beta-catenin/CREB binding protein (CBP) signaling reverses pulmonary fibrosis," Proc Natl Acad Sci U S A., 107(32):14309-14314, Epub Jul. 2010.
Hood et al., "Discovery of a small molecule inhibitor of the Wnt pathway (SM04690) as a potential disease modifying treatment for knee osteoarthritis," Osteoarthritis and Cartilage, Apr. 1, 2016, 24:S14-15.
Hu et al., "Discovery of indazoles as inhibitors of Tpl2 kinase," Bioorganic & Medicinal Chemistry Letters, (Aug. 2011) 21(16): 4758-4761.
Huang et al., "Tankyrase inhibition stabilizes axin and antagonizes Wnt signaling," Nature, (Oct. 2009), 461(7264): 614-620.
Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," Bioorganic & Medicinal Chemistry Letters, (2007) 17(5): 1243-1245.
Hübner et al., "Standardized quantification of pulmonary fibrosis in histological samples," Biotechniques, 44(4):507-511, 514-517, Apr. 2008.
Ikejima et al., "Interleukin-1 induces tumor necrosis factor (TNF) in human peripheral blood mononuclear cells in vitro and a circulating TNF-like activity in rabbits," J Infect Dis, Jul. 1990, 162(1):215-23.
Im et al., "Wnt inhibitors enhance chondrogenesis of human mesenchymal stem cells in a long-term pellet culture," Biotechnol Lett., 33(5):1061-1068, Epub Jan. 2011.
Inestrosa and Toledo, "The role of Wnt signaling in neuronal dysfunction in Alzheimer's Disease," Mol Neurodegener, 3:9, doi:10.1186/1750-1326-3-9, 13 pages, Jul. 2008.
International Preliminary Report on Patentability for Application No. PCT/US2017/057536, dated Apr. 23, 2019, 8 pages.
International Preliminary Report on Patentability for International Application No. PCT/US2016/45251, dated Feb. 15, 2018, 7 pages.
International Preliminary Report on Patentability for International Application No. PCT/US2016/45252, dated Feb. 15, 2018, 7 pages.
International Preliminary Report on Patentability for International Application No. PCT/US2016/45256, dated Feb. 15, 2018, 7 pages.
International Preliminary Report on Patentability for International Application No. PCT/US2016/45261, dated Feb. 15, 2018, 7 pages.
International Preliminary Report on Patentability for International Application No. PCT/US2016/45263, dated Feb. 15, 2018, 7 pages.
International Preliminary Report on Patentability for International Application No. PCT/US2016/45267, dated Feb. 15, 2018, 7 pages.
International Preliminary Report on Patentability for International Application No. PCT/US2016/45270, dated Feb. 15, 2018, 7 pages.
International Preliminary Report on Patentability for International Application No. PCT/US2016/45271, dated Feb. 15, 2018, 7 pages.
International Preliminary Report on Patentability for International Application No. PCT/US2016/45272, dated Feb. 15, 2018, 7 pages.
International Preliminary Report on Patentability for International Application No. PCT/US2016/45278, dated Feb. 15, 2018, 7 pages.
International Preliminary Report on Patentability for International Application No. PCT/US2016/45283, dated Feb. 15, 2018, 7 pages.
International Preliminary Report on Patentability for International Application No. PCT/US2016/45293, dated Feb. 15, 2018, 8 pages.
International Preliminary Report on Patentability for International Application No. PCT/US2016/45296, dated Feb. 15, 2018, 8 pages.
International Preliminary Report on Patentability for International Application No. PCT/US2016/45311, dated Feb. 15, 2018, 6 pages.
International Preliminary Report on Patentability for International Application No. PCT/US2016/45332, dated Feb. 15, 2018, 7 pages.
International Preliminary Report on Patentability for International Application No. PCT/US2016/045269, dated Feb. 15, 2018, 7 pages.
International Preliminary Report on Patentability for International Application No. PCT/US2016/045304, dated Feb. 15, 2018, 8 pages.
International Preliminary Report on Patentability for International Application No. PCT/US2016/45309, dated Feb. 15, 2018, 7 pages.
International Preliminary Report on Patentability for International Application No. PCT/US2016/45326, dated Feb. 15, 2018, 6 pages.
International Preliminary Report on Patentability for International Application No. PCT/US2016/45333, dated Feb. 15, 2018, 6 pages.

(56) References Cited

OTHER PUBLICATIONS

International Preliminary Report on Patentability for International Application No. PCT/US2016/60868, dated May 17, 2018, 9 pages.
International Preliminary Report on Patentability for International Application No. PCT/US2017/035411, dated Dec. 4, 2018, 12 pages.
International Preliminary Report on Patentability for PCT/US2010/060514 dated Jun. 26, 2012, 10 pages.
International Preliminary Report on Patentability for PCT/US2012/055172 dated Mar. 27, 2014, 8 pages.
International Preliminary Report on Patentability for PCT/US2013/031055, dated Oct. 16, 2014, 9 pages.
International Preliminary Report on Patentability for PCT/US2013/039484, dated Nov. 4, 2014, 7 pages.
International Preliminary Report on Patentability for PCT/US2014/010607, dated Jul. 23, 2015, 7 pages.
International Preliminary Report on Patentability in International Application No. PCT/US2016/60856, dated May 17, 2018, 9 pages.
International Preliminary Report on Patentability in International Application No. PCT/US2017/057536, dated Apr. 23, 2019, 10 pages.
International Preliminary Report on Patentability PCT/US2010/044865 dated Feb. 14, 2012, 7 pages.
International Preliminary Report on Patentability PCT/US2010/044872 dated Feb. 14, 2012, 12 pages.
International Preliminary Report on Patentability for Application No. PCT/US2015/048660, dated Mar. 23, 2017, 6 pages.
International Preliminary Report on Patentability for Application No. PCT/US2015/048663, dated Mar. 23, 2017, 6 pages.
International Preliminary Report on Patentability for Application No. PCT/US2015/048668, dated Mar. 14, 2017, 6 pages.
International Preliminary Report on Patentability for Application No. PCT/US2015/048680, dated Mar. 23, 2017, 6 pages.
International Preliminary Report on Patentability for Application No. PCT/US2015/048683, dated Mar. 14, 2017, 7 pages.
International Preliminary Report on Patentability for Application No. PCT/US2015/048689, dated Mar. 23, 2017, 6 pages.
International Preliminary Report on Patentability for Application No. PCT/US2015/048705, dated Mar. 23, 2017, 9 pages.
International Preliminary Report on Patentability for Application No. PCT/US2015/048709, dated Mar. 23, 2017, 9 pages.
International Search Report and Written Opinion for International Application No. PCT/US2016/045304, dated Sep. 29, 2016, 14 pages.
International Search Report and Written Opinion for International Application No. PCT/US2016/045269, dated Oct. 4, 2016, 13 pages.
International Search Report and Written Opinion for International Application No. PCT/US2016/45251, dated Oct. 4, 2016, 13 pages.
International Search Report and Written Opinion for International Application No. PCT/US2016/45252, dated Oct. 4, 2016, 13 pages.
International Search Report and Written Opinion for International Application No. PCT/US2016/45256, dated Oct. 4, 2016, 13 pages.
International Search Report and Written Opinion for International Application No. PCT/US2016/45261, dated Oct. 4, 2016, 13 pages.
International Search Report and Written Opinion for International Application No. PCT/US2016/45263, dated Oct. 4, 2016, 13 pages.
International Search Report and Written Opinion for International Application No. PCT/US2016/45267, dated Oct. 4, 2016, 13 pages.
International Search Report and Written Opinion for International Application No. PCT/US2016/45270, dated Oct. 4, 2016, 13 pages.
International Search Report and Written Opinion for International Application No. PCT/US2016/45271, dated Oct. 4, 2016, 13 pages.
International Search Report and Written Opinion for International Application No. PCT/US2016/45272, dated Oct. 7, 2016, 13 pages.
International Search Report and Written Opinion for International Application No. PCT/US2016/45278, dated Oct. 4, 2016, 13 pages.
International Search Report and Written Opinion for International Application No. PCT/US2016/45283, dated Oct. 4, 2016, 13 pages.
International Search Report and Written Opinion for International Application No. PCT/US2016/45293, dated Oct. 7, 2016, 10 pages.
International Search Report and Written Opinion for International Application No. PCT/US2016/45296, dated Oct. 7, 2016, 13 pages.
International Search Report and Written Opinion for International Application No. PCT/US2016/45309, dated Oct. 5, 2016, 12 pages.
International Search Report and Written Opinion for International Application No. PCT/US2016/45311, dated Nov. 4, 2016, 12 pages.
International Search Report and Written Opinion for International Application No. PCT/US2016/45326, dated Nov. 16, 2016, 13 pages.
International Search Report and Written Opinion for International Application No. PCT/US2016/45332, dated Sep. 30, 2016, 14 pages.
International Search Report and Written Opinion for International Application No. PCT/US2016/45333, dated Oct. 27, 2016, 12 pages.
International Search Report and Written Opinion for International Application No. PCT/US2016/60868, dated Jan. 19, 2017, 12 pages.
International Search Report and Written Opinion for International Application No. PCT/US2017/057536, dated Feb. 8, 2018, 15 pages.
International Search Report and Written Opinion for PCT/US2010/060514, dated Mar. 2, 2011, 11 pages.
International Search Report and Written Opinion for PCT/US2012/055172, dated Nov. 13, 2012, 10 pages.
International Search Report and Written Opinion for PCT/US2013/031055, dated May 21, 2013, 14 pages.
International Search Report and Written Opinion for PCT/US2014/10607, dated Aug. 15, 2014, 12 pages.
International Search Report and Written Opinion for PCT/US2015/048660, dated Jan. 11, 2016, 14 pages.
International Search Report and Written Opinion for PCT/US2015/048663, dated Jan. 11, 2016, 14 pages.
International Search Report and Written Opinion for PCT/US2015/048668, dated Jan. 11, 2016, 9 pages.
International Search Report and Written Opinion for PCT/US2015/048680, dated Jan. 11, 2016, 14 pages.
International Search Report and Written Opinion for PCT/US2015/048683, dated Jan. 12, 2016.
International Search Report and Written Opinion for PCT/US2015/048689, dated Jan. 11, 2016, 14 pages.
International Search Report and Written Opinion for PCT/US2015/048705, dated Dec. 15, 2015, 14 pages.
International Search Report and Written Opinion for PCT/US2015/048709, dated Dec. 4, 2015, 14 pages.
International Search Report and Written Opinion for PCT/US2017/035411 dated Oct. 6, 2017, 18 pages.
International Search Report and Written Opinion in International Application No. PCT/US2016/60856, dated Jan. 24, 2017, 11 pages.
International Search Report and Written Opinion PCT/US2010/044865 dated Sep. 29, 2010, 8 pages.
International Search Report and Written Opinion PCT/US2010/044872 dated Oct. 5, 2010, 13 pages.
International Search Report and Writtent Opinion for PCT/US2017/060481, dated Mar. 6, 2018, 13 pages.
International Search Report for PCT/US2013/039484 dated Dec. 5, 2013, 14 pages.
Invitation to Pay Additional Fees for Application No. PCT/US2017/035411, dated Aug. 4, 2017, 12 pages.
Invitation to Pay Additional Fees for Application No. PCT/US2017/057536, dated Dec. 14, 2017, 11 pages.
Invitation to Pay for International App. No. PCT/US2015/048668, dated Nov. 2, 2015, 2 pages.
Invitation to Pay for International App. No. PCT/US2015/048683, dated Nov. 5, 2015, 2 pages.
Ivanisevic et al., "Use of X-ray Powder Diffraction In the Pharmaceutical Industry," Pharm. Sci. Encycl., 2010, p. 1-42.
Jain & Mohammedi, "Polymorphism in Pharmacy," Indian Drugs, 1986, 23:(6):315-329.
Janssens et al., "The Wnt-dependent signaling pathways as target in oncology drug discovery," Invest New Drugs., 24(4):263-280, Jul. 2006.

(56) References Cited

OTHER PUBLICATIONS

Jenkins et al., "Germline mutations in WTX cause a sclerosing skeletal dysplasia but do not predispose to tumorigenesis," Nat. Genet. (Jan. 2009), 41(1), 95-100.

Jessen et al., "Peripheral white blood cell toxicity induced by broad spectrum cyclin-dependent kinase inhibitors," Journal of Applied Toxicology (Jan. 2007), 27(2), 133-142.

Johnson et al., "A stem cell-based approach to cartilage repair," Science, 336(6082):717-721, Epub Apr. 5, 2012.

Johnson et al., "Relationships between drug activity in NCI preclinical in vitro and in vivo models and early clinical trials," British Journal of Cancer 2001, 84, 1424-1431.

Jordan, "Tamoxifen: A Most Unlikely Pioneering Medicine," Nature Reviews, Mar. 2003, 2:205-213.

Kanazawa et al., "Association of the Gene Encoding Wingless-Type Mammary Tumor Virus Integration-Site Family Member 5B (WNT5B) with Type 2 Diabetes," Am. J. Hum. Genet. (2004), 75(5), 832-843.

Karlberg et al., "Structural basis for the interaction between tankyrase-2 and a potent Wnt-signaling inhibitor," J. Med. Chem. (2010), 53(14), 5352-5.

Kibar et al., "Mutations in VANGL1 Associated with Neural-Tube Defects," N. Engl. J. Med., (Apr. 2007), 356(14):1432-1437.

Kim et al., "Blockade of the Wnt/β-Catenin Pathway Attenuates Bleomycin-Induced Pulmonary Fibrosis," Tohoku J. Exp. Med., 2011, 223:45-54.

King et al., "Build-3: a randomized, controlled trial of bosentan in idiopathic pulmonary fibrosis," Am J Respir Crit Care Med., 184(1):92-99, Epub Apr. 2011.

Kishimoto et al., "Wnt/beta-catenin signaling suppresses expressions of Scx, Mkx, and Tnmd in tendon-derived cells," Plos One, Jul. 27, 2017, 12(7), E0182051, pp. 1-17.

Kittaka, Drug Discovery Science/Pharmaceutical Chemistry, 2013, 150-161.

Kuwajima et al., "Necdin Promotes GABAergic Neuron Differentiation in Cooperation with D1x Homeodomain Proteins," Journal of Neuroscience (May 2006), 26(20), 5383-5392.

Lacy et al., "Generation and characterization of ABT-981, a dual variable domain immunoglobulin (DVD-Ig(TM)) molecule that specifically and potently neutralizes both IL-1α and IL-1β," MAbs, May 2015, 7(3): 605-619.

Lala and Orucevic, "Role of nitric oxide in tumor progression: lessons from experimental tumors," Cancer and Metastasis Review, vol. 17, Mar. 1998, pp. 91-106.

Lammi et al., "Mutations in AXIN2 Cause Familial Tooth Agenesis and Predispose to Colorectal Cancer," Am. J. Hum. Genet. (2004), 74(5), 1043-1050.

Ledford "US cancer institute overhauls cell lines," Nature, Feb. 25, 2016 vol. 530 p. 391.

Leyns et al., "Frzb-1 Is a Secreted Antagonist of Wnt Signaling Expressed in the Spemann Organizer," Cell (Mar. 1997), 88(6), 747-756.

Li et al., "Artesunate attenuates the growth of human colorectal carcinoma and inhibits hyperactive Wnt/beta-catenin pathway," Int J Cancer., 121(6):1360-1365, Sep. 2007.

Lin et al., "Synthesis and evaluation of pyrazolo[3,4-b]pyridine CDK1 inhibitors as anti-tumor agents," Bioorganic & Medicinal Chemistry Letters, (Aug. 2007), 17(15): 4297-4302.

Liu et al., "Fibrotic lung fibroblasts show blunted inhibition by cAMP due to deficient cAMP response element-binding protein phosphorylation," J Pharmacol Exp Ther., 315(2):678-687, Epub Aug. 3, 2005.

Lories et al., "To Wnt or not to Wnt: the bone and joint health dilemma," Nat Rev Rheumatol., 9(6):328-339, Epub Mar. 2013.

Low et al., "Phenotypic fingerprinting of small molecule cell cycle kinase inhibitors for drug discovery," Curr Chem Genomics., 3:13-21, Mar. 2009.

Lu et al., "Structure-activity relationship studies of small-molecule inhibitors of Wnt response," Bioorganic & Medicinal Chemistry Letters, (Jul. 2009), 19(14):3825-3827.

Lui, "Histopathological changes in tendinopathy—potential roles of BMPs?" Rheumatology, May 2013, 52:2116-2126.

Luo et al., "Fragile X Mental Retardation Protein Regulates Proliferation and Differentiation of Adult Neural Stem/Progenitor Cells," PLoS Genetics, (Apr. 2010), 6(4):e1000898, 15 pages.

Luu et al., "Wnt/beta-catenin signaling pathway as a novel cancer drug target," Curr Cancer Drug Targets, 4(8):653-671, Dec. 2004.

Luyten et al., "Wnt signaling and osteoarthritis," Bone, 44(4):522-527, Epub Dec. 14, 2008.

MacDonald et al., "Wnt/beta-catenin signaling: components, mechanisms, and diseases," Dev. Cell (Jul. 2009), 17(1), 9-26.

Mandel et al., "SERKAL Syndrome: An Autosomal-Recessive Disorder Caused by a Loss-of-Function Mutation in WNT4," Am. J. Hum. Genet., (Jan. 2008), 82(1), 39-47.

Mani et al., "LRP6 Mutation in a Family with Early Coronary Disease and Metabolic Risk Factors," Science, (Mar. 2007), 315(5816), 1278-1282.

McBride et al., "Design and structure-activity relationship of 3-benzimidazol-2-yl-1H-indazoles as inhibitors of receptor tyrosine kinases," Bioorganic & Medicinal Chemistry Letters (2006), 16(13), 3595-3599.

McMahon et al., "VEGF receptor signaling in tumor angiogenesis," The Oncologist, 2005, pp. 3-10.

MedlinePlus, [online] "Cancer," [retrieved on Jul. 6, 2007], Retrieved from the internet, URL http://www.nInn.nih.govinnedlineplus/cancer.html>.

Misra et al., "1H-Pyrazolo[3,4-b]pyridine inhibitors of cyclin-dependent kinases: highly potent 2,6-Difluorophenacyl analogues," Bioorganic & Medicinal Chemistry Letters, (2003), 13:2405-2408.

Miyaura et al., "Palladium-catalyzed cross-coupling reactions of organoboron compounds," Chemical Reviews, Nov. 1, 1995, 95(7):2457-2483.

Monner et al., "Induction of lymphokine synthesis in peripheral blood mononuclear cells with phorbol ester and calcium ionophore allows precise measurement of individual variations in capacity to produce IL 2," Lymphokine Res. 1986;5 Suppl 1:S67-73.

Mora et al., "Emerging therapies for idiopathic pulmonary fibrosis, a progressive age-related disease," Nat Rev Drug Discov. Oct. 30, 2017; 16(11): 810.

Morissette et al., "High-throughput crystallization: polymorphs, salts, co-crystals and solvates of pharmaceutical solids," Advanced drug delivery reviews, Feb. 25, 2004, 56(3):275-300.

Morrisey, "Wnt signaling and pulmonary fibrosis," Am J Pathol., 162(5):1393-1397, May 2003.

Muddassar et al., "Elucidation of binding mode and three dimensional quantitative structure—activity relationship studies of a novel series of protein kinase B/Akt inhibitors," Journal of Molecular Modeling, (2009), 15(2): 183-192.

Ngkelo et al., "LPS induced inflammatory responses in human peripheral blood mononuclear cells is mediated through NOX4 and Gia dependent PI-3 kinase signaling," Journal of Inflammation, Dec. 2012, 9(1):1, 7 pages.

Niemann et al., "Homozygous WNT3 Mutation Causes Tetra-Amelia in a Large Consanguineous Family," Am. J. Hum. Genet. (2004), 74(3), 558-563.

Nishisho et al., "Mutations of chromosome 5q21 genes in FAP and colorectal cancer patients," Science, (Aug. 1991), 253(5020):665-669.

Nozaki et al., Drug Discovery Chemistry, 1995, 98-99.

Nusse, "Wnt signaling in disease and in development," Cell Res., 15(1):28-32, Jan. 2005.

Oates et al., "Increased DNA Methylation at the AXIN1 Gene in a Monozygotic Twin from a Pair Discordant for a Caudal Duplication Anomaly," Am. J. Hum. Genet. (2006 ), 79(1), 155-162.

Ocana, "Preclinical development of molecular targeted agents for cancer," Nat. Rev. Clin. Oncol. 2011, 8, 200-209.

Oduor et al., "Trypanosoma brucei glycogen synthase kinase-3, a target for anti-trypanosomal drug development: a public-private partnership to identify novel leads," PLoS Negl Trop Dis., 5(4):e1017, Apr. 2011.

Okerlund and Cheyette, "Synaptic Wnt signaling—a contributor to major psychiatric disorders?" J Neurodev Disord., (2011) 3(2):162-174.

(56) References Cited

OTHER PUBLICATIONS

Osteoarthritis, https://www.mayoclinic.org/diseases-conditions/osteoarthritis/diagnosis-treatment/drc-20351930—Sep. 2018, 8 pages.
Park et al., "Optimized THP-1 differentiation is required for the detection of responses to weak stimuli," Inflamm Res, Jan. 2007, 56(1):45-50.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," J Med Chem, May 2015, 58(9): 3859-3874.
Patani and Lavoie, "Bioisosterism: A Rational Approach in Drug Design," Chem. Rev, Jul. 25, 1996, vol. 96, p. 3147-3176.
Piersanti et al., "Synthesis of benzo[1,2-d;3,4-d']diimidazole and 1 H-pyrazolo[4,3-b]pyridine as putative A2A receptor antagonists," Organic and Biomolecular Chemistry, Aug. 2007, 5(16):2567-2571.
Pinedo & Slamon, "Translational Research: the role of VEGF in tumor angiogenesis," The Oncologist, 2005, pp. 1-2.
Polakis, "Wnt signaling and cancer," Genes Dev., 14: 1837-1851, 2000.
Pritzker et al., "Osteoarthritis cartilage histopathology: grading and staging," Osteoarthr. Cartil., Jan. 2006, 14(1):13-29.
Pubchem, Substance Record for SID 164345938. Deposit Date: Nov. 4, 2013. [retrieved on Nov. 16, 2015], Retrieved from the Internet. <URL: https://pubchem.ncbi.nlm.nih.gov/substance/164345938#section=Top>, 5 pages.
Qin et al., "Complexity of the genotype-phenotype correlation in familial exudative vitreoretinopathy with mutations in the LRP5 and/or FZD4 genes," Hum. Mutat. (2005), 26(2), 104-112.
Reya and Clevers, "Wnt signalling in stem cells and cancer," Nature 434: 843-850, Apr. 2005.
Richards et al., "Peripheral blood proteins predict mortality in idiopathic pulmonary fibrosis," Am J Respir Crit Care Med., 185(1):67-76, Jan. 2012.
Rivera et al., "An X Chromosome Gene, WTX, Is Commonly Inactivated in Wilms Tumor," Science, (Feb. 2007), 315(5812):642-645, published online Jan. 4, 2007.
Robitaille et al., "Mutant frizzled-4 disrupts retinal angiogenesis in familial exudative vitreoretinopathy," Nat. Genet., (Sep. 2002), 32(2):326-330.
Rodríguez-Spong et al., "General principles of pharmaceutical solid polymorphism: a supramolecular perspective," Advanced drug delivery reviews, Feb. 23, 2004, 56(3):241-274.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9): 1178-1183.
Ryu et al., "Natural derivatives of curcumin attenuate the Wnt/beta-catenin pathway through down-regulation of the transcriptional coactivator p300," Biochem Biophys Res Commun., 377(4):1304-1308, print Dec. 2008, Epub Nov. 2008.
Salinas, "Wnt signaling in the vertebrate central nervous system: from axon guidance to synaptic function," Cold Spring Harb Perspect Biol., (2012) 4(2). pii: a008003, 15 pages.
Sato, "Upregulation of the Wnt/beta-catenin pathway induced by transforming growth factor-beta in hypertrophic scars and keloids," Acta Derm Venereol., 86(4):300-307, 2006.
Seah et al., "Neuronal Death Resulting from Targeted Disruption of the Snf2 Protein ATRX Is Mediated by p53," Journal of Neuroscience (Nov. 2008), 28(47), 12570-12580.
Seddon "Pseudopolymorph: A Polemic," Crystal Growth & Design, 2004, v.4(6) p. 1087.
Shih et al., "Pharmacophore modeling and virtual screening to identify potential RET kinase inhibitors," Bioorg Med Chem Lett., 21(15):4490-4497, Epub Jun. 2011.
Shruster et al., "Wnt signaling enhances neurogenesis and improves neurological function after focal ischemic injury," PLoS One, (Jul. 2012), 7(7):e40843, 11 pages.
Shuto, Organic Drug Molecular Theory, 2012, 218-23.

Silva et al., "Advances in Prodrug Design," Mini-Revs. In Med. Chem. (2005), 5: 893-914.
Singapore Search Report for Application No. 11201400666P, dated Dec. 12, 2017, 7 pages.
Singapore Search Report for Application No. 11201400666P, dated Mar. 17, 2016, 12 pages.
Solowiej et al., "Characterizing the Effects of the Juxtamembrane Domain on Vascular Endothelial Growth Factor Receptor-2 Enzymatic Activity, Autophosphorylation, and Inhibition by Axitinib," Biochemistry, (2009), 48(29), 7019-7031.
Sperber et al., "Cytokine secretion induced by superantigens in peripheral blood mononuclear cells, lamina propria lymphocytes, and intraepithelial lymphocytes," Clin Diagn Lab Immunol, Jul. 1995, 2(4):473-477.
Staines et al., "Cartilage development and degeneration: a Wnt situation," Cell Biochem Funct., 30(8):633-642, Epub Jun. 2012.
Stomach cancer—Mayoclinic.com—Apr. 9, 2011, 8 pages.
Sutherland et al., "A robust high-content imaging approach for probing the mechanism of action and phenotypic outcomes of cell-cycle modulators," Molecular Cancer Therapeutics, (Feb. 2011), 10(2):242-254.
Swaney et al., "A novel, orally active LPA(1) receptor antagonist inhibits lung fibrosis in the mouse bleomycin model," Br J Pharmacol., 160(7):1699-1713, Aug. 2010.
Takahashi-Yanaga et al., "Celecoxib-induced degradation of T-cell factors-1 and -4 in human colon cancer cells," Biochem Biophys Res Commun,, 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," J Biol Chem., 280(19):19185-95. Epub Mar. 2005.
Thompson et al., "WNT/beta-catenin signaling in liver health and disease," Hepatology, 45(5):1298-1305, May 2007.
Trujillo et al., "2-(6-Phenyl-1H-indazol-3-yl)-1H-benzo[d]imidazoles: design and synthesis of a potent and isoform selective PKC-zeta inhibitor," Bioorg Med Chem Lett., 19(3):908-911, Epub Dec. 6, 2008.
Types of Brain Cancer at http://www.cancercenter.com/brain-cancer/types-of-brain-cancer.cfrn (Mar. 12, 2013), 3 pages.
"Types of Breast Cancer," published inbreastcancer.org (Sep. 30, 2012), 1 page.
Ugur et al., "Homozygous WNT10b mutation and complex inheritance in Split-Hand/Foot Malformation," Hum. Mol. Genet. (2008), 17(17), 2644-2653.
United States Court of Appeals for the Federal Circuit, *Eli Lilly and Company*, Plaintiff-Appellant, v. *Actavis Elizabeth LLC*, Defendant-Appellee, and *Sun Pharmaceutical Industries, Ltd.*, Defendant-Appellee, and *Sandoz, Inc.*, Defendant-Appellee, and *Mylan Pharmaceuticals Inc.*, Defendant-Appellee, and *Apotex Inc.*, Defendant-Appellee, and *Aurobindo Pharma Ltd.*, Defendant-Appellee, and *Teva Pharmaceuticals USA, Inc.*, Defendant-Appellee, Appeal from the United States District Court for the District of New Jersey in Case No. 07-CV-3770, Judge Dennis M. Cavanaugh, decided on Jul. 29, 2011, 20 pages.
Vippagunta et al., "Crystalline solids," Advanced Drug Delivery Reviews, 2001, 48:3-26.
Vulpetti et al., "Structure-Based Approaches to Improve Selectivity: CDK2-GSK3β Binding Site Analysis," Journal of Chemical Information and Modeling (2005), 45(5), 1282-1290.
Wagner et al., "The therapeutic potential of the Wnt signaling pathway in bone disorders," Curr Mol Pharmacol., 4(1):14-25, Jan. 2011.
Walters and Kleeberger, "Mouse models of bleomycin-induced pulmonary fibrosis," Current Protocols in Pharmacology, (2008) Chapter 5: Unit 5.46, 1-17.
Wang et al., "Mutations in X-linked PORCN, a putative regulator of Wnt signaling, cause focal dermal hypoplasia," Nat. Genet. (Jul. 2007), 39(7), 836-838.
Wantanabe and Dai, "Winning WNT: race to Wnt signaling inhibitors," Proc Natl Acad Sci U S A. 108(15):5929-5930, Epub Mar. 2011.

(56) References Cited

OTHER PUBLICATIONS

Watts et al., "RhoA signaling modulates cyclin D1 expression in human lung fibroblasts; implications for idiopathic pulmonary fibrosis," Respir Res., 7:88, Jun. 15, 2006.

Weng et al., "Control of Dkk-1 ameliorates chondrocyte apoptosis, cartilage destruction, and subchondral bone deterioration in osteoarthritic knees," Arthritis Rheum., 62(5):1393-1402, May 2010.

Wermuth ed., "The Practice of Medicinal Chemistry, Upper Volume," Technomics, Inc., Aug. 1998, 235-271.

Witherington et al., "5-Aryl-pyrazolo[3,4-b]pyridazines: potent inhibitors of glycogen synthase kinase-3 (GSK-3)," Bioorganic & Medicinal Chemistry Letters, (May 2003), 13(9):1581-1584.

Woods et al., "Mutations in WNT7A Cause a Range of Limb Malformations, Including Fuhrmann Syndrome and Al-Awadi/Raas-Rothschild/Schinzel Phocomelia Syndrome," Am. J. Hum. Genet. (Aug. 2006), 79(2), 402-408.

Yamada et al., "Emergence of TNIK inhibitors in cancer therapeutics," Cancer Sci, May 2017, 108(5):818-823.

Yan et al., "Discovery of small molecule inhibitors of the Wnt/b-catenin signaling pathway by targeting b-catenin/Tcf4 interactions," Experimental Biology and Medicine, vol. 242, Jun. 2017, 1185-1197.

Yardy and Brewster, "Wnt signalling and prostate cancer," Prostate Cancer Prostatic Dis, 8(2):119-126, 2005.

Yazici et al., "Abstract #: 312: Safety, Efficacy and Biomarker Outcomes of a Novel, Intra-Articular, Injectable, Wnt Inhibitor (SM04690) in the Treatment of Osteoarthritis of the Knee: Interim, Exploratory Analysis of Results from a Randomized, Double-Blind, Placebo-Controlled Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.

Yazici et al., "Abstract #: 313: Magnetic Resonance Imaging Outcomes Using an Intra-Articular Injection (SM04690) in the Treatment of Osteoarthritis of the Knee: Interim, Exploratory Analysis of Results from a Randomized, Double-Blind, Placebo-Controlled, Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.

Yu et al., "Physical characterization of polymorphic drugs: an integrated characterization strategy," PSTT, 1998, 1(3):118-127.

Zhan et al., "Wnt signaling in cancer" Oncogene (2017) 36, 1461-1473.

Zhang et al., "Small-molecule synergist of the Wnt/beta-catenin signaling pathway," Proc Natl Acad Sci U S A., 104(18):7444-7448, Epub Apr. 2007 and correction 104(30):12581, Jul. 2007.

Zheng, "Small-molecule inhibitors of Wnt signaling pathway: towards novel anticancer therapeutics," Future Med. Chem. (2015) 7(18), 2485-2505.

Zhong et al., "Characterization of in vitro and in vivo metabolism of AG-024322, a novel cyclin-dependent kinase (CDK) inhibitor," Health (2009), 1(4): 249-262.

Zhu et al., "Design and synthesis of pyridine-pyrazolopyridine-based inhibitors of protein kinase B/Akt," Bioorganic & Medicinal Chemistry, Mar. 2007, 15(6):2441-2452.

\* cited by examiner

TREATMENT OF OSTEOARTHRITIS

CROSS-REFERENCE TO RELATED APPLICATIONS

This application is a continuation of U.S. application Ser. No. 16/710,099, filed Dec. 11, 2019, which claims benefit of U.S. application Ser. No. 15/773,951, filed on May 4, 2018, which claims benefit of International Application No. PCT/US2016/060868, having an International Filing Date of Nov. 7, 2016, which claims priority to U.S. Provisional Application Nos. 62/252,332, filed Nov. 6, 2015, and 62/303,168, filed Mar. 3, 2016, all of which are incorporated by reference in their entirety.

TECHNICAL FIELD

This description relates to compositions and methods for treating osteoarthritis including administration of a compound of Formula (I), including polymorph and amorphous forms thereof. For example, provided herein are methods for treating osteoarthritis including administration, such as intra-articular administration, of compositions prepared from and/or including compounds of Formula (I), including polymorph and amorphous forms thereof.

BACKGROUND

Osteoarthritis is a chronic degenerative joint disease in which cartilage and bone are primarily affected and for which acceptable long-term therapy does not yet exist. Osteoarthritis is especially common among people over 50 years of age, and usually affects a joint on one side of the body. In osteoarthritis, the cartilage breaks down and wears away, causing pain, swelling, and loss of motion of the joint. Osteoarthritis of the knee can be unilateral, which affects just one knee joint in an individual, or bilateral, which affects both knees in the same individual. Reported prevalence of unilateral osteoarthritis has ranged from 12.6%-34.1% in individuals with osteoarthritis [*Ann. Rheum. Dis.* (1998), 57(12), 717-723 and *Joint Bone Spine* (2011), 78(3), 275-278]. To date, clinical efforts aimed at treating osteoarthritis have been primarily directed toward symptomatic relief of pain and inflammation.

SUMMARY

Provided herein are methods for treating osteoarthritis in a subject in need thereof, the methods comprising intra-articular administration of a pharmaceutical composition comprising a therapeutically effective amount of a compound of Formula (I), including amorphous and polymorph forms thereof.

Also provided herein is a method for treating osteoarthritis in a subject in need thereof, the method comprising intra-articular administration of a pharmaceutical composition comprising a therapeutically effective amount of a compound of Formula (I), wherein the compound of Formula (I) is substantially present as polymorph Form 13 having an X-ray powder diffraction pattern comprising peaks at ° 2θ values of 6.4±0.2, 11.0±0.2, and 18.4±0.2.

Also provided herein is a composition comprising a polymorph of a compound of Formula (I), wherein the polymorph is Form 1 and has an X-ray powder diffraction pattern comprising peaks at ° 2θ values of 6.8±0.2, 12.4±0.2, and 18.5±0.2; and wherein less than about 20% by weight of the amount of the compound of Formula (I) in the composition is polymorph Form 9 having X-ray powder diffraction pattern comprising peaks at ° 2θ values of 4.9±0.2, 18.6±0.2, and 21.1±0.2.

Also provided herein is a composition comprising a mixture of polymorphs of a compound of Formula (I): wherein the mixture comprises a polymorph Form 1 having an X-ray powder diffraction pattern comprising peaks at ° 2θ values of 6.8±0.2, 12.4±0.2, and 18.5±0.2; and a non-stoichiometric hydrate of Form 1 having between 1% and about 20% by weight water; wherein less than about 20% by weight of the amount of the compound of Formula (I) in the composition is polymorph Form 9 having X-ray powder diffraction pattern comprising peaks at ° 2θ values of 4.9±0.2, 18.6±0.2, and 21.1±0.2.

Also provided herein is a pharmaceutical composition comprising a compound of Formula (I), wherein the compound of Formula (I) is substantially present as a non-stoichiometric hydrate of Form 1 having between 1% and about 20% by weight water; and a pharmaceutically acceptable carrier; wherein less than about 20% by weight of the amount of the compound of Formula (I) in the composition is polymorph Form 9 having X-ray powder diffraction pattern comprising peaks at ° 2θ values of 4.9±0.2, 18.6±0.2, and 21.1±0.2.

Also provided herein is a pharmaceutical composition comprising a compound of Formula (I), wherein the compound of Formula (I) is substantially present as polymorph Form 1 having an X-ray powder diffraction pattern comprising peaks at ° 2θ values of 6.8±0.2, 12.4±0.2, and 18.5±0.2; and a pharmaceutically acceptable carrier; wherein less than about 20% by weight of the amount of the compound of Formula (I) in the composition is polymorph Form 9 having X-ray powder diffraction pattern comprising peaks at ° 2θ values of 4.9±0.2, 18.6±0.2, and 21.1±0.2.

Also provided herein is a pharmaceutical composition prepared by a process comprising mixing a pharmaceutically acceptable carrier and one or more polymorphs of a compound of Formula (I), wherein the polymorphs are selected from the group consisting of a polymorph Form 1 having an X-ray powder diffraction pattern comprising peaks at ° 2θ values of 6.8±0.2, 12.4±0.2, and 18.5±0.2; a non-stoichiometric hydrate of Form 1 having between 1% and about 20% by weight water; wherein less than about 20% by weight of the amount of the compound of Formula (I) is polymorph Form 9 having X-ray powder diffraction pattern comprising peaks at ° 2θ values of 4.9±0.2, 18.6±0.2, and 21.1±0.2.

Also provided herein is a process for preparing a polymorph of a compound of Formula (I), wherein the polymorph is Form 1 and has an X-ray powder diffraction pattern comprising peaks at ° 2θ values of 6.8±0.2, 12.4±0.2, and 18.5±0.2; wherein the process comprises drying a compound of Formula (I) to Form 1.

Also provided herein is a process for preparing a polymorph of a compound of Formula (I), wherein the polymorph is a non-stoichiometric hydrate of Form 1 having between 1% and about 20% by weight water; wherein the process comprises reslurrying a compound of Formula (I) in an aqueous solution.

Also provided herein is a method for treating osteoarthritis in a subject in need thereof, the method comprising intraarticular administration of a pharmaceutical composition comprising a therapeutically effective amount of a compound of Formula (I), or a pharmaceutically acceptable salt thereof; wherein the compound of Formula (I) is substantially present as a non-stoichiometric hydrate of Form 1 having between 1% and 20% by weight water.

Also provided herein is a composition comprising a polymorph of a compound of Formula (I), wherein the polymorph is a non-stoichiometric hydrate and has an X-ray powder diffraction pattern comprising peaks at ° 2θ values of 6.4±0.2, 11.0±0.2, and 18.4±0.2; and wherein less than about 20% by weight of the amount of the compound of Formula (I) in the composition is polymorph Form 9 having X-ray powder diffraction pattern comprising peaks at ° 2θ values of 4.9±0.2, 18.6±0.2, and 21.1±0.2.

Also provided herein is a pharmaceutical composition comprising a compound of Formula (I), wherein the compound of Formula (I) is substantially present as a non-stoichiometric hydrate of Form 1 having between 1% and about 20% by weight water; and a pharmaceutically acceptable carrier; wherein less than about 20% by weight of the amount of the compound of Formula (I) in the composition is polymorph Form 9 having X-ray powder diffraction pattern comprising peaks at ° 2θ values of 4.9±0.2, 18.6±0.2, and 21.1±0.2.

Also provided herein is a pharmaceutical composition prepared by a process comprising mixing a pharmaceutically acceptable carrier and one or more polymorphs of a compound of Formula (I), wherein the polymorphs are selected from the group consisting of a polymorph Form 1 having an X-ray powder diffraction pattern comprising peaks at ° 2θ values of 6.8±0.2, 12.4±0.2, and 18.5±0.2; a non-stoichiometric hydrate of Form 1 having between 1% and about 20% by weight water; and mixtures thereof; wherein less than about 20% by weight of the amount of the compound of Formula (I) is polymorph Form 9 having X-ray powder diffraction pattern comprising peaks at ° 2θ values of 4.9±0.2, 18.6±0.2, and 21.1±0.2.

A compound of Formula (I) has the structure:

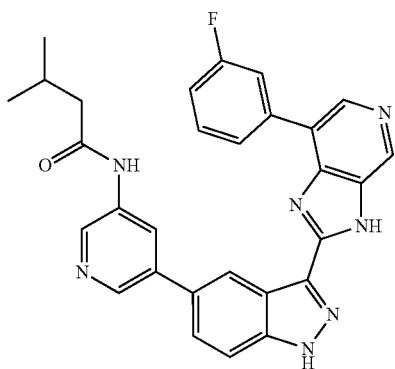

I

Other features and advantages of the compositions, methods and uses provided herein will be apparent from the following detailed description and figures, and from the claims.

DESCRIPTION OF DRAWINGS

FIG. 1A is an x-ray powder diffraction scan of fully dried Form 1. FIG. 1B is a differential scanning calorimetry scan of Form 1. FIG. 1C is a thermal gravimetric analysis scan of Form 1. FIG. 1D is a dynamic vapor sorption scan of Form 1.

FIG. 2A is an x-ray powder diffraction scan of fully dried Form 2. FIG. 2B is a differential scanning calorimetry scan of Form 2. FIG. 2C is a thermal gravimetric analysis scan of Form 2. FIG. 2D is an x-ray powder diffraction scan of fully dried Form 2*. FIG. 2E is a differential scanning calorimetry scan of Form 2*. FIG. 2F is a thermal gravimetric analysis scan of Form 2*. FIG. 2G is an x-ray powder diffraction scan of Form 2. FIG. 2H is a differential scanning calorimetry scan of Form 2.

FIG. 3A is an x-ray powder diffraction scan of fully dried Form 3. FIG. 3B is a differential scanning calorimetry scan of Form 3. FIG. 3C is a thermal gravimetric analysis scan of Form 3.

FIG. 4A is an x-ray powder diffraction scan of fully dried Form 4. FIG. 4B is a differential scanning calorimetry scan of Form 4. FIG. 4C is a thermal gravimetric analysis scan of Form 4. FIG. 4D is an x-ray powder diffraction scan of fully dried Form 4*. FIG. 4E is a differential scanning calorimetry scan of Form 4*. FIG. 4F is a thermal gravimetric analysis scan of Form 4*. FIG. 4G is an x-ray powder diffraction scan of Form 4. FIG. 4H is a differential scanning calorimetry scan of Form 4. FIG. 4I is a thermal gravimetric analysis scan of Form 4**.

FIG. 5A is an x-ray powder diffraction scan of fully dried Form 5. FIG. 5B is a differential scanning calorimetry scan of Form 5. FIG. 5C is a thermal gravimetric analysis scan of Form 5. FIG. 5D is an x-ray powder diffraction scan of Form 5*.

FIG. 6A is an x-ray powder diffraction scan of Form 6. FIG. 6B is a differential scanning calorimetry scan of Form 6.

FIG. 7A is an x-ray powder diffraction scan of fully dried Form 7. FIG. 7B is a differential scanning calorimetry scan of Form 7. FIG. 7C is a thermal gravimetric analysis scan of Form 7.

FIG. 8A is an x-ray powder diffraction scan of fully dried Form 8. FIG. 8B is a differential scanning calorimetry scan of Form 8. FIG. 8C is a thermal gravimetric analysis scan of Form 8.

FIG. 9A is an x-ray powder diffraction scan of fully dried Form 9. FIG. 9B is a differential scanning calorimetry scan of Form 9. FIG. 9C is a thermal gravimetric analysis scan of Form 9. FIG. 9D is a dynamic vapor sorption scan of Form 9.

FIG. 10A is an x-ray powder diffraction scan of fully dried Form 10. FIG. 10B is a differential scanning calorimetry scan of Form 10. FIG. 10C is a thermal gravimetric analysis scan of Form 10. FIG. 10D is an x-ray powder diffraction scan of Form 10*. FIG. 10E is a differential scanning calorimetry scan of Form 10*.

FIG. 11A is an x-ray powder diffraction scan of fully dried Form 11. FIG. 11B is a differential scanning calorimetry scan of Form 11. FIG. 11C is a thermal gravimetric analysis scan of Form 11. FIG.

11D is an x-ray powder diffraction scan of fully dried Form 11*. FIG. 11E is a differential scanning calorimetry scan of Form 11*.

FIG. 11F is a thermal gravimetric analysis scan of Form 11*.

FIG. 12A is an x-ray powder diffraction scan of Form 12. FIG. 12B is a differential scanning calorimetry scan of Form 12. FIG. 12C is a thermal gravimetric analysis scan of Form 12.

FIG. 13B is a differential scanning calorimetry scan of Form 13. FIG. 13C is a thermal gravimetric analysis scan of Form 13.

FIG. 13D is a dynamic vapor sorption scan of Form 13.

FIG. 16A shows chondrogenesis in cells stained with Nile Red and treated with the compound of Formula (I). FIG. 16B shows chondrogenesis in cells stained with Rhodamine B.

FIG. 18A shows upregulated chondrogenic gene expression.

FIG. 18B shows downregulated osteogenic gene expression.

FIG. 19A shows MMP1 production. FIG. 19B shows MMP3 production. FIG. 19C shows MMP13 production.

FIG. 20A shows levels of secreted GAG. FIG. 20B shows levels of released nitric oxide.

FIG. 21A shows inhibition of TNF-α.

FIG. 21B shows inhibition of IL-6.

FIG. 22A shows inhibition of TNF-α. FIG. 22B shows inhibition of IL-6.

DETAILED DESCRIPTION

1. Definitions

Figure 1A:
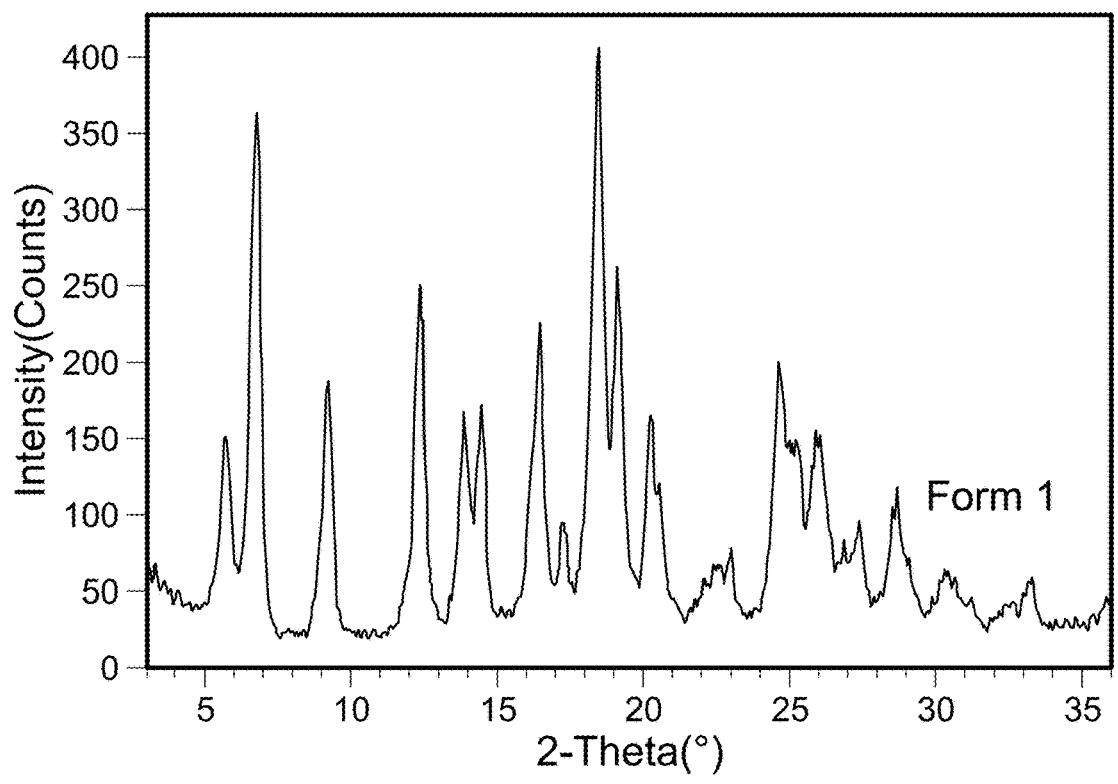
FIGS. 1A-1D are scans of polymorph Form 1 of the compound of Formula (I).

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The term "administration" or "administering" refers to a method of giving a dosage of a compound or pharmaceutical composition to a vertebrate or invertebrate, including a mammal, a bird, a fish, or an amphibian. The preferred method of administration can vary depending on various factors, e.g., the components of the pharmaceutical composition, the site of the disease, and the severity of the disease.

The term "mammal" is used herein in its usual biological sense. Thus, it specifically includes, e.g., humans, cattle, horses, dogs, and cats, but also includes many other species.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents, and the like, which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various excipients, such as are commonly used in the art, can be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

"Patient," as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate. In some embodiments, the patient is a human.

By "therapeutically effective amount" or "pharmaceutically effective amount" of a compound as provided herein is an amount which is sufficient to achieve the desired effect and can vary according to the nature and severity of the disease condition, and the potency of the compound. A therapeutic effect is the relief, to some extent, of one or more of the symptoms of the disease, and can include curing a disease. "Curing" means that the symptoms of active disease are eliminated. However, certain long-term or permanent effects of the disease can exist even after a cure is obtained (such as, e.g., extensive tissue damage).

"Treat," "treatment," or "treating," as used herein, refers to administering a compound or pharmaceutical composition, e.g., formulation, as provided herein for therapeutic purposes. The term "therapeutic treatment" refers to administering treatment to a patient already suffering from a disease, thus causing a therapeutically beneficial effect, such as ameliorating existing symptoms, preventing additional symptoms, ameliorating the underlying metabolic causes of symptoms, postponing or preventing the further development of a disorder and/or reducing the severity of symptoms that will or are expected to develop.

The term "polymorph," as used herein, refers to crystals of the same molecule having different physical properties as a result of the order of the molecules in the crystal lattice. Polymorphs of a single compound have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bio-availability), solubility, melting point, chemical stability, physical stability, powder flowability, water sorption, compaction, and particle morphology. Differences in stability can result from changes in chemical reactivity (e.g. differential oxidation, such that a dosage form discolors more rapidly when comprised of one polymorph than when comprised of another polymorph) or mechanical changes (e.g., crystal changes on storage as a kinetically favored polymorph converts to a thermodynamically more stable polymorph) or both (e.g., one polymorph is more hygroscopic than the other). As a result of solubility/dissolution differences, some transitions affect potency and/or toxicity. In addition, the physical properties of the crystal may be important in processing; for example, one polymorph might be more likely to form solvates or might be difficult to filter and wash free of impurities (i.e., particle shape and size distribution might be different between one polymorph relative to the other). "Polymorph" does not include amorphous forms of the compound. As used herein, "amorphous" refers to a non-crystalline form of a compound which may be a solid state form of the compound or a solubilized form of the compound. For example, "amorphous" refers to a compound without a regularly repeating arrangement of molecules or external face planes.

The term "anhydrous," as used herein, refers to a crystal form of the compound of Formula (I) that has 1% or less by weight water. For example, 0.5% or less, 0.25% or less, or 0.1% or less by weight water.

The term "solvate" as used herein refers to a crystalline form of a compound of Formula (I), such as a polymorph form of the compound, where the crystal lattice comprises one or more solvents of crystallization.

The term "non-stoichiometric hydrate" refers to a crystalline form of a compound of Formula I that comprises water, but wherein variations in the water content do not cause significant changes to the crystal structure. In some embodiments, a non-stoichiometric hydrate can refer to a crystalline form of a compound of Formula I that has channels or networks throughout the crystal structure into which water molecules can diffuse. During drying of non-stoichiometric hydrates, a considerable proportion of water can be removed without significantly disturbing the crystal network, and the crystals can subsequently rehydrate to give the initial non-stoichiometric hydrated crystalline form. Unlike stoichiometric hydrates, the dehydration and rehydration of non-stoichiometric hydrates is not accompanied by a phase transition, and thus all hydration states of a non-stoichiometric hydrate represent the same crystal form. In some embodiments, a non-stoichiometric hydrate can have up to about 20% by weight water, such as, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or greater than 1% water by weight. In some embodiments, a non-stoichiometric hydrate can have between 1% and about 20% by weight water, such as between 1% and about 5%, 1% and about 10%, 1% and about 15%, about 2% and about 5%, about 2% and about 10%, about 2% and about 15%, about 2% and about 20%, about 5% and about 10%, about 5% and about 15%, about 5% and about 20%, about 10% and about 15%, about 10% and about 20%, or about 15% and about 20% by weight water.

In some embodiments the % water by weight in a crystal form, such as a non-stoichiometric hydrate, is determined by the Karl Fischer titration method. In some embodiments, the crystal form is dried prior to Karl Fischer titration.

"Purity," when used in reference to a composition including a polymorph of a compound of Formula (I), refers to the percentage of one specific polymorph form relative to another polymorph form or an amorphous form of a compound of Formula (I) in the referenced composition. For example, a composition comprising polymorph Form 1 having a purity of 90% would comprise 90 weight parts Form 1 and 10 weight parts of other polymorph and/or amorphous forms of the compound of Formula (I).

As used herein, a compound or composition is "substantially free of" one or more other components if the compound or composition contains no significant amount of such other components. Such components can include starting materials, residual solvents, or any other impurities that can result from the preparation of and/or isolation of the compounds and compositions provided herein. In some embodiments, a polymorph form provided herein is substantially free of other polymorph forms. In some embodiments, a particular polymorph of the compound of Formula (I) is "substantially free" of other polymorphs if the particular polymorph constitutes at least about 95% by weight of the compound of Formula (I) present. In some embodiments, a particular polymorph of the compound of Formula (I) is "substantially free" of other polymorphs if the particular polymorph constitutes at least about 97%, about 98%, about 99%, or about 99.5% by weight of the compound of Formula (I) present. In certain embodiments, a particular polymorph of the compound of Formula (I) is "substantially free" of water if the amount of water constitutes no more than about 2%, about 1%, or about 0.5% by weight of the polymorph.

As used herein, a compound is "substantially present" as a given polymorph if at least about 50% by weight of the compound is in the form of that polymorph. In some embodiments, at least about 60% by weight of the compound is in the form of that polymorph. In some embodiments, at least about 70% by weight of the compound is in the form of that polymorph. In some embodiments, at least about 80% by weight of the compound is in the form of that polymorph. In some embodiments, at least about 90% by weight of the compound is in the form of that polymorph. In some embodiments, at least about 95% by weight of the compound is in the form of that polymorph. In some embodiments, at least about 96% by weight of the compound is in the form of that polymorph. In some embodiments, at least about 97% by weight of the compound is in the form of that polymorph. In some embodiments, at least about 98% by weight of the compound is in the form of that polymorph. In some embodiments, at least about 99% by weight of the compound is in the form of that polymorph. In some embodiments, at least about 99.5% by weight of the compound is in the form of that polymorph.

"Room temperature" or "RT" refers to the ambient temperature of a typical laboratory, which is typically around 25° C.

"Western Ontario and McMaster Universities Arthritis Index" or "WOMAC" refers to a widely used, proprietary set of standardized questionnaires used by health professionals to evaluate the condition of patients with osteoarthritis of the knee and hip, including pain, stiffness, and physical functioning of the joints. The WOMAC has also been used to assess back pain, rheumatoid arthritis, juvenile rheumatoid arthritis, systemic lupus erythematosus, and fibromyalgia. It can be self-administered and was developed at Western Ontario and McMaster Universities in 1982. The WOMAC measures five items for pain (score range 0-20), two for stiffness (score range 0-8), and 17 for functional limitation (score range 0-68). Physical functioning questions cover everyday activities such as stair use, standing up from a sitting or lying position, standing, bending, walking, getting in and out of a car, shopping, putting on or taking off socks, lying in bed, getting in or out of a bath, sitting, and heavy and light household duties.

2. Polymorphs

Provided herein is a compound of Formula (I):

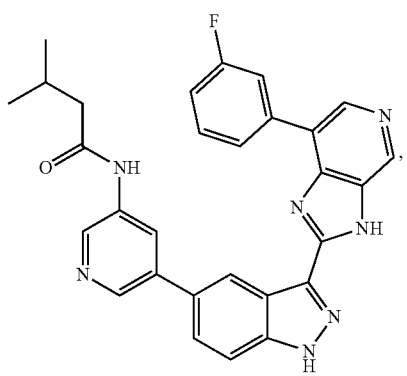

including amorphous and polymorph forms thereof.

The compound of Formula (I) provided herein can be prepared using methods known and understood by those of ordinary skill in the art. For example, synthetic methods such as those described in US 2013/0267495 can be used, and this application is herein incorporated by reference in its entirety.

Also provided herein are polymorph forms of the compound of Formula (I). The forms include, e.g., solvates, hydrates, non-stoichiometric hydrates, and non-solvated forms of the compound of Formula (I), including, for example, polymorph Forms 1, 2, 3, 4, 5, 6, 7, 8, 9, 10, 11, 12, and 13.

One such polymorph is a polymorph known as Form 1. Form 1 is an anhydrous polymorph of the compound of Formula (I). In one embodiment, Form 1 has an X-ray powder diffraction (XRPD or XRD) pattern, obtained with CuKα1-radiation, with at least peaks at ° 2θ values of 6.8±0.2, 12.4±0.2, and 18.5±0.2. In some embodiments, Form 1 has an XRPD pattern with at least peaks at ° 2θ values of 6.8±0.2, 12.4±0.2, 16.5±0.2, 18.5±0.2, and 19.2±0.2. In some embodiments, Form 1 has an XRPD pattern with at least peaks at ° 2θ values of 6.8±0.2, 9.3±0.2, 12.4±0.2, 13.9±0.2, 16.5±0.2, 18.5±0.2, 19.2±0.2, and 24.6±0.2. For example, in some embodiments, Form 1 has an XRPD pattern with at least peaks at ° 2θ values of 6.8±0.2, 9.3±0.2, 12.4±0.2, 13.9±0.2, 14.5±0.2, 16.5±0.2, 18.5±0.2, 19.2±0.2, 20.3±0.2, and 24.6±0.2.

In some embodiments, provided herein is a composition comprising polymorph Form 1. In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than about 15% by weight of other forms of the compound of Formula (I). For example, the composition can contain less than 14%, 13%, 12%, 11%, 10%, 9%, 8%, 7%, 6%, 5%, 4%, 3%, 2%, 1% or less by weight of other anhydrous forms of the compound of Formula (I). In some embodiments, the composition contains less than about 15% by weight of the polymorph Form 9. For example, the composition can contain less than 14%, 13%, 12%, 11%, 10%, 9%, 8%, 7%, 6%, 5%, 4%, 3%, 2%, 1% or less by weight of the polymorph of Form 9. In some embodiments, the composition contains less than about 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 2, Form 3, Form 4, Form 5, Form 6, Form 7, Form 8, Form 9, Form 10, Form 11, a non-stoichiometric hydrate of Form 1 having between 1% and about 20% by weight water, or a combination of two or more thereof.

In some embodiments, provided herein is polymorph Form 1 that exhibits an endotherm between about 50-100° C. as measured by differential scanning calorimetry (DSC) related to sorbed water. In some embodiments, polymorph Form 1 exhibits a recrystallization event that is observed between about 270-290° C., e.g., around 280° C. In some embodiments, the endotherm and exotherm are observed when using a scan rate of 10° C. per minute.

In some embodiments, provided herein is polymorph Form 1 that recrystallizes into Form 9 with a melting point of around 363° C. In some embodiments, polymorph Form 1 undergoes a total mass loss of about 0.33% before around 100° C., e.g., from about 39° C. to about 100° C., as measured by thermal gravimetric analysis (TGA).

Provided herein are methods of preparing polymorph Form 1. In some embodiments, the method comprises drying a composition comprising the compound of Formula (I), including amorphous and polymorph forms thereof, to generate polymorph Form 1. In some embodiments, the composition comprises a non-stoichiometric hydrate of Form 1 having between 1% and about 20% by weight water. In some embodiments, the method comprises reslurrying a composition comprising the compound of Formula (I), including amorphous and polymorph forms thereof, in a solvent or mixture of solvents to generate polymorph Form 1 as a residual solid. In some embodiments, the reslurrying takes place at room temperature (RT). In some embodiments, the reslurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising the compound of Formula (I), including amorphous and polymorph forms thereof in a solvent or mixture of solvents to generate polymorph Form 1 as a residual solid. In some embodiments, the compound of Formula (I) is a non-stoichiometric hydrate of Form 1 having between 1% and about 20% by weight water. In some embodiments, the solvent is methanol. In some embodiments, the solvent is toluene. In some embodiments, the solvent is heptane. In some embodiments, the solvent is dichloromethane (DCM). In some embodiments, the solvent is water. In some embodiments, the solvent is in a mixture with water, for example the solvent can be a mixture of water and acetonitrile, methanol, ethyl acetate (EA), methyl tert-butyl ether (MtBE), isopropyl alcohol (IPAc), methyl acetate (MA), methyl isobutyl ketone (MIBK), DCM, n-butyl acetate, heptane, toluene, or n-butanol. In some embodiments, the water is present in an amount of about 5% by weight. In some embodiments, the reslurrying takes place at room temperature. In some embodiments, the reslurrying takes place at around 50° C. In some embodiments, the method further comprises drying the residual solid, for example, under vacuum. In some embodiments, the drying is at a temperature of between about 60° C. and 90° C., such as, e.g., around 75° C.

Provided herein is a non-stoichiometric hydrate of Form 1 having between 1% and about 20% by weight water. In some embodiments, for example, above 30% relative humidity (RH), Form 1 readily sorbs water and shows a distinctive shift in Form 1 peaks from 6.8±0.2 to 6.2±0.2 and 12.6±0.2 to 11±0.2. In some embodiments, a non-stoichiometric hydrate of Form 1 comprises up to about 20% by weight water. For example, up to about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or greater than 1% water by weight. In some embodiments, a non-stoichiometric hydrate of Form 1 has between 1 to about 20% water by weight, e.g., between 1% and about 10%, about 5% and about 15%, about 10% and about 20%, 1% and about 5%, about 5% and about 10%, about 10% and about 15%, about 15% and about 20%, or about 17% and about 20% water by weight.

In some embodiments, provided herein is a composition comprising a non-stoichiometric hydrate of Form 1 having between 1% and about 20% by weight water. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I) (e.g., anhydrous forms of the compound of Formula (I)). In some embodiments, the composition contains less than 20% by weight of polymorph Form 9 having X-ray powder diffraction pattern comprising peaks at ° 2θ values of 4.9±0.2, 18.6±0.2, and 21.1±0.2. For example, the composition contains less than 15% by weight of Form 9, such as less than 14%, 13%, 12%, 11%, 10%, 9%, 8%, 7%, 6%, 5%, 4%, 3%, 2%, 1% or less by weight of other forms of the compound of Form 9. In some embodiments, the composition contains less than 15% of one or more other forms of the compound of Formula (I), such as less than 14%, 13%, 12%, 11%, 10%, 9%, 8%, 7%, 6%, 5%, 4%, 3%, 2%, 1% or less of one or more other forms of the compound of Formula (I). For example, the composition can contain less than about 15% of Form 1, Form 2, Form 3, Form 4, Form 5, Form 6, Form 7, Form 8, Form 9, Form 10, Form 11, or a combination of two or more thereof.

Another example of a non-stoichiometric hydrate of polymorph Form 1 is referred to as Form 12. Form 12 is a non-stoichiometric hydrate of polymorph Form 1 that has 1.42% water by weight.

In one embodiment, provided herein is a polymorph Form 12 having an XRPD pattern, obtained with CuKα1-radiation, with at least peaks at ° 2θ positions 6.4±0.2, 11.0±0.2, and 18.4±0.2. In some embodiments, Form 12 has an XRPD pattern with at least peaks at ° 2θ positions 6.4±0.2, 9.2±0.2, 11.0±0.2, 18.4±0.2, and 19.7±0.2. In some embodiments, Form 12 has an XRPD pattern with at least peaks at ° 2θ positions 6.4±0.2, 9.2±0.2, 11.0±0.2, 15.6±0.2, 18.4±0.2, 19.7±0.2, 24.4±0.2, and 25.2±0.2. For example, in some embodiments, Form 12 has an XRPD pattern with at least peaks at ° 2θ positions 6.4±0.2, 9.2±0.2, 11.0±0.2, 15.6±0.2, 16.1±0.2, 18.4±0.2, 19.7±0.2, 20.8±0.2, 24.4±0.2, and 25.2±0.2.

In some embodiments, provided herein is polymorph Form 12 that exhibits an endotherm between about 50-100° C. as measured by DSC. In some embodiments, polymorph Form 12 exhibits an exotherm at around 283° C. In some embodiments, the endotherms and exotherms are observed when using a scan rate of 10° C. per minute.

In some embodiments, provided herein is polymorph Form 12 that has a melting point of around 364° C. In some embodiments, polymorph Form 12 undergoes a weight loss of about 1.4% before around 100° C., e.g., from about 30° C. to about 100° C., as measured by TGA.

One example of a non-stoichiometric hydrate of polymorph Form 1 is referred to as Form 13. Form 13 is a non-stoichiometric hydrate of polymorph Form 1 that has 1.84% water by weight.

In one embodiment, provided herein is polymorph Form 13 having an XRPD pattern, obtained with CuKα1-radiation, with at least peaks at ° 2θ values of 6.8±0.2, 12.4±0.2, and 18.5±0.2. In some embodiments, Form 13 has an XRPD pattern with at least peaks at ° 2θ values of 6.8±0.2, 12.4±0.2, 16.5±0.2, 18.5±0.2, and 19.2±0.2. In some embodiments, Form 13 has an XRPD pattern with at least peaks at ° 2θ values of 6.8±0.2, 9.3±0.2, 12.4±0.2, 13.9±0.2, 16.5±0.2, 18.5±0.2, 19.2±0.2, and 24.6±0.2. For example, in some embodiments, Form 13 has an XRPD pattern with at least peaks at ° 2θ values of 6.8±0.2, 9.3±0.2, 12.4±0.2, 13.9±0.2, 14.5±0.2, 16.5±0.2, 18.5±0.2, 19.2±0.2, 20.3±0.2, and 24.6±0.2.

In some embodiments, provided herein is polymorph Form 13 that exhibits an endotherm between about 50-100° C. as measured by DSC. In some embodiments, polymorph Form 13 exhibits an exotherm at between about 265-285° C., e.g., around 278° C. For example, in some embodiments, the endotherms and exotherms are observed when using a scan rate of 10° C. per minute.

In some embodiments, provided herein is polymorph Form 13 that has a melting point of around 363° C. In some embodiments, polymorph Form 13 undergoes a weight loss of about 1.9% before around 100° C. as measured by TGA.

Provided herein are methods of preparing a non-stoichiometric hydrate of polymorph Form 1. In some embodiments, the method comprises reslurrying a composition comprising the compound of Formula (I), including amorphous and polymorph forms thereof, in a solvent or mixture of solvents to generate a non-stoichiometric hydrate of polymorph Form 1 as a residual solid. In some embodiments, the composition comprising the compound of Formula (I) is a mixture of a non-stoichiometric hydrate of polymorph Form 1 and Form 1. In some embodiments, the reslurrying takes place at RT. In some embodiments, the reslurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a mixture of a non-stoichiometric hydrate of polymorph Form 1 and Form 1 in a solvent or mixture of solvents to generate a non-stoichiometric hydrate of polymorph Form 1 as a residual solid. In some embodiments, the solvent is in a mixture with water, for example the solvent can be a mixture of water and acetonitrile, methanol, MtBE, MA, MIBK, DCM, IPAc, n-butyl acetate, heptane, toluene, or n-butanol. In some embodiments, the water is present in an amount of about 5% by weight. In some embodiments, the reslurrying takes place at RT. In some embodiments, the reslurrying takes place at around 50° C. Provided herein is a polymorph known as Form 2. Form 2 is an anhydrous polymorph of the compound of Formula (I). In one embodiment, provided herein is polymorph Form 2 having an XRPD pattern, obtained with CuKα1-radiation, with at least peaks at ° 2θ values of 7.0±0.2, 21.5±0.2, and 22.0±0.2. In some embodiments, Form 2 has an XRPD pattern with at least peaks at ° 2θ values of 7.0±0.2, 18.9±0.2, 21.5±0.2, 22.0±0.2, and 24.2±0.2. In some embodiments, Form 2 has an XRPD pattern with at least peaks at ° 2θ values of 7.0±0.2, 14.1±0.2, 18.9±0.2, 19.2±0.2, 21.5±0.2, 22.0±0.2, 24.2±0.2, and 26.4±0.2. For example, in some embodiments, Form 2 has an XRPD pattern with at least peaks at ° 2θ values of 7.0±0.2, 10.4±0.2, 14.1±0.2, 17.6±0.2, 18.9±0.2, 19.2±0.2, 21.5±0.2, 22.0±0.2, 24.2±0.2, and 26.4±0.2.

In some embodiments, provided herein is a composition comprising polymorph Form 2. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 3, Form 4, Form 5, Form 6, Form 7, Form 8, Form 9, Form 10, Form 11, a non-stoichiometric hydrate of Form 1, or a combination of two or more thereof.

In some embodiments, provided herein is polymorph Form 2 that exhibits an endotherm between about 50-100° C. as measured by DSC. In some embodiments, polymorph Form 2 exhibits an endotherm between about 220-230° C. In some embodiments, polymorph Form 2 exhibits an exotherm between about 233-238° C. In some embodiments, polymorph Form 2 exhibits an exotherm between about 290-295° C. In some embodiments, the endotherms and exotherms are observed when using a scan rate of 10° C. per minute.

In some embodiments, provided herein is polymorph Form 2 that has a melting point of around 363° C. In some embodiments, polymorph Form 2 undergoes a weight loss of about 2.7% before around 116° C., e.g., from about 36° C. to about 116° C., as measured by TGA.

Provided herein are methods of preparing polymorph Form 2. In some embodiments, the method comprises reslurrying a composition comprising the compound of Formula (I), including amorphous and polymorph forms thereof, in a solvent or mixture of solvents to generate Form 2 as a residual solid. In some embodiments, the composition comprising the compound of Formula (I) comprises a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 2 as a residual solid. In some embodiments, the solvent is acetonitrile. In some embodiments, the solvent is ethanol. In some embodiments, the solvent is in a mixture with water, for example the solvent can be a mixture of water and ethanol or water and n-propanol. In some embodiments, the water is present in an amount of about 5% by weight. In some embodiments, the reslurrying takes place at RT. In some embodiments, the reslurrying takes place at around 50° C.

Provided herein is a polymorph known as Form 3. Form 3 is an anhydrous polymorph of the compound of Formula (I). In one embodiment, provided herein is polymorph Form 3 having an XRPD pattern, obtained with CuKα1-radiation, with at least peaks at ° 2θ values of 7.2±0.2, 22.2±0.2, and 24.4±0.2. In some embodiments, Form 3 has an XRPD pattern with at least peaks at ° 2θ values of 6.3±0.2, 7.2±0.2, 21.6±0.2, 22.2±0.2, and 24.4±0.2. In some embodiments, Form 3 has an XRPD pattern with at least peaks at ° 2θ values of 6.3±0.2, 7.2±0.2, 11.0±0.2, 18.4±0.2, 19.0±0.2, 21.6±0.2, 22.2±0.2, and 24.4±0.2. For example, in some embodiments, Form 3 has an XRPD pattern with at least peaks at ° 2θ values of 6.3±0.2, 7.2±0.2, 11.0±0.2, 14.2±0.2, 17.8±0.2, 18.4±0.2, 19.0±0.2, 21.6±0.2, 22.2±0.2, and 24.4±0.2.

In some embodiments, provided herein is a composition comprising polymorph Form 3. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 4, Form 5, Form 6, Form 7, Form 8, Form 9, Form 10, Form 11, a non-stoichiometric hydrate of Form 1, or a combination of two or more thereof.

In some embodiments, provided herein is polymorph Form 3 that exhibits an exotherm between about 190-220° C., as measured by DSC. In some embodiments, polymorph Form 3 exhibits an exotherm at between about 225-235° C., e.g., around 230° C., as measured by DSC. In some embodiments, polymorph Form 3 exhibits an exotherm at between about 292-300° C., e.g., around 297° C., as measured by DSC. For example, in some embodiments, the endotherms and exotherms are observed when using a scan rate of 10° C. per minute.

In some embodiments, provided herein is polymorph Form 3 that has a melting point of around 365° C. In some embodiments, polymorph Form 3 undergoes a weight loss of about 1.6% before around 81° C. and a weight loss of about 1.7% between about 81-169° C. as measured by TGA.

Provided herein are methods of preparing polymorph Form 3. In some embodiments, the method comprises reslurrying a composition comprising the compound of Formula (I), including amorphous and polymorph forms thereof, in a solvent or mixture of solvents to generate Form 3 as a residual solid. In some embodiments, the composition comprising the compound of Formula (I) comprises a non-stoichiometric hydrate of Form 1 having between 1% and about 20% by weight water. In some embodiments, the reslurrying takes place at RT. In some embodiments, the reslurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 3 as a residual solid. In some embodiments, the solvent is IPAc. In some embodiments, the solvent is n-butyl acetate. In some embodiments, the reslurrying takes place at RT. In some embodiments, the reslurrying takes place at around 50° C.

Provided herein is a polymorph known as Form 4. Form 4 is an anhydrous polymorph of the compound of Formula (I). In one embodiment, provided herein is polymorph Form 4 having an XRPD pattern, obtained with CuKα1-radiation, with at least peaks at ° 2θ values of 7.0±0.2, 21.8±0.2, and 25.1±0.2. In some embodiments, Form 4 has an XRPD pattern with at least peaks at ° 2θ values of 7.0±0.2, 19.5±0.2, 21.8±0.2, 23.2±0.2, and 25.1±0.2. In some embodiments, Form 4 has an XRPD pattern with at least peaks at ° 2θ values of 7.0±0.2, 17.6±0.2, 18.3±0.2, 19.5±0.2, 21.8±0.2, 23.2±0.2, 25.1±0.2, and 25.8±0.2. For example, in some embodiments, Form 4 has an XRPD pattern with at least peaks at ° 2θ values of 7.0±0.2, 9.6±0.2, 17.6±0.2, 18.3±0.2, 19.5±0.2, 21.8±0.2, 23.2±0.2, 25.1±0.2, 25.8±0.2, and 29.3±0.2.

In some embodiments, provided herein is a composition comprising polymorph Form 4. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 5, Form 6, Form 7, Form 8, Form 9, Form 10, Form 11, a non-stoichiometric hydrate of Form 1, or a combination of two or more thereof.

In some embodiments, provided herein is polymorph Form 4 that exhibits an endotherm between about 50-100° C. as measured by DSC. In some embodiments, polymorph Form 4 exhibits an endotherm at between about 180-215° C. In some embodiments, polymorph Form 4 exhibits an endotherm between about 220-230° C. In some embodiments, polymorph Form 4 exhibits an exotherm at between about 230-240° C., e.g., around 235° C. In some embodiments, polymorph Form 4 exhibits an exotherm at between about 300-310° C. For example, in some embodiments, the endotherms and exotherms are observed when using a scan rate of 10° C. per minute.

In some embodiments, provided herein is polymorph Form 4 that has a melting point of between about 366-369° C., e.g., around 367° C. In some embodiments, polymorph Form 4 undergoes a weight loss of about 8.3% before around 200° C., e.g., from about 42° C. to about 200° C., as measured by TGA.

Provided herein are methods of preparing polymorph Form 4. In some embodiments, the method comprises reslurrying a composition comprising the compound of Formula (I), including amorphous and polymorph forms thereof, in a solvent or mixture of solvents to generate Form 4 as a residual solid. In some embodiments, the composition comprising the compound of Formula (I) comprises a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 4 as a residual solid. In some embodiments, the solvent is EA. In some embodiments, the solvent is MA. In some embodiments, the solvent is MtBE. In some embodiments, the solvent is n-propanol. In some embodiments, the solvent is acetone. In some embodiments, the solvent is in a mixture with water, for example the solvent can be a mixture of water and MA, EA, or acetone. In some embodiments, the water is present in an amount of about 5% by weight. In some embodiments, the reslurrying takes place at RT. In some embodiments, the reslurrying takes place at around 50° C.

Provided herein is a polymorph known as Form 5. Form 5 is an anhydrous polymorph of the compound of Formula (I). In one embodiment, provided herein is polymorph Form 5 having an XRPD pattern, obtained with CuKα1-radiation, with at least peaks at ° 2θ values of 7.3±0.2, 22.3±0.2, and 24.5±0.2. In some embodiments, Form 5 has an XRPD pattern with at least peaks at ° 2θ values of 6.3±0.2, 7.3±0.2, 21.7±0.2, 22.3±0.2, and 24.5±0.2. In some embodiments, Form 5 has an XRPD pattern with at least peaks at ° 2θ values of 6.3±0.2, 7.3±0.2, 11.0±0.2, 19.1±0.2, 19.5±0.2, 21.7±0.2, 22.3±0.2, and 24.5±0.2. For example, in some embodiments, Form 5 has an XRPD pattern with at least peaks at ° 2θ values of 6.3±0.2, 7.3±0.2, 11.0±0.2, 14.3±0.2, 19.1±0.2, 19.5±0.2, 21.7±0.2, 22.3±0.2, 24.5±0.2, and 26.5±0.2.

In some embodiments, provided herein is a composition comprising polymorph Form 5. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 6, Form 7, Form 8, Form 9, Form 10, Form 11, a non-stoichiometric hydrate of Form 1, or a combination of two or more thereof.

In some embodiments, provided herein is polymorph Form 5 that exhibits an endotherm between about 50-100° C. as measured by DSC. In some embodiments, polymorph Form 5 exhibits an endotherm at between about 210-235° C., e.g., around 222° C. In some embodiments, polymorph Form 5 exhibits an exotherm at between about 227-240° C., e.g., around 235° C. In some embodiments, polymorph Form 5 exhibits an exotherm at between about 280-300° C., e.g., around 293° C. For example, in some embodiments, the endotherms and exotherms are observed when using a scan rate of 10° C. per minute.

In some embodiments, provided herein is polymorph Form 5 that has a melting point of around 363° C. In some embodiments, polymorph Form 5 undergoes a weight loss of about 3.1% before around 100° C. and about 1.7% between about 100-250° C. as measured by TGA.

Provided herein are methods of preparing polymorph Form 5. In some embodiments, the method comprises reslurrying a composition comprising the compound of Formula (I), including amorphous and polymorph forms thereof, in a solvent or mixture of solvents to generate Form 5 as a residual solid. In some embodiments, the composition comprising the compound of Formula (I) comprises a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 5 as a residual solid. In some embodiments, the solvent is MtBE. In some embodiments, the reslurrying takes place at RT. In some embodiments, the reslurrying takes place at around 50° C.

Provided herein is a polymorph known as Form 6. Form 6 is an anhydrous polymorph of the compound of Formula (I).

In some embodiments, provided herein is a composition comprising polymorph Form 6. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 7, Form 8, Form 9, Form 10, Form 11, a non-stoichiometric hydrate of Form 1, or a combination of two or more thereof.

In some embodiments, provided herein is polymorph Form 6 that exhibits an exotherm between about 245-260° C. as measured by DSC. For example, in some embodiments, the endotherms and exotherms are observed when using a scan rate of 10° C. per minute. In some embodiments, provided herein is polymorph Form 6 that has a melting point of around 364° C.

Provided herein are methods of preparing polymorph Form 6. In some embodiments, the method comprises reslurrying a composition comprising the compound of Formula (I), including amorphous and polymorph forms thereof, in a solvent or mixture of solvents to generate Form 6 as a residual solid. In some embodiments, the composition comprising the compound of Formula (I) is a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 6 as a residual solid. In some embodiments, the solvent is IPAc. In some embodiments, the solvent is in a mixture with water, for example the solvent can be a mixture of water and IPAc. In some embodiments, the water is present in an amount of about 5% by weight. In some embodiments, the reslurrying takes place at RT. In some embodiments, the reslurrying takes place at around 50° C.

Provided herein is a polymorph known as Form 7. Form 7 is an anhydrous polymorph of the compound of Formula (I). In one embodiment, provided herein is polymorph Form 7 having an XRPD pattern, obtained with CuKα1-radiation, with at least peaks at ° 2θ values of 7.1±0.2, 21.6±0.2, and 23.2±0.2. In some embodiments, Form 7 has an XRPD pattern with at least peaks at ° 2θ values of 4.9±0.2, 7.1±0.2, 18.5±0.2, 21.6±0.2, and 23.2±0.2. In some embodiments, Form 7 has an XRPD pattern with at least peaks at ° 2θ values of 4.9±0.2, 7.1±0.2, 10.9±0.2, 18.5±0.2, 19.4±0.2, 21.6±0.2, 23.2±0.2, and 30.3±0.2. For example, in some embodiments, Form 7 has an XRPD pattern with at least peaks at ° 2θ values of 4.9±0.2, 7.1±0.2, 8.8±0.2, 10.9±0.2, 18.5±0.2, 19.4±0.2, 21.6±0.2, 22.1±0.2, 23.2±0.2, and 30.3±0.2.

In some embodiments, provided herein is a composition comprising polymorph Form 7. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 8, Form 9, Form 10, Form 11, a non-stoichiometric hydrate of Form 1, or a combination of two or more thereof.

In some embodiments, provided herein is polymorph Form 7 that exhibits an exotherm between about 227-235° C., e.g., around 232° C., as measured by DSC. In some embodiments, polymorph Form 7 exhibits an exotherm between about 299-305° C., e.g., around 303° C. For example, in some embodiments, the endotherms and exotherms are observed when using a scan rate of 10° C. per minute.

In some embodiments, provided herein is polymorph Form 7 that has a melting point of around 365° C. In some embodiments, polymorph Form 7 undergoes a weight loss of about 12% before around 200° C., e.g., from about 36° C. to about 200° C., as measured by TGA.

Provided herein are methods of preparing polymorph Form 7. In some embodiments, the method comprises reslurrying a composition comprising the compound of Formula (I), including amorphous and polymorph forms thereof, in a solvent or mixture of solvents to generate Form 7 as a residual solid. In some embodiments, the composition comprising the compound of Formula (I) is a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 7 as a residual solid. In some embodiments, the solvent is methyl ethyl ketone (MEK). In some embodiments, the solvent is in a mixture with water, for example the solvent can be a mixture of water and MEK. In some embodiments, the water is present in an amount of about 5% by weight. In some embodiments, the reslurrying takes place at RT. In some embodiments, the reslurrying takes place at around 50° C.

Provided herein is a polymorph known as Form 8. Form 8 is an anhydrous polymorph of the compound of Formula (I). In one embodiment, provided herein is polymorph Form 8 having an XRPD pattern, obtained with CuKα1-radiation, with at least peaks at ° 2θ values of 6.9±0.2, 17.7±0.2, and 21.5±0.2. In some embodiments, Form 8 has an XRPD pattern with at least peaks at ° 2θ values of 6.9±0.2, 11.5±0.2, 17.7±0.2, 21.5±0.2, and 27.6±0.2. In some embodiments, Form 8 has an XRPD pattern with at least peaks at ° 2θ values of 6.9±0.2, 11.5±0.2, 15.3±0.2, 16.9±0.2, 17.7±0.2, 21.5±0.2, 27.6±0.2, and 28.9±0.2. For example, in some embodiments, Form 8 has an XRPD pattern with at least peaks at ° 2θ values of 6.9±0.2, 11.5±0.2, 12.7±0.2, 14.2±0.2, 15.3±0.2, 16.9±0.2, 17.7±0.2, 21.5±0.2, 27.6±0.2, and 28.9±0.2.

In some embodiments, provided herein is a composition comprising polymorph Form 8. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 9, Form 10, Form 11, a non-stoichiometric hydrate of Form 1, or a combination of two or more thereof.

In some embodiments, provided herein is polymorph Form 8 that exhibits an endotherm between about 41-60° C. as measured by DSC. In some embodiments, polymorph Form 8 exhibits an exotherm at between about 221-235° C., e.g., around 231° C. In some embodiments, polymorph Form 8 exhibits an endotherm between about 279-290° C., e.g., around 285° C. For example, in some embodiments, the endotherms and exotherms are observed when using a scan rate of 10° C. per minute.

In some embodiments, provided herein is polymorph Form 8 that has a melting point of around 364° C. In some embodiments, polymorph Form 8 undergoes a weight loss of about 4.2% before around 190° C. and about 3.9% between about 190-261° C. as measured by TGA.

Provided herein are methods of preparing polymorph Form 8. In some embodiments, the method comprises reslurrying a composition comprising the compound of Formula (I), including amorphous and polymorph forms thereof, in a solvent or mixture of solvents to generate Form 8 as a residual solid. In some embodiments, the composition comprising the compound of Formula (I) a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 8 as a residual solid. In some embodiments, the solvent is MIBK. In some embodiments, the reslurrying takes place at RT. In some embodiments, the reslurrying takes place at around 50° C.

Provided herein is a polymorph known as Form 9. Form 9 is an anhydrous polymorph of the compound of Formula (I). In one embodiment, provided herein is polymorph Form 9 having an XRPD pattern, obtained with CuKα1-radiation, with at least peaks at ° 2θ values of 4.9±0.2, 18.6±0.2, and 21.1±0.2. In some embodiments, Form 9 has an XRPD pattern with at least peaks at ° 2θ values of 4.9±0.2, 18.6±0.2, 21.1±0.2, 24.1±0.2, and 25.2±0.2. In some embodiments, Form 9 has an XRPD pattern with at least peaks at ° 2θ values of 4.9±0.2, 15.3±0.2, 16.5±0.2, 18.6±0.2, 21.1±0.2, 22.4±0.2, 24.1±0.2, and 25.2±0.2. For example, in some embodiments, Form 9 has an XRPD pattern with at least peaks at ° 2θ values of 4.9±0.2, 10.1±0.2, 15.3±0.2, 16.5±0.2, 18.6±0.2, 21.1±0.2, 22.4±0.2, 24.1±0.2, 25.2±0.2, and 28.6±0.2.

In some embodiments, provided herein is a composition comprising polymorph Form 9. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 8, Form 10, Form 11, a non-stoichiometric hydrate of Form 1, or a combination of two or more thereof.

In some embodiments, provided herein is polymorph Form 9 that exhibits a single melting endotherm at around 364° C. as measured by DSC. For example, in some embodiments, the endotherm is observed when using a scan rate of 10° C. per minute. In some embodiments, other polymorph forms provided herein, such as, e.g., Form 1 and Form 2, can convert to Form 9 when heated to just before melting (i.e., around 364° C.).

In some embodiments, provided herein is polymorph Form 9 that has a melting point of around 364° C. In some embodiments, polymorph Form 9 undergoes a weight loss of about 0.28% before around 100° C., e.g., from about 30.5° C. to about 100° C., as measured by TGA.

Provided herein are methods of preparing polymorph Form 9. In some embodiments, the method comprises reslurrying a composition comprising the compound of Formula (I), including amorphous and polymorph forms thereof, in a solvent or mixture of solvents to generate Form 9 as a residual solid. In some embodiments, the composition comprising the compound of Formula (I) is a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 9 as a residual solid. In some embodiments, the solvent is n-butanol. In some embodiments, the solvent is IPAc. In some embodiments, the solvent is n-butyl acetate. In some embodiments, the solvent is in a mixture with water, for example the solvent can be a mixture of water and ethanol or water and n-propanol. In some embodiments, the water is present in an amount of about 5% by weight. In some embodiments, the reslurrying takes place at RT. In some embodiments, the reslurrying takes place at around 50° C.

Provided herein is a polymorph known as Form 10. Polymorph Form 10 is a polymorph of the compound of Formula (I) comprising DMSO. For example, DMSO is on the surface of the polymorph. In one embodiment, provided herein is polymorph Form 10 having an XRPD pattern, obtained with CuKα1-radiation, with at least peaks at ° 2θ values of 20.7±0.2, 21.7±0.2, and 24.2±0.2. In some embodiments, Form 10 has an XRPD pattern with at least peaks at ° 2θ values of 18.2±0.2, 19.0±0.2, 20.7±0.2, 21.7±0.2, and 24.2±0.2. In some embodiments, Form 10 has an XRPD pattern with at least peaks at ° 2θ values of 17.8±0.2, 18.2±0.2, 19.0±0.2, 20.7±0.2, 21.7±0.2, 23.4±0.2, 24.2±0.2, and 27.9±0.2. For example, in some embodiments, Form 10 has an XRPD pattern with at least peaks at ° 2θ values of 6.7±0.2, 17.8±0.2, 18.2±0.2, 19.0±0.2, 19.9±0.2, 20.7±0.2, 21.7±0.2, 23.4±0.2, 24.2±0.2, and 27.9±0.2.

In some embodiments, provided herein is a composition comprising polymorph Form 10. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 8, Form 9, Form 11, a non-stoichiometric hydrate of Form 1, or a combination of two or more thereof.

In some embodiments, provided herein is polymorph Form 10 that exhibits an endotherm between about 212-237° C. as measured by DSC. In some embodiments, polymorph Form 10 exhibits an endotherm at between about 234-245° C., e.g., around 237° C. In some embodiments, polymorph Form 10 exhibits an exotherm between about 300-325° C., e.g., around 308° C. For example, in some embodiments, the endotherms and exotherms are observed when using a scan rate of 10° C. per minute.

In some embodiments, provided herein is polymorph Form 10 that has a melting point of between about 364-372° C., such as, e.g., around 369° C. In some embodiments, polymorph Form 10 undergoes a weight loss of about 0.6% before around 100° C., a weight loss of about 3.8% between about 100-170° C., and a weight loss of about 7.1% between about 170-260° C. as measured by TGA.

Provided herein are methods of preparing polymorph Form 10. In some embodiments, the method comprises reslurrying a composition comprising the compound of Formula (I), including amorphous and polymorph forms thereof, in a solvent or mixture of solvents to generate Form 10 as a residual solid. In some embodiments, the composition comprising the compound of Formula (I) is a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 10 as a residual solid. In some embodiments, the solvent is DMSO. In some embodiments, the solvent is in a mixture with water, for example the solvent can be a mixture of water and DMSO. In some embodiments, the water is present in an amount of about 5% by weight. In some embodiments, the reslurrying takes place at RT. In some embodiments, the reslurrying takes place at around 50° C.

Provided herein is a polymorph known as Form 11. Form 11 is an anhydrous polymorph of the compound of Formula (I). In one embodiment, provided herein is polymorph Form 11 having an XRPD pattern, obtained with CuKα1-radiation, with at least peaks at ° 2θ values of 6.4±0.2, 18.5±0.2, and 22.4±0.2. In some embodiments, Form 11 has an XRPD pattern with at least peaks at ° 2θ values of 6.4±0.2, 17.8±0.2, 18.5±0.2, 19.9±0.2, and 22.4±0.2. In some embodiments, Form 11 has an XRPD pattern with at least peaks at ° 2θ values of 6.4±0.2, 8.4±0.2, 17.8±0.2, 18.5±0.2, 19.9±0.2, 22.4±0.2, 24.5±0.2, and 26.8±0.2. For example, in some embodiments, Form 11 has an XRPD pattern with at least peaks at ° 2θ values of 6.4±0.2, 8.4±0.2, 17.8±0.2, 18.5±0.2, 19.9±0.2, 20.3±0.2, 22.4±0.2, 22.9±0.2, 24.5±0.2, and 26.8±0.2.

In some embodiments, provided herein is a composition comprising polymorph Form 11. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 8, Form 9, Form 10, a non-stoichiometric hydrate of Form 1, or a combination of two or more thereof.

In some embodiments, provided herein is polymorph Form 11 that exhibits an endotherm between about 215-230° C. as measured by DSC. In some embodiments, polymorph Form 11 exhibits an exotherm at between about 230-240° C., e.g., around 235° C. In some embodiments, polymorph Form 11 exhibits an exotherm between about 300-315° C., e.g., around 310° C. For example, in some embodiments, the endotherms and exotherms are observed when using a scan rate of 10° C. per minute.

In some embodiments, provided herein is polymorph Form 11 that has a melting point of around 368° C. In some embodiments, polymorph Form 11 undergoes a weight loss of about 0.8% before around 100° C. and a weight loss of about 7.0% between about 100-249° C., as measured by TGA.

Provided herein are methods of preparing polymorph Form 11. In some embodiments, the method comprises reslurrying a composition comprising the compound of Formula (I), including amorphous and polymorph forms thereof, in a solvent or mixture of solvents to generate Form 11 as a residual solid. In some embodiments, the composition comprising the compound of Formula (I) is a non-stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a non-stoichiometric hydrate of Form 1 having between 1% and about 20% by weight water in a solvent or mixture of solvents to generate polymorph Form 11 as a residual solid. In some embodiments, the solvent is dimethylformamide (DMF). In some embodiments, the solvent is in a mixture with water, for example the solvent can be a mixture of water and DMF. In some embodiments, the water is present in an amount of about 5% by weight. In some embodiments, the reslurrying takes place at RT. In some embodiments, the reslurrying takes place at around 50° C.

3. Compositions and Administration

Provided herein are pharmaceutical compositions comprising a therapeutically effective amount of a compound of Formula (I), including amorphous and polymorph forms thereof, and a pharmaceutically acceptable carrier. Provided herein are pharmaceutical compositions prepared from a polymorph form of a compound of Formula (I). In some embodiments, the polymorph form is Form 1. In some embodiments, the polymorph form is a mixture of Form 1 and Form 9. In some embodiments, the polymorph is a non-stoichiometric hydrate of Form 1 having between 1% and about 20% by weight water.

In some embodiments, the pharmaceutical composition comprises a polymorph form of a compound of Formula (I). In some embodiments, the polymorph form is Form 1. In some embodiments, the pharmaceutical composition comprises a polymorph form of a compound of Formula (I) that is a mixture of forms. In some embodiments, the mixture of forms is a mixture of Forms 1 and 9. In some embodiments, the pharmaceutical composition comprises a polymorph form of a compound of Formula (I) that is a non-stoichiometric hydrate of Form 1 having between 1% and about 20% by weight water. In some embodiments the % water by weight in a crystal form, such as a non-stoichiometric hydrate, is determined by the Karl Fischer titration method. In some embodiments, the crystal form is dried prior to Karl Fischer titration. In some embodiments, the crystal form is dried prior to formulation as a composition, for example, with a pharmaceutically acceptable carrier.

In some embodiments, the pharmaceutical composition provided herein contains polymorph Form 1 that has a purity of at least about 90%. In some embodiments, the purity is at least about 95%. In some embodiments, the purity is at least about 98%. For example, the purity is at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition comprising Form 1 is substantially free of other forms of the compound of Formula (I), e.g., Form 9. In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of other forms of the compound of Formula (I). In some embodiments, the other forms of the compound of Formula (I) are other anhydrous forms of the compound of Formula (I). In some embodiments, the composition contains less than about 15% by weight of one or more other compounds of Formula (I). For example, the composition contains less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of one or more other forms of the compound of Formula (I). For example, the composition can contain less than about 15% by weight of Form 2, Form 3, Form 4, Form 5, Form 6, Form 7, Form 8, Form 9, Form 10, Form 11, a non-stoichiometric hydrate of Form 1, or combinations of two or more thereof.

In some embodiments, the pharmaceutical composition provided herein contains a non-stoichiometric hydrate of polymorph Form 1 having between 1% and about 20% by weight water that has a purity of at least about 90%. In some embodiments, the purity is at least about 95%. In some embodiments, the purity is at least about 98%. For example, the purity is at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition comprising the non-stoichiometric hydrate of Form 1 having between 1% and about 20% by weight water is substantially free of other forms of the compound of Formula (I), e.g., Form 9. In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of other forms of the compound of Formula (I). In some embodiments, the other forms of the compound of Formula (I) are other anhydrous forms of the compound of Formula (I). In some embodiments, the composition contains less than about 15% by weight of one or more other compounds of Formula (I). For example, the composition contains less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of one or more other forms of the compound of Formula (I). For example, the composition can contain less than about 15% by weight of Form 1, Form 2, Form 3, Form 4, Form 5, Form 6, Form 7, Form 8, Form 9, Form 10, Form 11, or combinations of two or more thereof.

In some embodiments, the composition can comprise between about 0.1% and 10% by weight of a compound of Formula (I), including amorphous and polymorph forms thereof. For example, the composition can comprise between about 0.1-10%, 0.1-5%, 0.1-4%, 0.15-3%, or 0.2-2% by weight of a compound of Formula (I), including amorphous and polymorph forms thereof. In some embodiments, the compound of Formula (I) is Form 1. In some embodiments, the compound of Formula (I) is a mixture of Form 1 and Form 9. In some embodiments, the compound of Formula (I) is a non-stoichiometric hydrate of polymorph Form 1 having between 1% and 20% by weight water.

In some embodiments, the composition comprises about 0.001 mg to about 5.0 mg per injection of a compound of Formula (I), including amorphous and polymorph forms thereof. For example, the composition in some embodiments comprises about 0.001 mg to about 4 mg, about 0.001 mg to about 3 mg, about 0.001 mg to about 2 mg, about 0.001 mg to about 1 mg, about 0.001 mg to about 0.5 mg, 0.001 mg to about 0.4 mg, about 0.001 mg to about 0.3 mg, about 0.001 mg to about 0.25 mg, about 0.001 mg to about 0.2 mg, about 0.001 mg to about 0.15 mg, about 0.001 mg to about 0.1 mg, about 0.001 mg to about 0.075 mg, about 0.001 mg to about 0.055 mg, about 0.001 mg to about 0.05 mg, about 0.001 mg to about 0.035 mg, about 0.001 mg to about 0.025 mg, about 0.001 mg to about 0.01 mg, about 0.001 mg to about 0.005 mg, about 0.005 mg to about 5.0 mg, about 0.0075 mg to about 5.0 mg, about 0.01 mg to about 5.0 mg, about 0.01 mg to about 4.0 mg, about 0.01 mg to about 3.0 mg, about 0.01 mg to about 2.0 mg, about 0.01 mg to about 1.0 mg, about 0.01 mg to about 0.7 mg, about 0.01 mg to about 0.5 mg, about 0.01 mg to about 0.3 mg, about 0.01 mg to about 0.23 mg, about 0.01 mg to about 0.1 mg, about 0.01 mg to about 0.07 mg, about 0.01 mg to about 0.05 mg, 0.01 mg to about 0.03 mg, about 0.03 mg to about 4.0 mg, about 0.03 mg to about 3.0 mg, about 0.03 mg to about 2.0 mg, about 0.03 mg to about 1.0 mg, about 0.03 mg to about 0.7 mg, about 0.03 mg to about 0.5 mg, about 0.03 mg to about 0.3 mg, about 0.03 mg to about 0.23 mg, about 0.03 mg to about 0.1 mg, about 0.03 mg to about 0.07 mg, about 0.03 mg to about 0.05 mg, about 0.07 mg to about 4.0 mg, about 0.07 mg to about 3.0 mg, about 0.07 mg to about 2.0 mg, about 0.07 mg to about 1.0 mg, about 0.07 mg to about 0.7 mg, about 0.07 mg to about 0.5 mg, about 0.07 mg to about 0.3 mg, about 0.07 mg to about 0.23 mg, about 0.07 mg to about 0.1 mg, about 0.025 mg to about 5.0 mg, about 0.045 mg to about 5.0 mg, about 0.05 mg to about 5.0 mg, about 0.075 mg to about 5.0 mg, about 0.1 mg to about 5.0 mg, about 0.25 mg to about 5.0 mg, about 0.01 mg to about 3.0 mg, about 0.025 mg to about 2.0 mg, about 0.01 mg to about 0.1 mg, and about 0.15 mg to about 0.25 mg of the compound of Formula (I), including amorphous and polymorph forms thereof. In some embodiments, the composition comprises about 0.001 mg, 0.005 mg, 0.01 mg, 0.03 mg, 0.05 mg, 0.07 mg, 0.1 mg, 0.23 mg, 0.25 mg, 0.5 mg, 0.75 mg, 1.0 mg, 1.2 mg, 1.5 mg, 1.7 mg, 2.0 mg, 2.2 mg, 2.5 mg, 2.7 mg, 3.0 mg, 3.2 mg, 3.5 mg, 3.7 mg, 4.0 mg, 4.2 mg, 4.5 mg, 4.7 mg, or 5.0 mg of the compound of Formula (I), including amorphous and polymorph forms thereof.

In the methods provided herein, in some embodiments relating to intra-articular administration of a compound provided herein, the therapeutically effective amount of the compound of Formula (I), including amorphous and polymorph forms thereof, is from about 1 µg to about 5000 µg. For example, the therapeutically effective amount can be from about 1 µg to about 4000 µg; from about 1 µg to about 3000 µg; from about 1 µg to about 2000 µg; from about 1 µg to about 1000 µg; from about 1 µg to about 500 µg; from about 1 µg to about 400 µg, about 1 µg to about 300 µg, from about 1 µg to about 250 µg; about 1 µg to about 200 µg, about 01 µg to about 150 µg, from about 1 µg to about 100 µg; from about 1 µg to about 75 µg; about 10 µg to about 100 µg; about 20 µg to about 80 µg; about 20 µg to about 40 µg; or about 60 µg to about 80 µg, from about 5 µg to about 5000 µg, about 7.5 µg to about 5000 µg, about 10 µg to about 5000 µg, about 10 µg to about 4000 µg, about 10 µg to about 3000 µg, about 10 µg to about 2000 µg, about 10 µg to about 1000 µg, about 10 µg to about 700 µg, about 10 µg to about 500 µg, about 10 µg to about 300 µg, about 10 µg to about 230 µg, about 10 µg to about 100 µg, about 10 µg to about 70 µg, about 10 µg to about 50 µg, about 10 µg to about 30 µg, about 30 µg to about 4000 µg, about 30 µg to about 3000 µg, about 30 µg to about 2000 µg, about 30 µg to about 1000 µg, about 30 µg to about 700 µg, about 30 µg to about 500 µg, about 30 µg to about 300 µg, about 30 µg to about 230 µg, about 30 µg to about 100 µg, about 30 µg to about 70 µg, about 30 µg to about 50 µg, about 70 µg to about 4000 µg, about 70 µg to about 3000 µg, about 70 µg to about 2000 µg mg, about 70 µg to about 1000 µg, about 70 µg to about 700 µg, about 70 µg to about 500 µg, about 70 µg to about 300 µg, about 70 µg to about 230 µg, about 70 µg to about 100 µg, about 25 µg to about 5000 µg, about 45 µg to about 5000 µg, about 50 µg to about 5000 µg, about 75 µg to about 5000 µg, about 100 µg to about 5000 µg, about 250 µg to about 5000 µg, about 10 µg to about 3000 µg, about 25 µg to about 2000 µg, about 10 µg to about 100 µg, and about 150 µg to about 250 µg of the compound of Formula (I), including amorphous and polymorph forms thereof. In some embodiments, the therapeutically effective amount is about 20 µg to about 80 µg. In some embodiments, the therapeutically effective amount is about 1 µg, 5 µg, 10 µg, 30 µg, 50 µg, 70 µg, 100 µg, 230 µg, 250 µg, 500 µg, 750 µg, 1000 µg, 1200 µg, 1500 µg, 1700 µg, 2000 µg, 2200 µg, 2500 µg, 2700 µg, 3000 µg, 3200 µg, 3500 µg, 3700 µg, 4000 µg, 4200 µg, 4500 µg, 4700 µg, or 5000 µg of the compound of Formula (I), including amorphous and polymorph forms thereof. In some embodiments, the total amount of the compound of Formula (I), including amorphous and polymorph forms thereof, that is administered in a 24-hour period is from about 1 µg to about 5000 µg, e.g., from about 1 to about 4000 µg; from about 1 µg to about 3000 µg; from about 1 µg to about 2000 µg; from about 1 µg to about 1000 µg; from about 1 µg to about 500 µg; from about 1 to about 250 µg; from about 1 µg to about 100 µg; from about 1 µg to about 75 µg; about 10 µg to about 100 µg; about 20 µg to about 80 µg; about 20 µg to about 40 µg; or about 60 µg to about 80 µg.

The compounds of Formula (I), including amorphous and polymorph forms thereof, can be administered either alone or more typically in combination with a conventional pharmaceutical carrier, excipient, or the like, e.g., as a composition. In some embodiments, the compounds of Formula (I), including amorphous and polymorph forms thereof, are formulated as a suspension. For example, the compound of Formula (I) is not completely dissolved in the pharmaceutically acceptable carrier, i.e., the compound of Formula (I) is suspended in the pharmaceutically acceptable carrier. In some embodiments, the composition comprises the compound of Formula (I) suspended in a pharmaceutically acceptable carrier. In some embodiments, the composition comprises a polymorph form of Formula (I) suspended in a pharmaceutically acceptable carrier. In some embodiments, the composition comprises Form 1 suspended in a pharmaceutically acceptable carrier. In some embodiments, the composition comprises a non-stoichiometric hydrate of Form 1 having between 1% and about 20% by weight water suspended in a pharmaceutically acceptable carrier. In some embodiments, the pharmaceutical composition is a solution, i.e., the compound of Formula (I) is completely dissolved in the pharmaceutically acceptable carrier.

In some embodiments, liquid pharmaceutically administrable compositions can, for example, be prepared by dissolving, dispersing or suspending a compound of Formula (I), including amorphous and polymorph forms thereof, and optional pharmaceutical excipients in a carrier, e.g., water, saline, aqueous dextrose, mannitol, glycerol, glycols, ethanol or the like, to form a solution, colloid, liposome, emulsion, complex, coacervate, or suspension. If desired, the pharmaceutical composition can also contain minor amounts of nontoxic auxiliary substances such as wetting agents, emulsifying agents (e.g., sodium carboxymethyl cellulose), co-solvents, solubilizing agents, pH buffering agents and the like (e.g., sodium acetate, sodium citrate, cyclodextrin derivatives, sorbitan monolaurate, triethanolamine acetate, triethanolamine oleate, phosphate, and the like).

In some embodiments, a pharmaceutical composition provided herein comprises water. For example, the pharmaceutical composition can include an aqueous buffer solution. Examples of buffer agents include, but are not limited to, acetic acid, acetic anhydride, adipic acid, alanine, albumin, alcohol, alfadex, ammonia, ammonium acetate, ammonium sulfate, anhydrous citric acid, anhydrous dextrose, anhydrous lactose, anhydrous trisodium citrate, arginine, ascorbic acid, aspartic acid, benzenesulfonic acid, benzoic acid, calcium chloride, calcium gluceptate, calcium hydroxide, calcium, caprylic acid, carbon dioxide, citric acid monohydrate, dibasic potassium phosphate, diethanolamine, disodium citrate sesquihydrate, disodium hydrogen citrate, edetate calcium disodium, edetate disodium, edetate sodium, edetic acid, ethanolamine hydrochloride, ferric chloride, gluceptate sodium, glycine hydrochloride, glycine, guanidine hydrochloride, histidine, hydrochloric acid, isoleucine, lactic acid, lactobionic acid, leucine, lysine acetate, lysine, lysine monohydrate, magnesium chloride, magnesium stearate, maleic acid, metaphosphoric acid, methanesulfonic acid, nitric acid, phosphate ion, phosphoric acid, potassium chloride, potassium hydroxide, potassium phosphate (monobasic), sodium acetate, sodium ascorbate, sodium benzoate, sodium bicarbonate, sodium bisulfate, sodium carbonate, sodium citrate, sodium hydroxide, sodium hypochlorite, sodium phosphate dihydrate, sodium phosphate, sodium phosphate p-32, sodium phosphate dibasic dihydrate, sodium phosphate dibasic dodecahydrate, sodium phosphate dibasic, sodium phosphate dibasic (anhydrous), sodium phosphate dibasic heptahydrate, sodium phosphate monobasic (anhydrous), sodium phosphate monobasic dihydrate, sodium phosphate monobasic monohydrate, sodium phosphate monobasic, sodium sulfate (anhydrous), sodium sulfate, sodium thioglycolate, sodium thiomalate, sodium thiosulfate, succinic acid, sulfuric acid, tartaric acid, tartaric acid (dl), trifluoroacetic acid, tromantadine, and tromethamine. In some embodiments, the pharmaceutical composition comprises phosphate buffered saline.

In some embodiments, a pharmaceutical composition provided herein comprises a cellulose derivative. In some embodiments, a pharmaceutical composition provided herein comprises a water-soluble cellulose or water-soluble cellulose derivative. Examples of cellulose and cellulose derivatives include, but are not limited to, microcrystalline cellulose (Avicel: Asahi Kasei Corp., etc.), microcrystalline cellulose carmellose sodium (Avicel RC: Asahi Kasei Corp., etc.), methyl cellulose (Metolose SM: Shin-Etsu Chemical Co., Ltd., etc.), ethyl cellulose (Ethocel: Dow Chemical Co., etc.), hydroxypropyl cellulose (Nisso HPC: Nippon Soda Co., Ltd., etc.), low-substituted hydroxypropyl cellulose (L-HPC: Shin-Etsu Chemical Co., Ltd., etc.), hydroxypropyl methyl cellulose 2208 (Metolose 90SH: Shin-Etsu Chemical Co., Ltd., etc.), hydroxypropyl methyl cellulose 2906 (Metolose 65SH: Shin-Etsu Chemical Co., Ltd., etc.), hydroxypropyl methyl cellulose 2910 (Metolose 60SH: Shin-Etsu Chemical Co., Ltd., etc.), hydroxypropyl cellulose phthalate 200731 (HPMCP: Shin-Etsu Chemical Co., Ltd., etc.), hydroxypropyl cellulose phthalate 220824 (HPMCP: Shin-Etsu Chemical Co., Ltd., etc.), hydroxypropyl methyl cellulose acetate succinate (Shin-Etsu AQOAT: Shin-Etsu Chemical Co., Ltd., etc.), carmellose (NS-300: Gotoku Chemical Co., Ltd., etc.), carmellose calcium (ECG-505: Gotoku Chemical Co., Ltd., etc.), carmellose sodium (Cellogen: Daiichi Kogyo Seiyaku Co., Ltd., etc.), croscarmellose sodium (Ac-Di-Sol: Asahi Kasei Corp., etc.), carboxymethyl ethyl cellulose (CMEC: Freund Corp., etc.), cellulose acetate phthalate (CAP: Wako Pure Chemical Industries, Ltd., etc.), hydroxyethyl cellulose (NATROSOL: Aqualon Corp., etc.) or mixtures thereof. In some embodiments, a cellulose derivative is a carboxymethylcellulose, or a pharmaceutically acceptable salt thereof. For example, a cellulose derivative is sodium carboxymethylcellulose. A cellulose derivative can be present in the composition in an amount of about 0.1% to about 5% by weight of the composition. For example, about 0.1% to about 2.5%; about 0.1% to about 1%; about 0.1% to about 0.75%; about 0.1% to about 0.5%; about 0.1% to about 0.25%; about 0.25% to about 5%; about 0.5% to about 5%; about 1% to about 5%; about 2.5% to about 5%; about 0.25% to about 0.75%; about 0.5% to about 1%; and about 1% to about 2% by weight of the composition. In some embodiments, the surfactant can be present in the composition at about 0.5% by weight of the composition.

In some embodiments, a pharmaceutical composition provided herein comprises a surfactant. Non-limiting examples of surfactants include polysorbates such as polysorbate 20, polysorbate 40, polysorbate 60, polysorbate 80, and polysorbate 85; polyoxyethylene hydrogenated castor oils such as polyoxyethylene hydrogenated castor oil 60 and polyoxyl 35 castor oil; sorbitan fatty acid esters; sucrose fatty acid esters; polyoxyethylene polyoxypropylene glycols; polyoxyethylene fatty acid ethers; polyoxyl stearates; and other surfactants, including, but not limited to, 1,2-dimyristoyl-sn-glycero-3-(phospho-s-(1-glycerol)), 1,2-dioleoyl-sn-glycero-3-phosphocholine, 1,2-dipalmitoyl-sn-glycero-3-(phospho-rac-(1-glycerol)), 1,2-distearoyl-sn-glycero-3-(phospho-rac-(1-glycerol)), 1,2-distearoyl-sn-glycero-3-phosphocholine, deoxycholic acid, dipalmitoylphosphatidylglycerol (dl), distearoylphosphatidylcholine (dl), docusate sodium, egg phospholipids, glyceryl palmitostearate, glyceryl trioleate, hydrogenated soybean lecithin, hydrolyzed soy protein (enzymatic; 2000 mw), hydroxyethylpiperazine ethane sulfonic acid, lecithin, miripirium chloride, n-(carbonyl-methoxypolyethylene glycol 2000)-1,2-distearoyl-sn-glycero-3-phiv, oleic acid, palmitic acid, peg vegetable oil, peg-20 sorbitan isostearate, peg-40 castor oil, phospholipid, poloxamer 188, polyethylene glycol 200, polyethylene glycol 300, polyethylene glycol 3350, polyethylene glycol 400, polyethylene glycol 4000, polyethylene glycol 600, polyoxyethylene fatty acid esters, sodium cholesteryl sulfate, sodium deoxycholate, sodium n-(carbonyl-methoxypolyethylene glycol 2000)-1,2-distearoyl-sn-glyc, sodium oleate, sorbitan monolaurate, sorbitan monopalmitate, stearic acid, tricaprylin, or mixtures thereof. In some embodiments, the surfactant is a polysorbate. For example, the pharmaceutical composition comprises polysorbate 80. A surfactant can be present in the composition in an amount of about 0.01% to about 0.5% by weight of the composition. For example, about 0.01% to about 0.25%; about 0.01% to about 0.1%; about 0.01% to about 0.075%; about 0.01% to about 0.05%; about 0.01% to about 0.025%; about 0.025% to about 0.5%; about 0.05% to about 0.5%; about 0.1% to about 0.5%; about 0.25% to about 0.5%; about 0.025% to about 0.075%; about 0.05% to about 0.1%; and about 0.1% to about 0.2% by weight of the composition. In some embodiments, the surfactant can be present in the composition at about 0.05% by weight of the composition.

In some embodiments, the pharmaceutical composition comprises a compound of Formula (I), including amorphous and polymorph forms thereof, and a pharmaceutically acceptable carrier. For example, the composition comprises a compound of Formula (I) and saline, e.g., phosphate buffered saline. In some embodiments, the pharmaceutical composition comprises a compound of Formula (I), a pharmaceutically acceptable carrier, and one or more excipients. For example, the composition comprises a compound of Formula (I), a pharmaceutically acceptable carrier, e.g., phosphate buffered saline, and one or more excipients, e.g., a surfactant and a cellulose derivative. In some embodiments, the surfactant is a polysorbate, e.g., polysorbate 80. In some embodiments, the cellulose derivative is sodium carboxymethylcellulose. In some embodiments, the pharmaceutical composition comprises a compound of Formula (I), e.g., a polymorph form of Formula (I), e.g., Form 1, a pharmaceutically acceptable carrier, e.g., phosphate buffered saline, and one or more excipients, e.g., sodium carboxymethylcellulose and a polysorbate, e.g., polysorbate 80.

In some embodiments, the pharmaceutical composition comprises a compound of Formula (I), e.g., a polymorph form of Formula (I), about 0.1% to about 5% by weight of a cellulose derivative, about 0.01% to about 0.5% by weight of a surfactant; in an aqueous buffer. For example, a pharmaceutical composition provided herein can include a compound of Formula (I), e.g., Form 1 or a non-stoichiometric hydrate of Form 1 having between 1% and about 20% by weight water, about 0.5% by weight sodium carboxymethylcellulose and about 0.05% by weight polysorbate 80 in phosphate buffered saline.

In some embodiments, a pharmaceutical composition provided herein has a pH of about 6.0 to about 8.0. For example, a pharmaceutical composition can have a pH of about 7.3 or 7.4. In some embodiments a pharmaceutical composition provided herein has a pH of about 3.0 to about 5.0. For example, a pharmaceutical composition can have a pH of about 3.8.

The compositions provided herein can contain an excipient. The term "excipient" is used herein to describe any ingredient other than the compound(s) provided herein, e.g., compound of Formula (I), including polymorph and amorphous forms thereof.

Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat, solubilizers, tonicity agents, stabilizers, preservatives, salt formation substances, chelators/chelating agents, viscosity enhancers, contrast agent, anti-foam agents, control release agents, lubricants, adhesives, analgesics, antiheparins, antivirals, colorants, emollients, propellants, and other excipients, including, but not limited to activated charcoal, barium sulfate, bibapcitide, brocrinat, calcobutrol, glutathione, zinc, zinc acetate, zinc carbonate, zinc chloride, and zinc oxide. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds described herein. Dosage forms or compositions containing a compound as described herein in the range of 0.005% to 100% with the balance made up from non-toxic carrier may be prepared. The contemplated compositions can contain 0.001%-100% active ingredient, in one embodiment 0.1-95%, in another embodiment 75-85%, in a further embodiment 20-80%. Actual methods of preparing such dosage forms are known, or will be apparent, to those skilled in the art; for example, see *Remington: The Science and Practice of Pharmacy*, $22^{nd}$ Edition (Pharmaceutical Press, London, U K. 2012).

In some embodiments, the pharmaceutical compositions provided herein contain a solubilizer. Examples of solubilizers include, but are not limited to, acetyltryptophan (dl), alanine, albumin (aggregated), alcohol, alfadex intracavitary powder, ammonia, anhydrous dextrose, anhydrous lactose, anhydrous trisodium citrate, arginine, ascorbic acid, aspartic acid, benzenesulfonic acid, benzyl alcohol, benzyl benzoate, benzyl chloride, betadex sulfobutyl ether sodium, butanol (mixed isomers), caprylic acid, carboxymethylcellulose, carboxymethylcellulose sodium, castor oil, cholesterol, corn oil, cottonseed oil, creatine, creatinine, croscarmellose sodium, crospovidone, cysteine hydrochloride, cysteine, cysteine (dl), dextran 40, dextran, diacetylated monoglycerides, diethanolamine, dimethyl sulfoxide, ethanolamine hydrochloride, ethyl acetate, ethylene-vinyl acetate copolymer (15% vinyl acetate), gamma cyclodextrin, gelatin, gentisic acid ethanolamide, gentisic acid, gluconolactone, glucuronic acid, glycerin, hetastarch, human albumin microspheres, hyaluronate sodium, hydroxypropyl betadex intramuscular injection, hypromellose, isopropyl alcohol, methylcellulose, methylpyrrolidone, microcrystalline cellulose, N,N-dimethylacetamide, niacinamide, oleic acid, palmitic acid, peanut oil, peg vegetable oil, peg-20 sorbitan isostearate, peg-40 castor oil, phenylethyl alcohol, polyethylene glycol 200, polyethylene glycol 300, polyethylene glycol 3350, polyethylene glycol 400, polyethylene glycol 4000, polyethylene glycol 600, polypropylene glycol, polyvinyl alcohol, poppy seed oil, povidone k12, povidone k17, povidone, proline, propyl gallate, propylene glycol, sesame oil, soybean oil, starch, stearic acid, trimethylsilyl treated dimethiconol/trimethylsiloxysilicate crosspolymer, and yellow wax, and combinations thereof.

In some embodiments, the pharmaceutical compositions provided herein contain a tonicity agent. Examples of tonicity agents include, but are not limited to, dextrose monohydrate, dextrose solution, dextrose, dimethyl sulfoxide, fructose, gluconolactone, glucuronic acid, glycerin, glycine hydrochloride, glycine, guanidine hydrochloride, histidine, hydrochloric acid, hypertonic sodium chloride solution, isoleucine, isopropyl alcohol, isotonic sodium chloride solution, lactic acid (dl), lactobionic acid, lactose monohydrate, lactose, leucine, lysine acetate, lysine, lysine monohydrate, magnesium chloride, magnesium stearate, maleic acid, mannitol, meglumine, methionine, methylboronic acid, polypropylene glycol, potassium chloride, potassium hydroxide, potassium phosphate (monobasic), proline, propyl gallate, propylene glycol, saccharin sodium, serine, sodium acetate, sodium ascorbate, sodium benzoate, sodium bicarbonate, sodium bisulfate, sodium carbonate, sodium chloride, sodium citrate, sodium gluconate, sodium hydroxide, sodium hypochlorite, sodium lactate, sodium phosphate dihydrate, sodium phosphate, sodium phosphate p-32, sodium phosphate dibasic dihydrate, sodium phosphate dibasic dodecahydrate, sodium phosphate dibasic, sodium phosphate dibasic (anhydrous), sodium phosphate dibasic heptahydrate, sodium phosphate monobasic (anhydrous), sodium phosphate monobasic dihydrate, sodium phosphate monobasic monohydrate, sodium phosphate monobasic, sodium sulfate (anhydrous), sodium sulfate, sodium thioglycolate, sodium thiomalate, sodium thiosulfate, sorbitol, succinic acid, sucrose, sulfuric acid, tartaric acid, tartaric acid (dl), threonine, trehalose, trifluoroacetic acid, trisodium citrate dihydrate, tromethamine, tryptophan, tyrosine, urea, urethane, and valine and combinations thereof.

In some embodiments, the pharmaceutical compositions provided herein contain a stabilizer. Examples of stabilizers include, but are not limited to, acetyltryptophan (dl), alanine, albumin (aggregated), alcohol, alfadex intracavitary powder, ammonia, anhydrous dextrose, anhydrous lactose, anhydrous trisodium citrate, arginine, ascorbic acid, aspartic acid, benzenesulfonic acid, benzyl alcohol, benzyl benzoate, benzyl chloride, betadex sulfobutyl ether sodium, boric acid, butanol (mixed isomers), caprylic acid, carboxymethylcellulose, carboxymethylcellulose sodium, castor oil, cholesterol, creatine, creatinine, croscarmellose sodium, crospovidone, cysteine hydrochloride, cysteine, cysteine (dl), dextran 40, dextran, ethylene-vinyl acetate copolymer (15% vinyl acetate), gelatin, gentisic acid ethanolamide, gentisic acid, hetastarch, human albumin microspheres, hyaluronate sodium, hypromellose, meglumine, methionine, methylboronic acid, methylcellulose, methylpyrrolidone, microcrystalline cellulose, miripirium chloride, N-(carbonyl-methoxypolyethylene glycol 2000)-1,2-distearoyl-sn-glycero-3-phiv, N,N-dimethylacetamide, niacinamide, phenylalanine, polyvinyl alcohol, povidone K12, povidone K17, povidone, serine, sodium citrate, sodium gluconate, sodium lactate, starch, threonine, trehalose, tricaprylin, trimethylsilyl treated dimethiconol/trimethylsiloxysilicate crosspolymer, trisodium citrate dihydrate, tryptophan, tyrosine, urea, and valine and combinations thereof.

In some embodiments, the pharmaceutical compositions provided herein contain a preservative. Examples of preservatives include, but are not limited to, acetone sodium bisulfite, alpha-tocopherol, benzalkonium chloride, benzyl alcohol, benzyl benzoate, benzyl chloride, boric acid, butylated hydroxyanisole, butylated hydroxytoluene, butylparaben, chlorobutanol, chlorobutanol hemihydrate, cresol, diethyl pyrocarbonate, edetate calcium disodium, edetate disodium, edetate sodium, edetic acid, hexylresorcinol, metacresol, methylparaben, miripirium chloride, monothioglycerol, nitrogen, phenol, phenylethyl alcohol, phenylmercuric nitrate, potassium bisulfite, potassium metabisulfite, propylparaben, sodium ascorbate, sodium benzoate, sodium bisulfate, sodium chlorate, sodium dithionite, sodium formaldehyde sulfoxylate, sodium iodide, sodium metabisulfite, sodium sulfite, sodium tartrate, sulfur dioxide, sulfurous acid, and thimerosal and combinations thereof.

In some embodiments, the pharmaceutical compositions provided herein contain a salt formation agent. Examples of salt formation agents include, but are not limited to, acetic acid, acetic anhydride, adipic acid, ammonium acetate, ammonium sulfate, anhydrous citric acid, benzoic acid, calcium chloride, calcium gluceptate, calcium hydroxide, calcium, carbon dioxide, citric acid monohydrate, dibasic potassium phosphate, diethanolamine, disodium citrate sesquihydrate, disodium hydrogen citrate, hydrochloric acid, isoleucine, lactic acid (dl), lactobionic acid, magnesium chloride, magnesium stearate, maleic acid, metaphosphoric acid, methanesulfonic acid, nitric acid, phosphate ion, phosphoric acid, sodium hydroxide, sodium hypochlorite, sodium phosphate dihydrate, sodium phosphate, sodium phosphate p-32, sodium phosphate dibasic dihydrate, sodium phosphate dibasic dodecahydrate, sodium phosphate dibasic, sodium phosphate dibasic (anhydrous), sodium phosphate dibasic heptahydrate, sodium phosphate monobasic (anhydrous), sodium phosphate monobasic dihydrate, sodium phosphate monobasic monohydrate, sodium phosphate monobasic, and trifluoroacetic acid and combinations thereof.

In some embodiments, the pharmaceutical compositions provided herein contain a chelator or chelating agent. Examples of chelators or chelating agents include, but are not limited to, caldiamide sodium, caloxetate trisodium, calteridol calcium, edetate calcium disodium, edetate disodium, edetate sodium, edetic acid, ferric chloride, gluceptate sodium, methylboronic acid, nioxime, oxidronate disodium, peg-60 hydrogenated castor oil, pentasodium pentetate, pentetate calcium trisodium, pentetic acid, sodium phosphite, sodium pyrophosphate, sodium succinate hexahydrate, sodium trimetaphosphate, succimer, and versetamide and combinations thereof.

In some embodiments, the pharmaceutical compositions provided herein contain a viscosity enhancer. Examples of viscosity enhancers include, but are not limited to, carboxymethylcellulose, carboxymethylcellulose sodium, croscarmellose sodium, crospovidone, ethylene-vinyl acetate copolymer (15% vinyl acetate), gelatin, hetastarch, human albumin microspheres, hyaluronate sodium, hypromellose, methylcellulose, methylpyrrolidone, microcrystalline cellulose, polyvinyl alcohol, povidone K12, povidone K17, povidone, starch, and trimethylsilyl treated dimethiconol/trimethylsiloxysilicate crosspolymer and combinations thereof.

In some embodiments, the pharmaceutical compositions provided herein contain a contrast agent. Examples of contrast agents include, but are not limited to, diatrizoic acid, perflutren, stannous chloride, stannous fluoride, stannous tartrate, tetrakis(2-methoxyisobutylisocyanide)copper(I) tetrafluoroborate, and tetrofosmin and combinations thereof.

In some embodiments, the pharmaceutical compositions provided herein contain an anti-foam agent. Examples of anti-foam agents include, but are not limited to, dimethicone, polysiloxane, silicone, and simethicone and combinations thereof.

In some embodiments, the pharmaceutical compositions provided herein contain a control release agent. Examples of control release agents include, but are not limited to, poly (dl-lactic-co-glycolic acid), (50:50; 12000 mw), polyglactin, and polylactide and combinations thereof.

In some embodiments, the pharmaceutical compositions provided herein contain a lubricant. Examples of lubricants include, but are not limited to, silicone and simethicone and combinations thereof.

In some embodiments, the pharmaceutical compositions provided herein contain an adhesive. An example of an adhesive includes, but is not limited to, Duro-Tak 87-2287.

In some embodiments, the pharmaceutical compositions provided herein contain an analgesic. An example of an analgesic includes, but is not limited to, disodium sulfosalicylate.

In some embodiments, the pharmaceutical compositions provided herein contain an anti-heparin agent. An example of an anti-heparin agent includes, but is not limited to, protamine sulfate.

In some embodiments, the pharmaceutical compositions provided herein contain an antiviral agent. An example of an antiviral agent includes, but is not limited to, tromantadine.

In some embodiments, the pharmaceutical compositions provided herein contain a colorant. An example of a colorant includes, but is not limited to, methylene blue.

In some embodiments, the pharmaceutical compositions provided herein contain an emollient. An example of an emollient includes, but is not limited to, urethane.

In some embodiments, the pharmaceutical compositions provided herein contain a propellant. An example of a propellant includes, but is not limited to, dichlorodifluoromethane.

In some embodiments, the pharmaceutical compositions provided herein are prepared as single-use injectable compositions. For example, the pharmaceutical composition is prepared to contain the therapeutically effective amount of the compound of Formula (I), including amorphous and polymorph forms thereof, and is intended to be used in a single subject for a single injection. In some embodiments, the pharmaceutical compositions provided herein are prepared as multi-dose compositions. For example, the pharmaceutical composition is prepared to contain more than the therapeutically effective amount of the compound of Formula (I), including amorphous and polymorph forms thereof, and is intended to be used in one or more subjects for more than one injection. In some embodiments, the multi-dose composition has a higher concentration of the compound of Formula (I), than is intended for a single dosage and is intended to be diluted on-site to achieve the appropriate dosage for the subject.

In some embodiments, the compositions are provided in unit dosage forms suitable for single administration of a dose. In some embodiments, the compositions are provided in unit dosage forms suitable for multiple administration of a dose. For example, one injection every three months, every six months, every nine months, etc.

Injectables can be prepared in conventional forms, either as liquid solutions, colloids, liposomes, complexes, coacervates, suspensions, or emulsions, or in solid forms suitable for reconstitution in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and could be higher if the composition is a solid or suspension, which could be subsequently diluted to the above percentages.

In some embodiments, the composition comprises a volume of about 1 mL to about 10 mL per injection. For example, about 1 mL to about 6 mL, about 1 mL to about 4 mL, about 1 mL to about 3 mL, about 2 mL to about 10 mL, about 4 mL to about 10 mL, about 7 mL to about 10 mL, about 1.5 mL to about 2.5 mL, about 2 mL to about 4 mL. In some embodiments, the composition comprises a volume of about 2 mL per injection.

In some embodiments, the unit dosage of compounds of Formula (I), including amorphous and polymorph forms thereof, is about 0.1 µg/kg to about 10 µg/kg in humans.

In some embodiments, the unit dosage of compounds of Formula (I), including amorphous and polymorph forms thereof, is about 0.1 µg/kg to about 5 µg/kg in humans. In some embodiments, the unit dosage of compounds of Formula (I), including amorphous and polymorph forms thereof, is about 0.2 µg/kg to about 9 µg/kg in humans.

In some embodiments, the unit dosage of compounds of Formula (I), including amorphous and polymorph forms thereof, is about 0.25 µg/kg to about 8 µg/kg in humans.

In some embodiments, the unit dosage of compounds of Formula (I), including amorphous and polymorph forms thereof, is about 0.3 µg/kg to about 7 µg/kg in humans.

In some embodiments, the unit dosage of compounds of Formula (I), including amorphous and polymorph forms thereof, is about 0.4 µg/kg to about 6 µg/kg in humans.

In some embodiments, the unit dosage of compounds of Formula (I), including amorphous and polymorph forms thereof, is about 0.5 µg/kg to about 5 µg/kg in humans. In some embodiments, the unit dosage of compounds of Formula (I), including amorphous and polymorph forms thereof, is about 0.6 µg/kg to about 5 µg/kg in humans.

In some embodiments, the unit dosage of compounds of Formula (I), including amorphous and polymorph forms thereof, is about 1.0 µg/kg to about 4 µg/kg in humans.

In some embodiments, the unit dosage of compounds of Formula (I), including amorphous and polymorph forms thereof, is about 2.0 µg/kg to about 4 µg/kg in humans.

In some embodiments, the unit dosage of compounds of Formula (I), including amorphous and polymorph forms thereof, is about 3.0 µg/kg to about 5 µg/kg in humans.

In some embodiments, the unit dosage of compounds of Formula (I), including amorphous and polymorph forms thereof, is about 4.0 µg/kg to about 6 µg/kg in humans. In some embodiments, the unit dosage of compounds of Formula (I), including amorphous and polymorph forms thereof, is about 5.0 µg/kg to about 10 µg/kg in humans.

In some embodiments, the unit dosage of compounds of Formula (I), including amorphous and polymorph forms thereof, is 0.01 mg to 1 mg in humans.

In some embodiments, the unit dosage of compounds of Formula (I), including amorphous and polymorph forms thereof, is 0.01 mg to 0.5 mg in humans.

In some embodiments, the unit dosage of compounds of Formula (I), including amorphous and polymorph forms thereof, is 0.01 mg to 0.3 mg in humans.

In some embodiments, the unit dosage of compounds of Formula (I), including amorphous and polymorph forms thereof, is 0.03 mg to 0.9 mg in humans.

In some embodiments, the unit dosage of compounds of Formula (I), including amorphous and polymorph forms thereof, is 0.03 mg to 0.23 mg in humans.

In some embodiments, the unit dosage of compounds of Formula (I), including amorphous and polymorph forms thereof, is 0.05 mg to 0.8 mg in humans.

In some embodiments, the unit dosage of compounds of Formula (I), including amorphous and polymorph forms thereof, is 0.07 mg to 0.7 mg in humans.

In some embodiments, the unit dosage of compounds of Formula (I), including amorphous and polymorph forms thereof, is 0.08 mg to 0.7 mg in humans.

In some embodiments, the unit dosage of compounds of Formula (I), including amorphous and polymorph forms thereof, is 0.1 mg to 0.6 mg in humans.

In some embodiments, the unit dosage of compounds of Formula (I), including amorphous and polymorph forms thereof, is 0.12 mg to 0.6 mg in humans.

In some embodiments, the unit dosage of compounds of Formula (I), including amorphous and polymorph forms thereof, is 0.14 mg to 0.5 mg in humans.

In some embodiments, the unit dosage of compounds of Formula (I), including amorphous and polymorph forms thereof, is 0.16 mg to 0.5 mg in humans.

In some embodiments, the unit dosage of compounds of Formula (I), including amorphous and polymorph forms thereof, is 0.18 mg to 0.4 mg in humans.

In some embodiments, the unit dosage of compounds of Formula (I), including amorphous and polymorph forms thereof, is 0.2 mg to 0.4 mg in humans.

In some embodiments, provided herein is a composition comprising a compound of Formula (I), including amorphous and polymorph forms thereof, and a pharmaceutically acceptable carrier. In some embodiments, the composition can be prepared from a polymorph form of Formula (I), e.g., Form 1. The compositions provided herein, e.g., suspensions and solutions, can maintain the effective drug concentration, i.e., the effective concentration of the compound of Formula (I), over an extended period of time, e.g., over a period of weeks, months, or years. In some embodiments, the compound of Formula (I) is present at the site of administration (e.g., the site of injection) at about 0.5% to about 10% of the initial dose, such as about 0.5%, 0.55%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the initial dose after a period of time. For example, about 0.5% to about 10% of the initial dose is at the site of injection after about 45 days, 90 days, or 180 days. In some embodiments, the compound of Formula (I) is radiolabeled. The compound can be radiolabeled at, for example, any carbon, hydrogen, or fluorine atom with a respective radioactive isotope. Examples of radioactive isotopes include, but are not limited to, deuterium, tritium, carbon-11, carbon 14, and fluorine-18. The signal can be measured using any imaging method known to those of skill in the art, including, but not limited to, magnetic resonance imaging (MRI), ultrasound, endoscopy, positron emission tomography (PET), and single-photon emission computed tomography (SPECT).

In some embodiments, the compositions and compositions provided herein are stable for at least 3 months. For example, the compositions do not exhibit a change in one or more of polymorph form (e.g., an increase or decrease of a certain form), appearance, pH, percent impurities, activity (as measured by in vitro assays), or osmolarity over time, e.g., at least 3 months. In some embodiments, the compositions and compositions provided herein are stable for at least 6 months. For example, the compositions do not exhibit a change in one or more of polymorph form (e.g., an increase or decrease of a certain form), appearance, pH, percent impurities, activity (as measured by in vitro assays), or osmolarity over time, e.g., at least 6 months. In some embodiments, the compositions and compositions provided herein are stable for at least 9 months. For example, the compositions do not exhibit a change in one or more of polymorph form (e.g., an increase or decrease of a certain form), appearance, pH, percent impurities, activity (as measured by in vitro assays), or osmolarity over time, e.g., at least 9 months. In some embodiments, the compositions and compositions provided herein are stable for at least 12 months. For example, the compositions do not exhibit a change in one or more of polymorph form (e.g., an increase or decrease of a certain form), appearance, pH, percent impurities, activity (as measured by in vitro assays), or osmolarity over time, e.g., at least 12 months. In the above, the phrase "do not exhibit a change" refers to a change of less than 5% (e.g., less than 4%, less than 3%, less than 2%, less than 1%) as measured for any of the parameters over the relevant time period.

In some embodiments, the pharmaceutical compositions provided herein exhibit slow dissolution of the compound of Formula (I), including amorphous and polymorph forms thereof. Dissolution time can vary according to the specific solvent, the concentration, the temperature, the polymorph form, etc. In some embodiments, a composition comprising a compound of Formula (I) exhibits a mean dissolution time of between about 5 days and 1500 days in solution, such as between about 5 days and 10 days, 10 days and 100 days, 100 days and 1000 days, or 1000 days and 1500 days in solution, e.g., about 5, 7, 10, 25, 50, 75, 100, 200, 300, 400, 500, 600, 700, 800, 900, 1000, 1100, 1200, 1300, 1400, or 1500 days in solution. In some embodiments, a pharmaceutical composition provided herein exhibits a mean dissolution time of greater than 7 days in solution; greater than 60 days in solution; greater than 120 days in solution; or greater than 1 year in solution. In some embodiments, a composition comprising a compound of Formula (I) exhibits a mean dissolution time of about 7 days in solution. In some embodiments, a composition comprising a compound of Formula (I) exhibits a mean dissolution time of about 89 days in solution. In some embodiments, a composition comprising a compound of Formula (I) exhibits a mean dissolution time of about 1116 days in solution. In some such embodiments, the pharmaceutical composition comprises about 100 mg/mL of the compound of Formula (I), including amorphous and polymorph forms thereof. In some embodiments, the dissolution time can depend upon, for example, pH or concentration or both. As used herein "mean dissolution time" refers to the rate of drug release from the dosage form, wherein the higher the value, the slower the rate of drug release.

In some such embodiments, the pharmaceutical composition comprises between about 0.005 mg/mL and 2.5 mg/mL of the compound of Formula (I), including amorphous and polymorph forms thereof, for example, between about 0.005 mg/mL to about 2 mg/mL, about 0.01 mg/mL to about 1.8 mg/mL, about 0.025 mg/mL to about 1.6 mg/mL, about 0.05 mg/mL to about 1.5 mg/mL, about 0.075 mg/mL to about 1.25 mg/mL, about 0.1 mg/mL to about 1 mg/mL, or about 0.25 mg/mL to about 0.75 mg/mL. In some such embodiments, the pharmaceutical composition comprises about 0.015 mg/mL to about 0.115 mg/mL of the compound of Formula (I), including amorphous and polymorph forms thereof. In some embodiments, the injection concentration comprises between about 0.1 mg/mL and 4 mg/mL. In some embodiments, the injection concentration is 2 mg/mL.

The compounds provided herein, e.g., compounds of Formula (I), including amorphous and polymorph forms thereof, can be formulated as a plurality of particles. For example, particles of a compound provided herein can have a median particle size of less than 20 µm (e.g., less than about 15 µm; less than about 10 µm; less than about 7.5 µm; less than about 5 µm; less than about 2.5 µm; less than about 1 µm; and less than about 0.5 µm). For example, the median particle size can be between about 0.1 µm and 20 µm, such as between about 0.5-20, 0.5-15, 0.5-10, 0.5-7.5, 0.5-5, 0.5-2.5, 0.5-1, 2.5-15, 5-10, 7.5-20, or 1-5 µm. In some embodiments, the particles also comprise a polymer. Examples of suitable polymers include biocompatible and biodegradable polymers like poly(lactic acid), a poly(glycolic acid), a poly(lactic-co-glycolic acid), a poly(lactide-co-glycolide), and mixtures thereof. In some embodiments, the particles comprise poly(lactic-co-glycolic acid) (PLGA).

In some embodiments, the compound of Formula (I), including amorphous and polymorph forms thereof, e.g., a polymorph form of Formula (I), e.g., Form 1, has a particle size distribution (D value), e.g., a D50, of between about 1 and about 6 µm, such as between about 1.5 and about 5 µm, or about 2.4 to about 2.55 µm. For example, the D50 can be about 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 4, 4.5, or 5 µm. In some embodiments, the D50 value is about 2.55 µm. In some embodiments, the D50 value is about 2.45 µm. In some embodiments, the D50 value is about 2.1 µm. In some embodiments, the D50 value is about 2 µm. In some embodiments, the D50 value is about 1.6 µm. The D50 can be measured by conventional particle size measuring techniques well known to those skilled in the art. Such techniques include, for example, sedimentation field flow fractionation, photon correlation spectroscopy, light scattering, laser diffraction and disc centrifugation.

Administration of the compositions and compounds provided herein, including amorphous and polymorph forms thereof, can be via any of the accepted modes of administration including, but not limited to, subcutaneous, intravenous, topical, transdermal, intraperitoneal, intramuscular, intrathecal, intra-articular, intracapsular, intraspinal, intrasynovial, epidural, intravascular, or via irrigation of infected bone. In some embodiments, administration is parenteral. In some embodiments, administration is intra-articular.

In some embodiments, the compound of Formula (I), including amorphous and polymorph forms thereof, and compositions provided herein are administered parenterally, including intramuscularly, intra-articularly, periarticularly, intraspinally, intrasynovially, and epidurally. For example, the compounds and compositions can be injected locally at the site of the osteoarthritis (e.g., knee, hip, shoulder, etc.). Injections can occur at one or more locations surrounding the joint. In some embodiments, the injection is guided using an imaging method such as ultrasound. In some embodiments, administration (e.g., injection) of a compound of Formula (I), including amorphous and polymorph forms thereof, is preceded or combined with a local anesthetic.

The compound of Formula (I) provided herein intended for pharmaceutical use can be administered as amorphous or polymorph compositions. Pharmaceutically acceptable compositions can include suspensions, liquids, solutions, colloidals, liposomes, emulsions, complexes, and coacervates. In some embodiments, the composition is formulated as a suspension. The compounds, including amorphous and polymorph forms thereof, and compositions can be administered as an injection.

The compounds and compositions provided herein can also be administered in combination (administered together or sequentially) with other known agents.

In some embodiments, a compound of Formula (I), including amorphous and polymorph forms thereof, can be used to treat osteoarthritis in combination with one or more of the following: (a) Nonsteroidal anti-inflammatory drugs (NSAIDs), including, but not limited to, ibuprofen, naproxen, aspirin, acetaminophen, indomethacin (e.g., INI-DOCIN® and TIVORBEX®), diclofenac by mouth or to the affected area (e.g., VOLTAREN®, ZIPSOR®, PENN-SAID®, FLECTOR®, and CATAFLAM®), meloxicam (e.g., MOBIC), celecoxib (e.g., CELEBREX®), piroxicam (e.g., FELDENE®), etodolac (e.g., LODINE®), nabumetone (e.g., RELAFEN®), lumiracoxib, valdecoxib (e.g., BEXTRA®), etoricoxib, parecoxib, fenoprofen (e.g., NALFON®), oxaprozin (e.g., DAYPRO®), mefanamic acid (e.g. PONSTEL®), diflunisal (e.g., DOLOBID®), fenoprofen (e.g., NALFON®), flurbirofen (e.g., ANSAID®), ketoprofen (e.g., ORUVAIL®), ketorolac (e.g., TORADOL®), sulindac (e.g., CLINORIL®), meclofenamate, choline salicylate-magnesium salicylate, salsalate (e.g., DISAL-CID®), and tolmetin (e.g., TOLECTIN®); (b) physical therapy; (c) injections of corticosteroid medications such as, e.g., prednisone, dexamethasone, hydrocortisone, and methylprenisolone; (d) injections of hyaluronic acid derivatives (e.g., HYALGAN®, SYNVISC®, EUIFLEXXA®, GEL-ONE®, MONOVISC®, ORTHOVISC®, and SUPARTZ®); (e) injections or topical application of Capsaicin (e.g., CAP-SAGEL®); (f) narcotics, such as, e.g., codeine, fentanyl, hydrocodone, hydromorphone, morphine, meperidine, oxycodone, and tramadol (e.g., ULTRAM®, CONZIP®, and RYZOLT®); (g) antidepressants such as duloxetine (e.g., CYMBALTA®); (h) braces and/or shoe inserts or any device that can immobilize or support the joints to help keep pressure off it (e.g., splints, braces, shoe inserts or other medical devices); (i) realigning bones (osteotomy); (j) joint replacement (arthroplasty); and (k) chronic pain class.

In some embodiments, a compound of Formula (I), including amorphous and polymorph forms thereof, can be used to treat osteoarthritis in combination with one or more of the following drugs or methods: prednisone, methylprednisolone, SYNVISC® (hylan G-F 20), ABT-981 [*MAbs* (2015) 7(3):605-619], stem cell injection, JNJ-42160443 (fulranumab), platelet rich plasma (PRGF) injection, tanezumab, venlafaxine, PH-797804, PG-530742 (the dihydrated sodium salt PG-116800), Sprifermin (AS902330, rhFGF-18), epicutaneous ketoprofen in transfersome (IDEA-033) [*Annals of the Rheumatic Diseases* (2007) 66(9):1178-1183], FX005 and FX006 (both by Flexion Therapeutics, Inc.), JNJ-39439335 (Mavatrep) [*J. Med. Chem.* (2015) 58(9):3859-3874], polmacoxib (Acelex, CG100649), balicatib (AAE581), GSK3196165, cebranopadol (GRT6005), fasinumab (REGN475), TPX-100 (by OrthoTrophix), PRX167700 (by Proximagen), EP 104IAR (extended release fluticasone propionate composition), LY2951742 and LY545694 (both by Eli Lilly & Co), Adalimumab (Humira®), GW842166 (by GSK), YY1201 (by Yooyoung Pharmaceutical Co., Ltd.), CF101 (IB-MECA) and CF602 (both by Can-Fite BioPharma), PLA-695 (by Pfizer), VX-150 (by Vertex), ADL5859 and ADL5747 (both by Adolor Corporation now Cubist Pharmaceuticals), funapide (INN) (TV-45070, XEN402), AGG-523 (by Pfizer) [*Osteoarthritis Cartilage* (2011) 19(3):315-323], CNTX- 4975 (capsaicin for injection by Centrexion Corporation), CR845 (by Cara Therapeutics), ASP7962 (by Astellas Pharma), DA-5202 (by Dong-A ST Co., Ltd.), GZ389988 (by Sanofi-Genzyme), and MEDI 7352 (by AstraZeneca), LNA043 (by Novartis).

4. Kits

Also provided herein are kits. Typically, a kit includes one or more compounds or compositions as described herein. In certain embodiments, a kit can include one or more delivery systems, e.g., for delivering or administering a compound or composition as provided herein, and directions for use of the kit (e.g., instructions for treating a patient). In some embodiments, the kit can include a compound or composition as described herein and a label that indicates that the contents are to be administered to a patient with bone or cartilage diseases or osteoarthritis.

5. Methods for Treating Osteoarthritis

Provided are methods for the treatment of osteoarthritis in a patient. The methods comprise administering to the patient a therapeutically effective amount of a compound of Formula (I), including amorphous and/or polymorph forms thereof, or a pharmaceutical composition comprising a compound of Formula (I), including amorphous and polymorph forms thereof, and a pharmaceutically acceptable carrier. In some embodiments, the methods provided herein include intra-articular administration of a pharmaceutical composition comprising a therapeutically effective amount of a compound of Formula (I), including amorphous and polymorph forms thereof. In some embodiments, the methods provided herein include intra-articular administration of a pharmaceutical composition prepared by a process comprising mixing a polymorph form of a compound of Formula (I) with a pharmaceutically acceptable carrier. In some embodiments, the polymorph form is dried prior to mixing with the pharmaceutically acceptable carrier. In some embodiments, the polymorph form is Form 1. In some embodiments, the polymorph form is Form 13. In some embodiments, the pharmaceutically acceptable carrier is an aqueous medium In some embodiments, provided herein are methods for treating osteoarthritis in a patient comprising intra-articular administration to the patient a pharmaceutical composition comprising a therapeutically effective amount of a compound of Formula (I), and a pharmaceutically acceptable carrier. In some embodiments, the compound of Formula (I) in the composition comprises Form 1. In some embodiments, the compound of Formula (I) in the composition comprises a non-stoichiometric hydrate of Form 1 having between 1% and about 20% by weight water. In some embodiments, the compound of Formula (I) in the composition is substantially present as a non-stoichiometric hydrate of Form 1 having between 1% and 20% by weight water. In some embodiments, the pharmaceutical composition is a composition. In some embodiments, the pharmaceutical composition is a suspension.

In some embodiments of the methods provided herein, a pharmaceutical composition provided herein delivers a therapeutically effective concentration of the compound of Formula (I), including amorphous and/or polymorph forms thereof, to the joint surrounding the site of administration for at least about two weeks following administration. For example, the pharmaceutical composition can provide a therapeutically effective concentration of the compound of Formula (I), including amorphous and/or polymorph forms thereof, in the joint surrounding the site of administration for at least about 30 days following administration. In some embodiments, the pharmaceutical composition provides a therapeutically effective concentration of the compound of Formula (I) in the joint surrounding the site of administration for at least about 45 days following administration. In some embodiments, the pharmaceutical composition provides a therapeutically effective concentration of the compound of Formula (I) in the joint surrounding the site of administration for at least about 60 days following administration. In some embodiments, the pharmaceutical composition provides a therapeutically effective concentration of the compound of Formula (I), including amorphous and/or polymorph forms thereof, in the joint surrounding the site of administration for at least about 90 days following administration. For example, the pharmaceutical composition can provide a therapeutically effective concentration of the compound of Formula (I), including amorphous and/or polymorph forms thereof, in the joint surrounding the site of administration for at least about 180 days following administration. In some embodiments, the compound of Formula (I) is radiolabeled before administration. In some embodiments, the compound of Formula (I) is radiolabeled with tritium ($^3$H). The concentration of the radiolabeled compound of Formula (I) can be measured by detection methods known to those of skill in the art. For example, the radiolabeled compound of Formula (I) can be measured by quantitative radiochemical analysis (QRA). In some embodiments, the radiolabeled compound of Formula (I) is measured by quantitative whole body autoradiography (QWBA). In some embodiments, the radiolabeled compound of Formula (I) is detected by radiographic imaging. In some embodiments, the compound of Formula (I) in the composition comprises Form 1. In some embodiments, the compound of Formula (I) in the composition comprises a non-stoichiometric hydrate of Form 1 having between 1% and about 20% by weight water. In some embodiments, the compound of Formula (I) in the composition is substantially present as a non-stoichiometric hydrate of Form 1 having between 1% and about 20% by weight water. In some embodiments, the pharmaceutical composition is a solution. In some embodiments, the pharmaceutical composition is a suspension.

In some embodiments of the methods provided herein, the compositions are formulated such that the compound of Formula (I), including amorphous and polymorph forms thereof, e.g., Form 1, is bioavailable over an extended period of time following administration. In some embodiments, the compound of Formula (I) maintains a concentration within a therapeutic window for a desired period of time.

Following intraarticular administration of a pharmaceutical composition, e.g., suspension, of a compound of Formula (I), including amorphous and polymorph forms thereof, little to no amount of the compound of Formula (I) is detected in the plasma of the subject. For example, a pharmaceutical composition, e.g., suspension, can provide a plasma concentration of less than about 0.1 ng/mL of the compound of Formula (I) following administration of the compound of Formula (I) at 4 hours after administration. In some embodiments, the pharmaceutical composition, e.g., suspension, provides a plasma concentration of less than about 0.1 ng/mL following administration of the compound of Formula (I) at 24 hours after administration. In some embodiments, the pharmaceutical composition, e.g., suspension, provides a plasma concentration of less than about 0.1 ng/mL of the compound of Formula (I) following administration of the compound of Formula (I) at 4 weeks following administration. For example, the pharmaceutical composition, e.g., suspension, can provide a plasma concentration of less than about 0.1 ng/mL of the compound of Formula (I) following administration of the compound at 24 weeks following administration.

In some embodiments, a pharmaceutical composition, e.g., suspension, can provide a plasma concentration of less than about 0.1 ng/mL of the compound of Formula (I) following a dose of up to 250 μg of the compound of Formula (I) at 4 hours after administration. In some embodiments, the pharmaceutical composition, e.g., suspension, provides a plasma concentration of less than about 0.1 ng/mL following a dose of up to 250 μg of the compound of Formula (I) at 24 hours after administration. In some embodiments, the pharmaceutical composition, e.g., suspension, provides a plasma concentration of less than about 0.1 ng/mL of the compound of Formula (I) following a dose of up to 250 μg of the compound of Formula (I) at 7 days following administration. In some embodiments, the pharmaceutical composition, e.g., suspension, provides a plasma concentration of less than about 0.1 ng/mL of the compound of Formula (I) following a dose of up to 250 μg of the compound of Formula (I) at 4 weeks following administration. For example, the pharmaceutical composition, e.g., suspension, can provide a plasma concentration of less than about 0.1 ng/mL of the compound of Formula (I) following a dose of up to 250 μg at 24 weeks following administration. In some embodiments, the pharmaceutical composition, e.g., suspension, can provide a plasma concentration of less than about 0.1 ng/mL of the compound of Formula (I) following a dose of up to 250 μg at 4 hours, 4 weeks, 12 weeks, and/or 24 weeks following administration.

In some embodiments, a pharmaceutical composition, e.g., suspension, can provide a plasma concentration of less than about 1 ng/mL of the compound of Formula (I) following administration of a dose of up to 250 μg of the compound of Formula (I) at 4 hours after administration. In some embodiments, the pharmaceutical composition, e.g., suspension, provides a plasma concentration of less than about 1 ng/mL following a dose of up to 250 μg of the compound of Formula (I) at 24 hours after administration. In some embodiments, the pharmaceutical composition, e.g., suspension, provides a plasma concentration of less than about 1 ng/mL of the compound of Formula (I) following administration at a dose of up to 250 μg of the compound of Formula (I) at 4 weeks following administration. For example, the pharmaceutical composition, e.g., suspension, can provide a plasma concentration of less than about 1 ng/mL of the compound of Formula (I) following a dose of up to 250 μg at 24 weeks following administration. In some embodiments, the pharmaceutical composition, e.g., suspension, can provide a plasma concentration of less than about 1 ng/mL of the compound of Formula (I) following a dose of up to 250 μg at 4 hours, 4 weeks, 12 weeks, and/or 24 weeks following administration.

In some embodiments of the methods herein, the compound of Formula (I) is not substantially systemically absorbed following administration of a dose of up to 250 μg of the compound of Formula (I) at 4 hours after administration. In some embodiments of the methods herein, the compound of Formula (I) is not substantially systemically absorbed following administration of a dose of up to 250 μg of the compound of Formula (I) at 4 weeks after administration. In some embodiments of the methods herein, the compound of Formula (I) is not substantially systemically absorbed following administration of a dose of up to 250 μg of the compound of Formula (I) at 12 weeks after administration. In some embodiments of the methods herein, the compound of Formula (I) is not substantially systemically absorbed following administration of a dose of up to 250 μg of the compound of Formula (I) at 24 weeks after administration.

In some embodiments of the methods herein, the composition comprises about 0.001 mg to about 0.5 mg per injection of a compound of Formula (I), including amorphous and polymorph forms thereof. For example, the composition in some embodiments comprises about 0.001 mg to about 0.4 mg, about 0.001 mg to about 0.3 mg, about 0.001 mg to about 0.25 mg, about 0.001 mg to about 0.2 mg, about 0.001 mg to about 0.15 mg, about 0.001 mg to about 0.1 mg, about 0.001 mg to about 0.075 mg, about 0.001 mg to about 0.055 mg, about 0.001 mg to about 0.05 mg, about 0.001 mg to about 0.035 mg, about 0.001 mg to about 0.025 mg, about 0.001 mg to about 0.01 mg, about 0.001 mg to about 0.005 mg, about 0.005 mg to about 0.5 mg, about 0.0075 mg to about 0.5 mg, about 0.01 mg to about 0.5 mg, about 0.025 mg to about 0.5 mg, about 0.045 mg to about 0.5 mg, about 0.05 mg to about 0.5 mg, about 0.075 mg to about 0.5 mg, about 0.1 mg to about 0.5 mg, about 0.25 mg to about 0.5 mg, about 0.01 mg to about 0.3 mg, about 0.025 mg to about 0.075 mg, about 0.01 mg to about 0.1 mg, and about 0.15 mg to about 0.25 mg of the compound of Formula (I), including amorphous and polymorph forms thereof.

In some embodiments, the compositions comprising a compound of Formula (I) provided herein are administered once. In some embodiments, the compositions comprising a compound of Formula (I) are administered more than once. In some embodiments, the composition is administered in doses spaced at least 4 weeks apart (e.g., at least 6 weeks apart, at least 8 weeks apart, at least 12 weeks apart). For example, the composition is administered in doses spaced at least 3 months apart up to about 60 months apart. In some embodiments, the composition is administered once every 3 months. In some embodiments, the composition is administered once every 6 months. In some embodiments, the composition is administered once every 12 months. In some embodiments, the composition is administered once every 24 months. In some embodiments, the composition is administered once every 60 months.

Also provided herein are methods of treating a patient that include first assessing the severity of the disease in the patient and then administering to the patient a dose of a compound of Formula (I), including amorphous and polymorph forms thereof, based on the assessment. Osteoarthritis can affect any joint in the body. In some embodiments, the osteoarthritis is present in one or more of the hands, feet, spine, shoulders, elbows, ankles, wrists, and the large weight bearing joints, such as the hips and knees. In some embodiments, the severity of the disorder is determined at one or more locations within a patient's body. For example, the severity of the disorder is determined at or near the target site of administration of a compound of Formula (I), including amorphous and polymorph forms thereof.

The severity of a patient's osteoarthritis can be determined using a variety of methods. For example, radiological criteria (e.g., X-rays, CT scans, MM, ultrasonography, and bone scanning), clinical criteria, pain assessments (e.g., visual analog scale (VAS) and Western Ontario and McMaster Universities Arthritis Index (WOMAC) scores), mobility assessments (e.g., physician global assessments), thickness of cartilage (e.g., at the target site of administration), total volume of cartilage (e.g., at the target site of administration), levels of anabolic or catabolic biomarkers indicative of cartilage synthesis or degradation (e.g., cartilage oligomeric matrix protein [COMP], N-terminal propeptides of procollagen type I [PINP], and β-C-terminal telopeptide [β-CTX]), plasma levels of cytokines related to inflammation (interleukin [IL] 1b, IL6, IL8, tumor necrosis factor (TNF), and interferon-alpha [IFNα]), levels of bone marrow edema (e.g., by MRI scans of the target site of administration), levels of synovial fluid, clarity of synovial fluid (e.g., levels of crystals present in the fluid when viewed under a polarized microscope), levels of metalloproteinases (e.g., collagenase, stromelysin), levels of free radicals (e.g., nitric oxide), and measurements of the space between bones. In some embodiments, one or more methods of assessing the severity of a patient's osteoarthritis or disease state can be used.

Assessments of a joint can be made at one or more locations at, around, or near a joint. For example, multiple measurements of the width, thickness, or volume of the cartilage can be made. In some embodiments, the results of multiple measurements can be combined into a composite score which can be used to assess the severity of the disorder. Various methods of assessing the joint can also be considered together to determine the severity of the disorder in any particular joint. For example, subjective measurements such as pain and mobility determinations can be combined with objective measurements in one or more locations of the joint such as width, thickness, or volume of the cartilage, measurements of the space between bones, and levels of synovial fluid.

In some embodiments, the severity of the disease is determined based on the stage of the disorder.

For example, osteoarthritis (OA) of the knee can be divided into five stages: 0 is assigned to a normal, healthy knee. The highest stage, 4, is assigned to severe OA. Exemplary diagnosis criteria and typical symptoms of the various stages are provided below in Table 1.

TABLE 1

| Stage | Symptoms |
|---|---|
| 0 | Stage 0 OA is classified as "normal" knee health. The knee joint shows no signs of OA, and the joint functions without any impairment or pain. |
| 1 | A person with stage 1 OA is showing very minor bone spur growth (bone spurs are boney growths that often develop where bones meet each other in the joint). Likely, a person with stage 1 OA is not experiencing any pain or discomfort as a result of the very minor wear on the components of the joint. |
| 2 | Stage 2 OA of the knee is considered a "mild" stage of the condition. X-rays of knee joints in this stage will likely reveal greater bone spur growth, but the cartilage likely remains at a healthy size - the space between the bones is normal, and the bones are not rubbing or scraping one another. Synovial fluid is also typically still present at sufficient levels for normal joint motion. However, this is the stage where people may first begin experiencing symptoms - pain after a long day of walking or running, greater stiffness in the joint when it's not used for several hours, tenderness when kneeling or bending. |
| 3 | Stage 3 OA is classified as "moderate" OA. The cartilage between bones is showing obvious damage, and the space between the bones is narrowing. People with stage 3 OA of the knee are likely experiencing frequent pain when walking, running, bending, or kneeling. They also may experience joint stiffness after sitting for long periods of time or when waking up in the morning. Joint swelling may be present after extended periods of motion, too. |
| 4 | Stage 4 OA is considered "severe." People in stage 4 OA of the knee experience great pain and discomfort when walking or moving the joint. The joint space between bones is dramatically reduced - the cartilage is almost completely gone, leaving the joint stiff and possibly immobile. The synovial fluid is decreased dramatically, and it no longer helps reduce the friction among the moving parts of a joint. |

Similarly, the stages of hip osteoarthritis can be divided into five stages according to the severity observed in various images. Exemplary diagnosis criteria and typical symptoms of the various stages are provided below in Table 2.

TABLE 2

| Stage | Plain film grading | MRI grading |
|---|---|---|
| 0 | Normal | Normal |
| 1 | Possible joint space narrowing and subtle osteophytes | Inhomogeneous high signal intensity in cartilage (T2WI) |
| 2 | Definite joint space narrowing, defined osteophytes and some sclerosis, especially in acetabular region | Inhomogeneity with areas of high signal intensity in articular cartilage (T2WI); indistinct trabeculae or signal intensity loss in femoral head & neck (T1WI) |
| 3 | Marked joint space narrowing, small osteophytes, some sclerosis and cyst formation and deformity of femoral head and acetabulum | Criteria of Stage 1 & 2 plus indistinct zone between femoral head & acetabulum; subchondral signal loss due to bone sclerosis |

TABLE 2-continued

| Stage | Plain film grading | MRI grading |
|---|---|---|
| 4 | Gross loss of joint space with above features plus large osteophytes and increased deformity of the femoral head and acetabulum | Above criteria plus femoral head deformity |

In some embodiments, a patient is diagnosed or identified as having moderate to severe symptomatic osteoarthritis. For example, the patient is diagnosed or identified as having moderate to severe symptomatic knee osteoarthritis. In some embodiments, the patient has grade 1 (or KL-1) osteoarthritis, as determined by the Kellgren-Lawrence system. In some embodiments, the patient has grade 2 (or KL-2) osteoarthritis, as determined by the Kellgren-Lawrence system. In some embodiments, the patient has grade 3 (or KL-3) osteoarthritis, as determined by the Kellgren-Lawrence system. In some embodiments, the patient has grade 4 (or KL-4) osteoarthritis, as determined by the Kellgren-Lawrence system. In some embodiments, a patient is administered the compound of Formula (I) as a preventative measure, for example, a patient with grade 1 osteoarthritis.

Based on the severity of the patient's disease state, a dosage amount of a compound of Formula (I), including amorphous and polymorph forms thereof, can be determined.

In some embodiments, the patient has unilateral osteoarthritis of the knee. In some embodiments, the patient has bilateral osteoarthritis of the knees.

In some embodiments, the patient is overweight or obese. In some embodiments, the patient has a body mass index (BMI) of between 25 and 30, for example, a BMI of 25, 26, 27, 28, or 29. In some embodiments, the patient has a BMI of 30 or greater, such as 30, 31, 32, 33, 34, 35, 40, or greater than 40.

One method of monitoring the progression and/or treatment of osteoarthritis involves measuring the joint space. As cartilage deteriorates or wears away, narrowing of the joint space of the affected joint can be observed (joint space narrowing). Given the difficulty in measuring cartilage, joint space width (JSW) measurements are often considered a surrogate for articular cartilage thickness as such measurements involve determining the distance between two bones (e.g., using X-ray techniques). Without being bound by any theory, an increase in the JSW is an indicator of cartilage growth. Methods of measurement of JSW can be completed following radiographic imaging of the affected joint. Measurements can be either manual using calipers or a simple graduated ruler and a micrometric eyepiece or semiautomated using computer software. In some embodiments, JSW measurements can involve radiographic images (e.g., X-ray) taken of the knee. For example, one or more of metatarsophalangeal, fixed flexion, semiflexed anteroposterior (AP) and Lyon-Schuss radiographs can be used to obtain the measurement. In some embodiments, the subject is imaged while standing. For example, standing, fixed-flexion (Synaflexer), posterior-anterior (PA) radiographs.

In some embodiments, the methods provided herein result in an increase in the joint space width in the joint surrounding the point of injection in a patient of a compound of Formula (I), including amorphous or polymorph forms thereof. In some embodiments, the dose administered by the injection in a patient of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 In some embodiments, the methods provided herein result in an increase in the joint space width in the joint surrounding the point of injection in a patient of about 5% to about 30% (e.g., about 9% to about 23%). In some embodiments, the methods provided herein result in an increase in the joint space width in the joint surrounding the point of injection in a patient of about 5% to about 30% (e.g., about 9% to about 23%) at week 24 following administration. In some embodiments, the methods provided herein result in an increase in the joint space width in the joint surrounding the point of injection in a patient of about 5% to about 30% (e.g., about 9% to about 23%) at a dose of about 70 µg of a compound of Formula (I) including amorphous or polymorph forms thereof, at week 24 following administration. For example, an increase in the joint space width in the joint surrounding the point of injection of about 10% to about 20% at a dose of about 70 µg at week 24 following administration; or about 15% to about 18% at a dose of about 70 µg at week 24 following administration. In some embodiments, the methods provided herein exhibit substantially no change in the joint space width at the joint surrounding the point of injection. Such a result can be indicative of an arrest of symptoms of the disease as no further loss in the joint space width is observed.

In some embodiments, the methods provided herein result in an increase in the joint space width in the joint surrounding the point of injection in a patient of a compound of Formula (I), including amorphous or polymorph forms thereof, of about 0.05 mm to about 2 mm. In some embodiments, the methods provided herein result in an increase in the joint space width in the joint surrounding the point of injection in a patient of a compound of Formula (I), including amorphous or polymorph forms thereof, of about 0.05 mm to about 2 mm at week 24 following administration. In some embodiments, the methods provided herein result in an increase in the joint space width in the joint surrounding the point of injection in a patient at a dose of about 70 µg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

In some embodiments, the methods provided herein result in an increase in the mean joint space width in the joint surrounding the point of injection, in a patient population, of a compound of Formula (I), including amorphous or polymorph forms thereof. In some embodiments, the dose administered by the injection, in a patient population, of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 µg. In some embodiments, the methods provided herein result in an increase in the mean joint space width in the joint surrounding the point of injection, in a patient population, of about 5% to about 30% (e.g., about 9% to about 23%). In some embodiments, the methods provided herein result in an increase in the mean joint space width in the joint surrounding the point of injection, in a patient population, of about 5% to about 30% (e.g., about 9% to about 23%) at week 24 following administration. In some embodiments, the methods provided herein result in an increase in the mean joint space width in the joint surrounding the point of injection, in a patient population, of about 5% to about 30% (e.g., about 9% to about 23%) at a dose of about 70 µg of a compound of Formula (I) including amorphous or polymorph forms thereof, at week 24 following administration. For example, an increase in the mean joint space width in the joint surrounding the point of injection of about 10% to about 20% at a dose of about 70 µg at week 24 following administration; or about 15% to about 18% at a dose of about 70 µg at week 24 following administration. In some embodiments, the methods provided herein exhibit substantially no change in the mean joint space width at the joint surrounding the point of injection. Such a result can be indicative of an arrest of symptoms of the disease as no further loss in the mean joint space width is observed.

In some embodiments, the methods provided herein result in an increase in the mean joint space width in the joint surrounding the point of injection, in a patient population, of a compound of Formula (I), including amorphous or polymorph forms thereof, of about 0.05 mm to about 2 mm. In some embodiments, the methods provided herein result in an increase in the mean joint space width in the joint surrounding the point of injection, in a patient population, of a compound of Formula (I), including amorphous or polymorph forms thereof, of about 0.05 mm to about 2 mm at week 24 following administration. In some embodiments, the methods provided herein result in an increase in the mean joint space width in the joint surrounding the point of injection in a patient population at a dose of about 70 µg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

In some embodiments, the methods provided herein result in an increase in the cartilage thickness in the joint surrounding the point of injection in a patient of a compound of Formula (I), including amorphous or polymorph forms thereof. In some embodiments, the dose administered by the injection in a patient of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 µg In some embodiments, the methods provided herein result in an increase in the cartilage thickness in the joint surrounding the point of injection in a patient of about 5% to about 30% (e.g., about 9% to about 23%). In some embodiments, the methods provided herein result in an increase in the cartilage thickness in the joint surrounding the point of injection in a patient of about 5% to about 30% (e.g., about 9% to about 23%) at week 24 following administration. In some embodiments, the methods provided herein result in an increase in the cartilage thickness in the joint surrounding the point of injection in a patient of about 5% to about 30% (e.g., about 9% to about 23%) at a dose of about 70 µg of a compound of Formula (I) including amorphous or polymorph forms thereof, at week 24 following administration. For example, an increase in the cartilage thickness in the joint surrounding the point of injection of about 10% to about 20% at a dose of about 70 µg at week 24 following administration; or about 15% to about 18% at a dose of about 70 µg at week 24 following administration. In some embodiments, the methods provided herein exhibit substantially no change in the cartilage thickness at the joint surrounding the point of injection. Such a result can be indicative of an arrest of symptoms of the disease as no further loss in the cartilage thickness is observed.

In some embodiments, the methods provided herein result in an increase in the cartilage thickness in the joint surrounding the point of injection in a patient of a compound of Formula (I), including amorphous or polymorph forms thereof, of about 0.05 mm to about 2 mm. In some embodiments, the methods provided herein result in an increase in the cartilage thickness in the joint surrounding the point of injection in a patient of a compound of Formula (I), including amorphous or polymorph forms thereof, of about 0.05 mm to about 2 mm at week 24 following administration. In some embodiments, the methods provided herein result in an increase in the cartilage thickness in the joint surrounding the point of injection in a patient at a dose of about 70 µg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

In some embodiments, the methods provided herein result in an increase in the mean cartilage thickness in the joint surrounding the point of injection, in a patient population, of a compound of Formula (I), including amorphous or polymorph forms thereof. In some embodiments, the dose administered by the injection, in a patient population, of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 µg. In some embodiments, the methods provided herein result in an increase in the mean cartilage thickness in the joint surrounding the point of injection, in a patient population, of about 5% to about 30% (e.g., about 9% to about 23%). In some embodiments, the methods provided herein result in an increase in the mean cartilage thickness in the joint surrounding the point of injection, in a patient population, of about 5% to about 30% (e.g., about 9% to about 23%) at week 24 following administration. In some embodiments, the methods provided herein result in an increase in the mean cartilage thickness in the joint surrounding the point of injection, in a patient population, of about 5% to about 30% (e.g., about 9% to about 23%) at a dose of about 70 µg of a compound of Formula (I) including amorphous or polymorph forms thereof, at week 24 following administration. For example, an increase in the mean cartilage thickness in the joint surrounding the point of injection of about 10% to about 20% at a dose of about 70 µg at week 24 following administration; or about 15% to about 18% at a dose of about 70 µg at week 24 following administration. In some embodiments, the methods provided herein exhibit substantially no change in the mean cartilage thickness at the joint surrounding the point of injection. Such a result can be indicative of an arrest of symptoms of the disease as no further loss in the mean cartilage thickness is observed.

In some embodiments, the methods provided herein result in an increase in the mean cartilage thickness in the joint surrounding the point of injection, in a patient population, of a compound of Formula (I), including amorphous or polymorph forms thereof, of about 0.05 mm to about 2 mm. In some embodiments, the methods provided herein result in an increase in the mean cartilage thickness in the joint surrounding the point of injection, in a patient population, of a compound of Formula (I), including amorphous or polymorph forms thereof, of about 0.05 mm to about 2 mm at week 24 following administration. In some embodiments, the methods provided herein result in an increase in the mean cartilage thickness in the joint surrounding the point of injection in a patient population at a dose of about 70 µg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

In some embodiments, the methods provided herein result in an increase from baseline in the joint space width in the joint surrounding the point of injection in a patient of a compound of Formula (I), including amorphous or polymorph forms thereof. In some embodiments, the dose administered by the injection in a patient of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 In some embodiments, the methods provided herein result in an increase in the joint space width in the joint surrounding the point of injection in a patient of about 5% to about 30% (e.g., about 9% to about 23%) from baseline. In some embodiments, the methods provided herein result in an increase in the joint space width in the joint surrounding the point of injection in a patient of about 5% to about 30% (e.g., about 9% to about 23%) from baseline at week 24 following administration. In some embodiments, the methods provided herein result in an increase in the joint space width in the joint surrounding the point of injection in a patient of about 5% to about 30% (e.g., about 9% to about 23%) from baseline at a dose of about 70 µg of a compound of Formula (I) including amorphous or polymorph forms thereof, at week 24 following administration. For example, an increase in the joint space width in the joint surrounding the point of injection of about 10% to about 20% from baseline at a dose of about 70 µg at week 24 following administration; or about 15% to about 18% from baseline at a dose of about 70 µg at week 24 following administration. In some embodiments, the methods provided herein exhibit substantially no change from baseline in the joint space width at the joint surrounding the point of injection. Such a result can be indicative of an arrest of symptoms of the disease as no further loss in the joint space width is observed.

In some embodiments, the methods provided herein result in an increase in the joint space width in the joint surrounding the point of injection in a patient of a compound of Formula (I), including amorphous or polymorph forms thereof, of about 0.05 mm to about 2 mm from baseline. In some embodiments, the methods provided herein result in an increase in the joint space width in the joint surrounding the point of injection in a patient of a compound of Formula (I), including amorphous or polymorph forms thereof, of about 0.05 mm to about 2 mm from baseline at week 24 following administration. In some embodiments, the methods provided herein result in an increase from baseline in the joint space width in the joint surrounding the point of injection in a patient at a dose of about 70 µg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

In some embodiments, the methods provided herein result in an increase from baseline in the mean joint space width in the joint surrounding the point of injection, in a patient population, of a compound of Formula (I), including amorphous or polymorph forms thereof. In some embodiments, the dose administered by the injection, in a patient population, of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 In some embodiments, the methods provided herein result in an increase in the mean joint space width in the joint surrounding the point of injection, in a patient population, of about 5% to about 30% (e.g., about 9% to about 23%) from baseline. In some embodiments, the methods provided herein result in an increase in the mean joint space width in the joint surrounding the point of injection, in a patient population, of about 5% to about 30%

(e.g., about 9% to about 23%) from baseline at week 24 following administration. In some embodiments, the methods provided herein result in an increase in the mean joint space width in the joint surrounding the point of injection, in a patient population, of about 5% to about 30% (e.g., about 9% to about 23%) from baseline at a dose of about 70 µg of a compound of Formula (I) including amorphous or polymorph forms thereof, at week 24 following administration. For example, an increase in the mean joint space width in the joint surrounding the point of injection of about 10% to about 20% from baseline at a dose of about 70 µg at week 24 following administration; or about 15% to about 18% from baseline at a dose of about 70 µg at week 24 following administration. In some embodiments, the methods provided herein exhibit substantially no change from baseline in the mean joint space width at the joint surrounding the point of injection. Such a result can be indicative of an arrest of symptoms of the disease as no further loss in the mean joint space width is observed.

In some embodiments, the methods provided herein result in an increase in the mean joint space width in the joint surrounding the point of injection, in a patient population, of a compound of Formula (I), including amorphous or polymorph forms thereof, of about 0.05 mm to about 2 mm from baseline. In some embodiments, the methods provided herein result in an increase in the mean joint space width in the joint surrounding the point of injection, in a patient population, of a compound of Formula (I), including amorphous or polymorph forms thereof, of about 0.05 mm to about 2 mm from baseline at week 24 following administration. In some embodiments, the methods provided herein result in an increase from baseline in the mean joint space width in the joint surrounding the point of injection in a patient population at a dose of about 70 µg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

In some embodiments, the methods provided herein result in an increase from baseline in the cartilage thickness in the joint surrounding the point of injection in a patient of a compound of Formula (I), including amorphous or polymorph forms thereof. In some embodiments, the dose administered by the injection in a patient of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 µg. In some embodiments, the methods provided herein result in an increase in the cartilage thickness in the joint surrounding the point of injection in a patient of about 5% to about 30% (e.g., about 9% to about 23%) from baseline. In some embodiments, the methods provided herein result in an increase in the cartilage thickness in the joint surrounding the point of injection in a patient of about 5% to about 30% (e.g., about 9% to about 23%) from baseline at week 24 following administration. In some embodiments, the methods provided herein result in an increase in the cartilage thickness in the joint surrounding the point of injection in a patient of about 5% to about 30% (e.g., about 9% to about 23%) from baseline at a dose of about 70 µg of a compound of Formula (I) including amorphous or polymorph forms thereof, at week 24 following administration. For example, an increase in the cartilage thickness in the joint surrounding the point of injection of about 10% to about 20% from baseline at a dose of about 70 µg at week 24 following administration; or about 15% to about 18% from baseline at a dose of about 70 µg at week 24 following administration. In some embodiments, the methods provided herein exhibit substantially no change in the cartilage thickness at the joint surrounding the point of injection. Such a result can be indicative of an arrest of symptoms of the disease as no further loss in the cartilage thickness is observed.

In some embodiments, the methods provided herein result in an increase in the cartilage thickness in the joint surrounding the point of injection in a patient of a compound of Formula (I), including amorphous or polymorph forms thereof, of about 0.05 mm to about 2 mm from baseline. In some embodiments, the methods provided herein result in an increase in the cartilage thickness in the joint surrounding the point of injection in a patient of a compound of Formula (I), including amorphous or polymorph forms thereof, of about 0.05 mm to about 2 mm from baseline at week 24 following administration. In some embodiments, the methods provided herein result in an increase from baseline in the cartilage thickness in the joint surrounding the point of injection in a patient at a dose of about 70 µg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

In some embodiments, the methods provided herein result in an increase from baseline in the mean cartilage thickness in the joint surrounding the point of injection, in a patient population, of a compound of Formula (I), including amorphous or polymorph forms thereof. In some embodiments, the dose administered by the injection, in a patient population, of the compound of Formula (I), including amorphous or polymorph forms thereof, is from about 10 µg to about 250 µg, such as from about 20 µg to about 230 µg, such as from about 20 µg to about 200 µg, such as from about 30 µg to about 150 µg, such as from about 50 µg to about 100 µg, such as about 70 In some embodiments, the methods provided herein result in an increase in the mean cartilage thickness in the joint surrounding the point of injection, in a patient population, of about 5% to about 30% (e.g., about 9% to about 23%) from baseline. In some embodiments, the methods provided herein result in an increase in the mean cartilage thickness in the joint surrounding the point of injection, in a patient population, of about 5% to about 30% (e.g., about 9% to about 23%) from baseline at week 24 following administration. In some embodiments, the methods provided herein result in an increase in the mean cartilage thickness in the joint surrounding the point of injection, in a patient population, of about 5% to about 30%

(e.g., about 9% to about 23%) from baseline at a dose of about 70 μg of a compound of Formula (I) including amorphous or polymorph forms thereof, at week 24 following administration. For example, an increase in the mean cartilage thickness in the joint surrounding the point of injection of about 10% to about 20% from baseline at a dose of about 70 μg at week 24 following administration; or about 15% to about 18% from baseline at a dose of about 70 μg at week 24 following administration. In some embodiments, the methods provided herein exhibit substantially no change in the mean cartilage thickness at the joint surrounding the point of injection. Such a result can be indicative of an arrest of symptoms of the disease as no further loss in the mean cartilage thickness is observed.

In some embodiments, the methods provided herein result in an increase in the mean cartilage thickness in the joint surrounding the point of injection, in a patient population, of a compound of Formula (I), including amorphous or polymorph forms thereof, of about 0.05 mm to about 2 mm from baseline. In some embodiments, the methods provided herein result in an increase in the mean cartilage thickness in the joint surrounding the point of injection, in a patient population, of a compound of Formula (I), including amorphous or polymorph forms thereof, of about 0.05 mm to about 2 mm from baseline at week 24 following administration. In some embodiments, the methods provided herein result in an increase from baseline in the mean cartilage thickness in the joint surrounding the point of injection in a patient population at a dose of about 70 μg of a compound of Formula (I) including amorphous or polymorph forms thereof, at week 24 following administration, of about 0.05 mm; about 0.1 mm; about 0.15 mm; about 0.2 mm; about 0.25 mm; about 0.3 mm; about 0.35 mm; about 0.4 mm; about 0.45 mm; about 0.5 mm; about 0.55 mm; about 0.6 mm; about 0.65 mm; about 0.7 mm; about 0.75 mm; about 0.8 mm; about 0.85 mm; about 0.9 mm; about 0.95 mm; about 1 mm; about 1.05 mm; about 1.1 mm; about 1.15 mm; about 1.2 mm; about 1.25 mm; about 1.3 mm; about 1.35 mm; about 1.4 mm; about 1.45 mm; about 1.5 mm; about 1.55 mm; about 1.6 mm; about 1.65 mm; about 1.7 mm; about 1.75 mm; about 1.8 mm; about 1.85 mm; about 1.9 mm; about 1.95 mm; or about 2 mm.

As used herein, "as used herein, the phrase "from baseline" refers to the change in the value of a parameter (such as JSW, cartilage thickness, WOMAC score, usw) relative to its value determined ≤28 days prior to the injection" In some embodiments, the methods provided herein result in a decrease in plasma cartilage oligomeric matrix protein (COMP) concentration at week 12 following administration.

In some embodiments, the methods provided herein result in a decrease in WOMAC total score in a subject. In some embodiments, the methods provided herein result in a decrease in WOMAC total score in the subject from baseline. For example, a decrease in WOMAC total score in the subject of at least 15 points from baseline; a decrease in WOMAC total score of at least 20 points from baseline; or a decrease in WOMAC total score of at least 24 points from baseline. In some embodiments, the methods provided herein result in a decrease in WOMAC total score in the subject from baseline at week 12 following administration. For example, a decrease in WOMAC total score in the subject of at least 15 points from baseline at week 12 following administration; a decrease in WOMAC total score of at least 20 points from baseline at week 12 following administration; or a decrease in WOMAC total score of at least 24 points from baseline at week 12 following administration.

In some embodiments, the WOMAC score can be broken down into individual pain, function, and stiffness scores.

In some embodiments, the methods provided herein result in a decrease in WOMAC function score in a subject. In some embodiments, the methods provided herein result in a decrease in WOMAC function score in the subject from baseline. For example, a decrease in WOMAC function score in the subject of at least 10 points from baseline; a decrease in WOMAC function score of at least 15 points from baseline; or a decrease in WOMAC function score of at least 19 points from baseline. In some embodiments, the methods provided herein result in a decrease in WOMAC function score in the subject from baseline at week 12 following administration. For example, a decrease in WOMAC function score in the subject of at least 10 points from baseline at week 12 following administration; a decrease in WOMAC function score of at least 15 points from baseline at week 12 following administration; or a decrease in WOMAC function score of at least 19 points from baseline at week 12 following administration.

In some embodiments, the methods provided herein result in a decrease in WOMAC pain score in a subject. In some embodiments, the methods provided herein result in a decrease in WOMAC pain score in the subject from baseline. For example, a decrease in WOMAC pain score in the subject of at least 4 points from baseline; or a decrease in WOMAC pain score of at least 5 points from baseline. In some embodiments, the methods provided herein result in a decrease in WOMAC pain score in the subject from baseline at week 12 following administration. For example, a decrease in WOMAC pain score in the subject of at least 4 points from baseline at week 12 following administration; or a decrease in WOMAC pain score of at least 5 points from baseline at week 12 following administration.

In some embodiments, the methods provided herein result in a decrease in WOMAC function score from baseline, such as, for example, a decrease in WOMAC function score of at least 10% from baseline; or a decrease in WOMAC function score of at least 20% from baseline; or a decrease in WOMAC function score of at least 30% from baseline; or a decrease in WOMAC function score of at least 40% from baseline; or a decrease in WOMAC function score of at least 50% from baseline. In some embodiments, the methods provided herein result in a decrease in WOMAC function score from baseline at week 12 following administration, such as, for example, a decrease in WOMAC function score of at least 10% from baseline at week 12 following administration; or a decrease in WOMAC function score of at least 20% from baseline at week 12 following administration; or a decrease in WOMAC function score of at least 30% from baseline at week 12 following administration; or a decrease in WOMAC function score of at least 40% from baseline at week 12 following administration; or a decrease in WOMAC function score of at least 50% from baseline at week 12 following administration.

In some embodiments, the methods provided herein result in a decrease in WOMAC pain score from baseline, such as, for example, a decrease in WOMAC pain score of at least 10% from baseline; or a decrease in WOMAC pain score of at least 20% from baseline; or a decrease in WOMAC pain score of at least 30% from baseline; or a decrease in WOMAC pain score of at least 40% from baseline; or a decrease in WOMAC pain score of at least 50% from baseline. In some embodiments, the methods provided herein result in a decrease in WOMAC pain score from baseline at week 12 following administration, such as, for example, a decrease in WOMAC pain score of at least 10% from baseline at week 12 following administration; or a decrease in WOMAC pain score of at least 20% from baseline at week 12 following administration; or a decrease in WOMAC pain score of at least 30% from baseline at week 12 following administration; or a decrease in WOMAC pain score of at least 40% from baseline at week 12 following administration; or a decrease in WOMAC pain score of at least 50% from baseline at week 12 following administration.

In some embodiments, the methods provided herein result in a decrease in WOMAC stiffness score from baseline, such as, for example, a decrease in WOMAC stiffness score of at least 10% from baseline; or a decrease in WOMAC stiffness score of at least 20% from baseline; or a decrease in WOMAC stiffness score of at least 30% from baseline; or a decrease in WOMAC stiffness score of at least 40% from baseline; or a decrease in WOMAC stiffness score of at least 50% from baseline. In some embodiments, the methods provided herein result in a decrease in WOMAC stiffness score from baseline at week 12 following administration, such as, for example, a decrease in WOMAC stiffness score of at least 10% from baseline at week 12 following administration; or a decrease in WOMAC stiffness score of at least 20% from baseline at week 12 following administration; or a decrease in WOMAC stiffness score of at least 30% from baseline at week 12 following administration; or a decrease in WOMAC stiffness score of at least 40% from baseline at week 12 following administration; or a decrease in WOMAC stiffness score of at least 50% from baseline at week 12 following administration.

In some embodiments, the methods provided herein result in a decrease in mean WOMAC total score in a subject population. In some embodiments, the methods provided herein result in a decrease in mean WOMAC total score in the subject population from baseline. For example, a decrease in mean WOMAC total score in the subject population of at least 15 points from baseline; a decrease in mean WOMAC total score of at least 20 points from baseline; or a decrease in mean WOMAC total score of at least 24 points from baseline. In some embodiments, the methods provided herein result in a decrease in mean WOMAC total score in the subject population from baseline at week 12 following administration. For example, a decrease in mean WOMAC total score in the subject population of at least 15 points from baseline at week 12 following administration; a decrease in mean WOMAC total score of at least 20 points from baseline at week 12 following administration; or a decrease in mean WOMAC total score of at least 24 points from baseline at week 12 following administration.

In some embodiments, the methods provided herein result in a decrease in mean WOMAC function score in a subject population. In some embodiments, the methods provided herein result in a decrease in mean WOMAC function score in the subject population from baseline. For example, a decrease in mean WOMAC function score in the subject population of at least 10 points from baseline; a decrease in mean WOMAC function score of at least 15 points from baseline; or a decrease in mean WOMAC function score of at least 19 points from baseline. In some embodiments, the methods provided herein result in a decrease in mean WOMAC function score in the subject population from baseline at week 12 following administration. For example, a decrease in mean WOMAC function score in the subject population of at least 10 points from baseline at week 12 following administration; a decrease in mean WOMAC function score of at least 15 points from baseline at week 12 following administration; or a decrease in mean WOMAC function score of at least 19 points from baseline at week 12 following administration.

In some embodiments, the methods provided herein result in a decrease in mean WOMAC pain score in a subject population. In some embodiments, the methods provided herein result in a decrease in mean WOMAC pain score in the subject population from baseline. For example, a decrease in mean WOMAC pain score in the subject population of at least 4 points from baseline; or a decrease in mean WOMAC pain score of at least 5 points from baseline.

In some embodiments, the methods provided herein result in a decrease in mean WOMAC pain score in a subject population. In some embodiments, the methods provided herein result in a decrease in mean WOMAC pain score in the subject population from baseline at week 12 following administration. For example, a decrease in mean WOMAC pain score in the subject population of at least 4 points from baseline at week 12 following administration; or a decrease in mean WOMAC pain score of at least 5 points from baseline at week 12 following administration.

In some embodiments, the methods provided herein result in a decrease in mean WOMAC function score from baseline, such as, for example, a decrease in mean WOMAC function score of at least 10% from baseline; or a decrease in mean WOMAC function score of at least 20% from baseline; or a decrease in mean WOMAC function score of at least 30% from baseline; or a decrease in mean WOMAC function score of at least 40% from baseline; or a decrease in mean WOMAC function score of at least 50% from baseline.

In some embodiments, the methods provided herein result in a decrease in mean WOMAC function score from baseline at week 12 following administration, such as, for example, a decrease in mean WOMAC function score of at least 10% from baseline at week 12 following administration; or a decrease in mean WOMAC function score of at least 20% from baseline at week 12 following administration; or a decrease in mean WOMAC function score of at least 30% from baseline at week 12 following administration; or a decrease in mean WOMAC function score of at least 40% from baseline at week 12 following administration; or a decrease in mean WOMAC function score of at least 50% from baseline at week 12 following administration.

In some embodiments, the methods provided herein result in a decrease in mean WOMAC pain score from baseline, such as, for example, a decrease in mean WOMAC pain score of at least 10% from baseline; or a decrease in mean WOMAC pain score of at least 20% from baseline; or a decrease in mean WOMAC pain score of at least 30% from baseline; or a decrease in mean WOMAC pain score of at least 40% from baseline; or a decrease in mean WOMAC pain score of at least 50% from baseline.

In some embodiments, the methods provided herein result in a decrease in mean WOMAC pain score from baseline at week 12 following administration, such as, for example, a decrease in mean WOMAC pain score of at least 10% from baseline at week 12 following administration; or a decrease in mean WOMAC pain score of at least 20% from baseline at week 12 following administration; or a decrease in mean WOMAC pain score of at least 30% from baseline at week 12 following administration; or a decrease in mean WOMAC pain score of at least 40% from baseline at week 12 following administration; or a decrease in mean WOMAC pain score of at least 50% from baseline at week 12 following administration.

In some embodiments, the methods provided herein result in a decrease in mean WOMAC stiffness score from baseline, such as, for example, a decrease in mean WOMAC stiffness score of at least 10% from baseline; or a decrease in mean WOMAC stiffness score of at least 20% from baseline; or a decrease in mean WOMAC stiffness score of at least 30% from baseline; or a decrease in mean WOMAC stiffness score of at least 40% from baseline; or a decrease in mean WOMAC stiffness score of at least 50% from baseline.

In some embodiments, the methods provided herein result in a decrease in mean WOMAC stiffness score from baseline at week 12 following administration, such as, for example, a decrease in mean WOMAC stiffness score of at least 10% from baseline at week 12 following administration; or a decrease in mean WOMAC stiffness score of at least 20% from baseline at week 12 following administration; or a decrease in mean WOMAC stiffness score of at least 30% from baseline at week 12 following administration; or a decrease in mean WOMAC stiffness score of at least 40% from baseline at week 12 following administration; or a decrease in mean WOMAC stiffness score of at least 50% from baseline at week 12 following administration.

In some embodiments, the values of certain parameters are as follows, in each case as a range from lowest median value (below zero) to highest median value (below zero):

In some embodiments, the change from baseline in WOMAC total score is from about −35 to about −75. For example, the change from baseline in WOMAC total score is from about −35 to about −60, about −35 to about −50, about −38 to about −73, about −40 to about −75, about −40 to about −70, about −40 to about −60, about −40 to about −50, about −50 to about −75, about −55 to about −70. In some embodiments, the change from baseline in WOMAC total score is from −38.6 to −73.4.

In some embodiments, the change in WOMAC total score as compared to placebo is from about 0 to about −20. For example, the change in WOMAC total score as compared to placebo is about 0 to about −15, about 0 to about −10, about 0 to about −5, about −5 to about −15, about −5 to about −10, about −10 to about −15. In some embodiments, the change in WOMAC total score as compared to placebo is from 0 to −14.7.

In some embodiments, the change from baseline in WOMAC pain score is from about −5 to about −20. For example, the change from baseline in WOMAC pain score is from about −5 to about −15, about −5 to about −10, about −7 to about −20, about −7 to about −15, about −10 to about −20, about −10 to about −15. In some embodiments, the change from baseline in WOMAC pain score is from −6.9 to −14.6.

In some embodiments, the change in WOMAC pain score as compared to placebo is from about 0 to about −5. For example, the change in WOMAC pain score as compared to placebo is about 0 to about −4, about 0 to about −3, about 0 to about −2, about 0 to about −1, about −1 to about −5, about −1 to about −4, about −1 to about −3, about −1 to about −2. In some embodiments, the change in WOMAC pain score as compared to placebo is from −0.35 to −2.79.

In some embodiments, the change from baseline in WOMAC function score is from about −25 to about −55. For example, the change from baseline in WOMAC function score is from about −25 to about −50, about −25 to about −40, about −25 to about −30, about −28 to about −55, about −28 to about −52, about −28 to about −50, about −28 to about −40, about −28 to about −35, about −35 to about −55, about −35 to about −45, about −40 to about −55. In some embodiments, the change from baseline in WOMAC function score is from −28.0 to −52.0.

In some embodiments, the change in WOMAC function score as compared to placebo is from about 0 to about −15. For example, the change in WOMAC function score as compared to placebo is about 0 to about −11, about 0 to about −10, about 0 to about −5, about −1 to about −15, about −1 to about −11, about −1 to about −5, about −5 to about −15, about −5 to about −10. In some embodiments, the change in WOMAC function score as compared to placebo is from −0.59 to −11.06.

In some embodiments, the change from baseline in WOMAC stiffness score is from about 0 to about −15. For example, the change from baseline in WOMAC stiffness score is from about 0 to about −10, about 1 to about −5, about −3 to about −15, about −3 to about −10, about −3 to about −7, about −5 to about −15, about −5 to about −10. In some embodiments, the change from baseline in WOMAC stiffness score is from −3.2 to −7.0.

In some embodiments, the change in WOMAC stiffness score as compared to placebo is from about 0 to about −5. For example, the change in WOMAC stiffness score as compared to placebo is about 0 to about −4, about 0 to about −3, about 0 to about −2, about −1 to about −5, about −1 to about −4, about −1 to about −3. In some embodiments, the change in WOMAC stiffness score as compared to placebo is from −0.07 to −1.95.

In some embodiments, the change from baseline in Medial Joint Space Width (mm) is from about 0 to about +0.5. For example, the change from baseline in Medial Joint Space Width (mm) is from about 0 to about +0.5, about 0 to about +0.4, about 0 to about +0.3, about 0 to about +0.2. In some embodiments, the change from baseline in Medial Joint Space Width (mm) is from 0 to +0.1.

In some embodiments, the change in Medial Joint Space Width (mm) as compared to placebo is from about 0 to about +1. For example, the change in Medial Joint Space Width (mm) as compared to placebo is about 0 to about +0.7, about 0 to about +0.5, about 0 to about +0.4, about 0 to about +0.2, about +0.1 to about +1, about +0.1 to about +0.5, about +0.1 to about +0.4. In some embodiments, the change in Medial Joint Space Width (mm) as compared to placebo is from +0.06 to +0.42.

In some of the embodiments wherein the methods result in a decrease in WOMAC total score in a subject, in WOMAC function score in a subject, in WOMAC pain score in a subject, and/or in WOMAC stiffness score in a subject, the subject is a patient.

In some embodiments, provided herein is a composition comprising a compound of Formula (I), including amorphous or polymorph forms thereof, wherein the composition is suitable for intraarticular injection in a patient, wherein the composition provides an increase in the joint space width in the joint surrounding the point of injection in the patient. In some embodiments, the increase is in an amount or a percentage disclosed herein. In some embodiments, the increase is at a time point disclosed herein.

In some embodiments, provided herein is a composition comprising a compound of Formula (I), including amorphous or polymorph forms thereof, wherein the composition is suitable for intraarticular injection in a patient, wherein the composition provides an increase in the cartilage thickness in the joint surrounding the point of injection in the patient. In some embodiments, the increase is in an amount or a percentage disclosed herein. In some embodiments, the increase is at a time point disclosed herein.

In some embodiments, provided herein is a composition comprising a compound of Formula (I), including amorphous or polymorph forms thereof, wherein the composition is suitable for intraarticular injection in a patient population, wherein the composition provides an increase in the mean joint space width in the joint surrounding the point of injection in the patient population. In some embodiments, the increase is in an amount or a percentage disclosed herein. In some embodiments, the increase is at a time point disclosed herein.

In some embodiments, provided herein is a composition comprising a compound of Formula (I), including amorphous or polymorph forms thereof, wherein the composition is suitable for intraarticular injection in a patient population, wherein the composition provides an increase in the mean cartilage thickness in the joint surrounding the point of injection in the patient population. In some embodiments, the increase is in an amount or a percentage disclosed herein. In some embodiments, the increase is at a time point disclosed herein.

In some embodiments, provided herein is a composition comprising a compound of Formula (I), including amorphous or polymorph forms thereof, wherein the composition is suitable for intraarticular injection in a patient, wherein the composition provides a decrease in the WOMAC total score. In some embodiments, the decrease is in an amount or a percentage disclosed herein. In some embodiments, the decrease is at a time point disclosed herein.

In some embodiments, provided herein is a composition comprising a compound of Formula (I), including amorphous or polymorph forms thereof, wherein the composition is suitable for intraarticular injection in a patient, wherein the composition provides a decrease in the WOMAC function score. In some embodiments, the decrease is in an amount or a percentage disclosed herein. In some embodiments, the decrease is at a time point disclosed herein.

In some embodiments, provided herein is a composition comprising a compound of Formula (I), including amorphous or polymorph forms thereof, wherein the composition is suitable for intraarticular injection in a patient, wherein the composition provides a decrease in the WOMAC pain score. In some embodiments, the decrease is in an amount or a percentage disclosed herein. In some embodiments, the decrease is at a time point disclosed herein.

In some embodiments, provided herein is a composition comprising a compound of Formula (I), including amorphous or polymorph forms thereof, wherein the composition is suitable for intraarticular injection in a patient, wherein the composition provides a decrease in the WOMAC stiffness score. In some embodiments, the decrease is in an amount or a percentage disclosed herein. In some embodiments, the decrease is at a time point disclosed herein.

In some embodiments, provided herein is a composition comprising a compound of Formula (I), including amorphous or polymorph forms thereof, wherein the composition is suitable for intraarticular injection in a patient population, wherein the composition provides a decrease in the mean WOMAC total score. In some embodiments, the decrease is in an amount or a percentage disclosed herein. In some embodiments, the decrease is at a time point disclosed herein.

In some embodiments, provided herein is a composition comprising a compound of Formula (I), including amorphous or polymorph forms thereof, wherein the composition is suitable for intraarticular injection in a patient population, wherein the composition provides a decrease in the mean WOMAC function score. In some embodiments, the decrease is in an amount or a percentage disclosed herein. In some embodiments, the decrease is at a time point disclosed herein.

In some embodiments, provided herein is a composition comprising a compound of Formula (I), including amorphous or polymorph forms thereof, wherein the composition is suitable for intraarticular injection in a patient population, wherein the composition provides a decrease in the mean WOMAC pain score. In some embodiments, the decrease is in an amount or a percentage disclosed herein. In some embodiments, the decrease is at a time point disclosed herein.

In some embodiments, provided herein is a composition comprising a compound of Formula (I), including amorphous or polymorph forms thereof, wherein the composition is suitable for intraarticular injection in a patient population, wherein the composition provides a decrease in the mean WOMAC stiffness score. In some embodiments, the decrease is in an amount or a percentage disclosed herein. In some embodiments, the decrease is at a time point disclosed herein.

In some embodiments, the methods provided herein result in a decrease in mean physician global assessment from baseline at week 12 following administration. For example, a decrease in mean physician global assessment from baseline of at least 25 points at week 12 following administration; or a decrease in mean physician global assessment from baseline of at least 30 points at week 12 following administration.

In some embodiments, a compound of Formula (I), including amorphous and polymorph forms thereof, increases chondrocyte formation. For example, the compound of Formula (I), including amorphous and polymorph forms thereof, increases chondrocyte formation in human mesenchymal stem cells. In some embodiments, chondrocyte formation is increased between about 30 and 67-fold change over DMSO. In some embodiments, a compound of Formula (I), including amorphous and polymorph forms thereof, inhibits expression of MMP1, MMP3, MMP13, or any combination thereof. For example, the compound of Formula (I), including amorphous and polymorph forms thereof, inhibits expression of MMP1, MMP3, MMP13, or any combination thereof in chondrocytes treated with TNFα and oncostatin M.

Other measurements that can be taken include, but are not limited to, Daily Pain VAS (visual analog scale) for Weekly Average Pain Score; NSAID Rescue Medication Use, which is a measurement of the amount of pain medication used after administration of the compound of Formula (I) vs. placebo; Patient Global Assessment, a 5- or 6-point scoring system used to assess disease severity by the patient, taking into consideration overall health; quantitative computed tomography (QCT) for bone density, a fast, non-invasive bone mineral density (BMD) exam perform on a CT scanner that can be used to detect low bone mass and monitor the effects of bone mass therapy in patients undergoing treatment; biomarkers from periphery, including, but not limited to B-CTX (beta CTX-I; (C-terminal telopeptide of collagen type I), P1NP (serum type 1 procollagen (C-terminal/N-terminal)), COMP (cartilage oligomeric matrix protein), and CTX-II (C-terminal telopeptide of collagen type II); biomarkers in joint space fluid, including, but not limited to B-CTX, P1NP, COMP, and CTX-II; histopathology of cartilage, including, but not limited to cartilage quality (fibro vs. hyaline) for both the meniscus (two pads of fibrocartilaginous tissue which serve to disperse friction in the knee joint between the lower leg (tibia) and the thigh (femur), where the most common injury is the rupturing (tearing) of one or more of the fibrocartilage strips) and articular (hyaline) cartilage in the synovial joints, glycosaminoglycans (GAG; including hyaluronic acid, a major component of synovial tissues and fluid), aggrecan (a large proteoglycan which plays a role in fluid pressurization of the cartilage which supports the articular surface and so may facilitate its function. Aggrecan degradation cause cleavage of all components of the aggregate which are detrimental to cartilage function and are enhanced in osteoarthritic cartilage, resulting in aggrecan depletion and predisposing to cartilage erosion), and type 2 and type 10 collagen content (for joint health); and visual grading of cartilage field.

EXAMPLES

Example 1: Polymorph Screen

A polymorph screen was performed on the compound of Formula (I) to determine solubility, polymorphism, and thermodynamic stability.

A. Analysis of the starting solid (a mixture of Form 1 and a non-stoichiometric hydrate of Form 1)

X-ray powder diffraction (XRD), differential scanning calorimetry (DSC), and thermal gravimetric analysis (TGA) scans of the starting solid compound of Formula (I), indicated that the starting solid was a crystalline material and was a mixture of Form I and a non-stoichiometric hydrate of Form 1 having between 1% and about 20% by weight water. According to the DSC scan (FIG. 12B), the solid showed a wide endotherm between 50° C.-100° C.; it also showed a sharp exotherm at 284° C.; and the solid eventually melted at 364° C. According to the TGA scan (FIG. 12C), a 1.4% weight loss was observed before 100° C.

The solubility of the mixture of Form 1 and a non-stoichiometric hydrate of Form 1 was measured by the gravimetric method and indicated that the compound had low solubility at RT and at 50° C. in all solvents tested except DMF and DMSO. Results from the solubility data test at RT and at 50° C. are shown in Table 3.

TABLE 3

Solubility data of the starting solid
(non-stoichiometric hydrate of Form 1)

| Solvents | Solubility at RT (mg/mL) | Solubility at 50° C. (mg/mL) |
|---|---|---|
| Acetone | 1 | 1 |
| Acetonitrile | ~0 | 0 |
| MeOH | 1 | 1 |
| Toluene | 1 | 1 |
| EtOH | 2 | 2 |
| IPAc | ~0 | ~0 |
| EA | 1 | 1 |
| MtBE | ~0 | ~0 |
| IPA | 2 | 5 |
| MEK | 1 | 1 |
| MA | ~0 | ~0 |
| n-Propanol | 1 | 2 |
| MIBK | 1 | 1 |
| n-Butyl acetate | ~0 | ~0 |
| water | 1 | 1 |
| Heptane | ~0 | ~0 |
| n-Butanol | 1 | 2 |
| DMSO | n/a | n/a |
| DMF | 12 | 16 |
| DCM | 2 | 2 |
| Acetic acid | ~0 | 3 |

Slurry experiments in various solvents were performed. Approximately 30-80 mg of the starting solid (a non-stoichiometric hydrate of Form 1 having between 1% and about 20% by weight water) was slurried in 39 different solvents (pure and binary solvents; the ratio of organic solvent/water (V/V) was 95%/5%) at RT and 50° C. for 5 days. Three solvates, one non-stoichiometric hydrate, and eleven non-solvated forms were identified. A "*" after a particular Form, e.g., Form 2*, indicates that the forms had similar XRD scans with minor differences and were considered to belong to the same class. Generally, the identified forms showed multiple endotherms/exotherms on differential scanning calorimetry (DSC) scans; Form 9 showed a single endotherm. XRD of both wet and dry samples were scanned (FIG. 12A (dry sample)). The data is shown in Tables 4 and 5 below.

TABLE 4

Results of slurry experiments at RT

| Solvent | Crystalline Form (wet/dry) | | Solvent | Crystalline Form (wet/dry) | |
|---|---|---|---|---|---|
| Acetone | Solvate 1 | Form 2 | Acetone/water | Solvate 2 | Form 4** |
| Acetonitrile | Form 2 | Form 1 | Acetonitrile/water | Form 12 | Form 1 |
| MeOH | Form 13 | Form 1 | MeOH/water | Form 12 | Form 1 |
| Toluene | Form 1 | Form 2* | Toluene/water | Form 13 | Form 1 |
| EtOH | Form 2* | Form 3 | EtOH/water | Solvate 3 | Form 2 |
| IPAc | Form 3 | Form 4 | IPAc/water | Form 12 | Form 1 |
| EA | Form 4* | Form 5 | EA/water | Form 12 | Form 1 |
| MtBE | Form 5* | Form 6 | MtBE/water | Form 12 | Form 1 |
| IPA | Form 6 | Form 7 | IPA/water | Form 6 | Form 6 |
| MEK | Form 7 | Form 4 | MEK/water | Form 7 | Form 7 |
| MA | Form 4 | Form 4* | MA/water | Form 13 | Form 1 |
| n-Propanol | Form 4* | Form 8 | n-Propanol/water | Form 2** | Form 2** |
| MIBK | Form 8 | Form 3 | MIBK/water | Form 12 | Form 1 |
| n-Butyl acetate | Form 3* | Form 1 | n-Butyl acetate/water | Form 13 | Form 12 |
| Water | Form 13 | Form 1 | Heptane/water | Form 13 | Form 12 |
| Heptane | Form 1 | Form 9 | n-Butanol/water | Form 13 | Form 13 |
| n-Butanol | Form 9 | Form 10 | DMSO/water | amorphous | Form 10 |
| DMSO | amorphous | Form 11 | DMF/water | Form 11 | Form 11 |
| DMF | Form 11 | Form 1 | DCM/water | Form 13 | Form 1 |
| DCM | Form 1 | Form 2 | | | |

TABLE 5

Results of slurry experiments at 50° C.

| Solvent | Crystalline Form (wet/dry) | | Solvent | Crystalline Form (wet/dry) | |
|---|---|---|---|---|---|
| Acetone | Solvate 2 | Form 4** | Acetone/water | Form 4** | Form 4** |
| Acetonitrile | Form 2* | Form 2 | Acetonitrile/water | Form 13 | Form 13 |
| MeOH | Form 1 | Form 1 | MeOH/water | Form 13 | Form 13 |
| Toluene | Form 1 | Form 1 | Toluene/water | Form 13 | Form 13 |
| EtOH | Form 2* | Form 2* | EtOH/water | Form 9 | Form 9 |
| IPAc | Form 9 | Form 9 | IPAc/water | Form 13 | Form 13 |
| EA | Form 4* | Form 4 | EA/water | Form 4* | Form 4* |
| MtBE | Form 5* | Form 4 | MtBE/water | Form 13 | Form 13 |
| IPA | Form 6 | Form 6 | IPA/water | Form 6 | Form 6 |
| MEK | Form 7 | Form 7 | MEK/water | Form 7 | Form 7 |
| MA | Form 4 | Form 4 | MA/water | Form 12 | Form 4 |
| n-Propanol | Form 4 | Form 4** | n-Propanol/water | Form 9 | Form 9 |
| MIBK | Form 8 | Form 8 | MIBK/water | Form 13 | Form 1 |
| n-Butyl acetate | Form 9 | Form 9 | n-Butyl acetate/water | Form 13 | Form 1 |
| water | Form 13 | Form 13 | Heptane/water | Form 13 | Form 1 |
| Heptane | Form 13 | Form 13 | n-Butanol/water | Form 13 | Form 1 |
| n-Butanol | Form 9 | Form 9 | DMSO/water | Amorphous | Form 10 |
| DMSO | Amorphous | Form 10* | DMF/water | Form 11 | Form 11 |
| DMF | Form 11 | Form 11* | DCM/water | Form 13 | Form 1 |
| DCM | Form 13 | Form 13 | | | |

The slurry experiments identified 3 solvated forms from wet samples (Solvates 1, 2, and 3); 2 non-stoichiometric hydrates of Form 1 (Forms 12 and 13); and 11 non-solvated forms (Forms 1-11). In some instances, similar XRD scans with minor differences were obtained. These were considered to be part of the same class (e.g., the same form). For example, XRD scans of Form 2 and Form 2* were similar and were considered to belong to the same class. The solvated forms were obtained from wet sample analysis; after drying, the sample indicated a different XRD.

Solvate 1 was obtained from acetone at RT, and after drying, a low crystallinity solid was generated. Solvate 2 was obtained from acetone (at RT) and acetone/water (at RT), and after drying, Form 4** was generated. Solvate 3 was obtained from EtOH/water at RT, and after drying, Form 2 was generated.

B. Form 1

The experiments that generated Form 1 are shown in Table 6, below. Form 1 was generally obtained from drying of Form 13 or Form 12. Form 1 may be considered as a dehydrated hydrate. Reslurry in many binary solvents (with 5% water) generated Form 1. Purity of the residual solid was 98.9%. KF of Form 1 (one sample) solid was 5.8%; residual MeOH of Form 1 solid was 0.01%. A TGA scan of fully dried Form 1 solid was performed (FIG. 1C). A 0.33% weight loss was observed before 100° C.

Figure 1B:
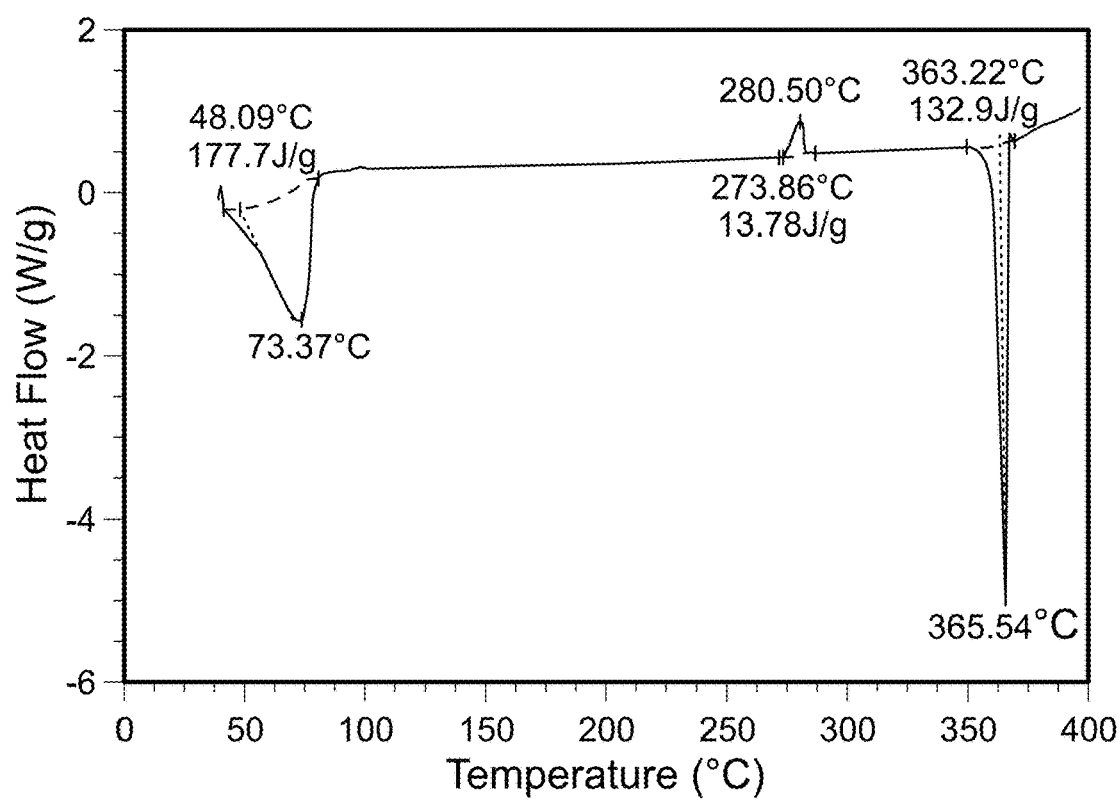
Figure 1C:
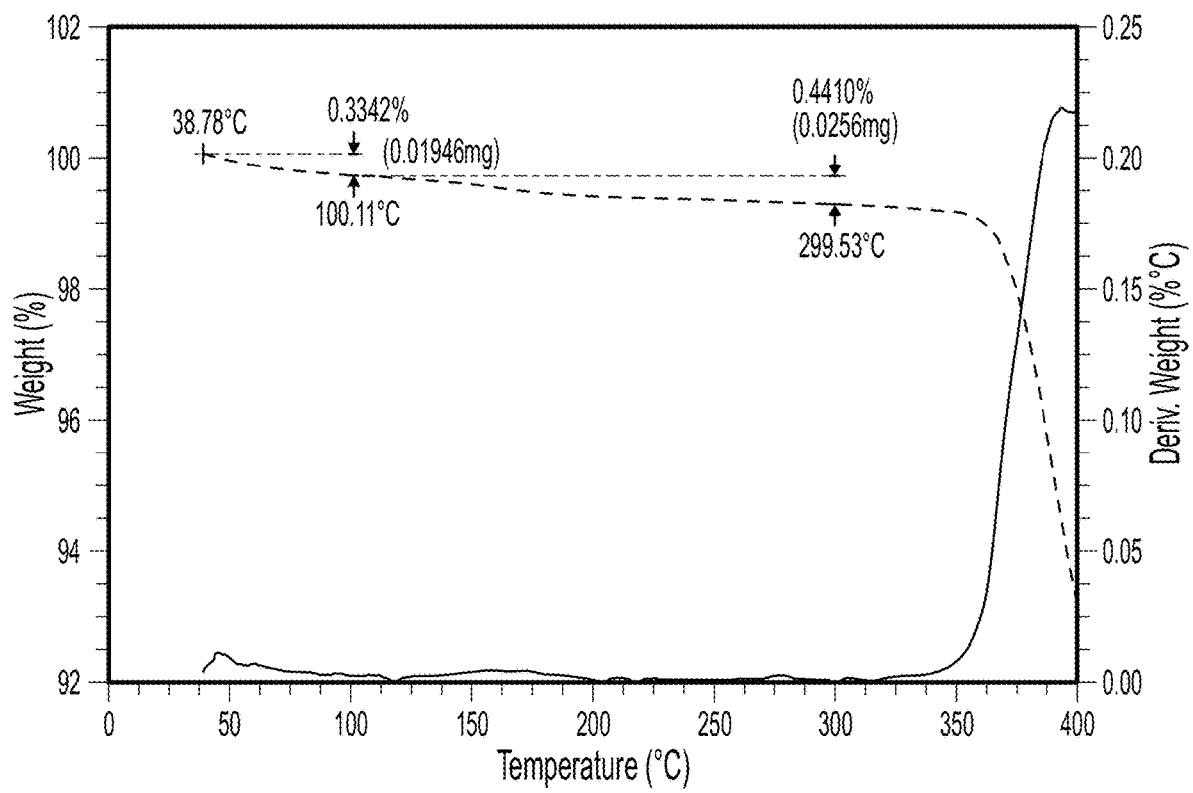

Form 1 showed sharp crystalline peaks on the XRD scan (FIG. 1A). The XRD peaks of Form 1 are shown in Table 7, below. According to the DSC scan (FIG. 1B), the solid showed a wide endotherm between 50-100° C.; it showed a sharp exotherm at 281° C.; and the melting point was 363° C.

The Form 1 solid was dried at 75° C. under vacuum overnight, and XRD, DSC, and TGA scans were performed. Comparison of the first and the second XRD scans (after drying at 75° C. under vacuum overnight), showed no change. However, the DSC scans indicated the absence of endotherm. The loss of the early peak on the DSC scan had no effect on the XRD trace, showing that the wide endotherm between 50-100° C. on DSC scan was due to the free solvent.

The Form 1 solid was heated in a DSC chamber to 305° C. (past the endotherm/exotherm around 280° C.), and then scanned by XRD. Comparison of the first and the third XRD and DSC scans shows that after heating to 305° C., Form 1 converted to Form 9. It can be concluded that the endotherm/exotherm around 280° C. might be due to melting/crystallization events.

Form 1 tended to convert to a non-stoichiometric hydrate of Form 1 having between 1% and about 20% by weight water (e.g., Form 13) at RH above 4050%. The hydrate lost its water below 30% RH. Form 1 converts to Form 13 when exposed to air.

Figure 1D:
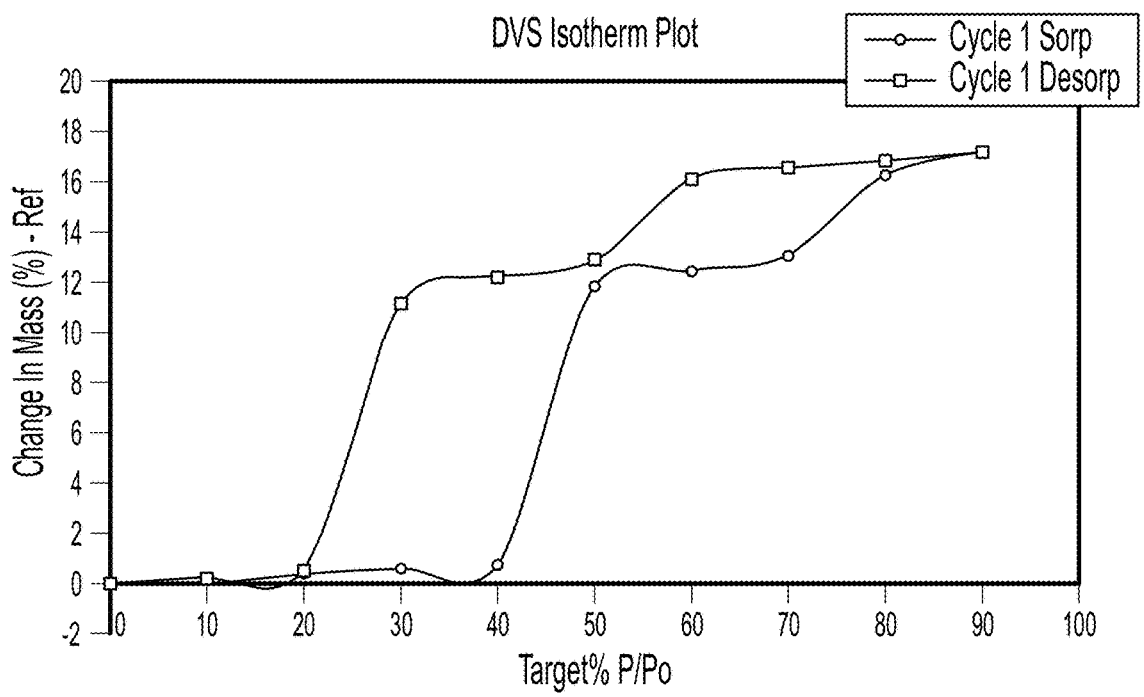

The dynamic vapor sorption (DVS) scan of Form 1 solid showed a 17% water absorption at 90% RH (FIG. 1D). The XRD data indicated that the solid used in the DVS test converted to the hydrate form before the start of the DVS test. However, at 0% RH, water was lost, perhaps indicating that the solid was Form 1.

TABLE 6

Summary of experiments that generated Form 1

| Form | Solvent | Temperature | Wet | Dry |
|---|---|---|---|---|
| Form 1 | MeOH | RT | Form 13 | Form 1 |
| | MeOH | 50° C. | Form 1 | Form 1 |
| | Toluene | RT | Form 1 | Form 1 |
| | Toluene | 50° C. | Form 1 | Form 1 |
| | water | RT | Form 13 | Form 1 |
| | Heptane | RT | Form 1 | Form 1 |
| | DCM | RT | Form 1 | Form 1 |
| | Acetonitrile/water | RT | Form 12 | Form 1 |
| | MeOH/water | RT | Form 12 | Form 1 |
| | Toluene/water | RT | Form 13 | Form 1 |
| | IPAc/water | RT | Form 13 | Form 1 |
| | EA/water | RT | Form 12 | Form 1 |
| | MtBE/water | RT | Form 12 | Form 1 |
| | MA/water | RT | Form 13 | Form 1 |
| | MIBK/water | RT | Form 12 | Form 1 |
| | MIBK/water | 50° C. | Form 13 | Form 1 |
| | DCM/water | RT | Form 13 | Form 1 |
| | DCM/water | 50° C. | Form 13 | Form 1 |
| | n-Butyl acetate/water | 50° C. | Form 13 | Form 1 |

TABLE 6-continued

Summary of experiments that generated Form 1

| Form | Solvent | Temperature | Wet | Dry |
|---|---|---|---|---|
| | Heptane/water | 50° C. | Form 13 | Form 1 |
| | n-Butanol/water | 50° C. | Form 13 | Form 1 |

*Amount of water in binary solvents is 5%

TABLE 7

XRD peaks of Form 1

| 2-Theta | d(A) | BG | Height | I % | Area | I % | FWHM |
|---|---|---|---|---|---|---|---|
| 5.778 | 15.2835 | 57 | 97 | 28.3 | 1765 | 18.5 | 0.309 |
| 6.801 | 12.9871 | 19 | 343 | 100 | 8306 | 87.1 | 0.412 |
| 9.26 | 9.5427 | 20 | 178 | 51.9 | 3884 | 40.7 | 0.371 |
| 12.421 | 7.1203 | 30 | 231 | 67.3 | 4862 | 51 | 0.358 |
| 13.919 | 6.357 | 35 | 147 | 42.9 | 3668 | 38.5 | 0.424 |
| 14.501 | 6.1033 | 40 | 133 | 38.8 | 3439 | 36.1 | 0.44 |
| 16.5 | 5.3681 | 47 | 196 | 57.1 | 4286 | 44.9 | 0.372 |
| 17.26 | 5.1333 | 53 | 46 | 13.4 | 560 | 5.9 | 0.207 |
| 18.52 | 4.7868 | 68 | 342 | 99.7 | 9539 | 100 | 0.474 |
| 19.161 | 4.6282 | 54 | 215 | 62.7 | 4130 | 43.3 | 0.327 |
| 20.302 | 4.3706 | 49 | 133 | 38.8 | 2823 | 29.6 | 0.361 |
| 20.619 | 4.304 | 43 | 80 | 23.3 | 2047 | 21.5 | 0.435 |
| 23.056 | 3.8543 | 41 | 38 | 11.1 | 765 | 8 | 0.342 |
| 24.642 | 3.6098 | 33 | 175 | 51 | 7235 | 75.8 | 0.703 |
| 25.302 | 3.5171 | 86 | 80 | 23.3 | 2345 | 24.6 | 0.498 |
| 26.1 | 3.4113 | 83 | 69 | 20.1 | 1545 | 16.2 | 0.381 |
| 27.46 | 3.2453 | 52 | 46 | 13.4 | 872 | 9.1 | 0.322 |
| 28.739 | 3.1038 | 39 | 84 | 24.5 | 2146 | 22.5 | 0.434 |
| 30.444 | 2.9337 | 34 | 32 | 9.3 | 1080 | 11.3 | 0.54 |
| 33.302 | 2.6882 | 30 | 27 | 7.9 | 683 | 7.2 | 0.405 |

C. Forms 2, 2*, and 2***

Figure 2A:
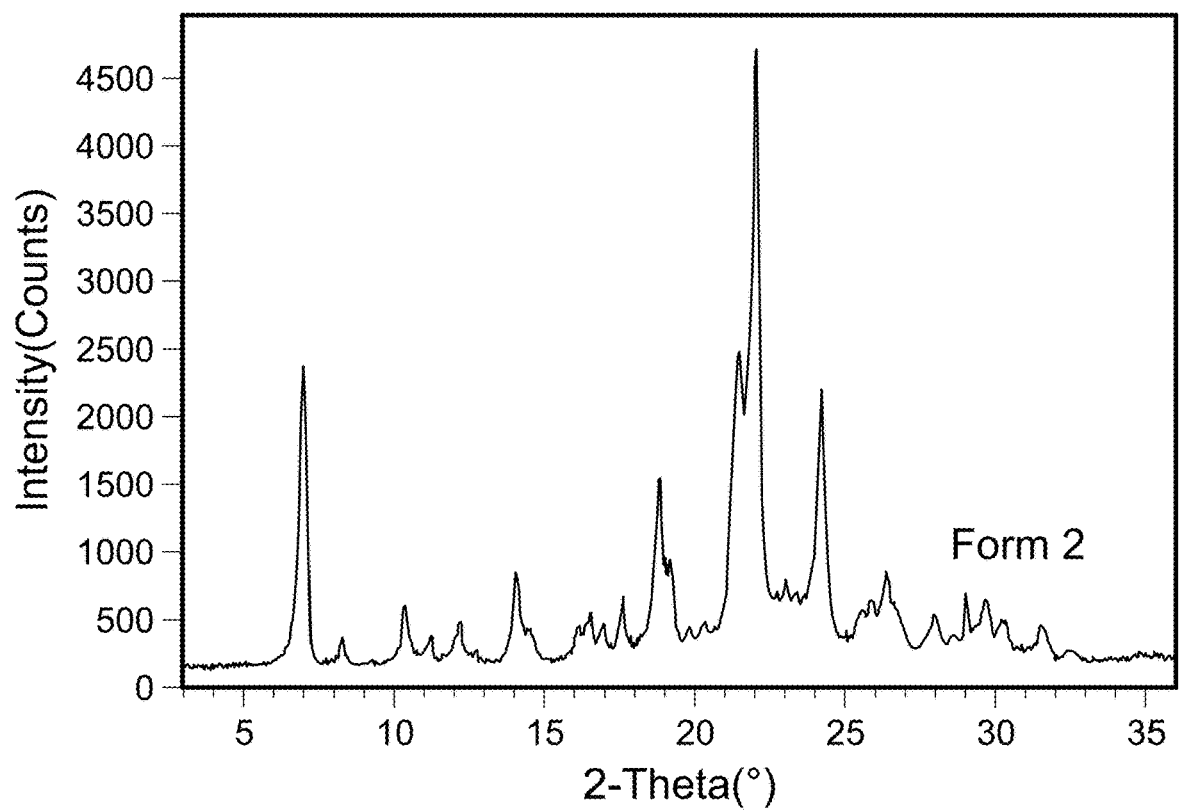
FIGS. 2A-2H are scans of polymorph Forms 2, 2*, and 2** of the compound of Formula (I).
Figure 2B:
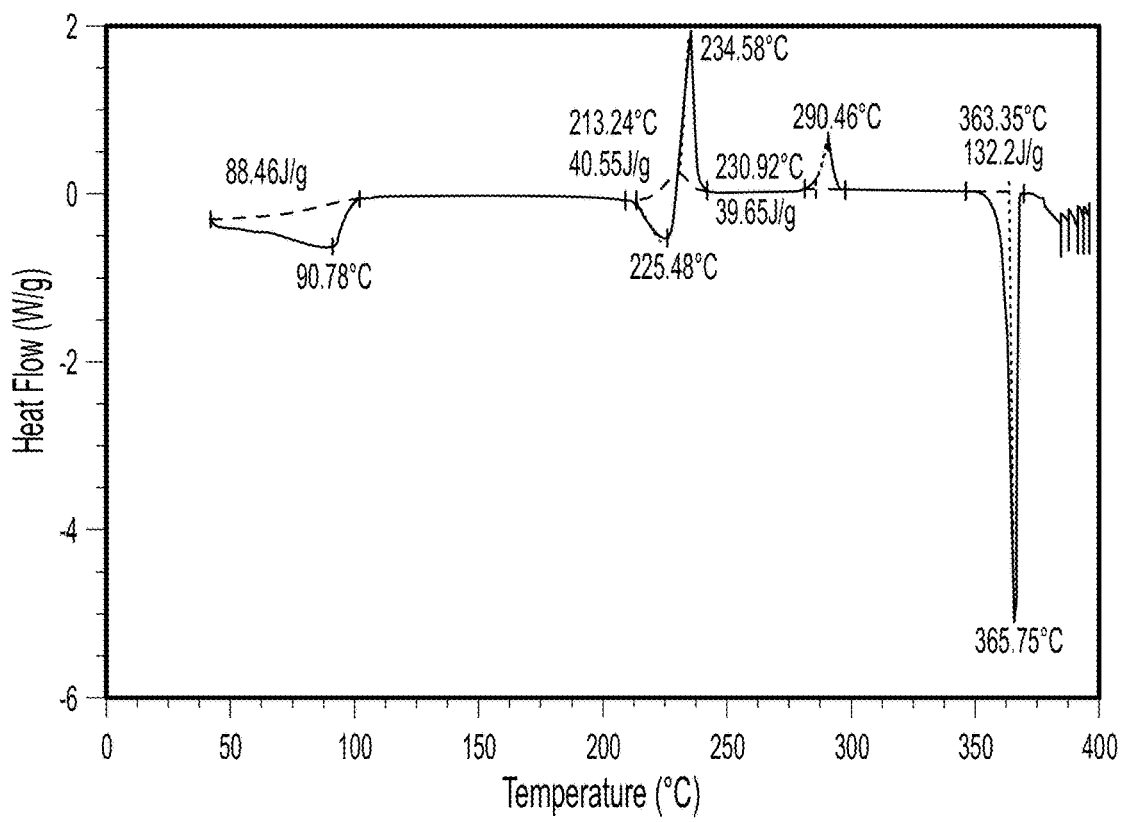
Figure 2C:
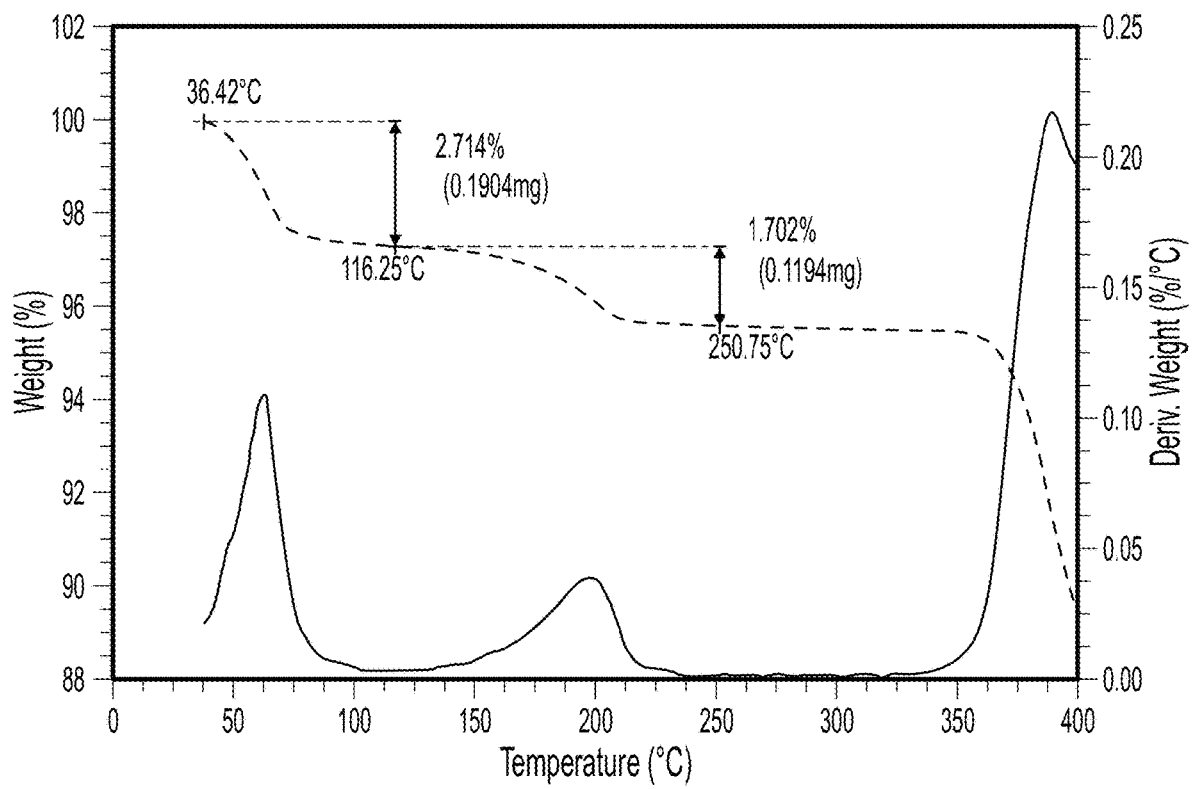
Figure 2D:
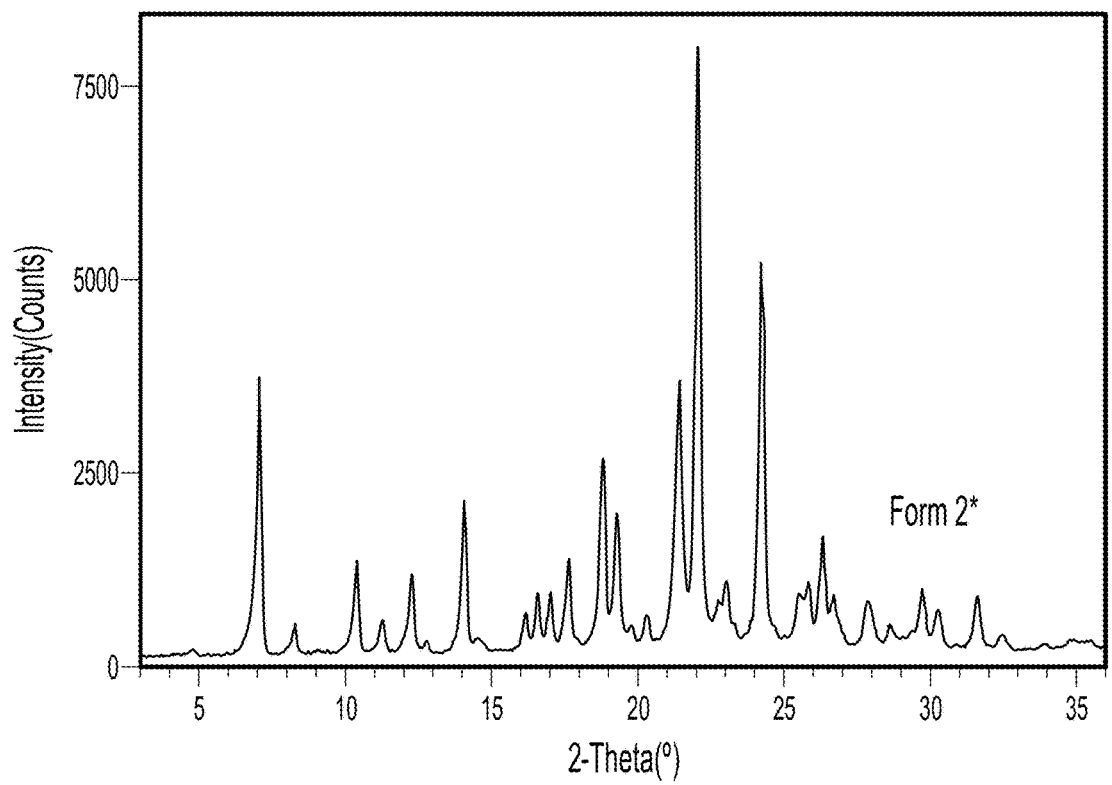
Figure 2E:
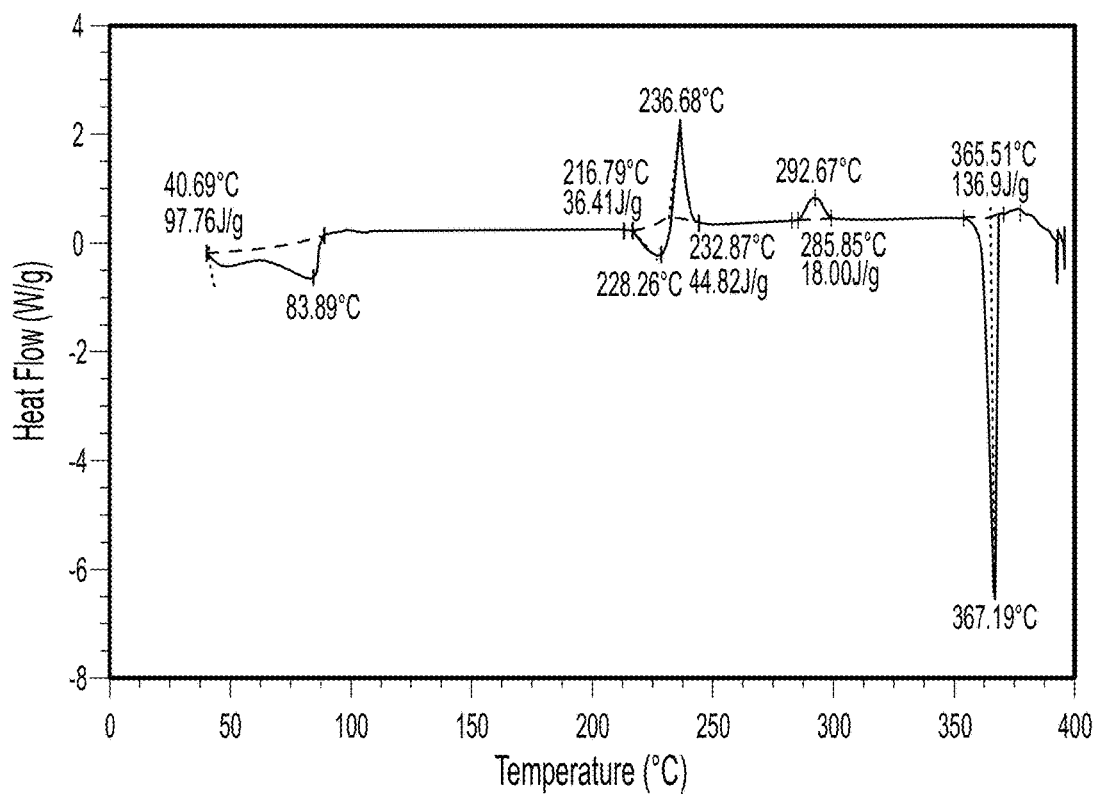
Figure 2F:
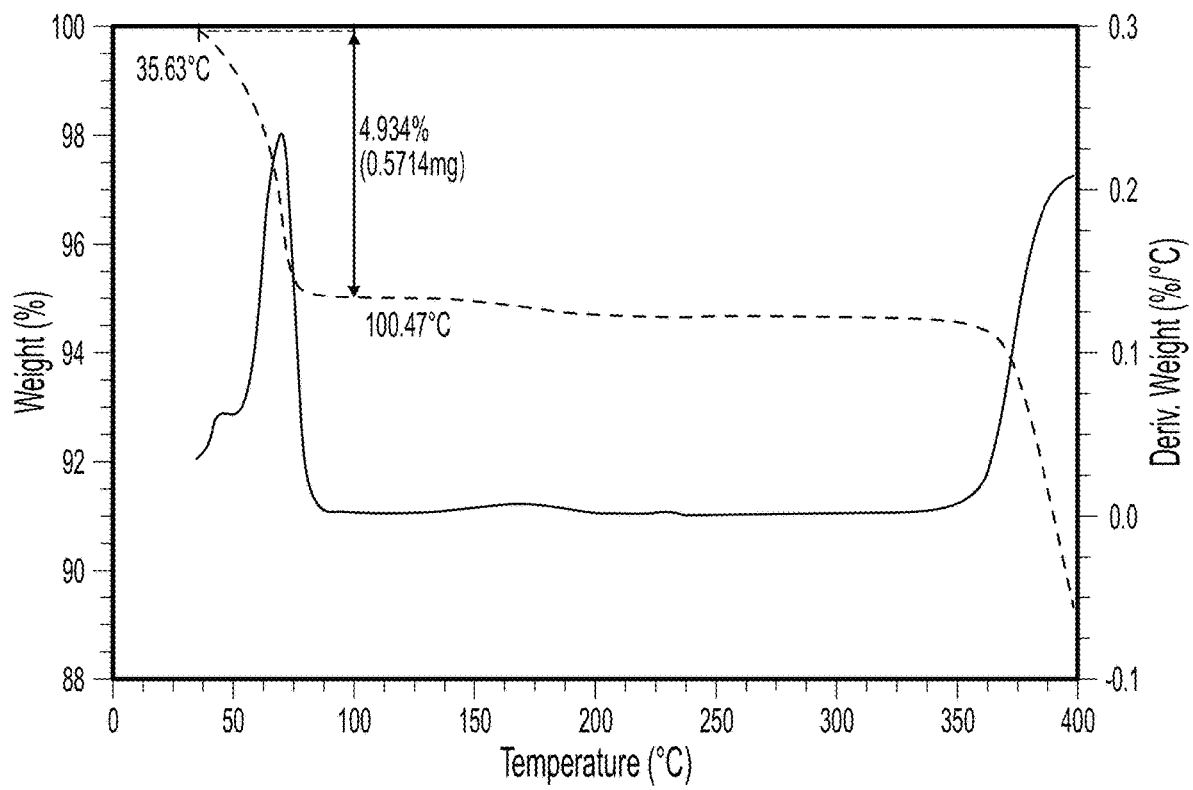
Figure 2G:
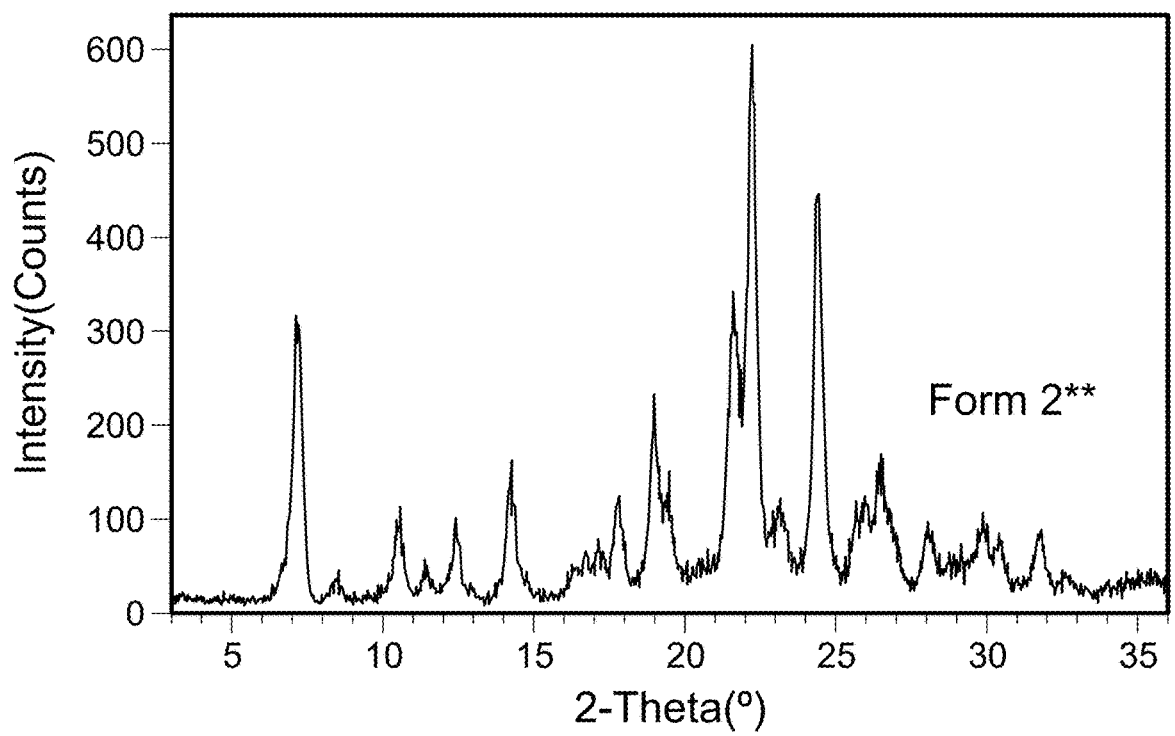
Figure 2H:
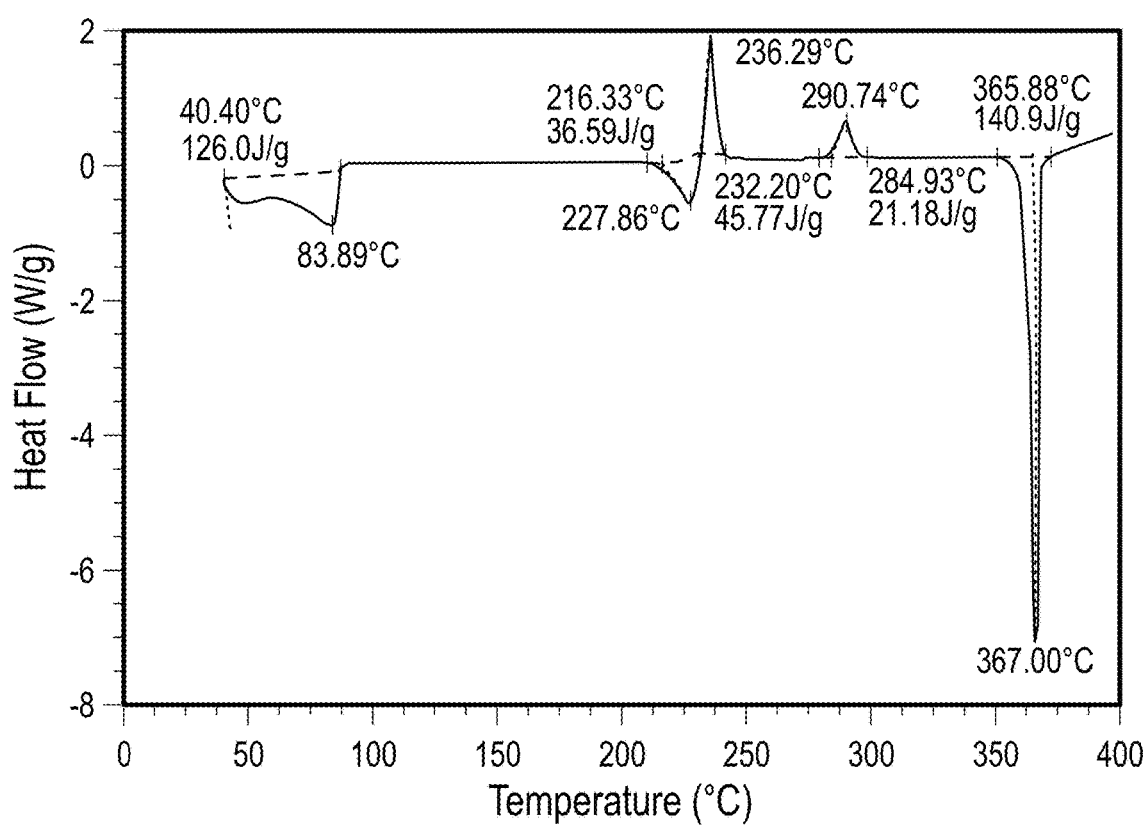

The experiments that generated Forms 2, 2*, and 2** are shown in Table 8, below. XRD scans of Forms 2, 2* and 2** were performed (FIGS. 2A, 2D, and 2G show the XRD scans of Forms 2, 2*, and 2**, respectively). The XRD peaks of Forms 2 and 2* are shown in Tables 9 and 10, below, respectively. DSC scans were also performed (FIGS. 2B, 2E, and 2H show the DSC scans of Forms 2, 2*, and 2**, respectively). According to the DSC scans, Forms 2, 2* and 2** each showed a wide endotherm between 50° C.-100° C., and multiple endotherms and exotherms before melting at 363° C. The wide endotherm before 100° C. may be due to the containment of water/solvent in the solid. Form 2 was obtained from acetonitrile; Form 2* from ethanol; Form 2** from n-propanol/5% water.

A TGA scan of Form 2 (FIG. 2C) showed a 2.7% weight loss before 116° C. FIG. 2F shows the TGA scan of Form 2*

A PLM photo of Form 2 was taken, indicating that the particle size of this solid was around 50 um.

The Form 2 solid was heated in a DSC machine to 90° C. (past the wide endotherm between 50-100° C.); to 270° C. (past the endotherm/exotherm around 240° C.); and finally to 330° C. (past the exotherm around 330° C.). The residual solid was analyzed by XRD. According to the first and second XRD and DSC scans, the form did not change before and after heating to 90° C. The wide endotherm between 50-100° C. might be free solvent or hydrate. According to the first and third XRD and DSC scans, after heating a Form 2 sample to 270° C., the solid converted to low crystalline solids. According to the first and fourth XRD and DSC scans, after heating the sample to 330° C., the solid converted to Form 9. Thus, the exotherm around 290° C. was a re-crystallization event. According to an XRD and DSC overlay, the behavior of Form 2* was similar to Form 2.

Residual acetonitrile and EtOH in Form 2 and 2* was not detected.

TABLE 8

Summary of experiments that generated Forms 2, 2*, and 2**

| Form | Solvent | Temperature | Wet | Dry |
|---|---|---|---|---|
| Form 2 | Acetonitrile | RT | Form 2 | Form 2 |
| | Acetonitrile | 50° C. | Form 2* | Form 2 |
| | EtOH/water | RT | Solvate 3 | Form 2 |
| Form 2* | EtOH | RT | Form 2* | Form 2* |
| | EtOH | 50° C. | Form 2* | Form 2* |
| | Acetonitrile | 50° C. | Form 2* | Form 2 |
| Form 2** | n-Propanol/water | RT | Form 2** | Form 2** |

*Amount of water in binary solvents is 5%

TABLE 9

XRD peaks of Form 2

| 2-Theta | d(A) | BG | Height | I % | Area | I % | FWHM |
|---|---|---|---|---|---|---|---|
| 7.021 | 12.5802 | 164 | 2202 | 54.1 | 36151 | 38.2 | 0.279 |
| 8.298 | 10.6462 | 156 | 194 | 4.8 | 2332 | 2.5 | 0.204 |
| 10.399 | 8.5 | 193 | 397 | 9.8 | 6246 | 6.6 | 0.267 |
| 11.258 | 7.8531 | 206 | 151 | 3.7 | 1407 | 1.5 | 0.158 |
| 12.239 | 7.2259 | 181 | 287 | 7 | 5980 | 6.3 | 0.354 |
| 14.1 | 6.2759 | 186 | 648 | 15.9 | 14147 | 15 | 0.371 |
| 14.597 | 6.0632 | 195 | 182 | 4.5 | 7983 | 8.4 | 0.746 |
| 16.18 | 5.4734 | 235 | 201 | 4.9 | 4033 | 4.3 | 0.341 |
| 16.561 | 5.3484 | 251 | 280 | 6.9 | 8382 | 8.9 | 0.509 |
| 17.033 | 5.2013 | 288 | 160 | 3.9 | 1810 | 1.9 | 0.192 |
| 17.639 | 5.0238 | 295 | 366 | 9 | 3542 | 3.7 | 0.165 |
| 18.878 | 4.6968 | 316 | 1210 | 29.7 | 29303 | 31 | 0.412 |
| 19.22 | 4.614 | 333 | 585 | 14.4 | 21169 | 22.4 | 0.615 |
| 19.863 | 4.4662 | 340 | 95 | 2.3 | 437 | 0.5 | 0.078 |
| 20.411 | 4.3474 | 385 | 86 | 2.1 | 671 | 0.7 | 0.133 |
| 21.48 | 4.1335 | 532 | 1944 | 47.8 | 61345 | 64.8 | 0.536 |
| 22.04 | 4.0297 | 647 | 4071 | 100 | 94605 | 100 | 0.395 |
| 23.036 | 3.8576 | 634 | 142 | 3.5 | 1478 | 1.6 | 0.177 |
| 24.24 | 3.6686 | 497 | 1688 | 41.5 | 28976 | 30.6 | 0.292 |
| 25.561 | 3.482 | 422 | 120 | 2.9 | 2545 | 2.7 | 0.361 |
| 25.918 | 3.4349 | 365 | 271 | 6.7 | 11426 | 12.1 | 0.717 |
| 26.379 | 3.3759 | 349 | 497 | 12.2 | 15133 | 16 | 0.518 |
| 26.739 | 3.3313 | 387 | 181 | 4.4 | 2845 | 3 | 0.267 |
| 27.979 | 3.1863 | 297 | 235 | 5.8 | 4050 | 4.3 | 0.293 |
| 29.043 | 3.072 | 338 | 347 | 8.5 | 4584 | 4.8 | 0.225 |
| 29.661 | 3.0094 | 321 | 310 | 7.6 | 7879 | 8.3 | 0.432 |
| 30.204 | 2.9565 | 355 | 135 | 3.3 | 1501 | 1.6 | 0.189 |
| 31.58 | 2.8308 | 232 | 206 | 5.1 | 3991 | 4.2 | 0.329 |
| 32.602 | 2.7443 | 193 | 63 | 1.5 | 1129 | 1.2 | 0.305 |

TABLE 10

XRD peaks of Form 2*

| 2-Theta | d(A) | BG | Height | I % | Area | I % | FWHM |
|---|---|---|---|---|---|---|---|
| 4.859 | 18.1701 | 127 | 87 | 1.2 | 1714 | 1.9 | 0.335 |
| 7.119 | 12.4067 | 148 | 3587 | 48.4 | 44853 | 50.4 | 0.213 |
| 8.321 | 10.6166 | 149 | 407 | 5.5 | 4871 | 5.5 | 0.203 |
| 10.439 | 8.4669 | 186 | 1184 | 16 | 13629 | 15.3 | 0.196 |
| 11.319 | 7.8109 | 190 | 413 | 5.6 | 4673 | 5.3 | 0.192 |
| 12.3 | 7.1899 | 179 | 1010 | 13.6 | 13220 | 14.9 | 0.223 |
| 12.803 | 6.9089 | 182 | 140 | 1.9 | 1587 | 1.8 | 0.193 |
| 14.121 | 6.2667 | 179 | 1966 | 26.5 | 27290 | 30.7 | 0.236 |
| 14.559 | 6.0791 | 199 | 169 | 2.3 | 4381 | 4.9 | 0.441 |
| 16.236 | 5.4546 | 244 | 436 | 5.9 | 5696 | 6.4 | 0.222 |
| 16.62 | 5.3297 | 271 | 674 | 9.1 | 7919 | 8.9 | 0.2 |
| 17.059 | 5.1935 | 313 | 629 | 8.5 | 6279 | 7.1 | 0.17 |
| 17.699 | 5.0071 | 303 | 1094 | 14.7 | 12619 | 14.2 | 0.196 |
| 18.858 | 4.7018 | 359 | 2334 | 31.5 | 31734 | 35.7 | 0.231 |
| 19.321 | 4.5903 | 325 | 1650 | 22.2 | 28313 | 31.8 | 0.292 |
| 19.823 | 4.4751 | 412 | 127 | 1.7 | 582 | 0.7 | 0.078 |

TABLE 10-continued

XRD peaks of Form 2*

| 2-Theta | d(A) | BG | Height | I % | Area | I % | FWHM |
|---|---|---|---|---|---|---|---|
| 20.321 | 4.3665 | 327 | 333 | 4.5 | 3361 | 3.8 | 0.172 |
| 21.479 | 4.1336 | 451 | 3245 | 43.8 | 56365 | 63.3 | 0.295 |
| 22.119 | 4.0154 | 612 | 7417 | 100 | 89000 | 100 | 0.204 |
| 22.782 | 3.9 | 536 | 327 | 4.4 | 11890 | 13.4 | 0.618 |
| 23.098 | 3.8475 | 466 | 638 | 8.6 | 11127 | 12.5 | 0.296 |
| 24.3 | 3.6597 | 361 | 4873 | 65.7 | 61170 | 68.7 | 0.213 |
| 25.599 | 3.4769 | 487 | 475 | 6.4 | 7278 | 8.2 | 0.26 |
| 25.88 | 3.4399 | 541 | 562 | 7.6 | 10968 | 12.3 | 0.332 |
| 26.361 | 3.3782 | 372 | 1289 | 17.4 | 20859 | 23.4 | 0.275 |
| 26.739 | 3.3312 | 266 | 660 | 8.9 | 13196 | 14.8 | 0.34 |
| 27.938 | 3.1909 | 284 | 560 | 7.6 | 9888 | 11.1 | 0.3 |
| 28.641 | 3.1142 | 319 | 210 | 2.8 | 2324 | 2.6 | 0.188 |
| 29.398 | 3.0357 | 357 | 100 | 1.3 | 2376 | 2.7 | 0.404 |
| 29.779 | 2.9977 | 295 | 708 | 9.5 | 13168 | 14.8 | 0.316 |
| 30.3 | 2.9473 | 283 | 451 | 6.1 | 6600 | 7.4 | 0.249 |
| 31.658 | 2.8239 | 239 | 667 | 9 | 9228 | 10.4 | 0.235 |
| 32.519 | 2.7511 | 221 | 191 | 2.6 | 2896 | 3.3 | 0.258 |
| 33.903 | 2.6419 | 213 | 72 | 1 | 876 | 1 | 0.207 |
| 34.82 | 2.5744 | 229 | 110 | 1.5 | 3822 | 4.3 | 0.591 |
| 35.504 | 2.5264 | 230 | 97 | 1.3 | 3876 | 4.4 | 0.679 |

D. Form 3

Figure 3A:
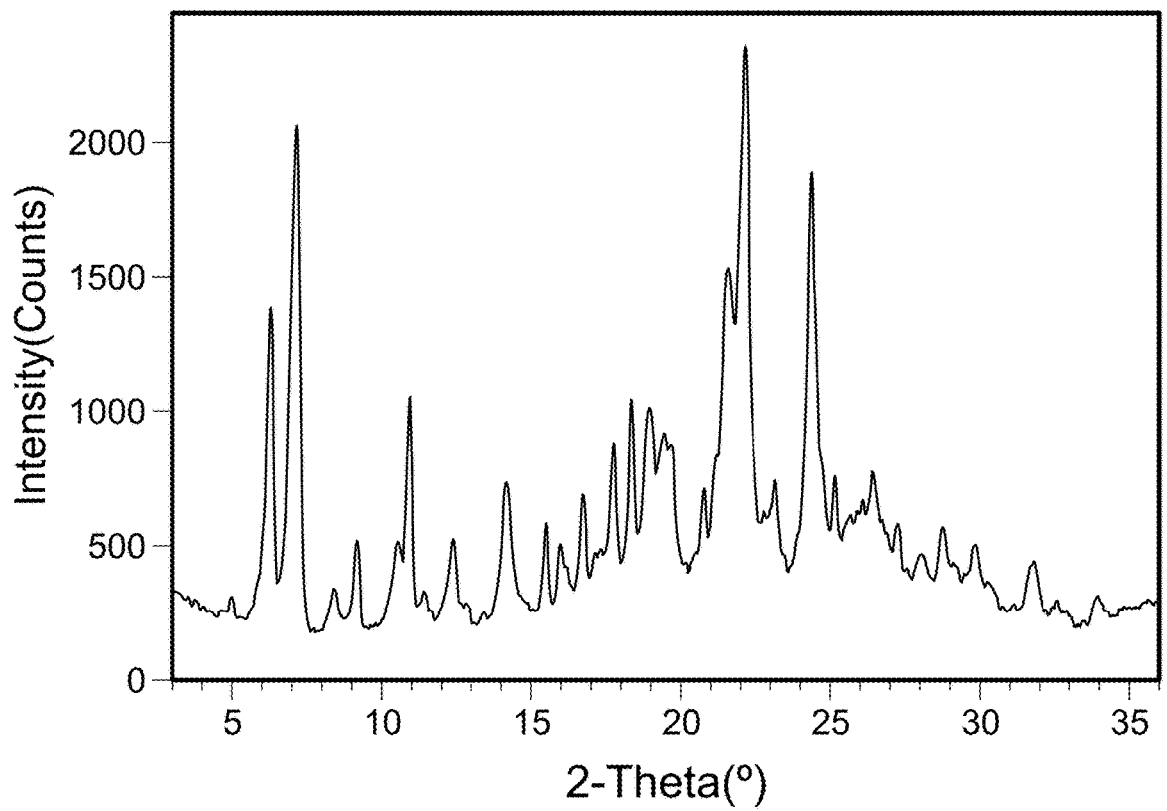
FIGS. 3A-3C are scans of polymorph Form 3 of the compound of Formula (I).
Figure 3B:
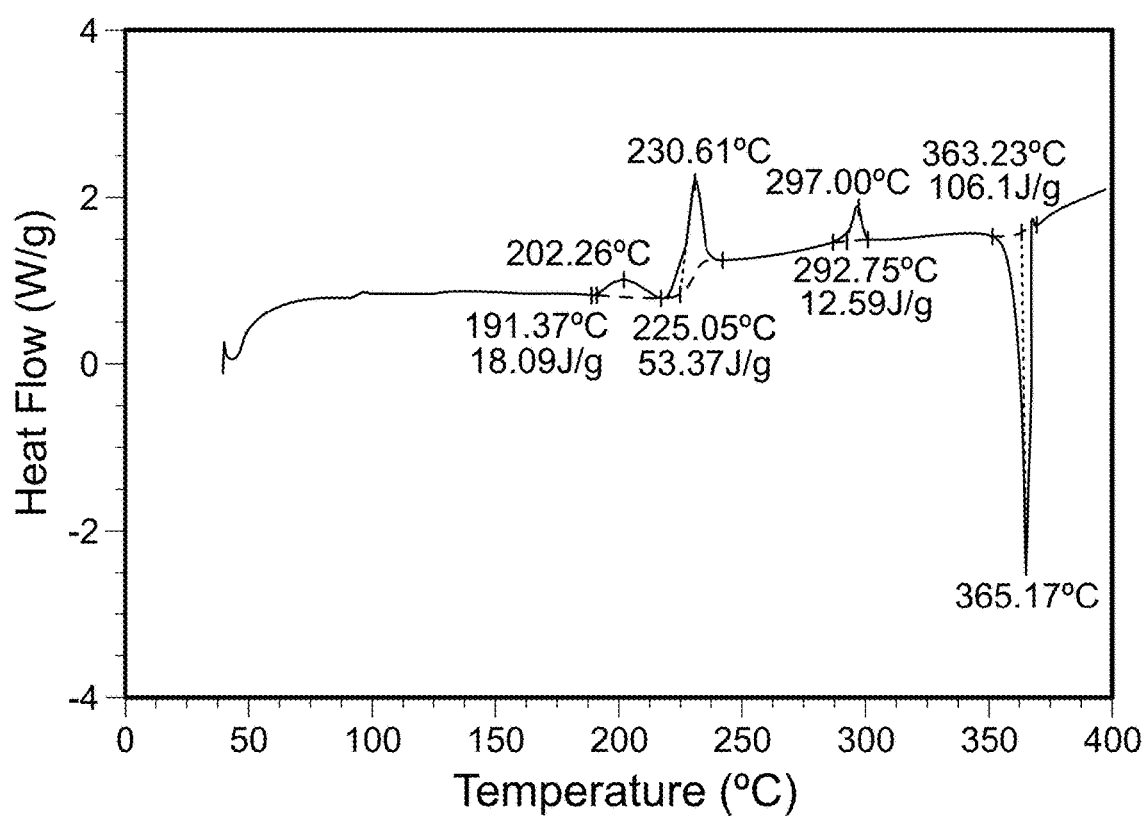

The experiments that generated Form 3 are shown in Table 11, below. XRD and DSC scans of Form 3 were taken (FIGS. 3A and 3B, respectively). Table 12, below, shows the XRD peaks of Form 3. Multiple exotherms and endotherms were observed from the DSC scan of Form 3.

Figure 3C:
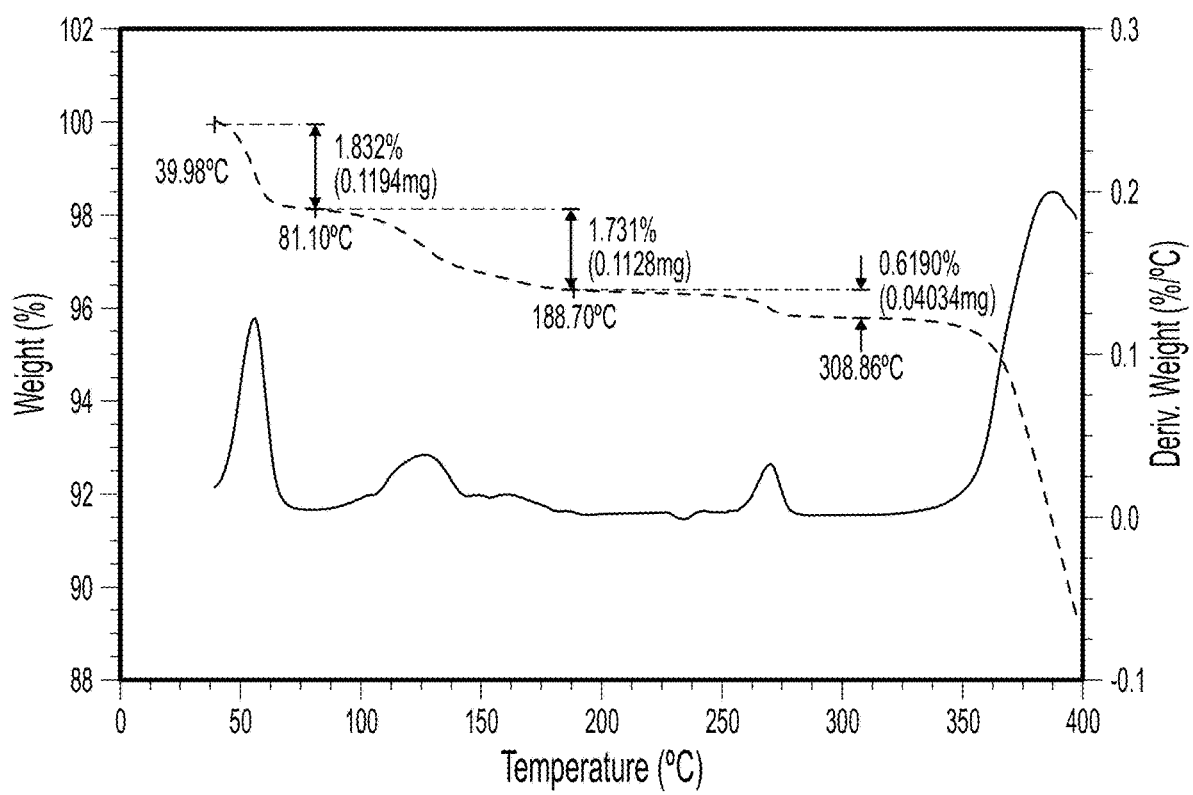

A TGA scan of Form 3 was taken (FIG. 3C) and showed a 1.6% weight loss of the solid before 81° C., followed by a 1.7% weight loss between 81° C. and 169° C.

Form 3 was obtained from IPAc at RT, while Form 3* was obtained from reslurry in n-butyl acetate.

TABLE 11

Summary of experiments that generated Form 3 and Form 3*

| Form | Solvent | Temperature | Wet | Dry |
|---|---|---|---|---|
| Form 3 | IPAc | RT | Form 3 | Form 3 |
|  | n-Butyl acetate | RT | Form 3* | Form 3 |
| Form 3* | n-Butyl acetate | RT | Form 3* | Form 3 |

TABLE 12

XRD peaks of Form 3

| 2-Theta | d(A) | BG | Height | I % | Area | I % | FWHM |
|---|---|---|---|---|---|---|---|
| 5.024 | 17.5739 | 231 | 87 | 4.4 | 845 | 1.9 | 0.165 |
| 6.34 | 13.9294 | 368 | 1030 | 52.5 | 12361 | 27.5 | 0.204 |
| 7.219 | 12.2357 | 182 | 1962 | 100 | 36491 | 81.1 | 0.316 |
| 8.441 | 10.4665 | 188 | 159 | 8.1 | 3261 | 7.2 | 0.349 |
| 9.237 | 9.5659 | 207 | 320 | 16.3 | 3365 | 7.5 | 0.179 |
| 10.561 | 8.37 | 240 | 278 | 14.2 | 6270 | 13.9 | 0.383 |
| 10.998 | 8.0381 | 217 | 849 | 43.3 | 17119 | 38.1 | 0.343 |
| 11.46 | 7.715 | 256 | 87 | 4.4 | 662 | 1.5 | 0.129 |
| 12.439 | 7.11 | 215 | 311 | 15.9 | 6502 | 14.5 | 0.355 |
| 12.865 | 6.8756 | 209 | 92 | 4.7 | 1599 | 3.6 | 0.295 |
| 14.22 | 6.2233 | 231 | 522 | 26.6 | 12265 | 27.3 | 0.399 |
| 15.524 | 5.7034 | 273 | 311 | 15.9 | 2957 | 6.6 | 0.162 |
| 16.021 | 5.5276 | 309 | 218 | 11.1 | 2669 | 5.9 | 0.208 |
| 16.78 | 5.2792 | 368 | 330 | 16.8 | 3780 | 8.4 | 0.195 |
| 17.181 | 5.1567 | 384 | 99 | 5 | 2614 | 5.8 | 0.449 |
| 17.782 | 4.9837 | 428 | 496 | 25.3 | 6264 | 13.9 | 0.215 |
| 18.381 | 4.8227 | 509 | 551 | 28.1 | 5102 | 11.3 | 0.157 |
| 19.02 | 4.6622 | 447 | 589 | 30 | 20513 | 45.6 | 0.592 |
| 19.758 | 4.4896 | 487 | 423 | 21.6 | 14362 | 31.9 | 0.577 |
| 20.8 | 4.267 | 520 | 214 | 10.9 | 1518 | 3.4 | 0.121 |
| 21.19 | 4.1893 | 408 | 418 | 21.3 | 4581 | 10.2 | 0.186 |

TABLE 12-continued

XRD peaks of Form 3

| 2-Theta | d(A) | BG | Height | I % | Area | I % | FWHM |
|---|---|---|---|---|---|---|---|
| 21.6 | 4.1107 | 553 | 1017 | 51.8 | 41986 | 93.3 | 0.702 |
| 22.181 | 4.0044 | 662 | 1736 | 88.5 | 44981 | 100 | 0.44 |
| 23.185 | 3.8333 | 508 | 259 | 13.2 | 3327 | 7.4 | 0.218 |
| 24.44 | 3.6392 | 467 | 1441 | 73.4 | 29510 | 65.6 | 0.348 |
| 25.198 | 3.5313 | 551 | 232 | 11.8 | 1362 | 3 | 0.1 |
| 25.618 | 3.4745 | 557 | 79 | 4 | 365 | 0.8 | 0.079 |
| 26.103 | 3.4109 | 512 | 180 | 9.2 | 7374 | 16.4 | 0.696 |
| 26.479 | 3.3634 | 475 | 306 | 15.6 | 11652 | 25.9 | 0.647 |
| 27.3 | 3.264 | 455 | 133 | 6.8 | 1016 | 2.3 | 0.13 |
| 28.04 | 3.1796 | 378 | 93 | 4.7 | 1485 | 3.3 | 0.271 |
| 28.82 | 3.0953 | 372 | 201 | 10.2 | 3455 | 7.7 | 0.292 |
| 29.258 | 3.0499 | 362 | 76 | 3.9 | 2580 | 5.7 | 0.577 |
| 29.88 | 2.9878 | 334 | 191 | 9.7 | 4011 | 8.9 | 0.357 |
| 31.802 | 2.8115 | 251 | 205 | 10.4 | 4094 | 9.1 | 0.34 |
| 32.62 | 2.7429 | 231 | 87 | 4.4 | 1109 | 2.5 | 0.217 |
| 32.943 | 2.7167 | 215 | 52 | 2.7 | 1107 | 2.5 | 0.362 |
| 33.961 | 2.6375 | 217 | 101 | 5.1 | 1686 | 3.7 | 0.284 |

E. Form 4

Figure 4A:
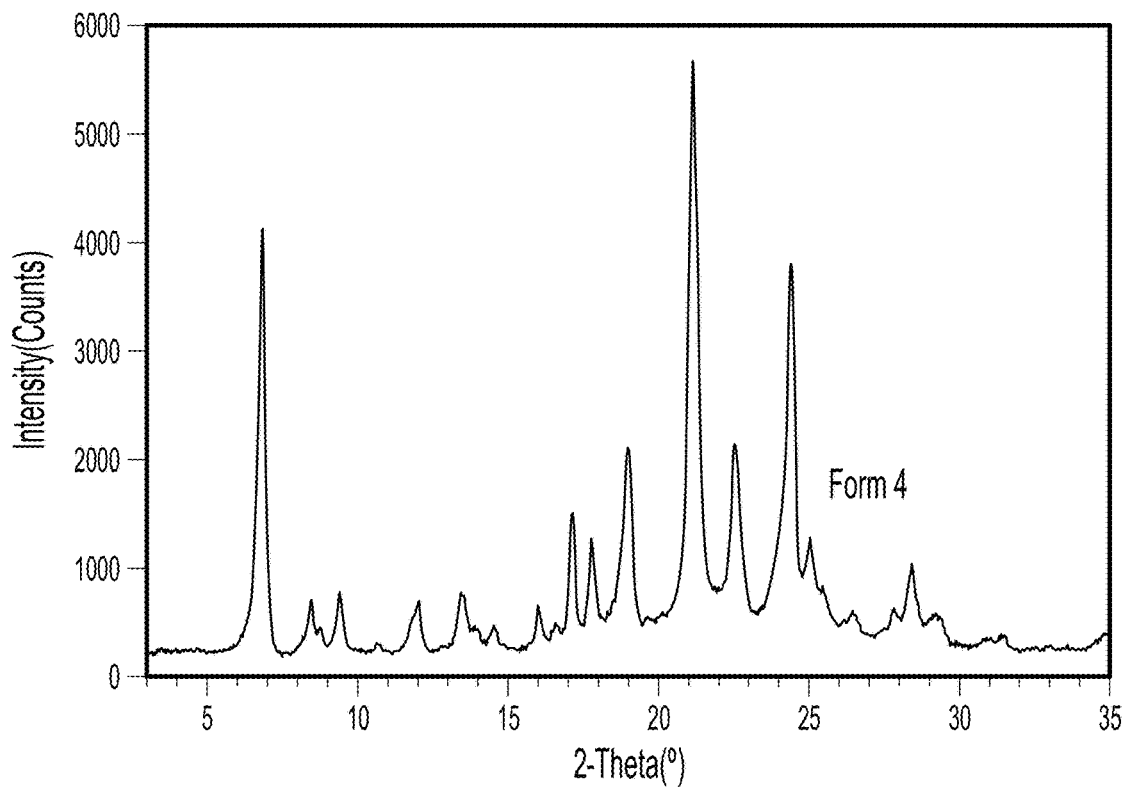
FIGS. 4A-4I are scans of polymorph Forms 4, 4*, and 4** of the compound of Formula (I).
Figure 4B:
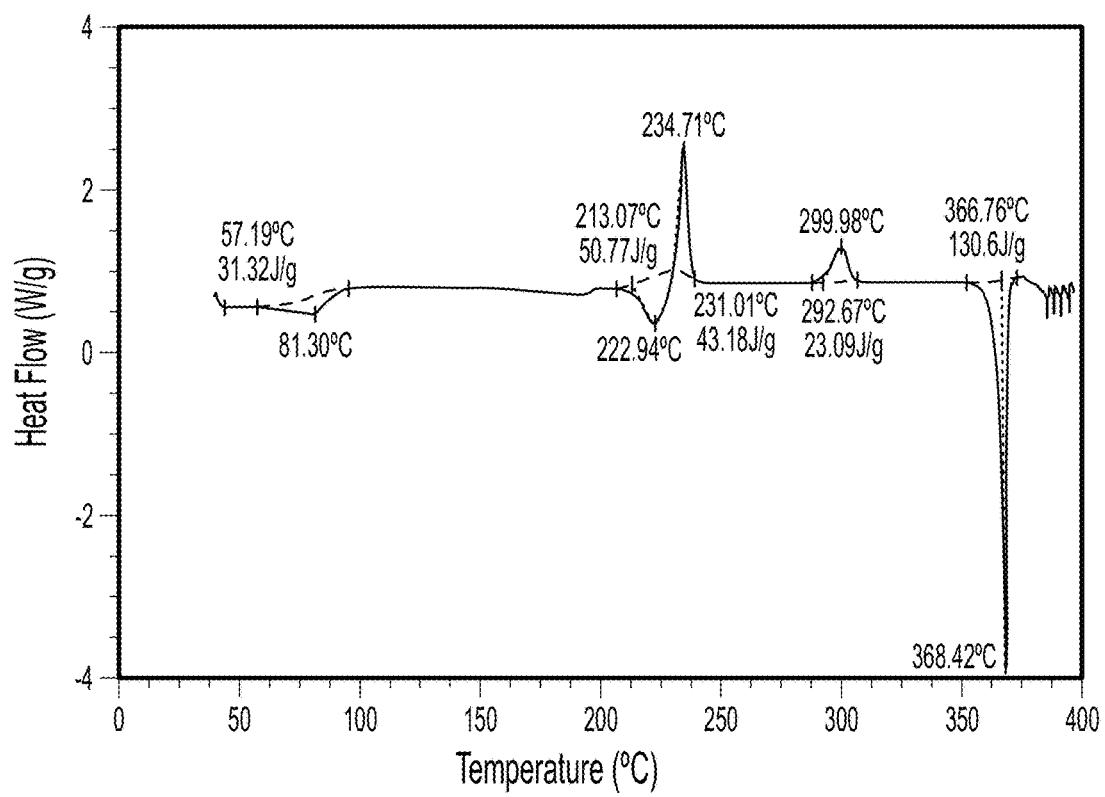

The experiments that generated Forms 4, 4*, and 4** are shown in Table 13, below. XRD of Forms 4, 4*, and 4** were taken (FIGS. 4A, 4D, and 4G, respectively). Tables 14 and 15, below, show the XRD peaks of Form 4 and Form 4*, respectively. DSC scans of Forms 4, 4*, and 4** were also performed (FIGS. 4B, 4E, and 4H, respectively). According to the DSC scans, Form 4 showed a wide endotherm between 50° C.-100° C., followed by multiple endotherms/exotherms, and then melted at around 367° C. Forms 4* and 4** showed similar DSC patterns as Form 4.

Figure 4C:
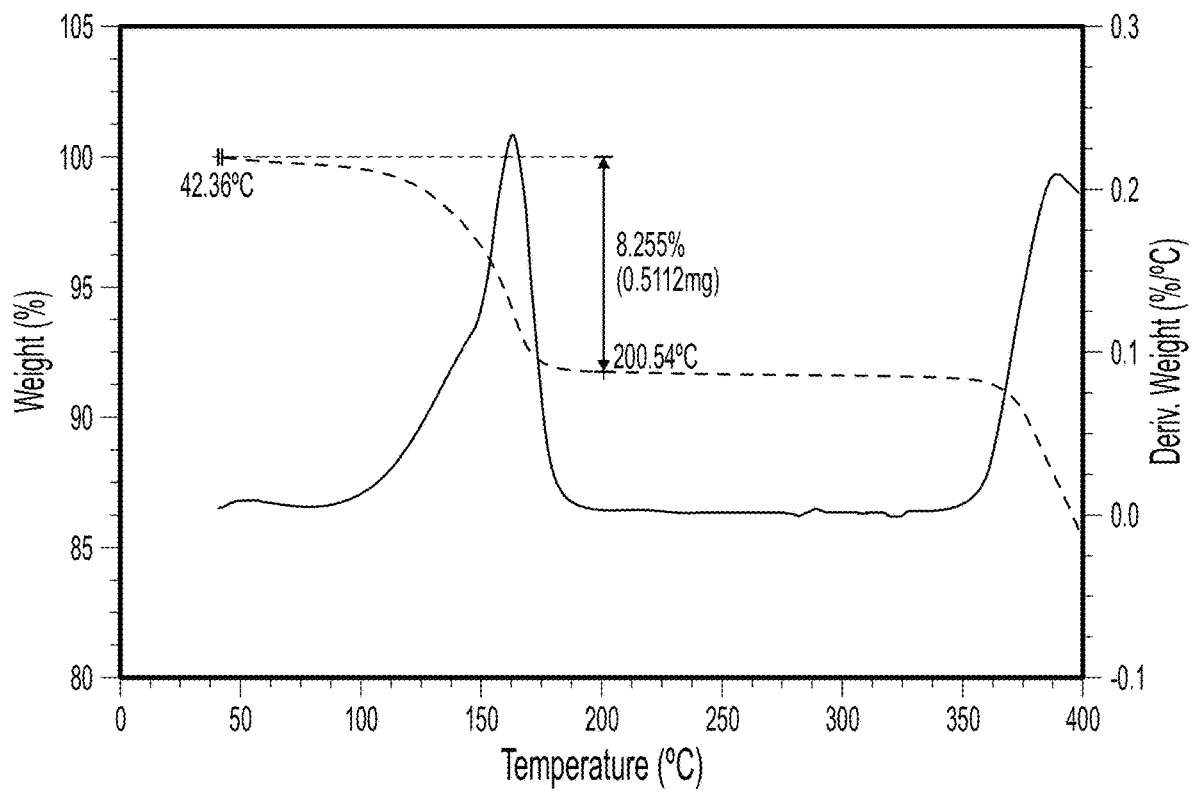
Figure 4D:
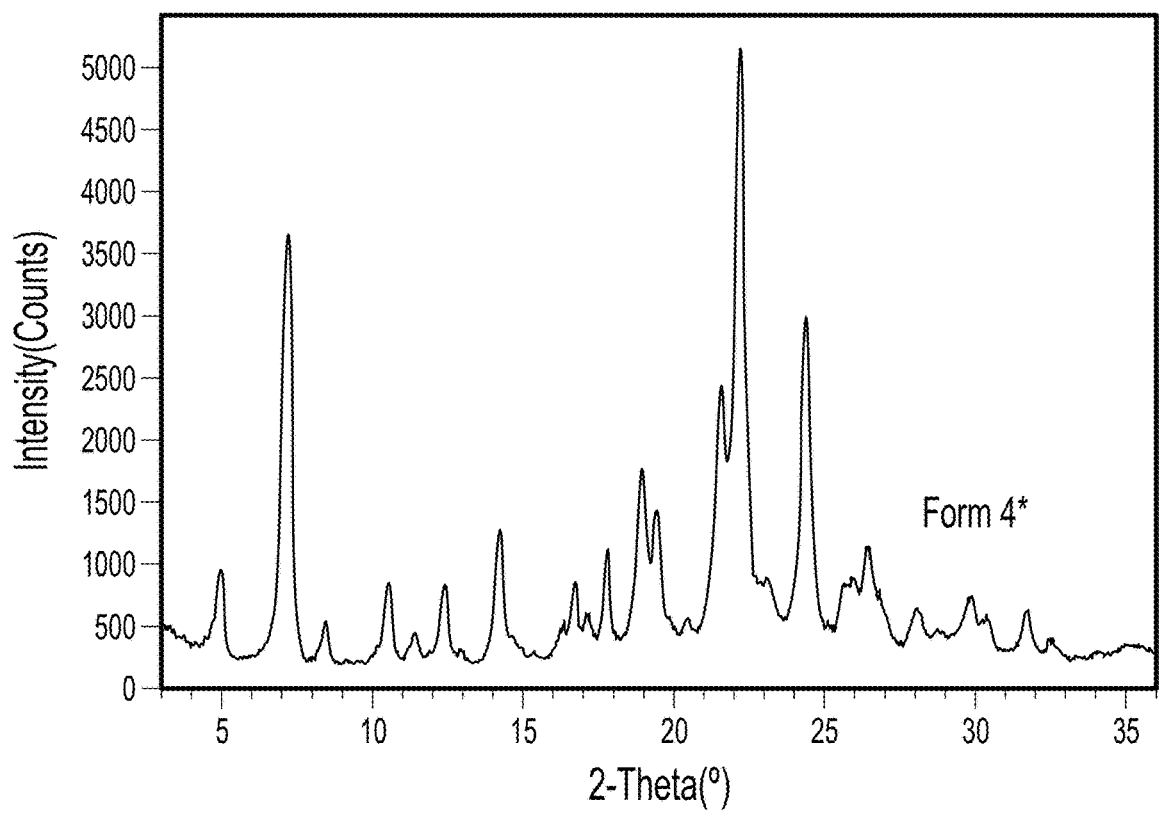
Figure 4E:
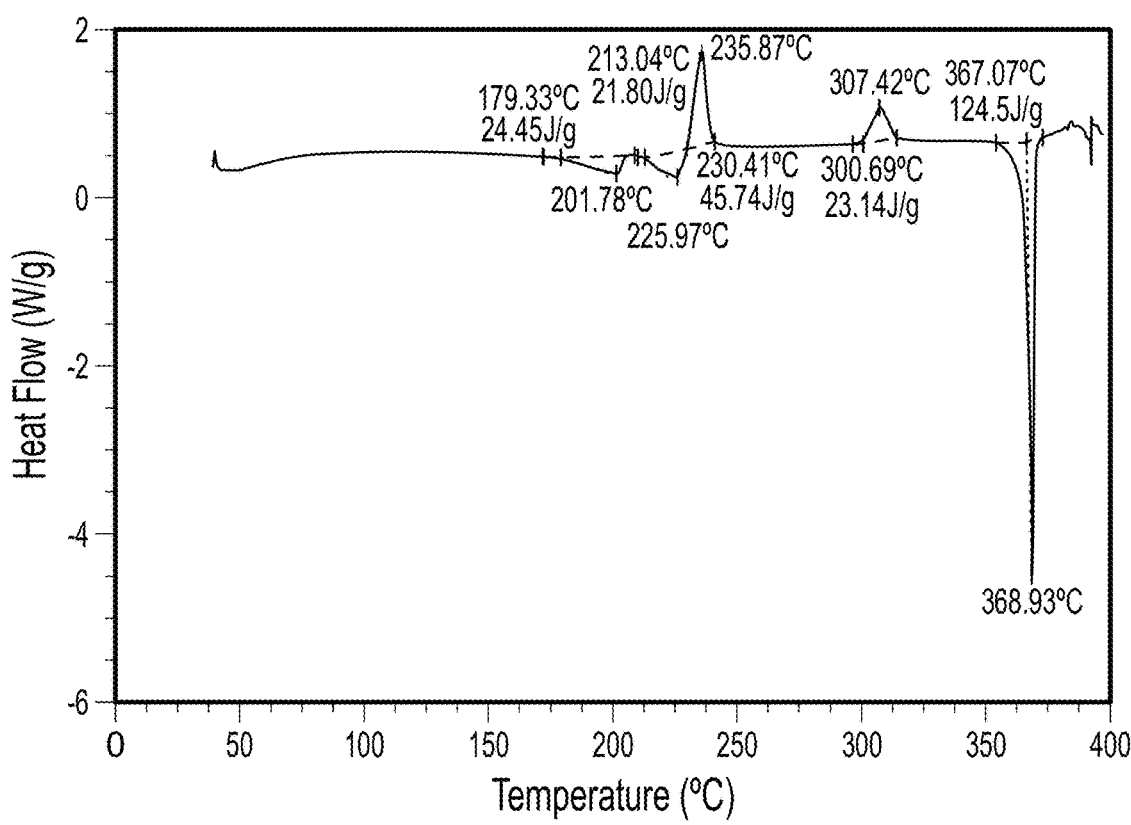
Figure 4F:
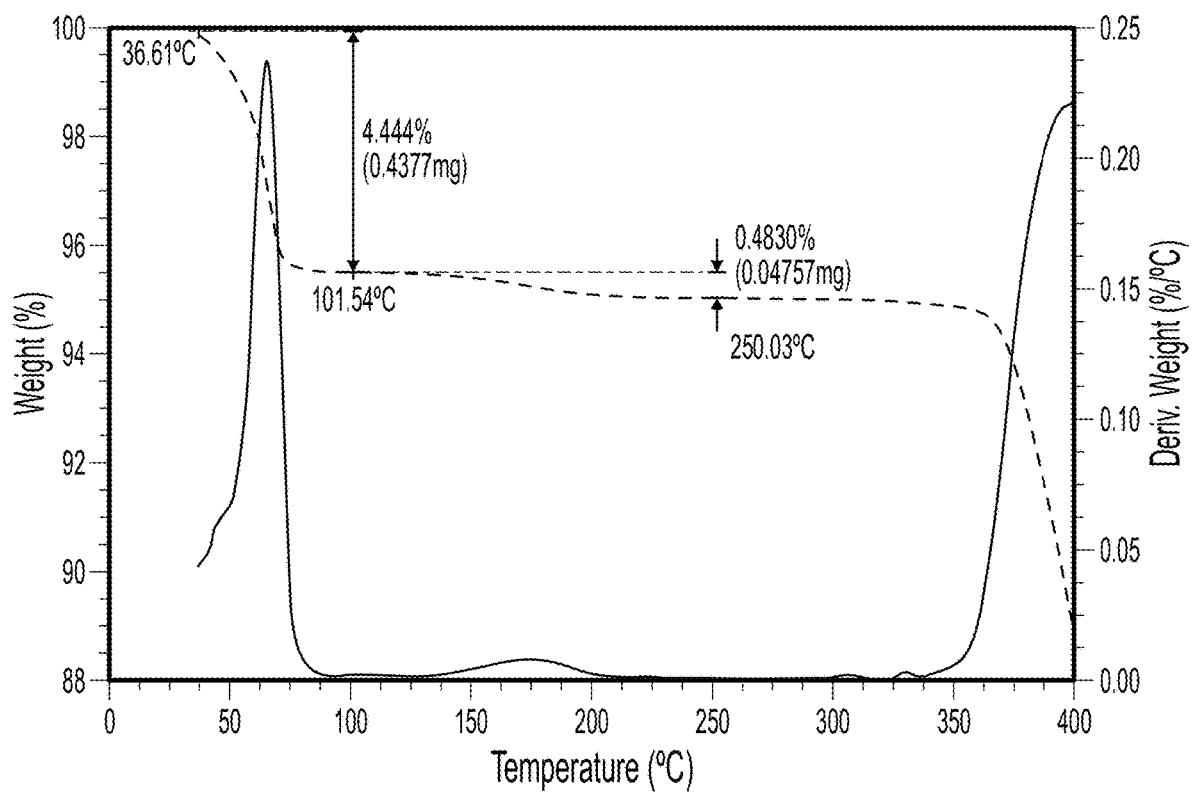
Figure 4G:
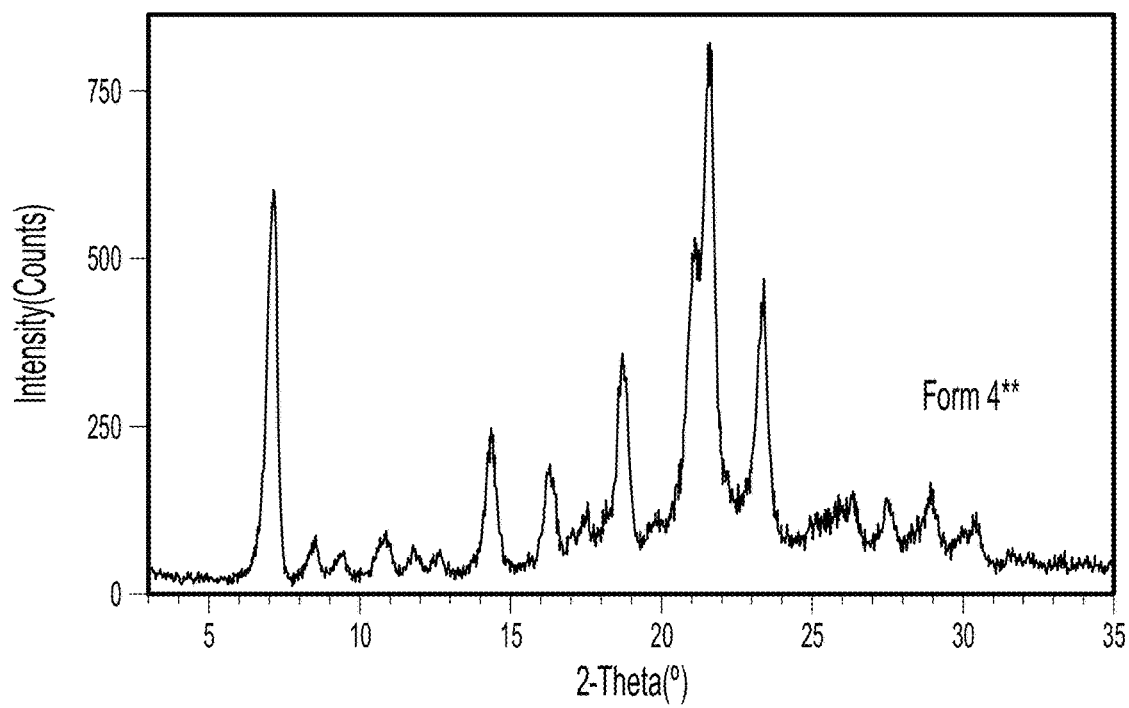
Figure 4H:
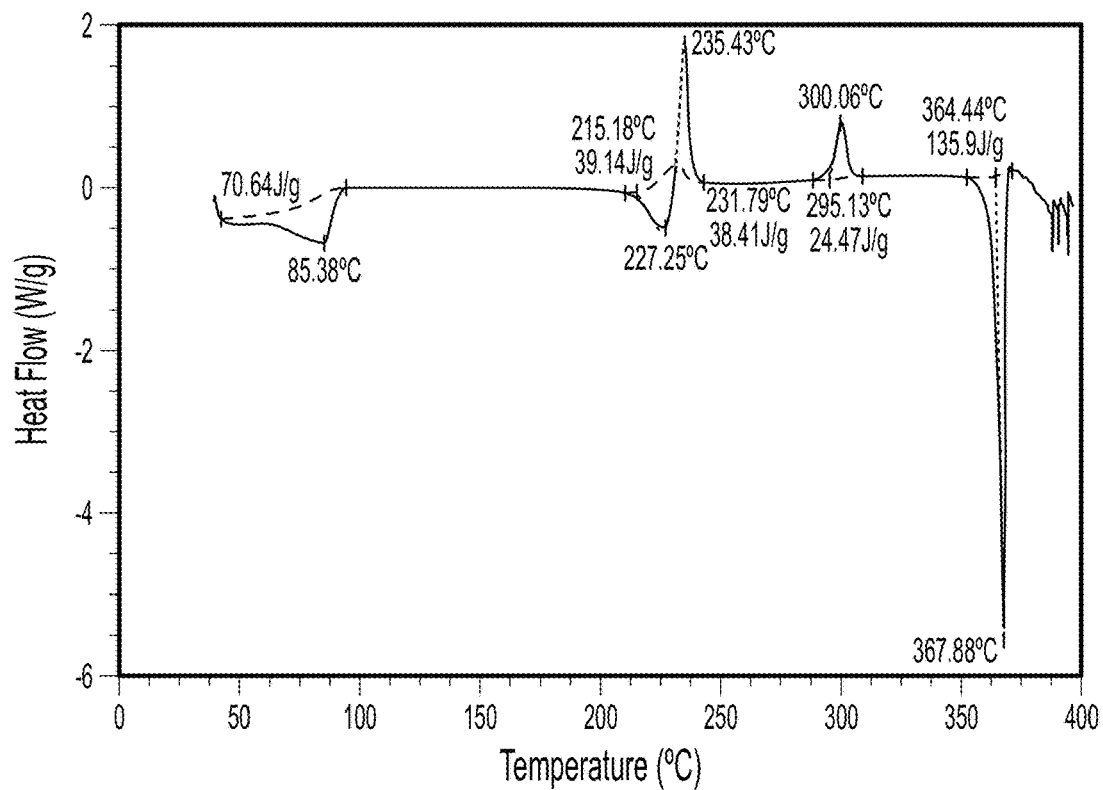
Figure 4I:
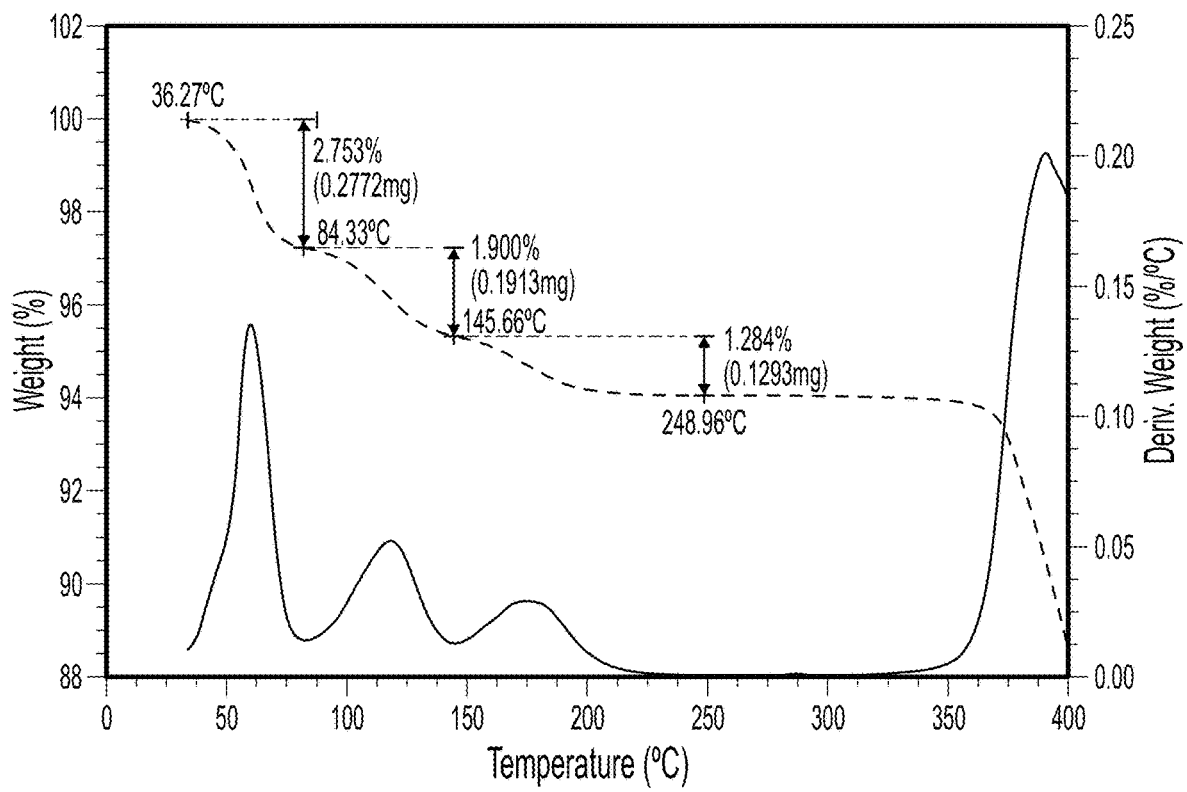

TGA scans of Form 4, Form 4*, and Form 4** were taken (FIGS. 4C, 4F, and 4I, respectively). For Form 4, there was an 8.3% weight loss before 200° C.; for Form 4*, there was a 4.4% weight loss before 102° C., followed by a 0.5% weight loss between 102° C. and 250° C.; and for Form 4**, there were three stages of weight loss, which were 2.8%, 1.9%, and 1.3%, respectively.

These solid forms were obtained from methyl acetate, n-propanol, MIBK, MtBE, ethyl acetate, acetone/water, and ethyl acetate/water.

TABLE 13

Summary of experiments that generated Forms 4, 4*, and 4**

| Form | Solvent | Temperature | Wet | Dry |
|---|---|---|---|---|
| Form 4 | EA | RT | Form 4* | Form 4 |
|  | EA | 50° C. | Form 4* | Form 4 |
|  | MA | RT | Form 4 | Form 4 |
|  | MA | 50° C. | Form 4 | Form 4 |
|  | MA/water | 50° C. | Form 12 | Form 4 |
|  | MtBE | 50° C. | Form 5* | Form 4 |
|  | n-Propanol | RT | Form 4 | Form 4* |
| Form 4* | EA | RT | Form 4* | Form 4* |
|  | EA | 50° C. | Form 4* | Form 4 |
|  | EA/water | 50° C. | Form 4* | Form 4* |
|  | n-Propanol | RT | Form 4 | Form 4* |
| Form 4** | Acetone/water | RT | Solvate 2 | Form 4** |
|  | Acetone | 50° C. | Solvate 2 | Form 4** |
|  | n-Propanol | 50° C. | Form 4 | Form 4** |
|  | Acetone/water | 50° C. | Form 4** | Form 4** |

*Amount of water in binary solvents is 5%

TABLE 14

XRD peaks of Form 4

| 2-Theta | d(A) | BG | Height | I % | Area | I % | FWHM |
|---|---|---|---|---|---|---|---|
| 3.433 | 25.7129 | 197 | 48 | 1 | 697 | 0.7 | 0.247 |
| 7.019 | 12.5829 | 222 | 3897 | 77.3 | 66968 | 69.4 | 0.292 |
| 8.659 | 10.203 | 242 | 448 | 8.9 | 8198 | 8.5 | 0.311 |
| 8.98 | 9.8395 | 223 | 219 | 4.3 | 7649 | 7.9 | 0.594 |
| 9.64 | 9.1672 | 251 | 516 | 10.2 | 6969 | 7.2 | 0.23 |
| 10.917 | 8.0978 | 210 | 77 | 1.5 | 1041 | 1.1 | 0.23 |
| 12.339 | 7.1673 | 220 | 465 | 9.2 | 9572 | 9.9 | 0.35 |
| 13.82 | 6.4023 | 268 | 501 | 9.9 | 11493 | 11.9 | 0.39 |
| 14.278 | 6.1981 | 271 | 192 | 3.8 | 7288 | 7.6 | 0.645 |
| 14.923 | 5.9314 | 288 | 172 | 3.4 | 1636 | 1.7 | 0.162 |
| 16.462 | 5.3804 | 310 | 329 | 6.5 | 3066 | 3.2 | 0.158 |
| 17.041 | 5.199 | 375 | 105 | 2.1 | 942 | 1 | 0.153 |
| 17.638 | 5.0241 | 435 | 1073 | 21.3 | 13511 | 14 | 0.214 |
| 18.281 | 4.8488 | 487 | 772 | 15.3 | 9782 | 10.1 | 0.215 |
| 19.52 | 4.5437 | 504 | 1590 | 31.5 | 31949 | 33.1 | 0.342 |
| 21.759 | 4.081 | 677 | 5040 | 100 | 96504 | 100 | 0.326 |
| 23.22 | 3.8275 | 693 | 1457 | 28.9 | 28109 | 29.1 | 0.328 |
| 25.12 | 3.5421 | 710 | 3091 | 61.3 | 69330 | 71.8 | 0.381 |
| 25.76 | 3.4556 | 455 | 827 | 16.4 | 22029 | 22.8 | 0.453 |
| 27.221 | 3.2733 | 419 | 180 | 3.6 | 2915 | 3 | 0.275 |
| 28.638 | 3.1145 | 409 | 210 | 4.2 | 4338 | 4.5 | 0.351 |
| 29.259 | 3.0498 | 461 | 568 | 11.3 | 11998 | 12.4 | 0.359 |
| 30.137 | 2.9629 | 409 | 149 | 3 | 1946 | 2 | 0.222 |
| 31.817 | 2.8102 | 253 | 110 | 2.2 | 4034 | 4.2 | 0.623 |
| 32.319 | 2.7677 | 245 | 137 | 2.7 | 3829 | 4 | 0.475 |

TABLE 15

XRD peaks of Form 4*

| 2-Theta | d(A) | BG | Height | I % | Area | I % | FWHM |
|---|---|---|---|---|---|---|---|
| 4.981 | 17.7282 | 270 | 684 | 15.8 | 12231 | 12.6 | 0.304 |
| 7.22 | 12.2329 | 244 | 3416 | 79 | 65744 | 67.8 | 0.327 |
| 8.459 | 10.4447 | 202 | 335 | 7.7 | 4814 | 5 | 0.244 |
| 10.56 | 8.3707 | 219 | 629 | 14.5 | 10739 | 11.1 | 0.29 |
| 11.42 | 7.7419 | 240 | 203 | 4.7 | 2908 | 3 | 0.244 |
| 12.42 | 7.1209 | 221 | 614 | 14.2 | 11445 | 11.8 | 0.317 |
| 13.019 | 6.7947 | 238 | 59 | 1.4 | 423 | 0.4 | 0.122 |
| 14.26 | 6.2057 | 227 | 1052 | 24.3 | 20787 | 21.4 | 0.336 |
| 16.318 | 5.4274 | 409 | 85 | 2 | 665 | 0.7 | 0.133 |
| 16.722 | 5.2973 | 332 | 496 | 11.5 | 8980 | 9.3 | 0.308 |
| 17.199 | 5.1515 | 393 | 226 | 5.2 | 3448 | 3.6 | 0.259 |
| 17.82 | 4.9733 | 402 | 725 | 16.8 | 8502 | 8.8 | 0.199 |
| 18.98 | 4.672 | 432 | 1352 | 31.3 | 36895 | 38.1 | 0.464 |
| 19.44 | 4.5623 | 439 | 990 | 22.9 | 28546 | 29.4 | 0.49 |
| 20.46 | 4.3371 | 444 | 119 | 2.8 | 1163 | 1.2 | 0.166 |
| 21.58 | 4.1144 | 458 | 1982 | 45.8 | 71568 | 73.8 | 0.614 |
| 22.22 | 3.9974 | 837 | 4325 | 100 | 96937 | 100 | 0.381 |
| 23.16 | 3.8373 | 758 | 114 | 2.6 | 1085 | 1.1 | 0.162 |
| 24.42 | 3.6421 | 522 | 2466 | 57 | 48977 | 50.5 | 0.338 |
| 25.679 | 3.4663 | 590 | 252 | 5.8 | 5211 | 5.4 | 0.352 |
| 26.5 | 3.3607 | 470 | 671 | 15.5 | 23177 | 23.9 | 0.587 |
| 26.95 | 3.3056 | 356 | 313 | 7.2 | 3645 | 3.8 | 0.198 |
| 28.118 | 3.1709 | 385 | 255 | 5.9 | 5045 | 5.2 | 0.336 |
| 29.9 | 2.9858 | 360 | 383 | 8.9 | 13112 | 13.5 | 0.582 |
| 30.421 | 2.9359 | 346 | 239 | 5.5 | 5602 | 5.8 | 0.398 |
| 31.779 | 2.8134 | 293 | 336 | 7.8 | 5905 | 6.1 | 0.299 |
| 32.618 | 2.743 | 267 | 124 | 2.9 | 1934 | 2 | 0.265 |

F. Forms 5 and 5*

Figure 5A:
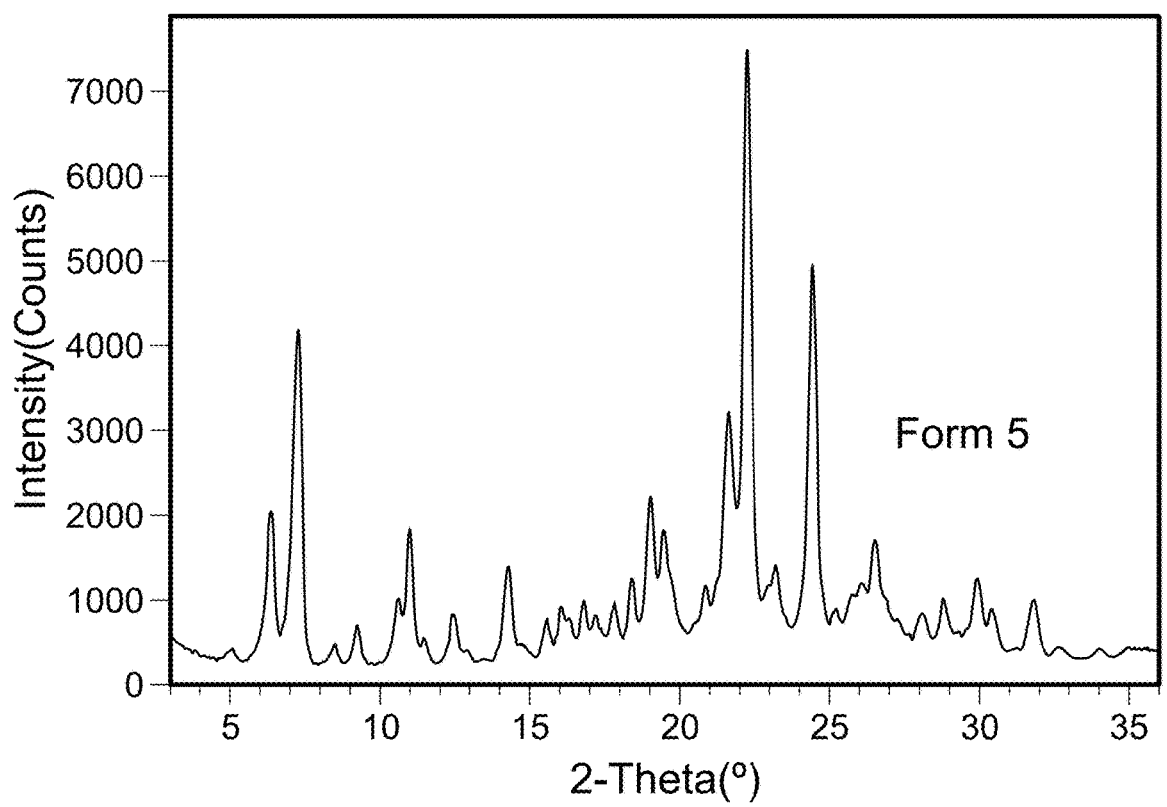
FIGS. 5A-5D are scans of polymorph Forms 5 and 5* of the compound of Formula (I).
Figure 5B:
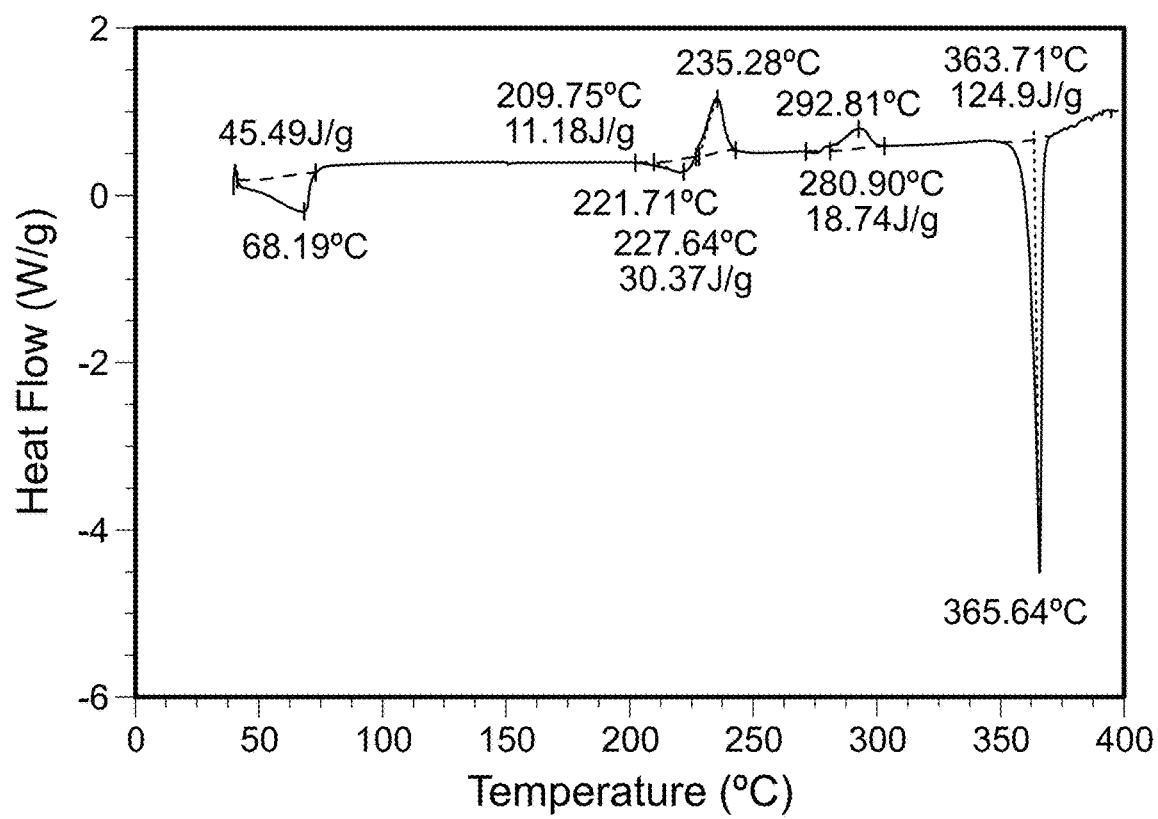
Figure 5C:
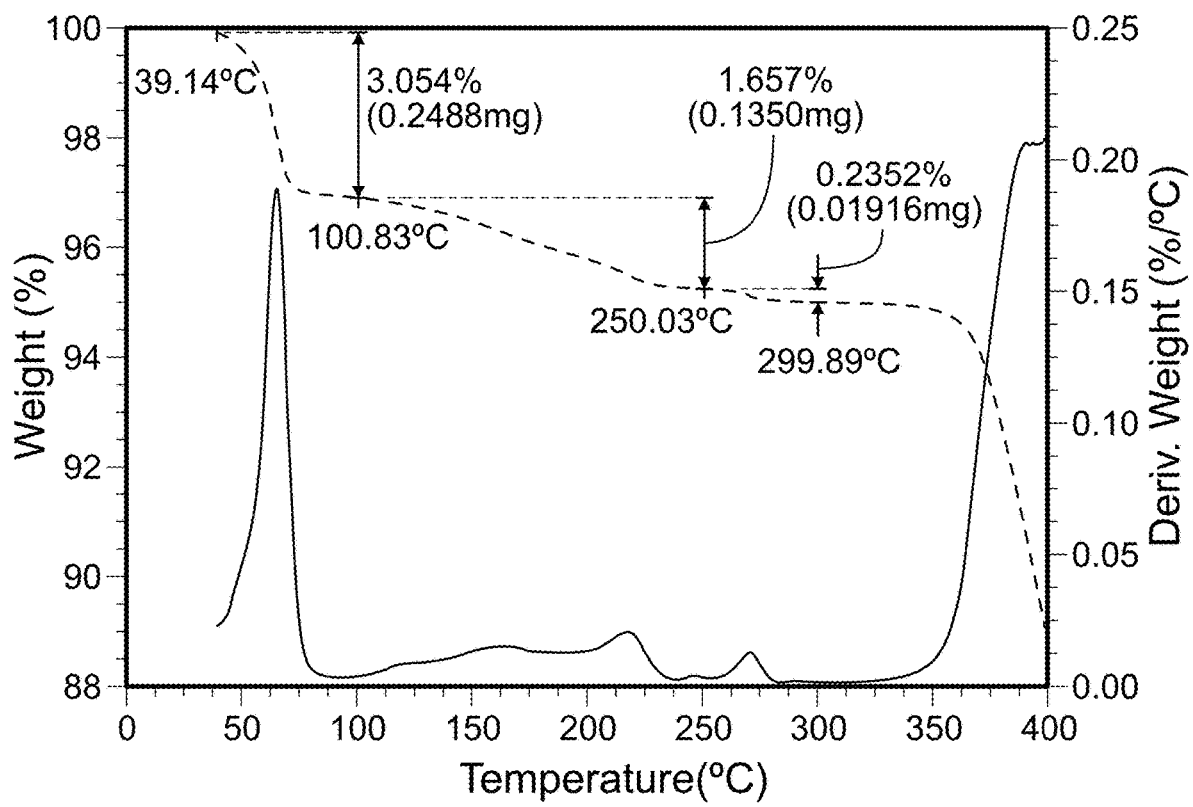
Figure 5D:
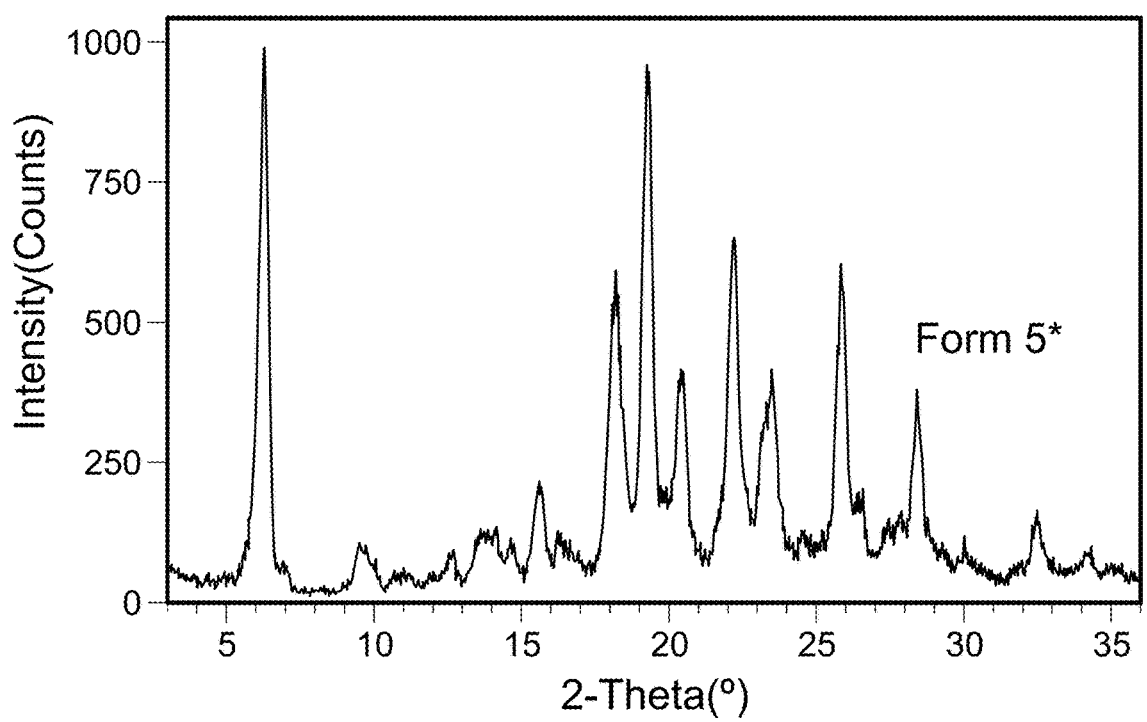

The experiments that generated Forms 5 and 5* are shown in Table 16, below. XRD scans of Forms 5 and 5* were taken (FIGS. 5A and 5D, respectively). The XRD peaks of Form 5 are shown in Table 17, below. A DSC scan of Form 5 was also performed and showed a wide endotherm between 50° C.-100° C., and multiple endotherms and exotherms before melting at 363° C. (FIG. 5B).

A TGA scan of Form 5 solid showed a 3.1% weight loss before 100° C., followed by a 1.7% weight loss between 100° C. and 250° C. (FIG. 5C).

Forms 5 and 5* were obtained from slurrying Form 12 in MtBE at RT and 50° C. Wet solid showed Form 5*, while dry solid indicated Form 5.

TABLE 16

Summary of experiments that generated Forms 5 and 5*

| Form | Solvent | Temperature | Wet | Dry |
|---|---|---|---|---|
| Form 5 | MtBE | RT | Form 5* | Form 5 |
| Form 5* | MtBE | RT | Form 5* | Form 5 |
|  | MtBE | 50° C. | Form 5* | Form 4 |

TABLE 17

XRD peaks of Form 5

| 2-Theta | d(A) | BG | Height | I % | Area | I % | FWHM |
|---|---|---|---|---|---|---|---|
| 5.098 | 17.3185 | 260 | 155 | 2.4 | 2464 | 2.1 | 0.27 |
| 6.38 | 13.8428 | 256 | 1778 | 27.7 | 34733 | 29.6 | 0.332 |
| 7.28 | 12.1332 | 214 | 3964 | 61.6 | 78158 | 66.5 | 0.335 |
| 8.518 | 10.3715 | 234 | 241 | 3.7 | 3170 | 2.7 | 0.224 |
| 9.24 | 9.5627 | 227 | 472 | 7.3 | 6614 | 5.6 | 0.238 |
| 10.639 | 8.3083 | 266 | 765 | 11.9 | 20508 | 17.5 | 0.456 |
| 11.019 | 8.0226 | 242 | 1596 | 24.8 | 37620 | 32 | 0.401 |
| 11.483 | 7.6998 | 398 | 133 | 2.1 | 949 | 0.8 | 0.121 |
| 12.44 | 7.1091 | 246 | 584 | 9.1 | 11910 | 10.1 | 0.347 |
| 12.94 | 6.8358 | 249 | 152 | 2.4 | 4189 | 3.6 | 0.469 |
| 14.301 | 6.1883 | 279 | 1114 | 17.3 | 22226 | 18.9 | 0.339 |
| 14.839 | 5.9648 | 300 | 167 | 2.6 | 5989 | 5.1 | 0.61 |
| 15.581 | 5.6827 | 404 | 376 | 5.8 | 4045 | 3.4 | 0.183 |
| 16.08 | 5.5073 | 452 | 459 | 7.1 | 9013 | 7.7 | 0.334 |
| 16.357 | 5.4146 | 509 | 260 | 4 | 11967 | 10.2 | 0.782 |
| 16.839 | 5.2606 | 521 | 473 | 7.4 | 7195 | 6.1 | 0.259 |
| 17.254 | 5.1351 | 550 | 258 | 4 | 4373 | 3.7 | 0.288 |
| 17.839 | 4.968 | 562 | 414 | 6.4 | 4207 | 3.6 | 0.173 |
| 18.439 | 4.8078 | 667 | 590 | 9.2 | 5946 | 5.1 | 0.171 |
| 19.059 | 4.6527 | 616 | 1603 | 24.9 | 35964 | 30.6 | 0.381 |
| 19.5 | 4.5486 | 671 | 1163 | 18.1 | 30384 | 25.9 | 0.444 |
| 20.882 | 4.2506 | 850 | 305 | 4.7 | 2860 | 2.4 | 0.159 |
| 21.679 | 4.0959 | 935 | 2272 | 35.3 | 66194 | 56.4 | 0.495 |
| 22.28 | 3.9867 | 1083 | 6430 | 100 | 117449 | 100 | 0.311 |
| 23.221 | 3.8273 | 856 | 564 | 8.8 | 9429 | 8 | 0.284 |
| 24.461 | 3.6361 | 697 | 4250 | 66.1 | 74709 | 63.6 | 0.299 |
| 25.276 | 3.5206 | 726 | 170 | 2.6 | 1349 | 1.1 | 0.135 |
| 26.081 | 3.4137 | 756 | 442 | 6.9 | 17518 | 14.9 | 0.674 |
| 26.52 | 3.3582 | 689 | 1014 | 15.8 | 34615 | 29.5 | 0.58 |
| 28.139 | 3.1686 | 528 | 306 | 4.8 | 4846 | 4.1 | 0.269 |
| 28.821 | 3.0952 | 533 | 463 | 7.2 | 7067 | 6 | 0.259 |
| 29.94 | 2.9819 | 499 | 755 | 11.7 | 15565 | 13.3 | 0.35 |
| 30.458 | 2.9324 | 435 | 467 | 7.3 | 9861 | 8.4 | 0.359 |
| 31.86 | 2.8065 | 343 | 648 | 10.1 | 13697 | 11.7 | 0.359 |
| 32.642 | 2.741 | 314 | 125 | 1.9 | 2403 | 2 | 0.327 |
| 34.002 | 2.6344 | 298 | 123 | 1.9 | 1956 | 1.7 | 0.27 |

G. Form 6

Figure 6A:
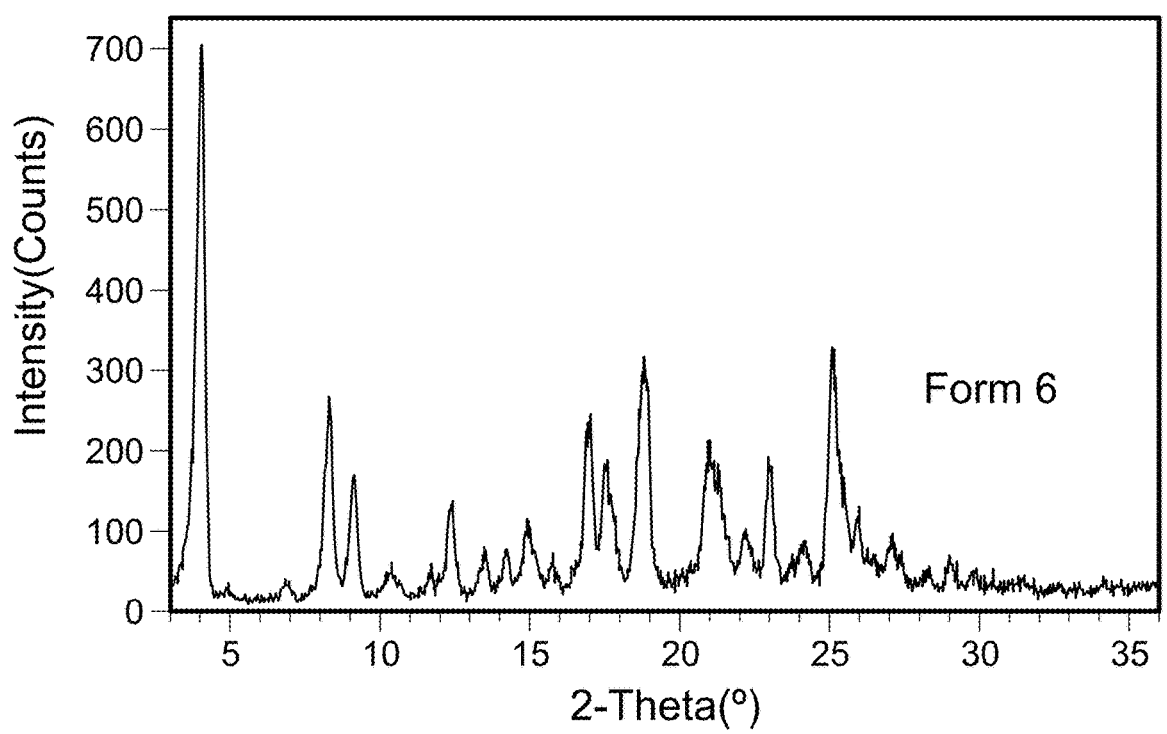
FIGS. 6A and 6B are scans of polymorph Form 6 of the compound of Formula (I).
Figure 6B:
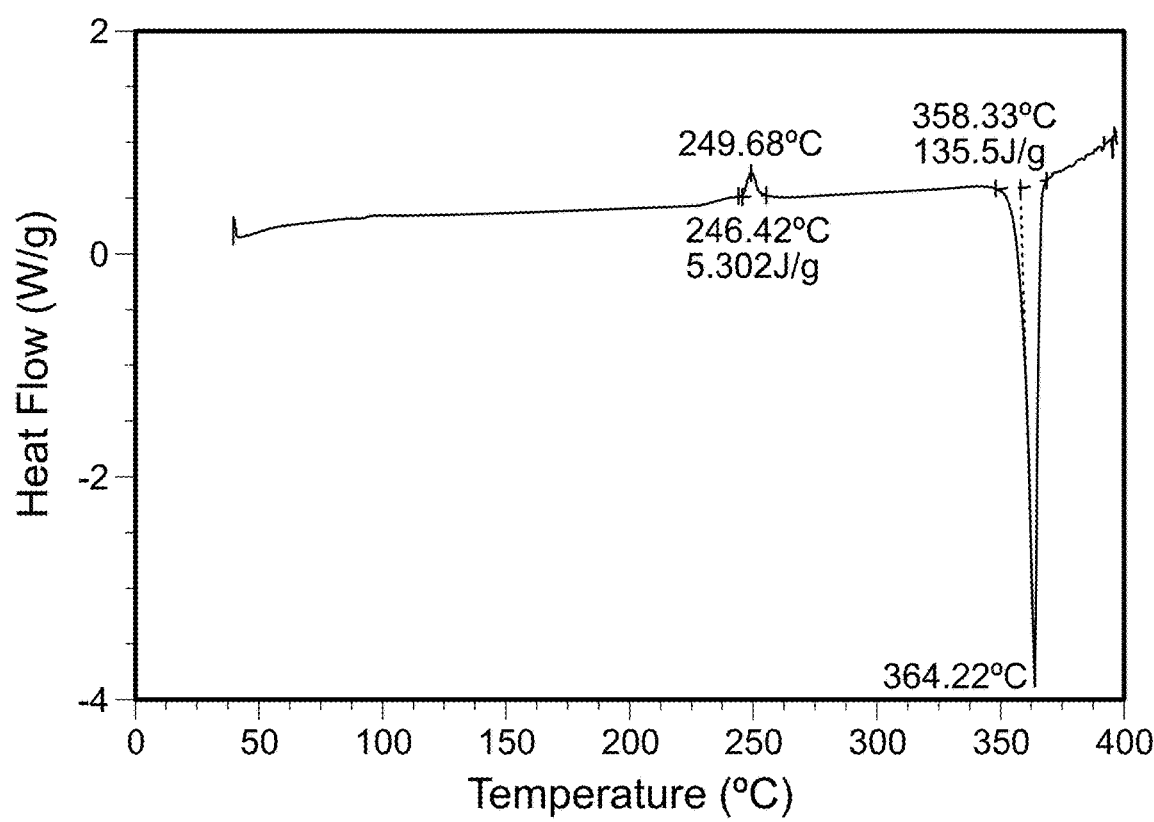

The experiments that generated Form 6 are shown in Table 18, below. XRD and DSC scans of Form 6 were taken (FIGS. 6A and 6B, respectively). According to the DSC scan, the solid showed a small exotherm at 250° C. and a sharp melting endotherm at 358° C. Form 6 was obtained by slurrying starting material in IPA and IPA/5% water at RT and 50° C.

TABLE 18

Summary of experiments that generated Form 6

| Form | Solvent | Temperature | Wet | Dry |
|---|---|---|---|---|
| Form 6 | IPA | RT | Form 6 | Form 6 |
|  | IPA | 50° C. | Form 6 | Form 6 |

TABLE 18-continued

Summary of experiments that generated Form 6

| Form | Solvent | Temperature | Wet | Dry |
|---|---|---|---|---|
| | IPA/water | RT | Form 6 | Form 6 |
| | IPA/water | 50° C. | Form 6 | Form 6 |

*Amount of water in binary solvents is 5%

H. Form 7

Figure 7A:
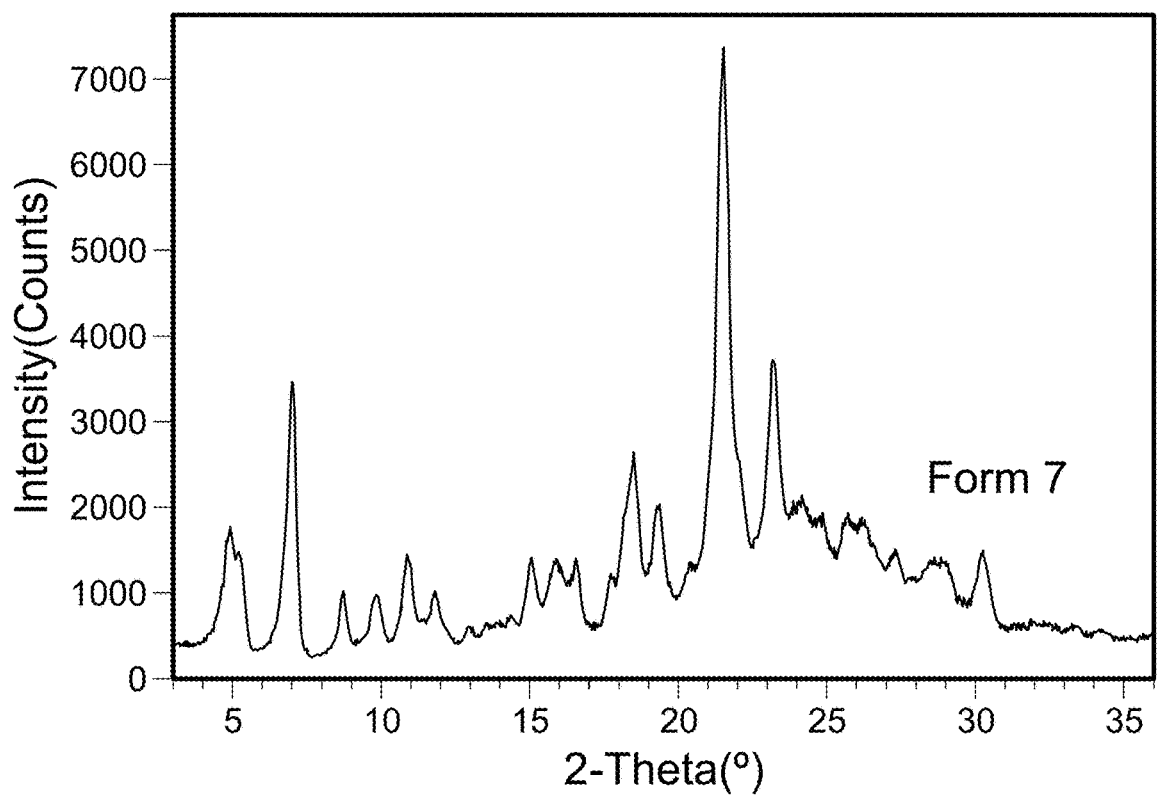
FIGS. 7A-7C are scans of polymorph Form 7 of the compound of Formula (I).
Figure 7B:
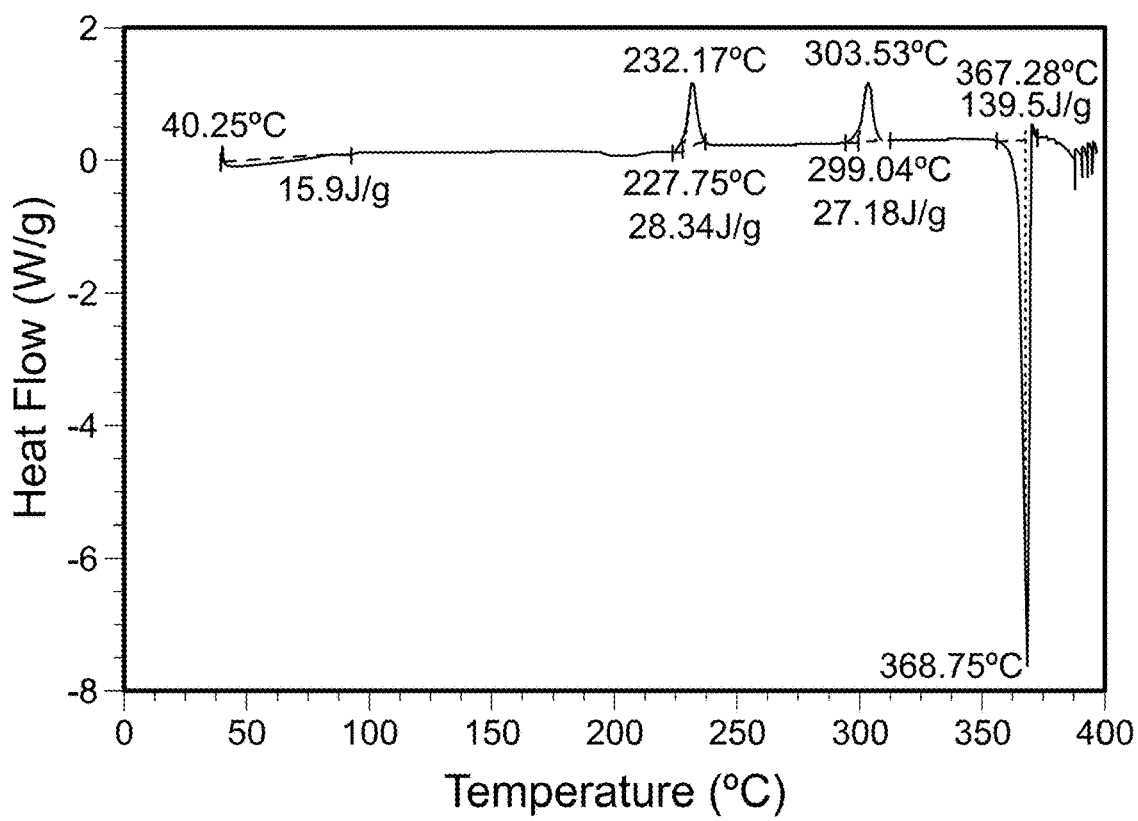

The experiments that generated Form 7 are shown in Table 19, below. XRD and DSC scans of Form 7 were taken (FIGS. 7A and 7B, respectively). The XRD peaks of Form 7 are shown in Table 20, below. According to the DSC scan, the solid showed two exotherms at 227° C. and 299° C., followed by a melting endotherm at 365° C. Form 7 showed low degree of crystallinity on XRD. The double exotherm on the DSC scans may be associated with the low crystallinity observed on the XRD scan.

Figure 7C:
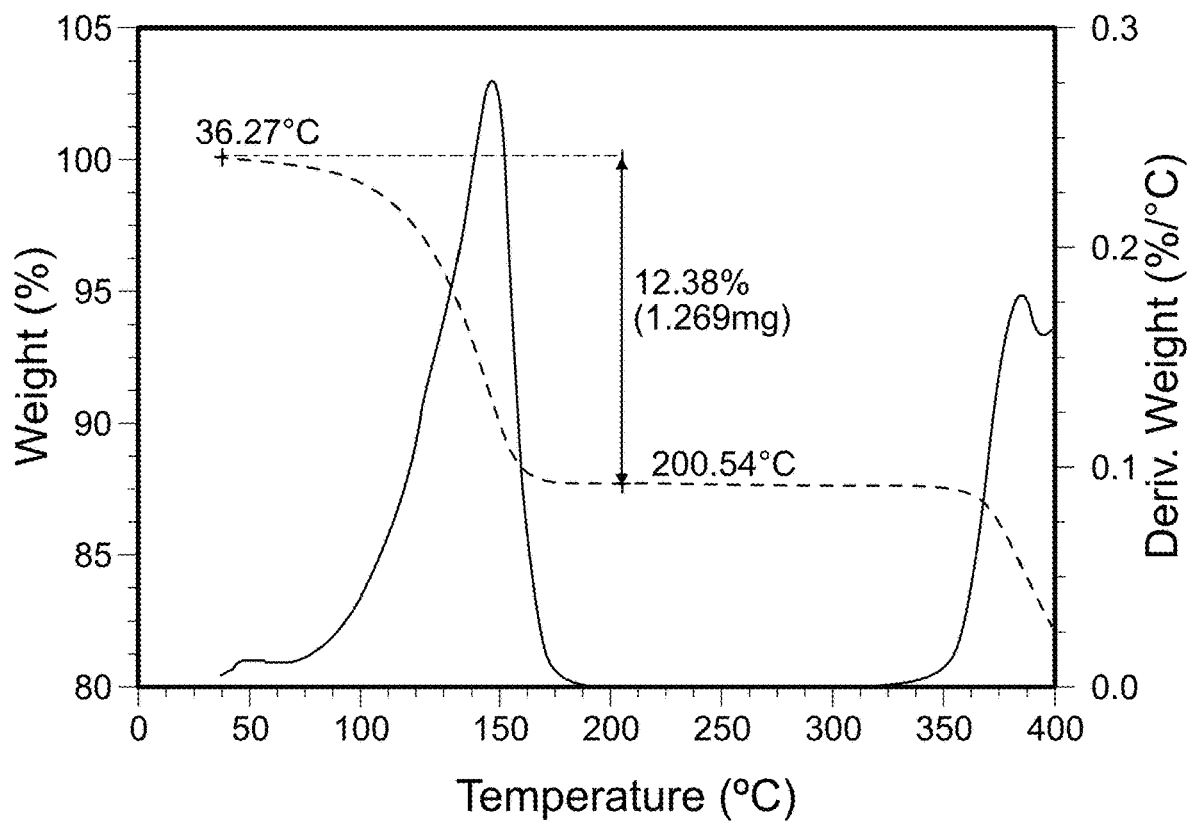

A TGA scan of Form 7 solid showed a 12% weight loss before 200° C. (FIG. 7C).

Form 7 was obtained from MEK and MEK/5% water at RT and 50° C.

TABLE 19

Summary of experiments that generated Form 7

| Form | Solvent | Temperature | Wet | Dry |
|---|---|---|---|---|
| Form 7 | MEK | RT | Form 7 | Form 7 |
| | MEK | 50° C. | Form 7 | Form 7 |
| | MEK/water | RT | Form 7 | Form 7 |
| | MEK/water | 50° C. | Form 7 | Form 7 |

*Amount of water in binary solvents is 5%

TABLE 20

XRD peaks of Form 7

| 2-Theta | d(A) | BG | Height | I % | Area | I % | FWHM |
|---|---|---|---|---|---|---|---|
| 4.94 | 17.8745 | 362 | 1384 | 23.3 | 50829 | 29.2 | 0.624 |
| 7.06 | 12.5111 | 286 | 3171 | 53.3 | 69159 | 39.8 | 0.371 |
| 8.759 | 10.0876 | 370 | 628 | 10.6 | 9606 | 5.5 | 0.26 |
| 9.9 | 8.9272 | 429 | 537 | 9 | 11110 | 6.4 | 0.352 |
| 10.881 | 8.1241 | 546 | 879 | 14.8 | 16425 | 9.4 | 0.318 |
| 11.84 | 7.4681 | 588 | 413 | 6.9 | 7187 | 4.1 | 0.296 |
| 12.997 | 6.8061 | 463 | 135 | 2.3 | 1351 | 0.8 | 0.17 |
| 14.404 | 6.1442 | 604 | 126 | 2.1 | 3331 | 1.9 | 0.449 |
| 15.1 | 5.8626 | 791 | 596 | 10 | 8819 | 5.1 | 0.252 |
| 15.92 | 5.5622 | 792 | 593 | 10 | 24460 | 14.1 | 0.701 |
| 16.581 | 5.3421 | 739 | 641 | 10.8 | 14919 | 8.6 | 0.396 |
| 18.5 | 4.7919 | 1066 | 1555 | 26.1 | 43174 | 24.8 | 0.472 |
| 19.4 | 4.5717 | 1087 | 930 | 15.6 | 17521 | 10.1 | 0.32 |
| 20.382 | 4.3535 | 1178 | 154 | 2.6 | 867 | 0.5 | 0.096 |
| 21.56 | 4.1183 | 1424 | 5949 | 100 | 173972 | 100 | 0.497 |
| 22.098 | 4.0192 | 1830 | 692 | 11.6 | 17678 | 10.2 | 0.434 |
| 23.22 | 3.8275 | 1749 | 1971 | 33.1 | 42151 | 24.2 | 0.364 |
| 24.203 | 3.6743 | 1776 | 351 | 5.9 | 11935 | 6.9 | 0.578 |
| 24.884 | 3.5751 | 1658 | 271 | 4.6 | 2378 | 1.4 | 0.149 |
| 25.759 | 3.4556 | 1416 | 492 | 8.3 | 19894 | 11.4 | 0.687 |
| 26.3 | 3.3858 | 1335 | 499 | 8.4 | 23631 | 13.6 | 0.805 |
| 27.34 | 3.2594 | 1192 | 307 | 5.2 | 4494 | 2.6 | 0.249 |
| 28.641 | 3.1142 | 1004 | 382 | 6.4 | 18030 | 10.4 | 0.802 |
| 29.078 | 3.0684 | 979 | 324 | 5.4 | 14234 | 8.2 | 0.747 |
| 30.28 | 2.9492 | 759 | 711 | 12 | 16004 | 9.2 | 0.383 |
| 31.985 | 2.7959 | 551 | 111 | 1.9 | 4816 | 2.8 | 0.738 |
| 33.402 | 2.6804 | 509 | 102 | 1.7 | 2060 | 1.2 | 0.343 |
| 34.24 | 2.6167 | 474 | 92 | 1.5 | 1901 | 1.1 | 0.351 |

I. Form 8

Figure 8A:
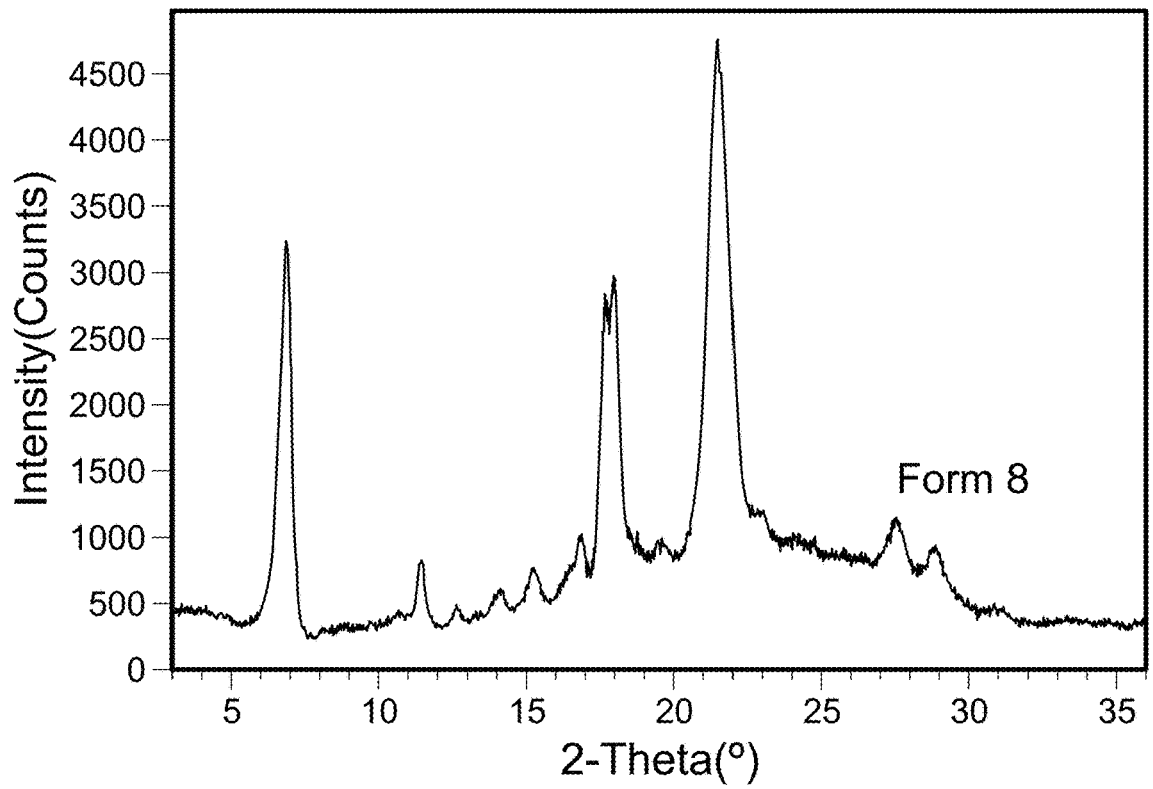
FIGS. 8A-8C are scans of polymorph Form 8 of the compound of Formula (I).
Figure 8B:
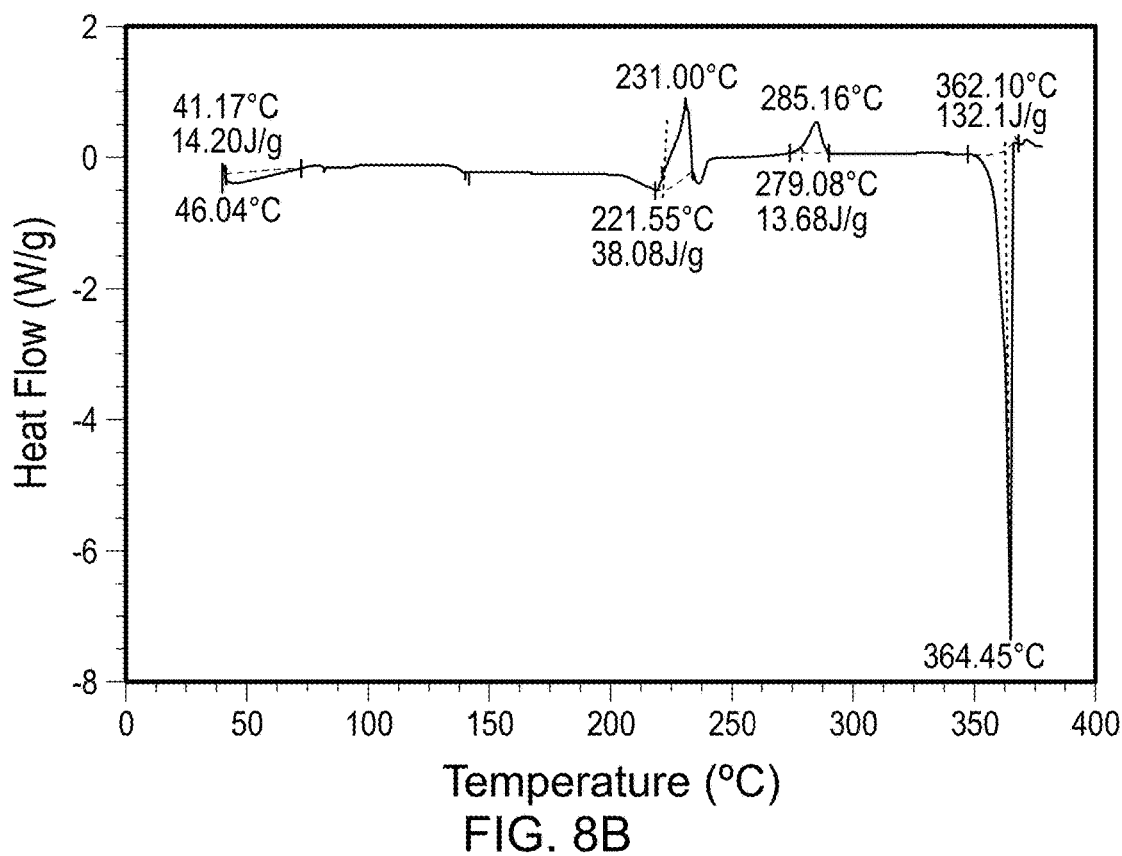

The experiments that generated Form 8 are shown in Table 21, below. XRD and DSC scans of Form 8 were taken (FIGS. 8A and 8B, respectively). The XRD peaks of Form 8 are shown in Table 22, below. According to the DSC scan, the solid showed two endotherms at 205° C. and 231° C., followed by an exotherm at 279° C., followed by a melting endotherm at 362° C. Form 8 showed a low degree of crystallinity on the XRD scan. The double exotherm on the DSC scan may confirm the low crystallinity seen on XRD (low crystalline material convert to higher crystallinity solid).

Figure 8C:
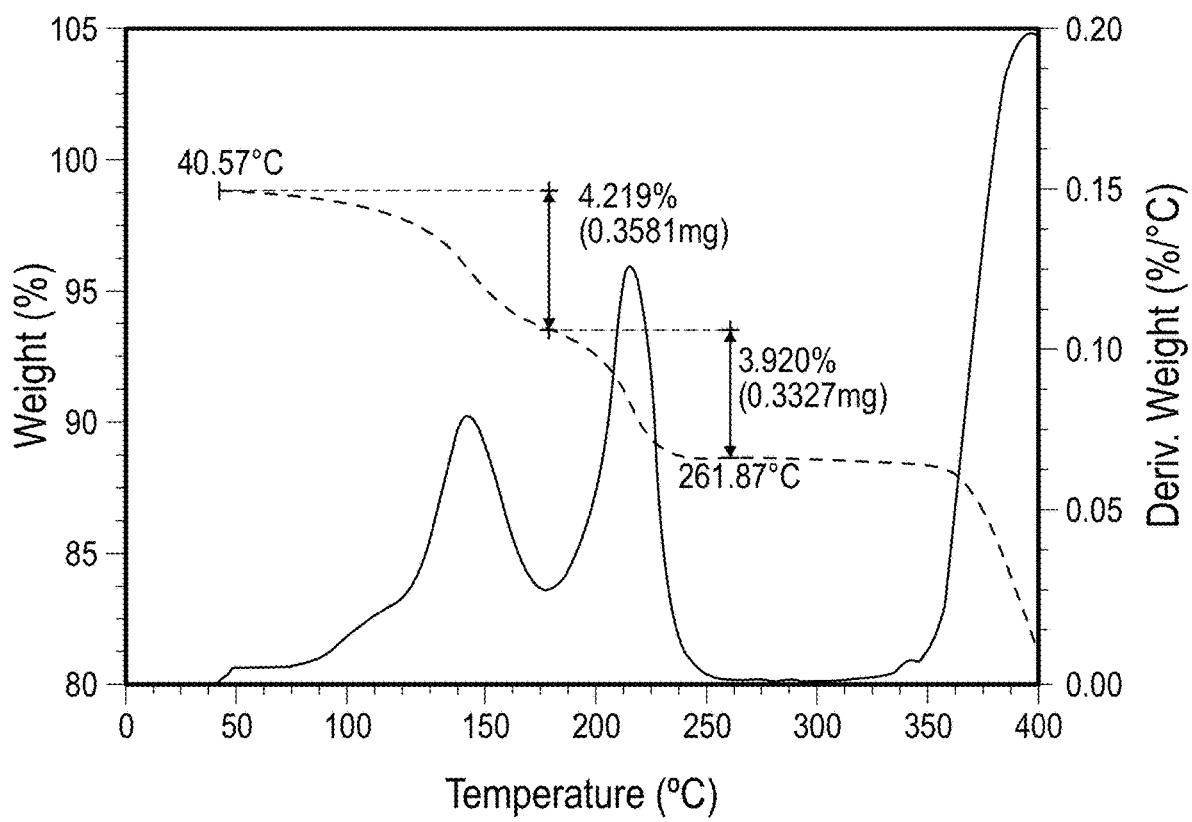

A TGA scan of Form 8 showed a 4.2% weight loss before 190° C., followed by a 3.9% weight loss between 190° C. and 261° C. (FIG. 8C).

Form 8 was obtained from MIBK at RT and 50° C. MIBK/5% water reslurry does not produce the same form.

TABLE 21

Summary of experiments that generated Form 8

| Form | Solvent | Temperature | Wet | Dry |
|---|---|---|---|---|
| Form 8 | MIBK | RT | Form 8 | Form 8 |
| | MIBK | 50° C. | Form 8 | Form 8 |

TABLE 22

XRD peaks of Form 8

| 2-Theta | d(A) | BG | Height | I % | Area | I % | FWHM |
|---|---|---|---|---|---|---|---|
| 6.88 | 12.8368 | 318 | 2815 | 80.8 | 71578 | 51.7 | 0.432 |
| 10.699 | 8.2619 | 380 | 70 | 2 | 722 | 0.5 | 0.175 |
| 11.48 | 7.7016 | 344 | 466 | 13.4 | 9513 | 6.9 | 0.347 |
| 12.66 | 6.9866 | 348 | 136 | 3.9 | 1759 | 1.3 | 0.22 |
| 14.16 | 6.2496 | 435 | 166 | 4.8 | 3298 | 2.4 | 0.338 |
| 15.259 | 5.8017 | 483 | 269 | 7.7 | 6267 | 4.5 | 0.396 |
| 16.879 | 5.2484 | 669 | 333 | 9.6 | 7638 | 5.5 | 0.39 |
| 17.681 | 5.0121 | 780 | 1959 | 56.2 | 76035 | 54.9 | 0.66 |
| 19.618 | 4.5213 | 833 | 134 | 3.8 | 2110 | 1.5 | 0.268 |
| 21.5 | 4.1296 | 1116 | 3484 | 100 | 138450 | 100 | 0.676 |
| 24.244 | 3.6682 | 899 | 99 | 2.8 | 2643 | 1.9 | 0.454 |
| 27.559 | 3.234 | 753 | 366 | 10.5 | 11182 | 8.1 | 0.519 |
| 28.881 | 3.0889 | 636 | 279 | 8 | 8137 | 5.9 | 0.496 |
| 30.878 | 2.8935 | 403 | 87 | 2.5 | 1890 | 1.4 | 0.369 |
| 31.221 | 2.8624 | 386 | 69 | 2 | 1898 | 1.4 | 0.468 |

J. Form 9

Figure 9A:
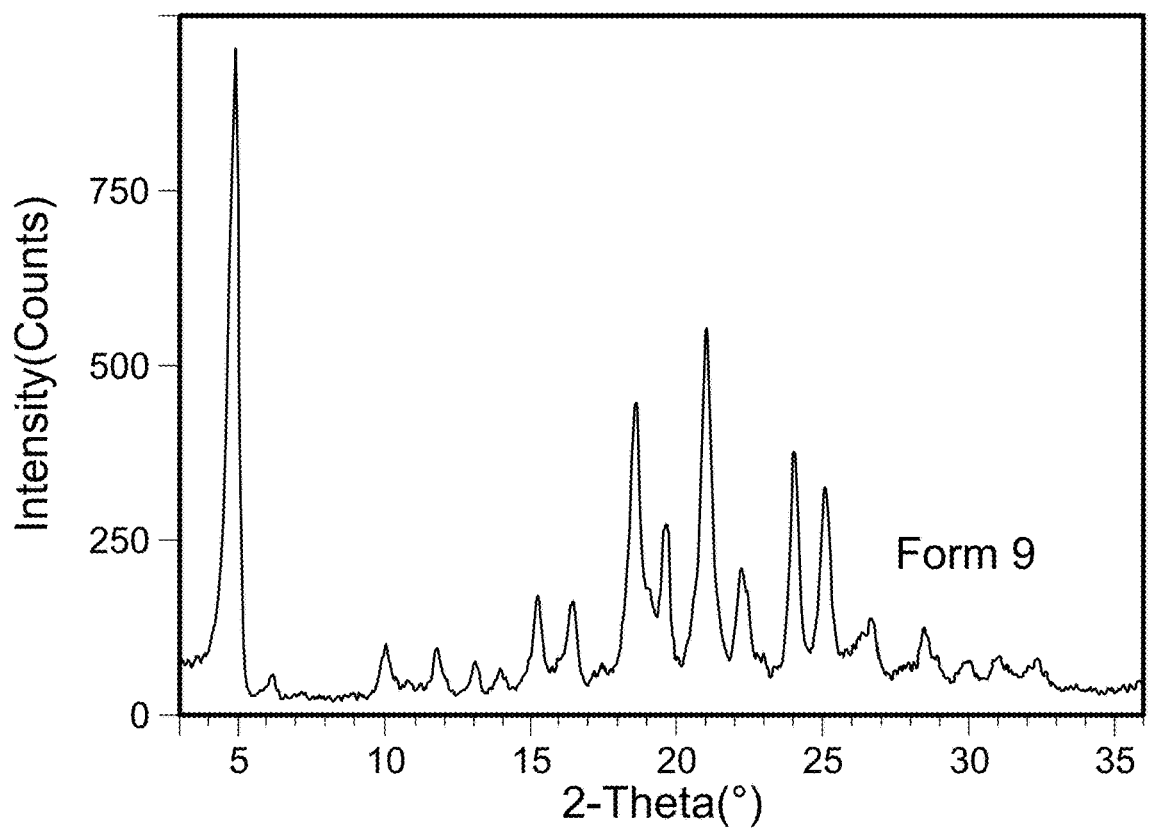
FIGS. 9A-9D are scans of polymorph Form 9 of the compound of Formula (I).
Figure 9B:
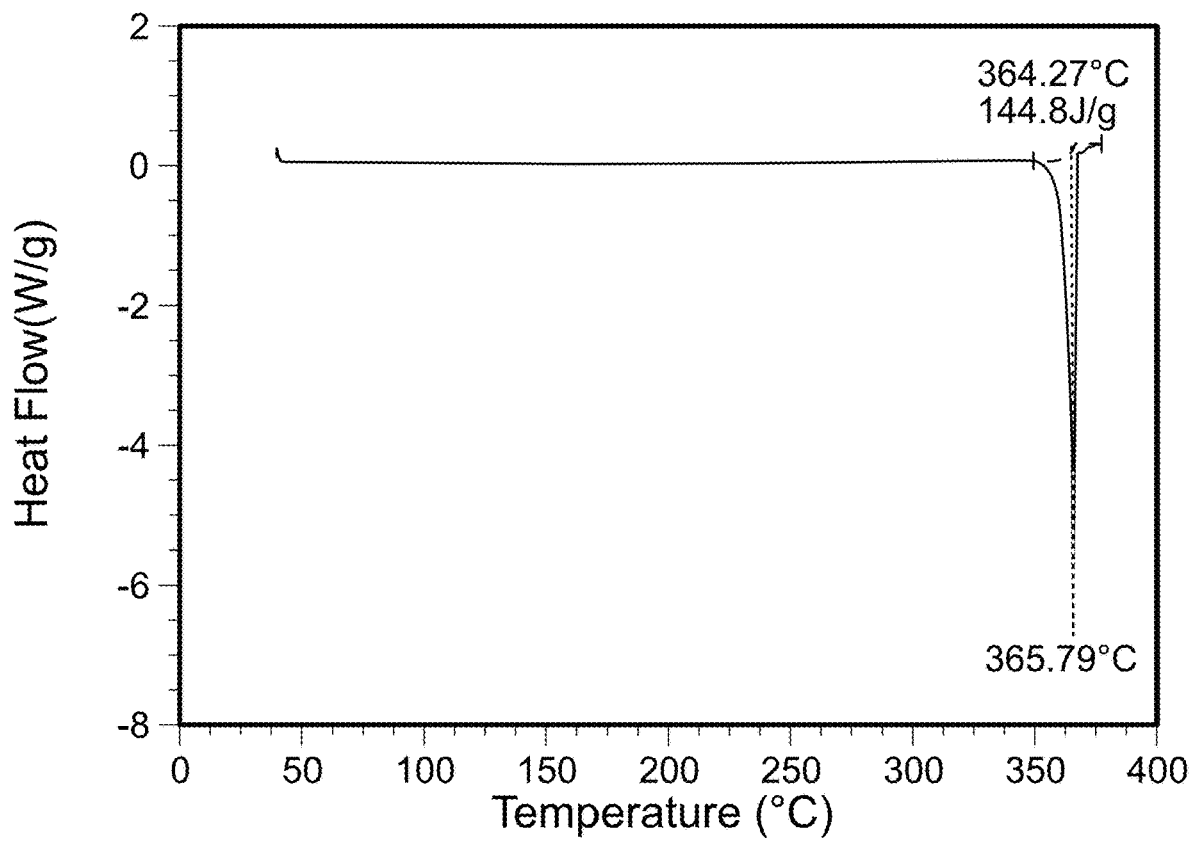

The experiments that generated Form 9 are shown in Table 23, below. XRD and DSC scans of Form 9 were taken (FIGS. 9A and 9B, respectively). The XRD peaks of Form 9 are shown in Table 24, below. According to the DSC scan, the solid showed a single melting endotherm at 364° C.

Figure 9C:
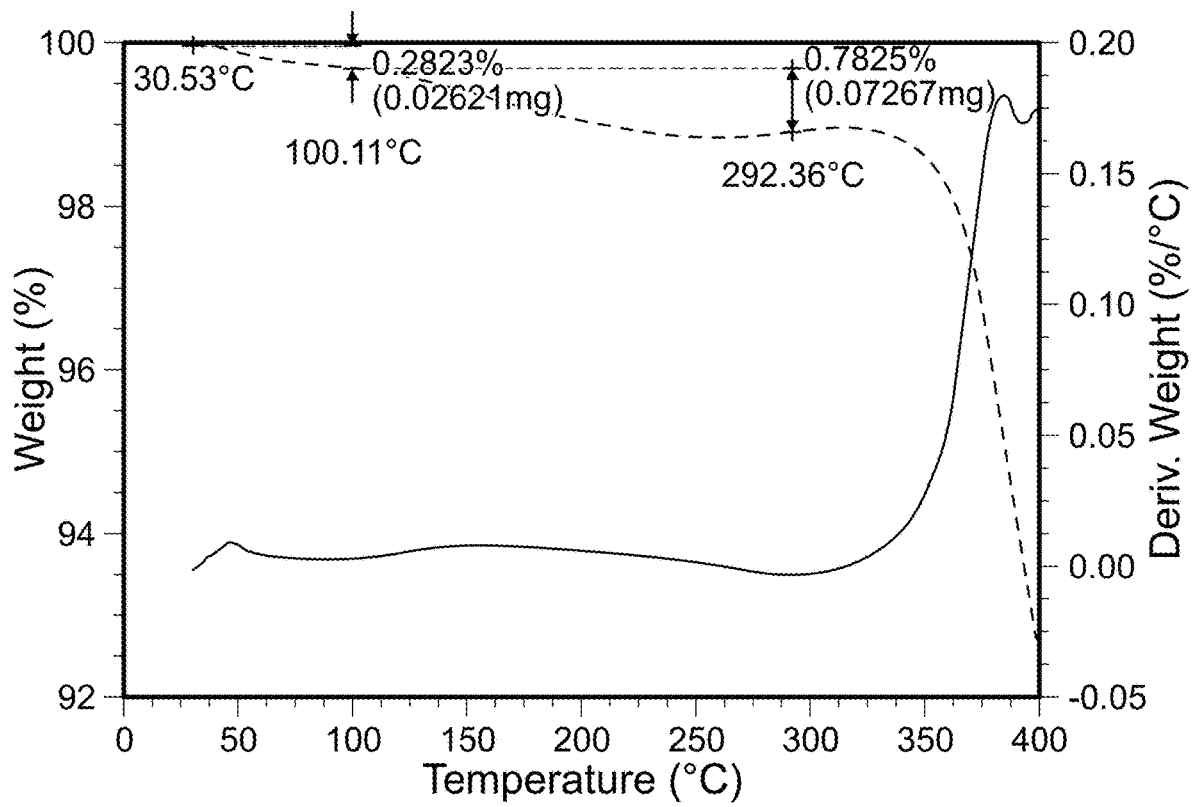

A TGA scan of Form 9 showed a 0.28% weight loss before 100° C. (FIG. 9C).

Other forms, when heated to just before melting at 364° C., seemed to convert to Form 9. This has been confirmed for Forms 1 and 2.

Figure 9D:
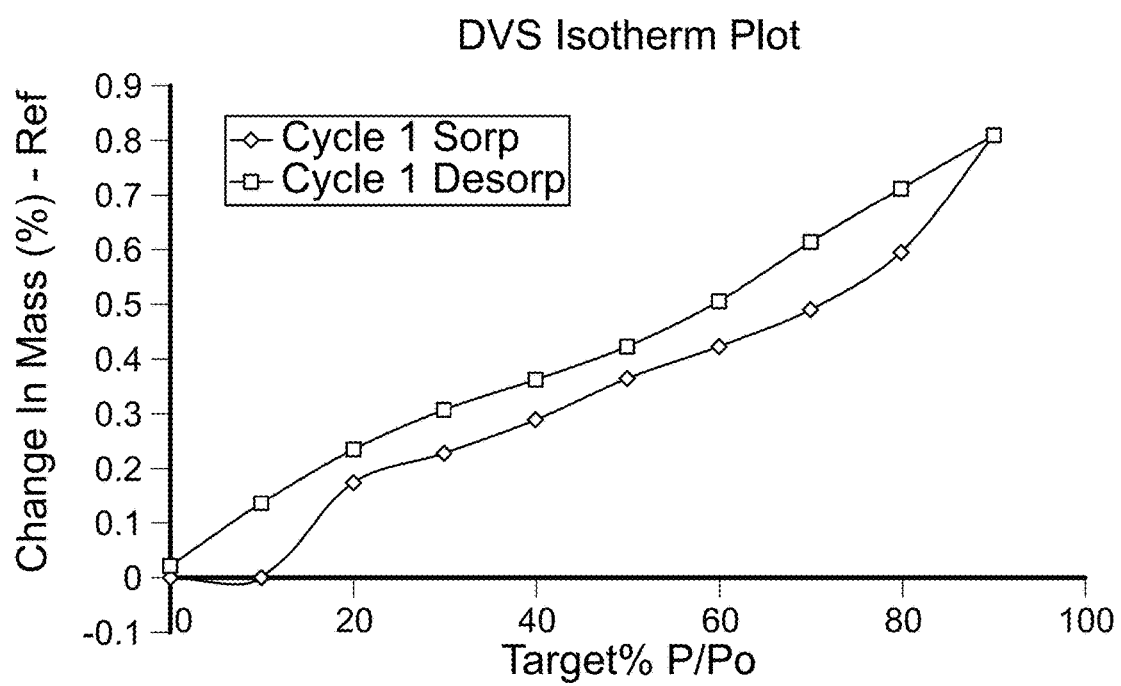

A DVS scan of Form 9 showed a 0.8% water absorption at 90% RH. Form 9 did not change its form before and after the DVS scan (FIG. 9D).

TABLE 23

Summary of experiments that generated Form 9

| Form | Solvent | Temperature | Wet | Dry |
|---|---|---|---|---|
| Form 9 | n-Butanol | RT | Form 9 | Form 9 |
| | IPAc | 50° C. | Form 9 | Form 9 |
| | n-Butyl acetate | 50° C. | Form 9 | Form 9 |
| | n-Butanol | 50° C. | Form 9 | Form 9 |

TABLE 23-continued

Summary of experiments that generated Form 9

| Form | Solvent | Temperature | Wet | Dry |
|---|---|---|---|---|
| | EtOH/water | 50° C. | Form 9 | Form 9 |
| | n-Propanol/water | 50° C. | Form 9 | Form 9 |

*Amount of water in binary solvents is 5%

TABLE 24

XRD peaks of Form 9

| 2-Theta | d(A) | BG | Height | I % | Area | I % | FWHM |
|---|---|---|---|---|---|---|---|
| 4.94 | 17.8746 | 21 | 895 | 100 | 23398 | 100 | 0.444 |
| 6.26 | 14.1076 | 21 | 34 | 3.8 | 513 | 2.2 | 0.257 |
| 10.099 | 8.7516 | 28 | 66 | 7.4 | 1172 | 5 | 0.302 |
| 11.883 | 7.4413 | 30 | 46 | 5.1 | 828 | 3.5 | 0.306 |
| 13.16 | 6.7221 | 27 | 37 | 4.1 | 400 | 1.7 | 0.184 |
| 15.341 | 5.771 | 39 | 71 | 7.9 | 1541 | 6.6 | 0.369 |
| 16.518 | 5.3622 | 40 | 93 | 10.4 | 1728 | 7.4 | 0.316 |
| 18.622 | 4.7608 | 46 | 260 | 29.1 | 7069 | 30.2 | 0.462 |
| 19.74 | 4.4938 | 80 | 138 | 15.4 | 1937 | 8.3 | 0.239 |
| 21.101 | 4.2068 | 64 | 342 | 38.2 | 8314 | 35.5 | 0.413 |
| 22.42 | 3.9622 | 56 | 77 | 8.6 | 1721 | 7.4 | 0.38 |
| 24.1 | 3.6897 | 58 | 198 | 22.1 | 3904 | 16.7 | 0.335 |
| 25.2 | 3.5311 | 63 | 157 | 17.5 | 3615 | 15.5 | 0.391 |
| 26.897 | 3.312 | 46 | 44 | 4.9 | 1307 | 5.6 | 0.505 |
| 28.577 | 3.121 | 35 | 54 | 6 | 1754 | 7.5 | 0.552 |
| 29.884 | 2.9874 | 32 | 30 | 3.4 | 477 | 2 | 0.254 |
| 30.926 | 2.8891 | 35 | 32 | 3.6 | 682 | 2.9 | 0.341 |

K. Forms 10 and 10*

Figure 10A:
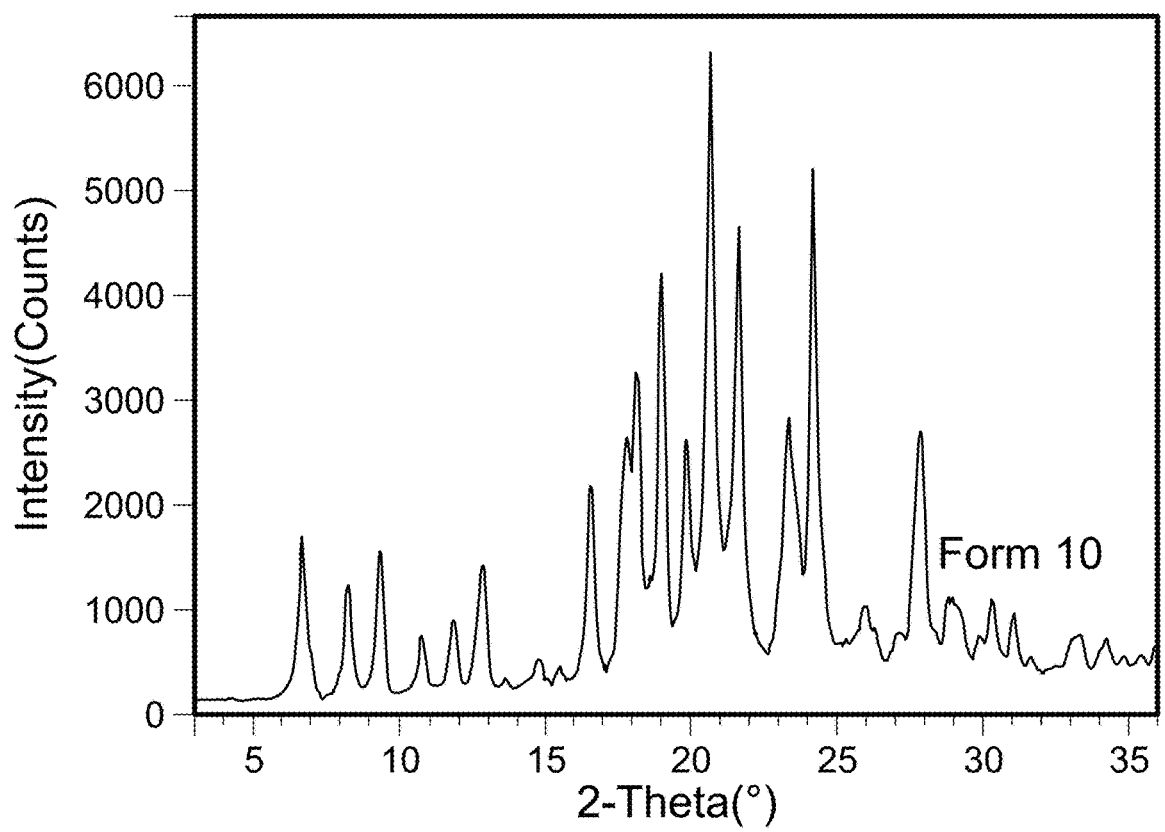
FIGS. 10A-10E are scans of polymorph Forms 10 and 10* of the compound of Formula (I).
Figure 10B:
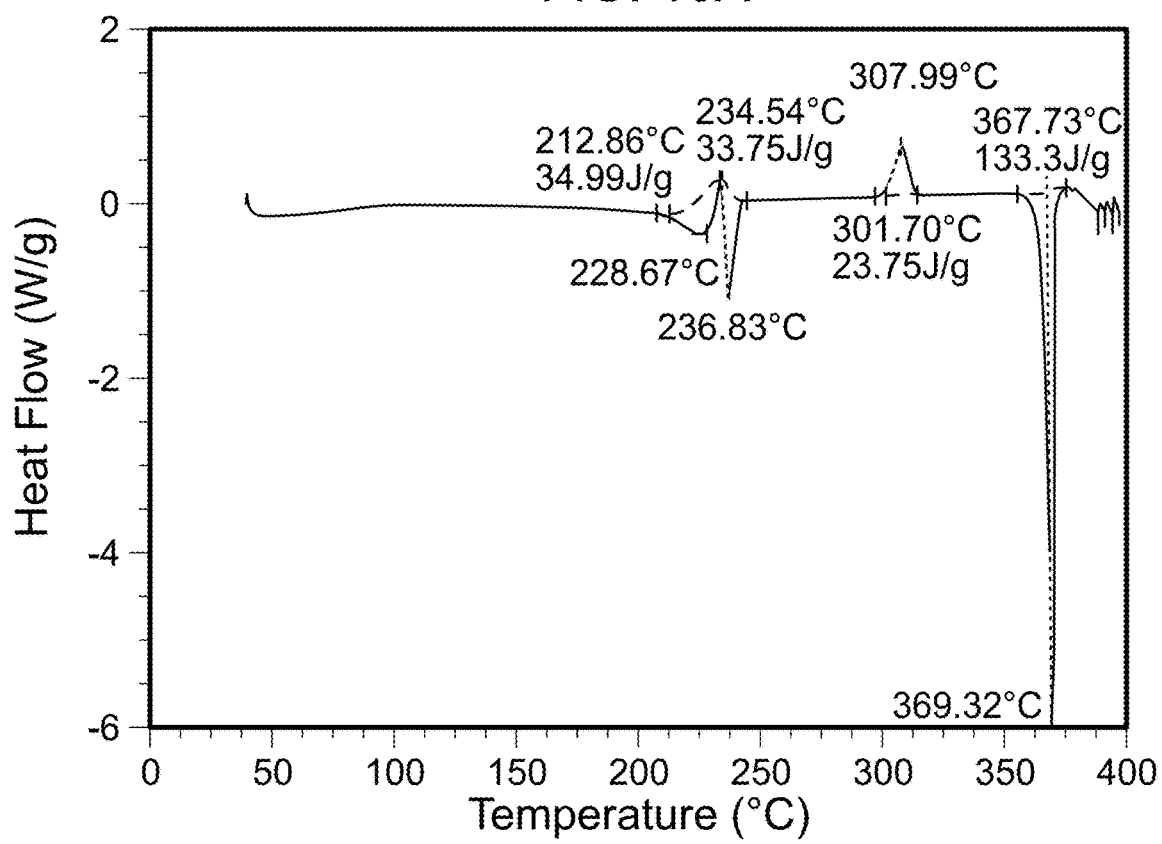
Figure 10C:
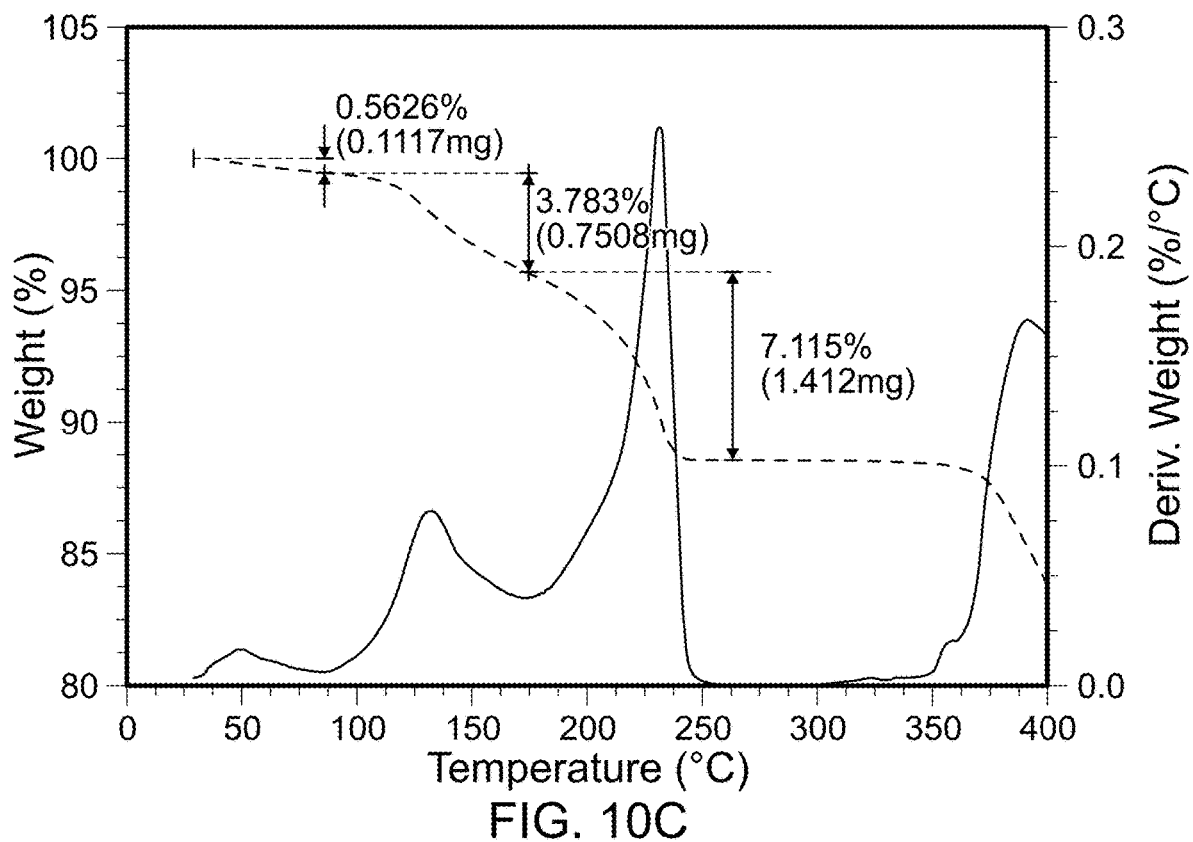
Figure 10D:
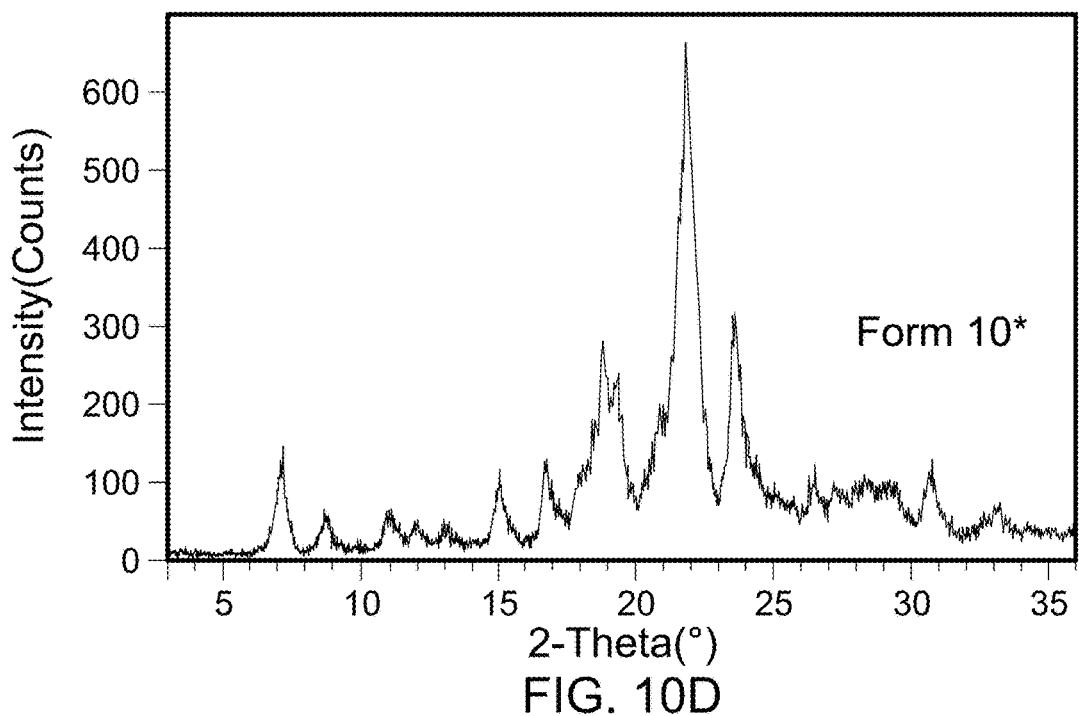
Figure 10E:
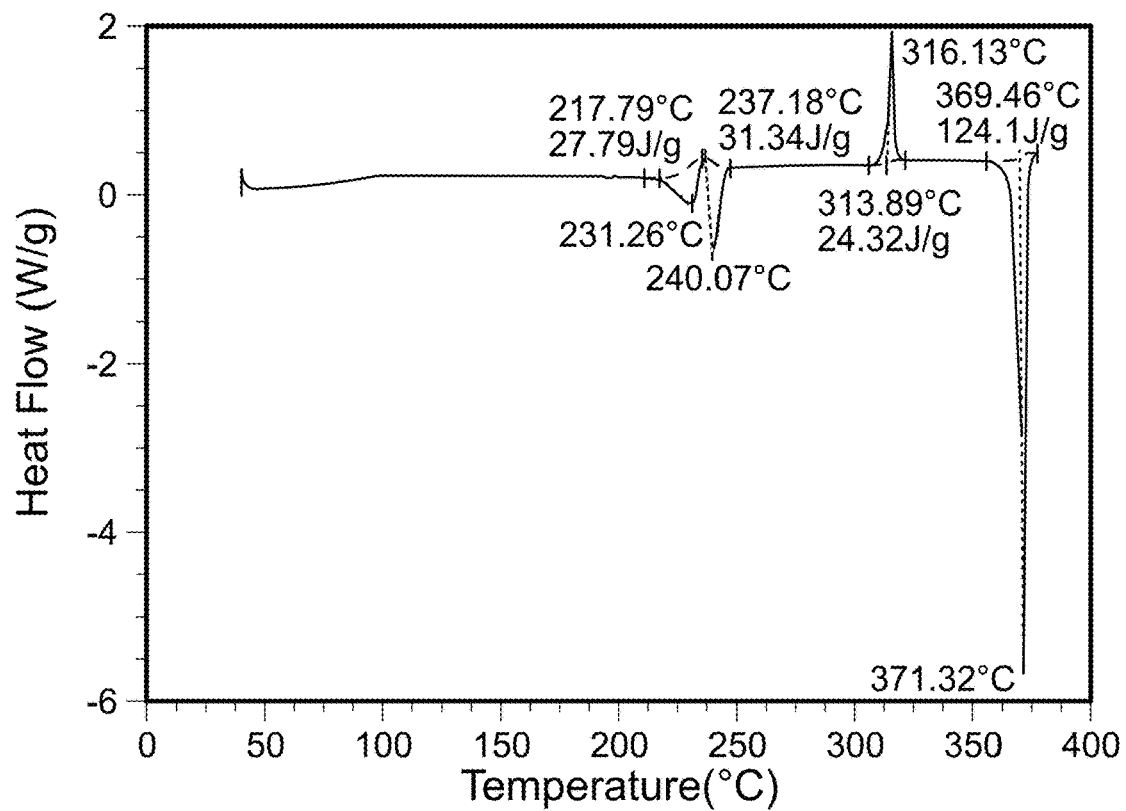

The experiments that generated Forms 10 and 10* are shown in Table 25, below. XRD scans of Forms 10 and 10* were taken (FIGS. 10A and 10D, respectively). The XRD peaks of Form 10 are shown in Table 26, below. DSC scans of Forms 10 and 10* were also taken and indicated multiple endotherms/exotherms, followed by melting at 367° C. (FIGS. 10B and 10E, respectively).

Forms 10 and 10* were produced by drying of amorphous solids (obtained from DMSO and DMSO/water reslurry at RT and 50° C.). Both Form 10 and 10* are associated with DMSO.

A TGA scan of Form 10 solid showed a 0.6% weight loss before 100° C., followed by a 3.8% weight loss between 100° C. and 170° C., followed by a 7.1% weight loss between 170° C. and 260° C. (FIG. 10C).

TABLE 25

Summary of experiments that generated Forms 10 and 10*

| Form | Solvent | Temperature | Wet | Dry |
|---|---|---|---|---|
| Form 10 | DMSO | RT | amorphous | Form 10 |
| | DMSO/water | RT | amorphous | Form 10 |
| | DMSO/water | 50° C. | amorphous | Form 10 |
| Form 10* | DMSO | 50° C. | amorphous | Form 10* |

*Amount of water in binary solvents is 5%

TABLE 26

XRD peaks of Form 10

| 2-Theta | d(A) | BG | Height | I % | Area | I % | FWHM |
|---|---|---|---|---|---|---|---|
| 6.701 | 13.1792 | 148 | 1553 | 32.1 | 31364 | 34.4 | 0.343 |
| 8.3 | 10.6444 | 207 | 1026 | 21.2 | 17914 | 19.6 | 0.297 |
| 9.38 | 9.4203 | 212 | 1352 | 27.9 | 21528 | 23.6 | 0.271 |
| 10.819 | 8.1705 | 223 | 514 | 10.6 | 8714 | 9.6 | 0.288 |
| 11.919 | 7.4192 | 271 | 635 | 13.1 | 9435 | 10.3 | 0.253 |
| 12.919 | 6.8469 | 266 | 1160 | 24 | 22094 | 24.2 | 0.324 |
| 13.718 | 6.45 | 242 | 81 | 1.7 | 856 | 0.9 | 0.18 |
| 14.84 | 5.9646 | 271 | 244 | 5 | 4716 | 5.2 | 0.329 |
| 15.536 | 5.6988 | 312 | 147 | 3 | 1304 | 1.4 | 0.151 |
| 16.58 | 5.3424 | 392 | 1813 | 37.5 | 30451 | 33.4 | 0.286 |
| 17.821 | 4.9731 | 434 | 2208 | 45.6 | 58342 | 64 | 0.449 |
| 18.16 | 4.881 | 434 | 2862 | 59.2 | 89029 | 97.6 | 0.529 |
| 19.001 | 4.6667 | 1021 | 3215 | 66.5 | 45840 | 50.2 | 0.242 |
| 19.88 | 4.4623 | 1163 | 1454 | 30.1 | 19014 | 20.8 | 0.222 |
| 20.701 | 4.2873 | 1514 | 4838 | 100 | 78140 | 85.7 | 0.275 |
| 21.66 | 4.0994 | 596 | 4067 | 84.1 | 91229 | 100 | 0.381 |
| 23.38 | 3.8017 | 596 | 2251 | 46.5 | 64928 | 71.2 | 0.49 |
| 24.22 | 3.6717 | 663 | 4578 | 94.6 | 84228 | 92.3 | 0.313 |
| 26 | 3.4242 | 595 | 430 | 8.9 | 11172 | 12.2 | 0.442 |
| 27.12 | 3.2853 | 639 | 146 | 3 | 1986 | 2.2 | 0.231 |
| 27.88 | 3.1974 | 642 | 2073 | 42.8 | 48132 | 52.8 | 0.395 |
| 28.88 | 3.089 | 638 | 477 | 9.9 | 14155 | 15.5 | 0.504 |
| 29.867 | 2.9891 | 544 | 205 | 4.2 | 4572 | 5 | 0.379 |
| 30.32 | 2.9454 | 528 | 568 | 11.7 | 11936 | 13.1 | 0.357 |
| 31.098 | 2.8735 | 517 | 443 | 9.2 | 5841 | 6.4 | 0.224 |
| 31.661 | 2.8236 | 433 | 118 | 2.4 | 953 | 1 | 0.137 |
| 33.379 | 2.6822 | 433 | 311 | 6.4 | 9235 | 10.1 | 0.505 |
| 34.22 | 2.6181 | 444 | 281 | 5.8 | 6059 | 6.6 | 0.367 |
| 34.822 | 2.5743 | 460 | 84 | 1.7 | 2707 | 3 | 0.548 |
| 35.438 | 2.5309 | 465 | 89 | 1.8 | 858 | 0.9 | 0.164 |

L. Forms 11 and 11*

Figure 11A:
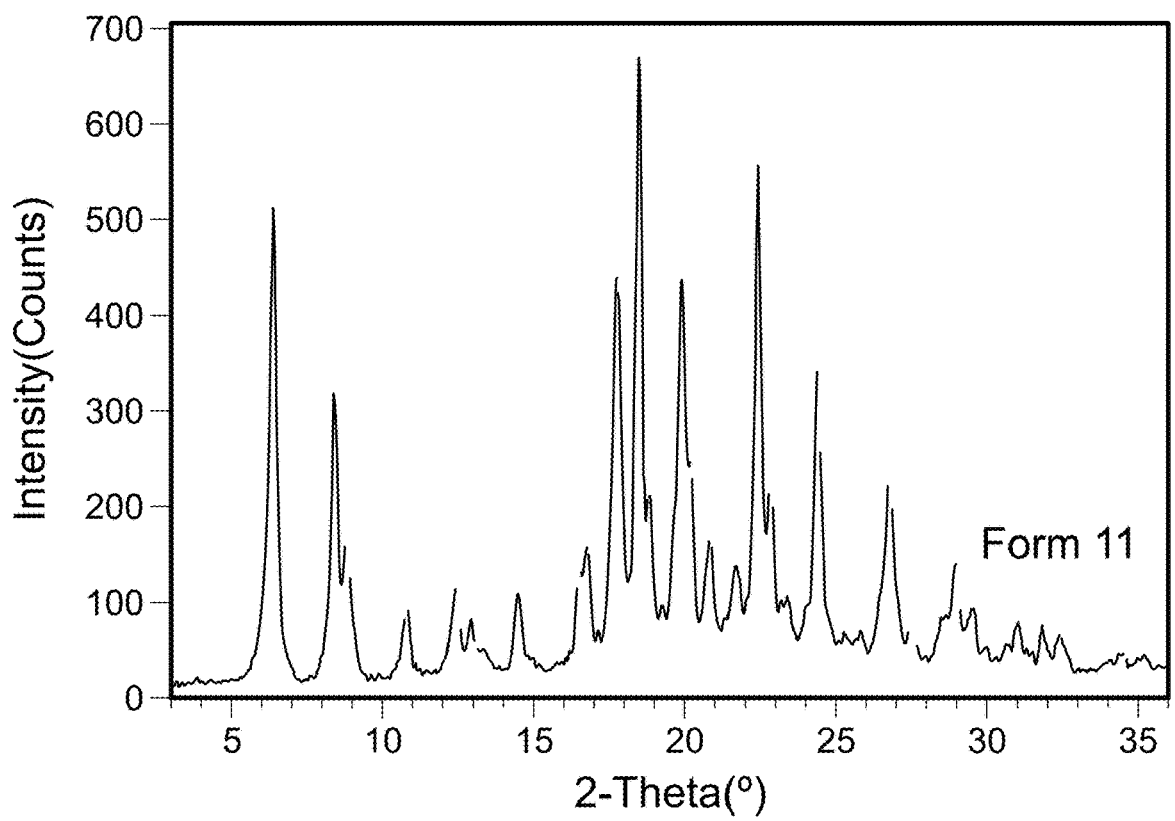
FIGS. 11A-11F are scans of polymorph Forms 11 and 11* of the compound of Formula (I).
Figure 11B:
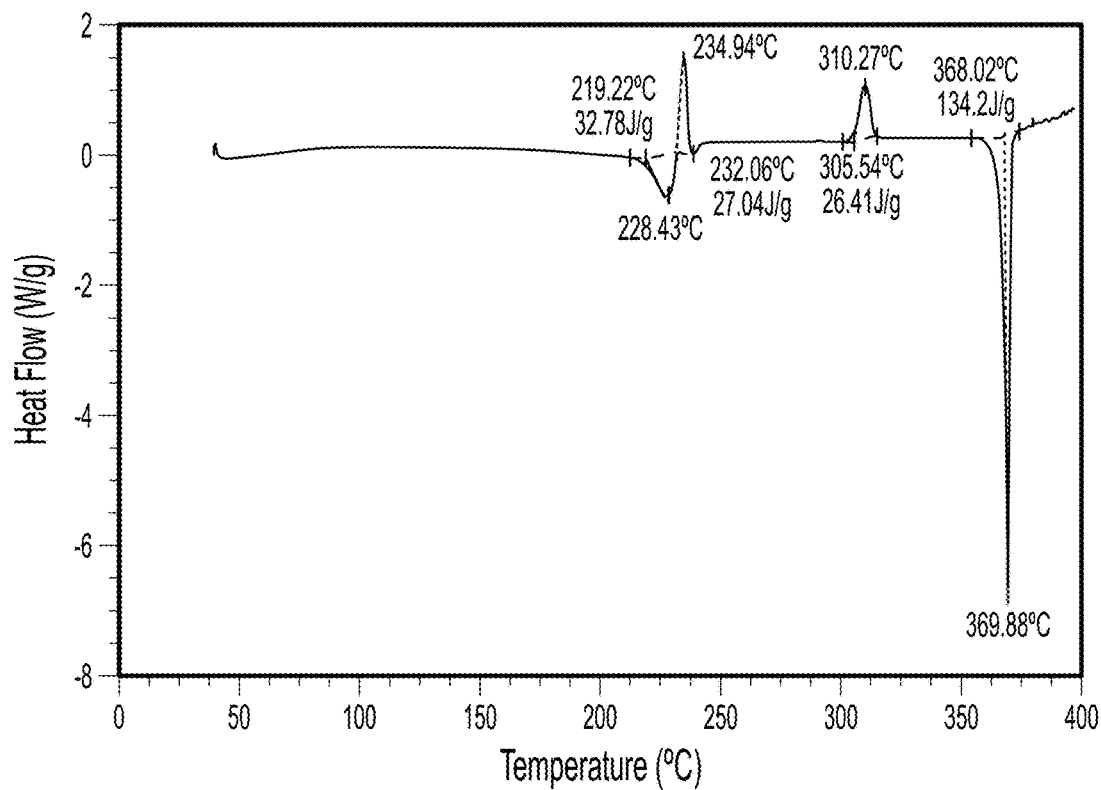

The experiments that generated Forms 11 and 11* are shown in Table 27, below. XRD scans of Forms 11 and 11* were taken (FIGS. 11A and 11D, respectively). The XRD peaks of Form 11 and Form 11* are shown in Tables 28 and 29, below, respectively. DSC scans of Forms 11 and 11* were also taken (FIGS. 11B and 11E, respectively). According to the DSC scans, the solid showed multiple endotherms/exotherms and eventually melted at 368° C. Amorphous halo was observed in the XRD of both Forms. The double exotherm on the DSC of both forms may be also associated with the amorphous halo observed on XRD scans.

Figure 11C:
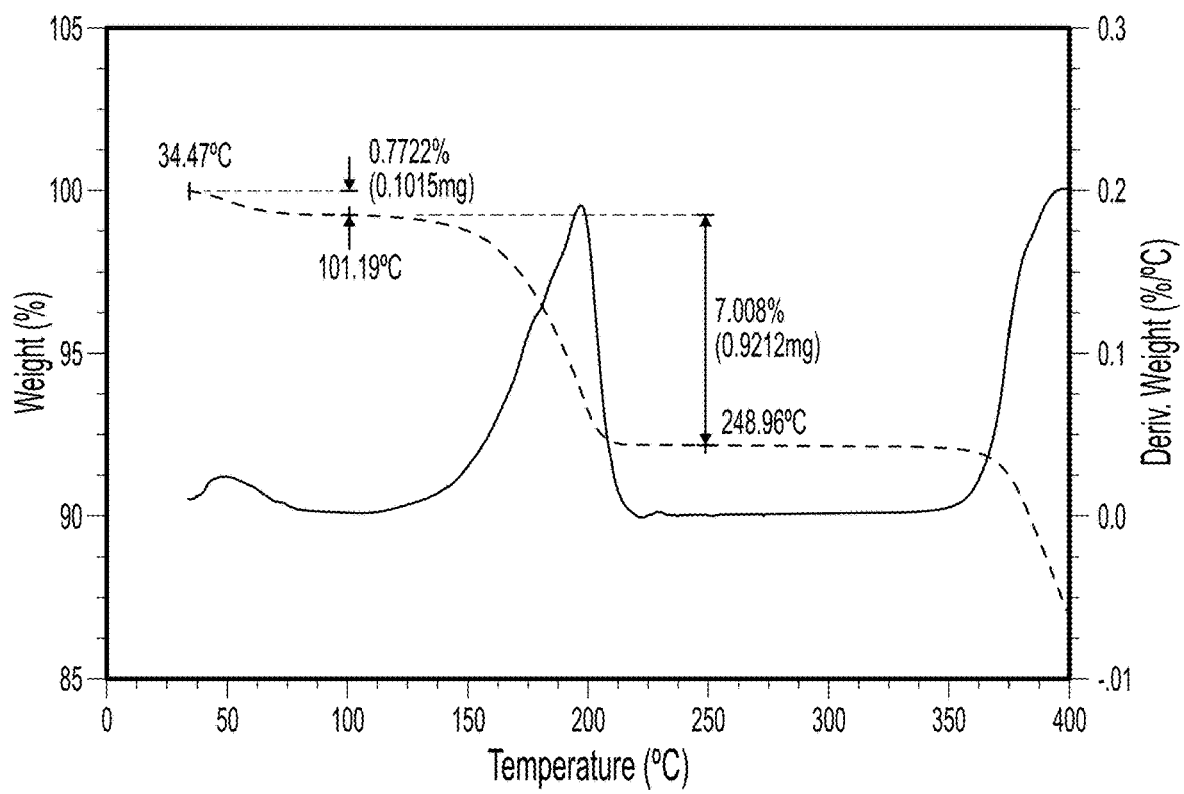
Figure 11D:
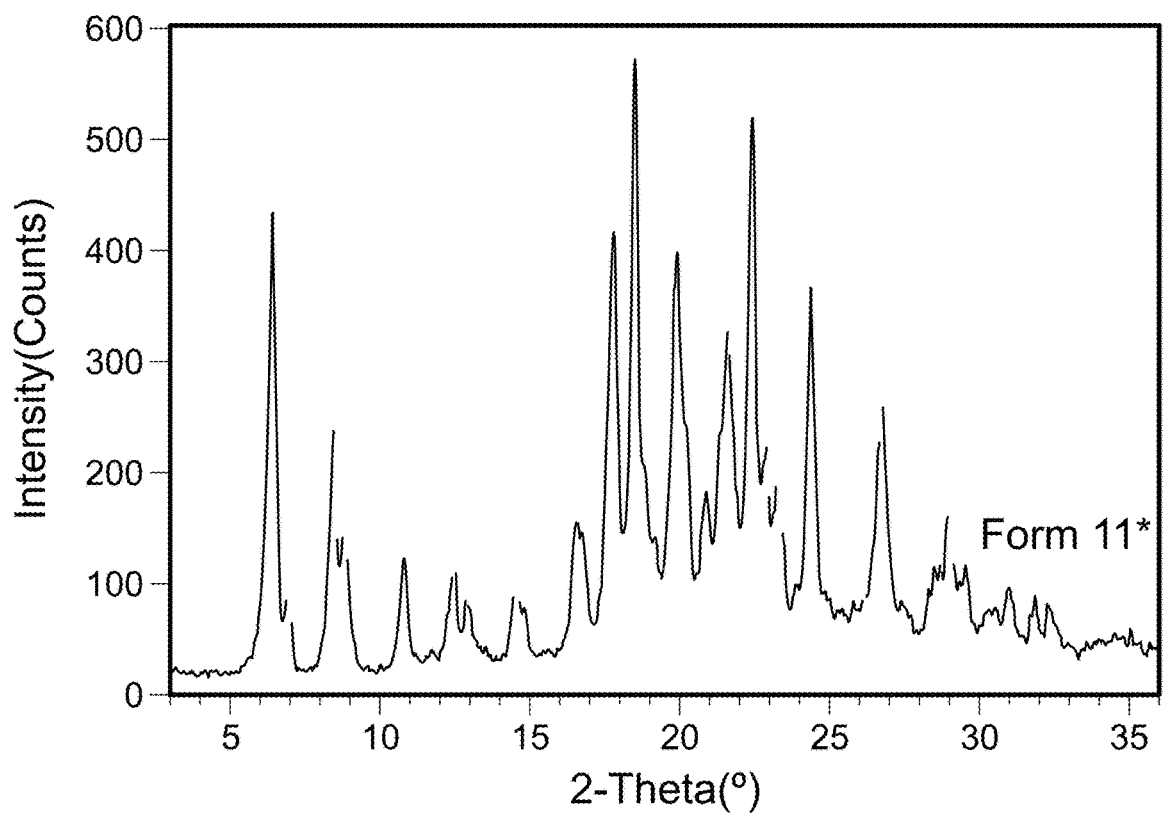
Figure 11E:
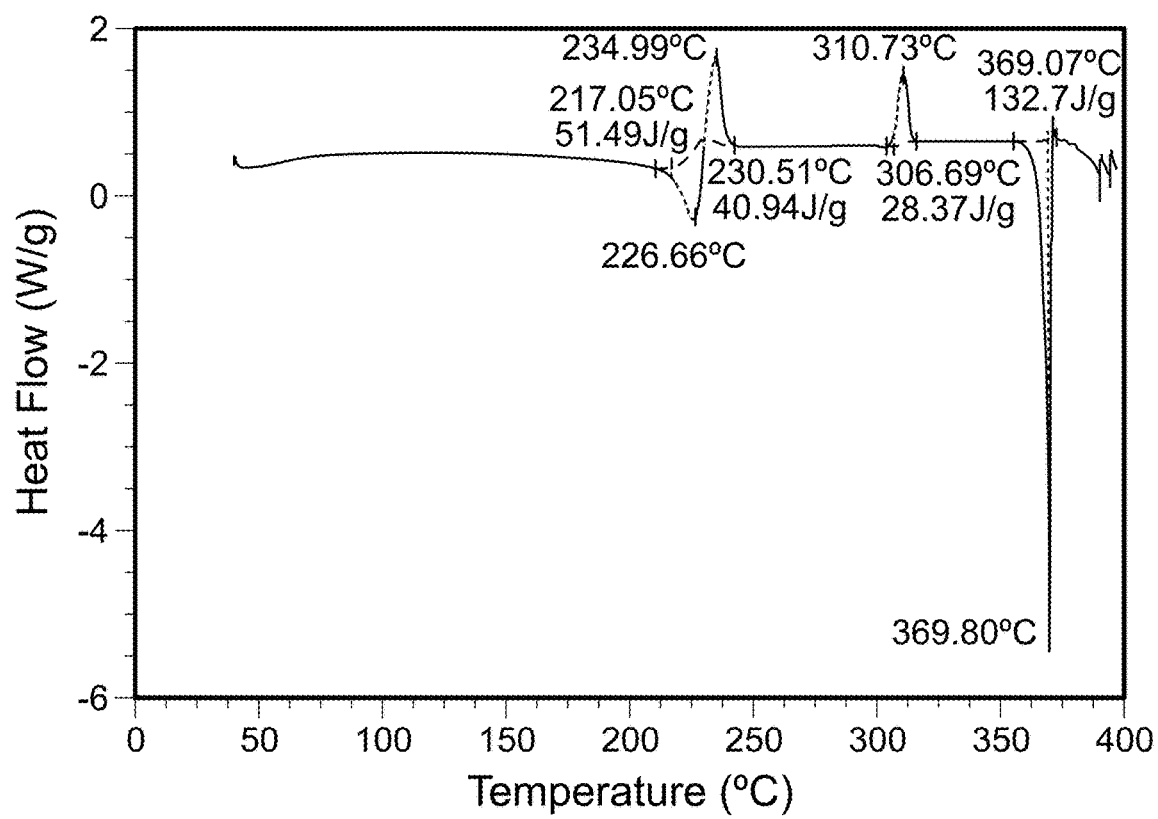
Figure 11F:
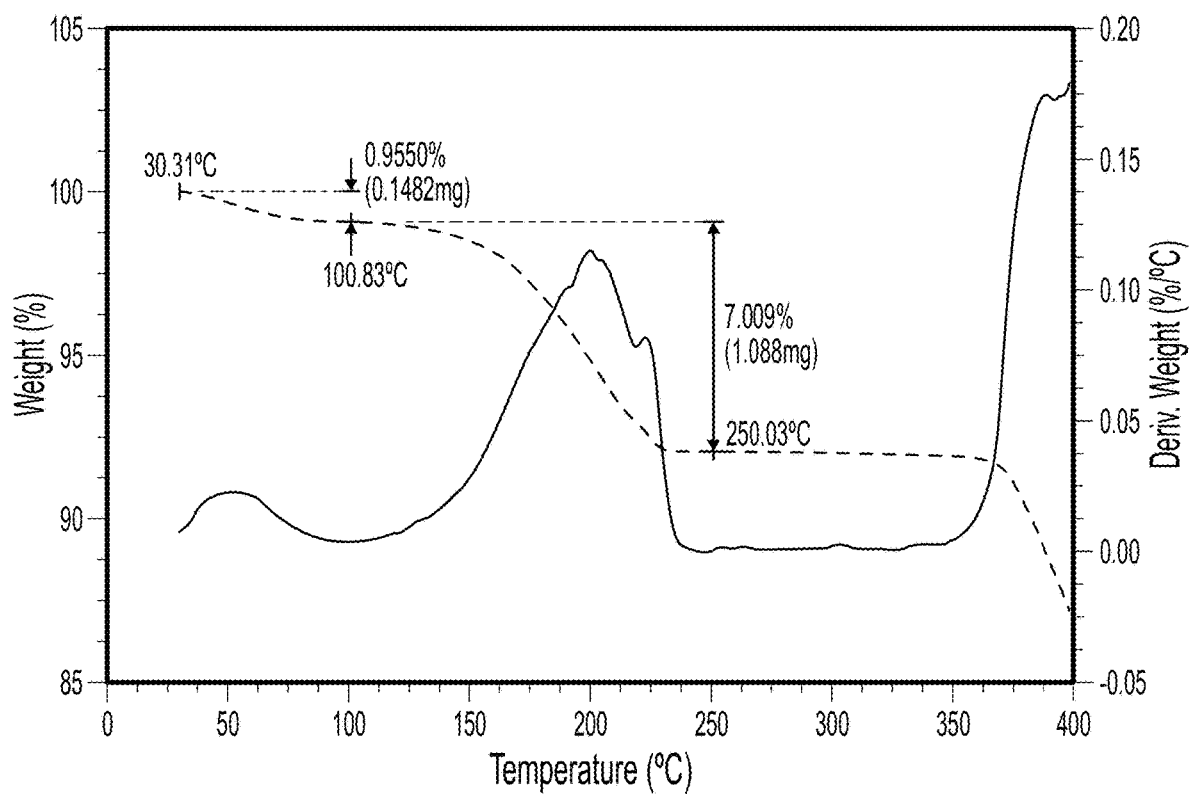

TGA scans of Form 11 and 11* were taken (FIGS. 11C and 11F, respectively). Form 11 solids showed a 0.8% weight loss before 100° C., followed by a 7.0% weight loss between 100° C. and 249° C. Form 11* solids showed a 1.0% weight loss before 100° C., and followed by a 7.0% weight loss before 250° C.

Forms 11 and 11* were obtained from DMF and DMF/5% water at RT and 50° C.

TABLE 27

Summary of experiments that generated Forms 11 and 11*

| Form | Solvent | Temperature | Wet | Dry |
|---|---|---|---|---|
| Form 11 | DMF | RT | Form 11 | Form 11 |
| | DMF | 50° C. | Form 11 | Form 11* |
| | DMF/water | RT | Form 11 | Form 11 |
| | DMF/water | 50° C. | Form 11 | Form 11 |
| Form 11* | DMF | 50° C. | Form 11 | Form 11* |

*Amount of water in binary solvents is 5%

TABLE 28

XRD peaks of Form 11

| 2-Theta | d(A) | BG | Height | I % | Area | I % | FWHM |
|---|---|---|---|---|---|---|---|
| 6.42 | 13.7554 | 19 | 496 | 81.7 | 9502 | 100 | 0.326 |
| 8.421 | 10.4908 | 20 | 335 | 55.2 | 5775 | 60.8 | 0.293 |
| 8.86 | 9.9726 | 24 | 166 | 27.3 | 4268 | 44.9 | 0.437 |
| 10.859 | 8.1404 | 21 | 91 | 15 | 1292 | 13.6 | 0.241 |
| 12.479 | 7.0871 | 44 | 83 | 13.7 | 1004 | 10.6 | 0.206 |
| 12.977 | 6.8165 | 29 | 51 | 8.4 | 1542 | 16.2 | 0.514 |
| 14.519 | 6.0957 | 28 | 91 | 15 | 1421 | 15 | 0.265 |
| 16.801 | 5.2727 | 57 | 104 | 17.1 | 2226 | 23.4 | 0.364 |
| 17.801 | 4.9787 | 103 | 358 | 59 | 5109 | 53.8 | 0.243 |
| 18.519 | 4.7871 | 101 | 607 | 100 | 8460 | 89 | 0.237 |
| 18.861 | 4.7011 | 102 | 125 | 20.6 | 1763 | 18.6 | 0.24 |
| 19.922 | 4.453 | 85 | 383 | 63.1 | 7376 | 77.6 | 0.327 |
| 20.258 | 4.38 | 79 | 180 | 29.7 | 5778 | 60.8 | 0.546 |
| 20.899 | 4.247 | 76 | 105 | 17.3 | 1291 | 13.6 | 0.209 |
| 21.738 | 4.085 | 86 | 55 | 9.1 | 757 | 8 | 0.234 |
| 22.441 | 3.9585 | 94 | 471 | 77.6 | 7125 | 75 | 0.257 |
| 22.859 | 3.8871 | 78 | 167 | 27.5 | 3724 | 39.2 | 0.379 |
| 24.458 | 3.6365 | 60 | 298 | 49.1 | 4544 | 47.8 | 0.259 |
| 26.82 | 3.3213 | 45 | 195 | 32.1 | 4777 | 50.3 | 0.416 |
| 29 | 3.0764 | 43 | 99 | 16.3 | 3112 | 32.8 | 0.534 |
| 29.524 | 3.023 | 63 | 37 | 6.1 | 190 | 2 | 0.087 |
| 31.04 | 2.8788 | 38 | 46 | 7.6 | 826 | 8.7 | 0.305 |
| 31.825 | 2.8095 | 36 | 56 | 9.2 | 737 | 7.8 | 0.224 |
| 32.456 | 2.7563 | 31 | 40 | 6.6 | 857 | 9 | 0.364 |

TABLE 29

XRD peaks of Form 11*

| 2-Theta | d(A) | BG | Height | I % | Area | I % | FWHM |
|---|---|---|---|---|---|---|---|
| 6.441 | 13.7116 | 24 | 424 | 93.4 | 8643 | 100 | 0.347 |
| 6.944 | 12.7196 | 20 | 84 | 18.5 | 2078 | 24 | 0.421 |
| 8.518 | 10.3718 | 22 | 227 | 50 | 4871 | 56.4 | 0.365 |
| 8.86 | 9.9721 | 23 | 147 | 32.4 | 3581 | 41.4 | 0.414 |
| 10.859 | 8.141 | 26 | 107 | 23.6 | 1695 | 19.6 | 0.269 |
| 12.519 | 7.0648 | 34 | 90 | 19.8 | 2165 | 25 | 0.409 |
| 13.021 | 6.7935 | 31 | 54 | 11.9 | 1517 | 17.6 | 0.478 |
| 14.618 | 6.0547 | 32 | 76 | 16.7 | 1605 | 18.6 | 0.359 |
| 16.638 | 5.3238 | 55 | 115 | 25.3 | 2410 | 27.9 | 0.356 |
| 17.838 | 4.9684 | 71 | 368 | 81.1 | 6709 | 77.6 | 0.31 |
| 18.522 | 4.7864 | 130 | 454 | 100 | 7473 | 86.5 | 0.28 |
| 19.96 | 4.4447 | 109 | 315 | 69.4 | 6433 | 74.4 | 0.347 |
| 20.26 | 4.3795 | 109 | 146 | 32.2 | 5359 | 62 | 0.624 |
| 20.904 | 4.2461 | 127 | 58 | 12.8 | 559 | 6.5 | 0.164 |
| 21.639 | 4.1034 | 142 | 194 | 42.7 | 4690 | 54.3 | 0.411 |
| 22.441 | 3.9586 | 161 | 368 | 81.1 | 5409 | 62.6 | 0.25 |
| 22.94 | 3.8735 | 78 | 150 | 33 | 6057 | 70.1 | 0.686 |
| 23.398 | 3.7988 | 78 | 116 | 25.6 | 2330 | 27 | 0.341 |
| 24.44 | 3.6391 | 75 | 305 | 67.2 | 5097 | 59 | 0.284 |
| 26.819 | 3.3215 | 68 | 206 | 45.4 | 4795 | 55.5 | 0.396 |
| 29.018 | 3.0745 | 56 | 109 | 24 | 4093 | 47.4 | 0.638 |
| 29.566 | 3.0188 | 82 | 43 | 9.5 | 341 | 3.9 | 0.135 |
| 31.022 | 2.8804 | 58 | 55 | 12.1 | 509 | 5.9 | 0.157 |
| 31.881 | 2.8047 | 49 | 48 | 10.6 | 482 | 5.6 | 0.171 |
| 32.338 | 2.7661 | 42 | 50 | 11 | 1360 | 15.7 | 0.462 |

M. Form 13 and Form 12

Figure 12A:
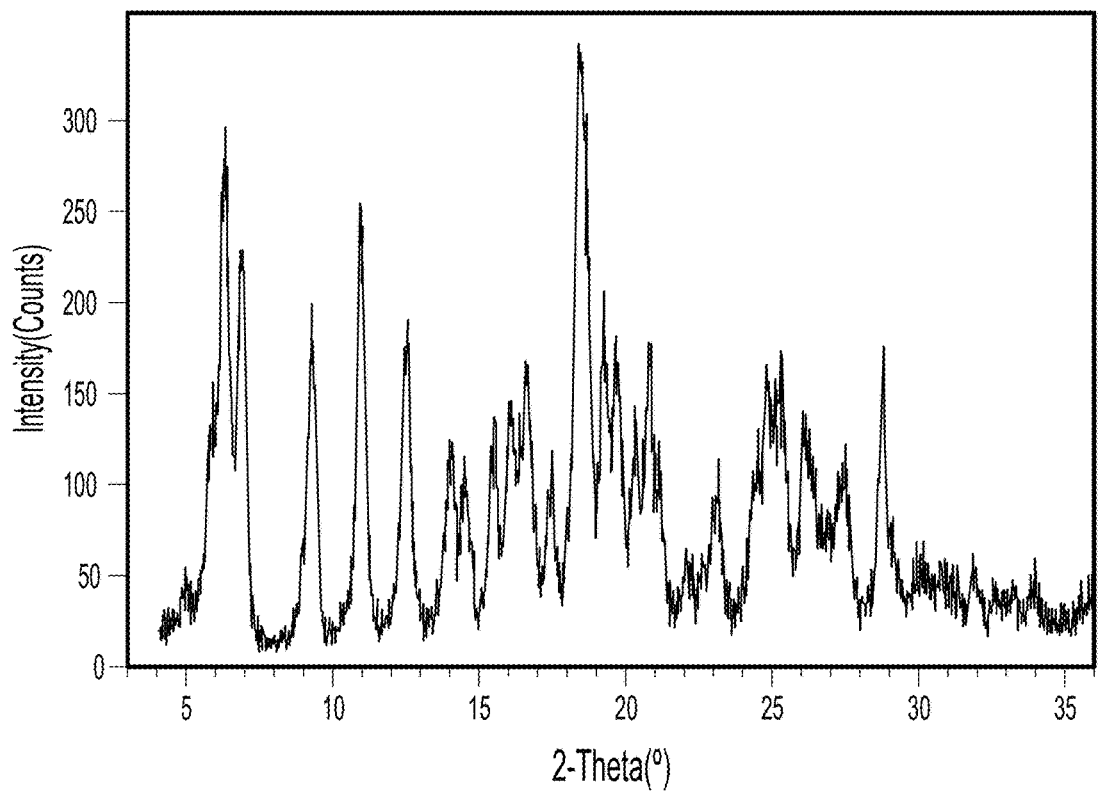
FIGS. 12A-12C are scans of Form 12, an example of a non-stoichiometric hydrate of polymorph Form 1 of the compound of Formula (I).
Figure 12B:
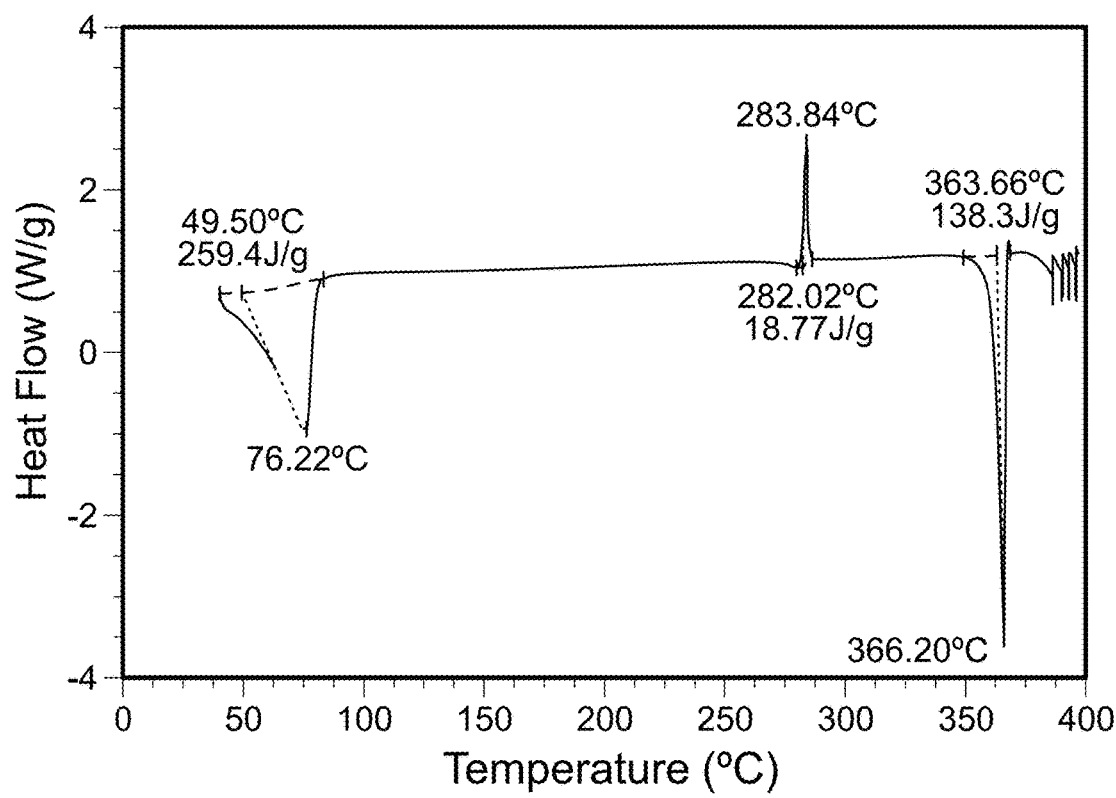
Figure 12C:
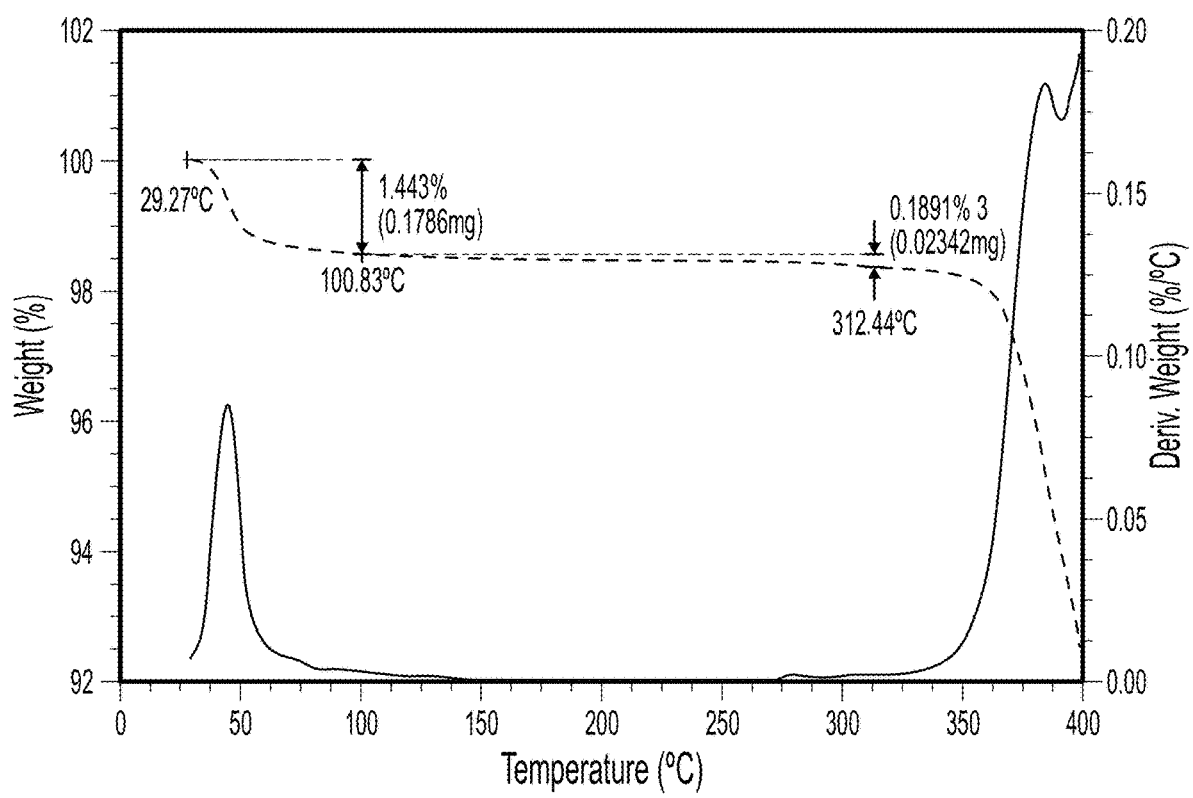
Figure 13A:
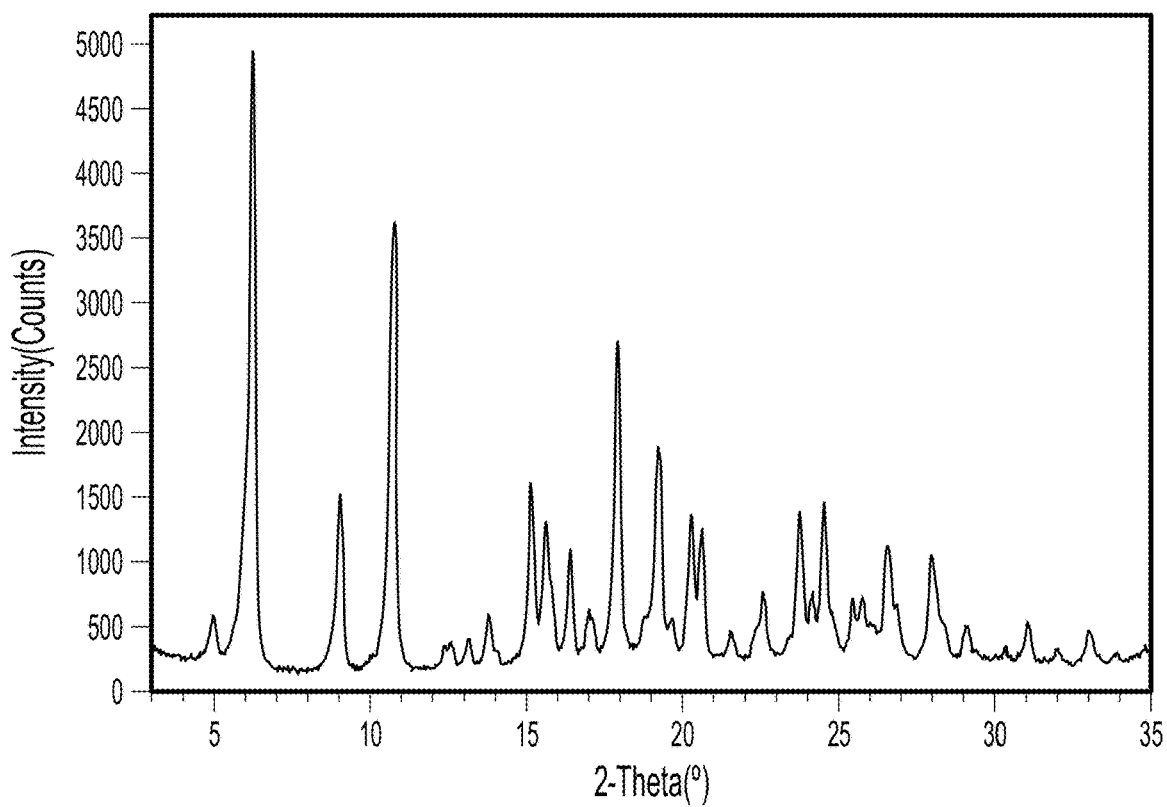
FIGS. 13A-13D are scans of Form 13, an example of a non-stoichiometric hydrate of polymorph Form 1 of the compound of Formula (I).
Figure 13B:
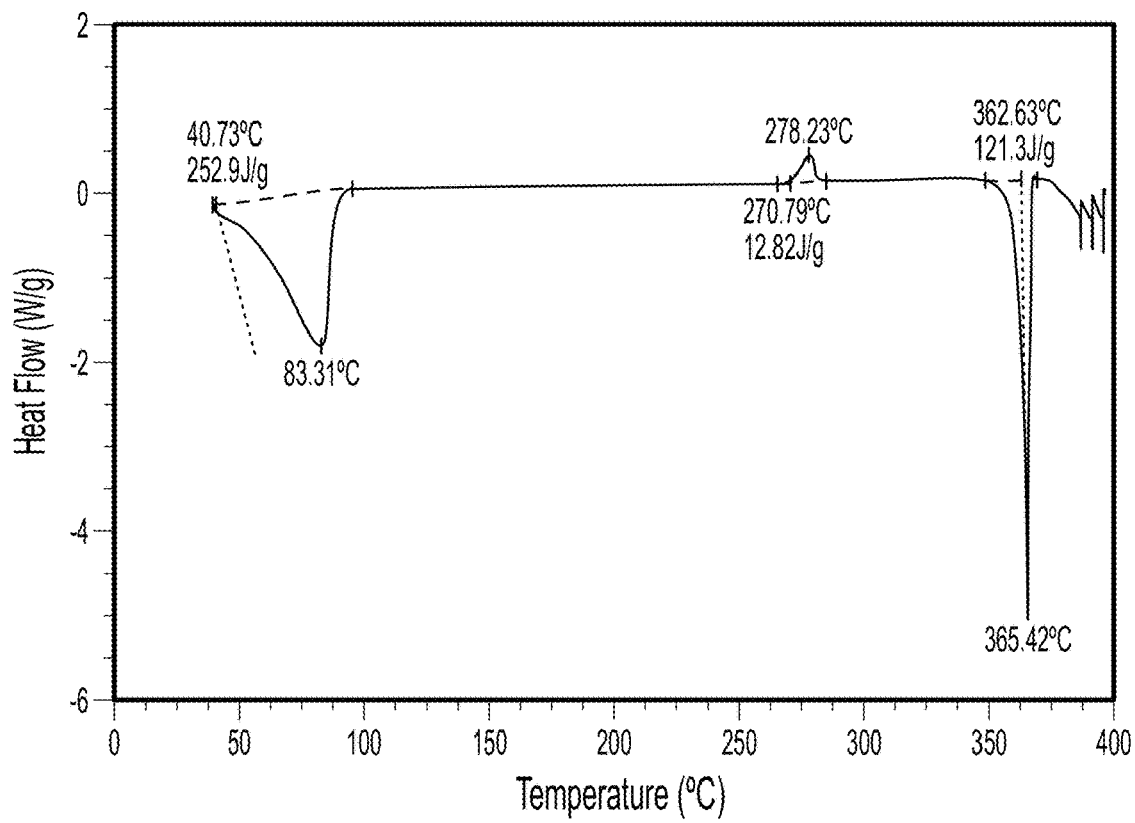

The experiments that generated Form 13 and Form 12 are shown in Tables 30 and 32, below, respectively. Forms 12 and 13 are examples of non-stoichiometric hydrates of Form 1 that have between 1% and about 20% by weight water. XRD scans of Form 13 and Form 12 were taken (FIGS. 13A and 12A, respectively). The XRD peaks of Form 13 are shown in Table 31, below. DSC scans of Form 13 and Form 12 were also taken (FIGS. 13B and 12B, respectively). According to the DSC scan, Form 13 solids showed a wide endotherm between 50° C.-100° C., followed by a small exotherm at 278° C.; and a melting endotherm at 363° C. According to the DSC scan, Form 12 solids showed a wide endotherm between 50° C.-100° C., followed by a sharp exotherm at 283° C.; and a melting endotherm at 364° C.

Figure 13C:
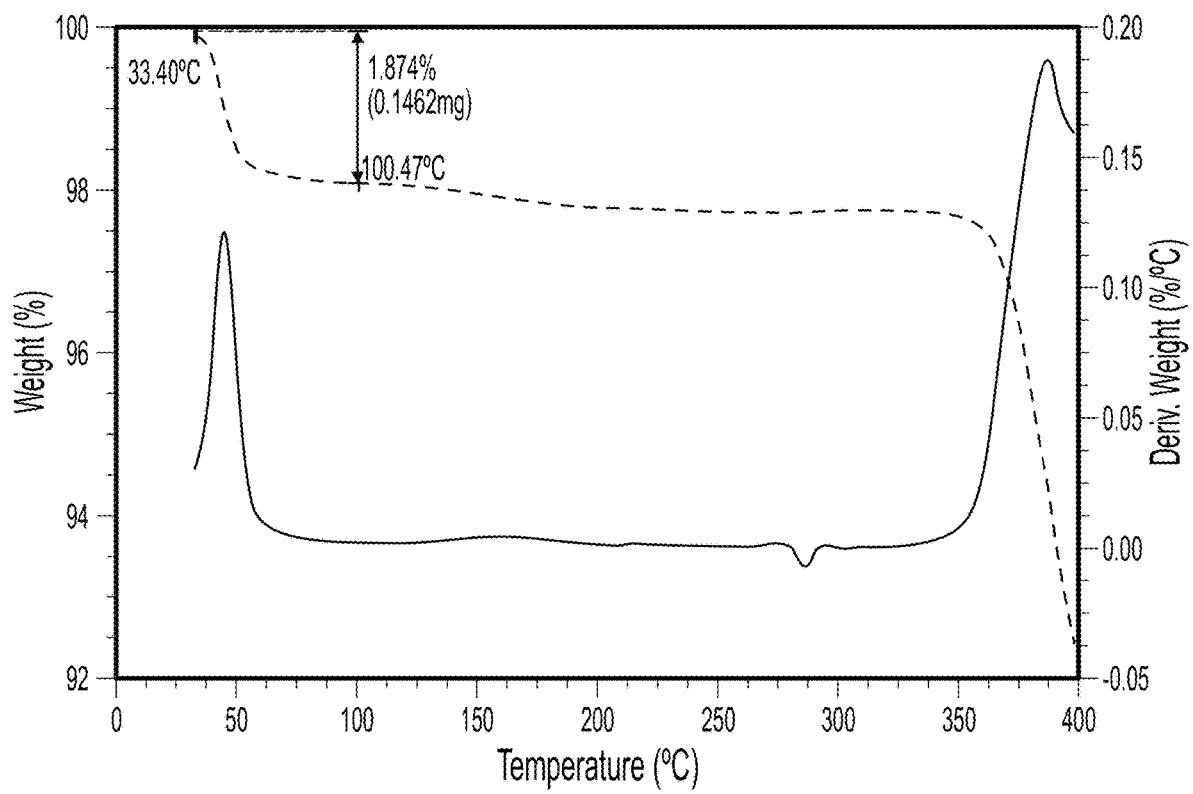
Figure 13D:
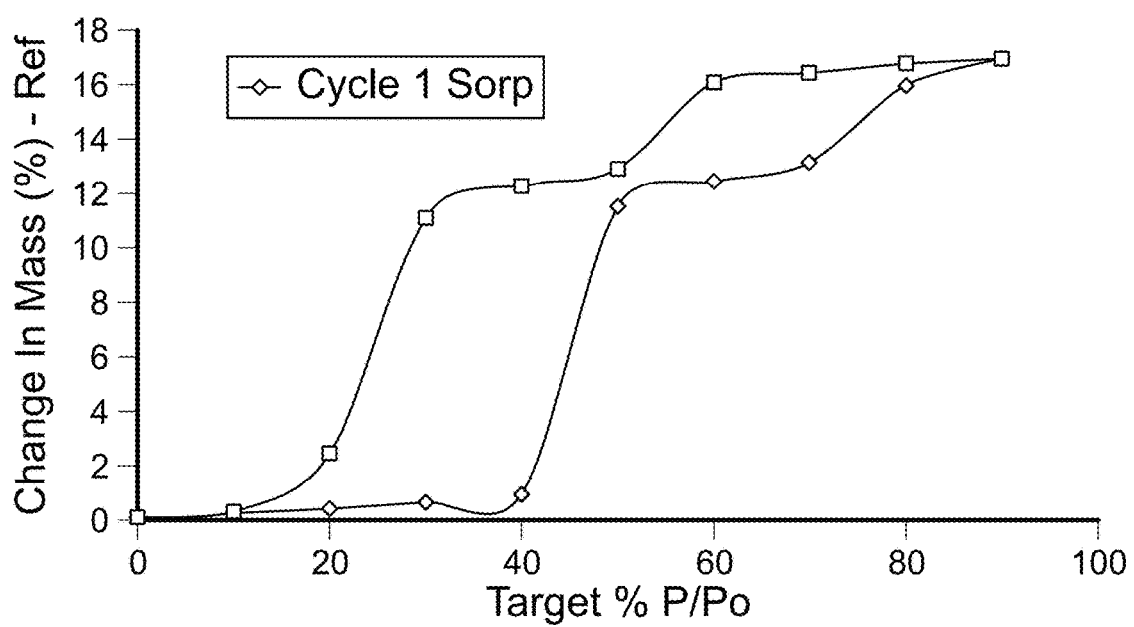

The purity of the Form 13 sample was 98.8%; the KF of an undried Form 13 sample was 35.7%. A DVS scan of Form 13 solid showed a 17% water sorption at 90% RH (FIG. 13D). Form 13 converted to Form 1 upon drying.

A TGA scan of Form 13 solid showed a 1.9% weight loss before 100° C. (FIG. 13C).

Form 13 solid was heated in a DSC chamber to 170° C. (past the endotherm between 50-100° C.), and then scanned by XRD. A comparison of the first and the second XRD and DSC scans, after heating to 170° C., showed that Form 13 converted to Form 1. It can be concluded that the endotherm between 50-100° C. is due to bonded water.

Form 13 solid was heated in a DSC chamber to 330° C. (past the endotherm/exotherm around 300° C.), and then scanned by XRD. A comparison of the first and the third XRD and DSC scans, after heating to 170° C., showed that Form 13 converted to Form 9. It can be concluded that the endotherm/exotherm is due to melting/crystallization events.

TABLE 30

Summary of experiments that generated Form 13

| Form | Solvent | Temperature | Wet | Dry |
|---|---|---|---|---|
| Form 13 | MeOH | RT | Form 13 | Form 1 |
| | MeOH/water | 50° C. | Form 13 | Form 13 |
| | water | RT | Form 13 | Form 1 |
| | water | 50° C. | Form 13 | Form 13 |
| | Toluene/water | RT | Form 13 | Form 1 |
| | Toluene/water | 50° C. | Form 13 | Form 13 |
| | MA/water | RT | Form 13 | Form 1 |
| | n-Butyl acetate/water | RT | Form 13 | Form 12 |
| | n-Butyl acetate/water | 50° C. | Form 13 | Form 1 |
| | Heptane | 50° C. | Form 13 | Form 13 |
| | Heptane/water | RT | Form 13 | Form 12 |
| | Heptane/water | 50° C. | Form 13 | Form 1 |
| | n-Butanol/water | RT | Form 13 | Form 13 |
| | n-Butanol/water | 50° C. | Form 13 | Form 1 |
| | DCM | 50° C. | Form 13 | Form 13 |
| | DCM/water | RT | Form 13 | Form 1 |
| | DCM/water | 50° C. | Form 13 | Form 1 |
| | Acetonitrile/water | 50° C. | Form 13 | Form 13 |
| | IPAc/water | 50° C. | Form 13 | Form 13 |
| | MtBE/water | 50° C. | Form 13 | Form 13 |
| | MIBK/water | 50° C. | Form 13 | Form 1 |

*Amount of water in binary solvents is 5%

TABLE 31

XRD peaks of Form 13

| 2-Theta | d(A) | BG | Height | I % | Area | I % | FWHM |
|---|---|---|---|---|---|---|---|
| 5.06 | 17.45 | 278 | 309 | 6.5 | 3685 | 4.8 | 0.203 |
| 6.379 | 13.8451 | 223 | 4743 | 100 | 76110 | 100 | 0.273 |
| 9.24 | 9.5632 | 164 | 1370 | 28.9 | 20018 | 26.3 | 0.248 |
| 11 | 8.0364 | 173 | 3445 | 72.6 | 51777 | 68 | 0.256 |
| 12.899 | 6.8574 | 195 | 173 | 3.6 | 3114 | 4.1 | 0.306 |
| 13.462 | 6.572 | 199 | 204 | 4.3 | 2376 | 3.1 | 0.198 |
| 14.159 | 6.2498 | 202 | 390 | 8.2 | 5424 | 7.1 | 0.236 |
| 15.56 | 5.6901 | 262 | 1335 | 28.1 | 19295 | 25.4 | 0.246 |
| 16.059 | 5.5145 | 302 | 1002 | 21.1 | 17561 | 23.1 | 0.298 |
| 16.841 | 5.26 | 313 | 774 | 16.3 | 7797 | 10.2 | 0.171 |
| 17.46 | 5.075 | 322 | 314 | 6.6 | 3863 | 5.1 | 0.209 |
| 18.419 | 4.8128 | 339 | 2354 | 49.6 | 29374 | 38.6 | 0.212 |
| 19.3 | 4.5951 | 357 | 210 | 4.4 | 8112 | 10.7 | 0.657 |
| 19.741 | 4.4935 | 329 | 1566 | 33 | 30236 | 39.7 | 0.328 |
| 20.202 | 4.3919 | 342 | 210 | 4.4 | 2880 | 3.8 | 0.233 |

TABLE 31-continued

XRD peaks of Form 13

| 2-Theta | d(A) | BG | Height | I % | Area | I % | FWHM |
|---|---|---|---|---|---|---|---|
| 20.84 | 4.2589 | 300 | 1054 | 22.2 | 18033 | 23.7 | 0.291 |
| 21.201 | 4.1873 | 284 | 964 | 20.3 | 15700 | 20.6 | 0.277 |
| 22.121 | 4.015 | 259 | 197 | 4.2 | 2208 | 2.9 | 0.191 |
| 23.2 | 3.8307 | 268 | 482 | 10.2 | 7844 | 10.3 | 0.277 |
| 24.42 | 3.642 | 280 | 1101 | 23.2 | 16244 | 21.3 | 0.251 |
| 24.839 | 3.5816 | 303 | 468 | 9.9 | 9306 | 12.2 | 0.338 |
| 25.219 | 3.5284 | 385 | 1093 | 23 | 16646 | 21.9 | 0.259 |
| 26.164 | 3.4032 | 359 | 357 | 7.5 | 5064 | 6.7 | 0.241 |
| 26.499 | 3.3609 | 402 | 317 | 6.7 | 7316 | 9.6 | 0.392 |
| 26.798 | 3.324 | 346 | 179 | 3.8 | 8025 | 10.5 | 0.762 |
| 27.339 | 3.2594 | 394 | 720 | 15.2 | 13063 | 17.2 | 0.308 |
| 27.639 | 3.2247 | 341 | 318 | 6.7 | 5673 | 7.5 | 0.303 |
| 28.799 | 3.0974 | 256 | 805 | 17 | 16756 | 22 | 0.354 |
| 29.902 | 2.9857 | 262 | 234 | 4.9 | 3508 | 4.6 | 0.255 |
| 31.234 | 2.8613 | 230 | 106 | 2.2 | 1473 | 1.9 | 0.236 |
| 31.96 | 2.798 | 226 | 308 | 6.5 | 3908 | 5.1 | 0.216 |
| 32.939 | 2.717 | 208 | 117 | 2.5 | 1444 | 1.9 | 0.21 |
| 33.962 | 2.6375 | 199 | 266 | 5.6 | 4617 | 6.1 | 0.295 |
| 34.917 | 2.5675 | 217 | 73 | 1.5 | 736 | 1 | 0.171 |

TABLE 32

Summary of experiments that generated Form 12

| Form | Solvent | Temperature | Wet | Dry |
|---|---|---|---|---|
| Form 12 | Acetonitrile/water | RT | Form 12 | Form 1 |
| | MeOH/water | RT | Form 12 | Form 1 |
| | IPAc/water | RT | Form 12 | Form 1 |
| | EA/water | RT | Form 12 | Form 1 |
| | MtBE/water | RT | Form 12 | Form 1 |
| | MIBK/water | RT | Form 12 | Form 1 |
| | n-Butyl acetate/water | RT | Form 13 | Form 12 |
| | Heptane/water | RT | Form 13 | Form 12 |
| | MA/water | 50° C. | Form 12 | Form 4 |

*Amount of water in binary solvents is 5%

N. Solvates 1-3

The experiments that generated Solvates 1, 2, and 3 are shown in Table 33, below. Solvates 1 and 2 solids were exposed to air overnight, and then analyzed by XRD. After the analysis, the solids were dried at 50° C. under vacuum, and then analyzed by XRD again.

After exposure to air overnight, Solvate 1 converted to low crystallinity; after drying at 50° C., the sample was still low crystallinity solid. After exposure to air overnight, the XRD pattern of Solvate 2 changed a little; after drying at 50° C., the form remained the same as the solid exposed to air overnight.

TABLE 33

Summary of experiments that generated solvates 1-3

| Form | Solvent | Temperature | Wet | Dry |
|---|---|---|---|---|
| Solvate 1 | Acetone | RT | Solvate 1 | Low crystallinity |
| Solvate 2 | Acetone/water | RT | Solvate 2 | Form 4** |
| | Acetone | 50° C. | Solvate 2 | Form 4** |
| Solvate 3 | EtOH/water | RT | Solvate 3 | Form 2 |

*Amount of water in binary solvent is 5%

Example 2: Competitive Slurry Experiments Between Polymorph Forms

In order to find out the thermodynamic stability between the different forms, several competitive slurry experiments were carried out. Form 1, Form 2, Form 2*, Form 3, Form 4, Form 4*, Form 4**, Form 5, Form 7, Form 8, Form 9, Form 10, Form 11, Form 11*, and Form 13 (10 mg for each) was mixed and slurried in 2 mL of solvent at both RT and 50° C. The solids were slurried for 3-5 days and then analyzed by XRD. According to the analytical data, Form 2* was the most stable form in a MeOH, EtOH, and acetone system at both RT and 50° C. Form 4 or 4* was most stable in EA at RT and 50° C. Form 13 was most stable in water at RT and 50° C. Table 34 shows the XRD scan results from the competitive slurry experiments.

TABLE 34

XRD scan results of competitive slurry experiments

| Temperature | Solvent | Form after 3 days; wet/dry | Form after 5 days; wet/dry |
|---|---|---|---|
| RT | MeOH | Form 2*/Form 2* | Form 2*/Form 2* |
| | EtOH | Form 2*/Form 2* | Form 2*/Form 2* |
| | Acetone | Form 2*/Form 2* | Form 2*/Form 2* |
| | EA | Form 4/Form 4 | Form 4/Form 4 |
| | water | Form 13/Form 13 | Form 13/Form 1&Form 13 |
| 50° C. | MeOH | Form 2*/Form 2* | Form 2*/Form 2* |
| | EtOH | Form 2*/Form 2* | Form 2*/Form 2* |
| | Acetone | Form 2*/Form 2* | Form 2*/Form 2* |
| | EA | Form 4/Form 4 | Form 4*/Form 4* |
| | water | Form 13/Form 13 | Form 13/Form 13 |

In order to find out the thermodynamic stability between Form 13 and Form 9, several competitive slurry experiments were carried out. 15 mg of Form 1, Form 9 and Form 13 solid were mixed in 1 mL of toluene, IPAc, and n-butyl acetate, and slurried for 3 days at RT and 50° C.

The residual solid was analyzed by XRD. After a three-day slurry, it was difficult to tell which one was more stable between Form 13 and Form 9. The XRD scan results of the experiment is shown in Table 35, below.

TABLE 35

XRD scan results competitive slurry experiments

| Temperature | Solvent | Form after 3 days; wet/dry |
|---|---|---|
| RT | Toluene | Form 13/Form 1 |
| | IPAc | Form 9 + Form 13/Form 9 + Form 1 |
| | n-Butyl acetate | Form 9 + Form 13/Form 9 + Form 1 |
| 50° C. | Toluene | Form 9 + Form 13/Form 9 + Form 1 |
| | IPAc | Form 9/Form 9 |
| | n-Butyl acetate | Form 9 + Form 13/Form 9 + Form 1 |

Example 3: Composition Studies

The stability and pharmaceutical acceptability of a 0.22 mg/mL suspension of the compound of Formula (I) and a 2.1 mg/mL solution of the compound of Formula (I) were evaluated.

A. Stability studies

1. Preparation of a 2.1 mg/mL Solution of the Compound of Formula (I)

250 mg of the compound of Formula (I) was added to a small jar/vial and dried in an oven at 60° C. (55-65° C.) for 2 hours (without placing the jar/vial directly in contact with the walls of the oven). While still hot, the sample was taken out and the vial was closed and allowed to equilibrate to room temperature.

An empty, dry, and sterile 150 mL media bottle containing a cap and a stir bar was weighed and the weight recorded. About 120 mL of a 75% w/w propylene glycol/water in a 250 mL sterile container (90 g of propylene glycol+30 g of water for injection (WFI)) was prepared and 50 g of the solution was added to the media bottle, followed by 400 µL of 1N HCl, and 134 mg of the compound of Formula (I). The mixture was stirred and sonicated until dissolution occurred.

If the compound was not completely dissolved, a 40 µL aliquot of 1N HCl was added, followed by 10 minutes of stirring. Additional 40 µL aliquots of 1N HCl were added, each with subsequent stirring, until a solution was obtained.

Once dissolved, the 75% w/w propylene glycol solution was added until the solution containing the compound of Formula (I) weighed 60 g. The resulting solution was mixed for no less than 10 minutes. Using aseptic techniques, all the solutions were filtered into a 100 mL sterile vial using a 0.22 µm PES sterile syringe filter (Millex GP) and 10 mL syringes. The 2.1 mg/mL solution of the compound of Formula (I) (75% PG) was stored at controlled room temperature and was tested initially and again after storage for one month and 26 months. The stability profile, including assay (%), purity, pH, and appearance, are shown below in Table 36.

TABLE 36

Stability profile of 2.1 mg/mL solution (75% PG) of a compound of Formula (I) stored at controlled room temperature

| Test | Initial | 1 month | 26 months |
|---|---|---|---|
| % Assay | 98% | 96% | 98% |
| Purity | 98.7% | 98.7% | 98.3% |
| pH | 3.8 | 3.8 | 3.8 |
| Appearance | Clear colorless solution essentially free of visible particulates | Clear colorless solution essentially free of visible particulates | Clear colorless solution essentially free of visible particulates |

2. Preparation of a 0.22 mg/mL Suspension of the Compound of Formula (I)

In a laminar flow hood, an empty, dry, and sterile 500 mL Kimble-Kontes media bottle with cap and stir bar was weighed. 250.0 g±0.5 g of filtered vehicle (propylene glycol solution) was added to the media bottle. 56.3±0.5 mg of the dried compound of Formula (I) (Form 1) was added to the media bottle. The container was closed, and the mixture stirred and sonicated to produce a suspension until no aggregates were observed.

The resulting suspension was stirred for at least 10 minutes. While using aseptic techniques, the vial was filled using a sterile 25-50 mL glass pipette while maintaining mixing during the filling procedure. The vials were crimp sealed and labeled according to protocol. The vials were autoclaved at 122° C. for not less than 20 minutes. The 0.22 mg/mL suspension of the compound of Formula (I) was stored at 30° C. with 65% relative humidity and was analyzed initially and again after storage for 3 months, 6 months, 9 months, and 12 months. The stability profile, including pH, assay (%), % impurities, and osmolality are shown below in Table 37.

TABLE 37

Stability profile of a 0.22 mg/mL suspension of Formula (I) stored at 30° C./65% RH

| Test | Initial | 3 Months | 6 Months | 9 Months | 12 Months |
|---|---|---|---|---|---|
| Appearance | opaque off-white suspension | opaque off-white suspension | opaque off-white suspension | opaque off-white suspension | opaque off-white suspension |
| pH | 7.3 | 7.3 | 7.3 | 7.4 | 7.3 |
| Assay (%) | 104.5 | 100.0 | 100.0 | 100.5 | 100.0 |

TABLE 37-continued

Stability profile of a 0.22 mg/mL suspension of Formula (I) stored at 30° C./65% RH

| Test | Initial | 3 Months | 6 Months | 9 Months | 12 Months |
|---|---|---|---|---|---|
| % impurities | 1.17 | 0.99 | 1.17 | 0.97 | 0.91 |
| Osmolality (mOsm/kg) | 308 | 307 | 307 | N/A | N/A |

As the results above indicate, both compositions of the compound of Formula (I) (i.e., the suspension and the solution) are pharmaceutically acceptable and are stable for extended periods of time.

B. Release Study

The release properties of the compound of Formula (I) were manipulated by formulating it as a plurality of particles in a buffered media to slow the release or dissolution of the active ingredient from the solution.

An accelerated in vitro release profile was performed in 6.5 mm, 0.4 µm polycarbonate costar transwells (Corning catalog #3413). The release profile was carried out by placing 1 mL of 10% propylene glycol/1% Tween 80 in 0.1 mg/mL citric acid in the well and 50 µL of either a 2.1 mg/mL solution or 0.22 mg/mL, 5 mg/mL or 100 mg/mL suspension of the compound of Formula (I) on the insert-membrane. Samples were placed in an incubator set at 37° C. with a rotation speed of 140 rpm. Samples (1.0 mL) were taken every day and replaced with a fresh 1.0 mL aliquot of 10% propylene glycol/1% Tween 80 in 0.1 mg/mL citric acid. Quantitation was performed using HPLC against an external calibration curve.

Results were fitted to the Korsmeyer-Peppas equation and the mean dissolution time (MDT) was calculated (Table 38).

TABLE 38

Mean Dissolution Times

| Sample | MDT |
|---|---|
| 2.1 mg/mL solution of the compound of Formula (I) | minutes |
| 0.22 mg/mL suspension of the compound of Formula (I) | 7 days |
| 5 mg/mL suspension of the compound of Formula (I) | 89 days |
| 100 mg/mL suspension of the compound of Formula (I) | 1116 days |

Example 4: Preliminary In Vitro Studies

A. Wnt pathway inhibition

1. Sp5 assay

The compound of Formula (I) was screened for Wnt activity. The screening assay is described as follows. Reporter cell lines were generated by stably transducing cancer cell lines (e.g., colon cancer) or primary cells (e.g., IEC-6 intestinal cells) with a lentiviral construct that included a Wnt-responsive promoter driving expression of the firefly luciferase gene.

Figure 14:
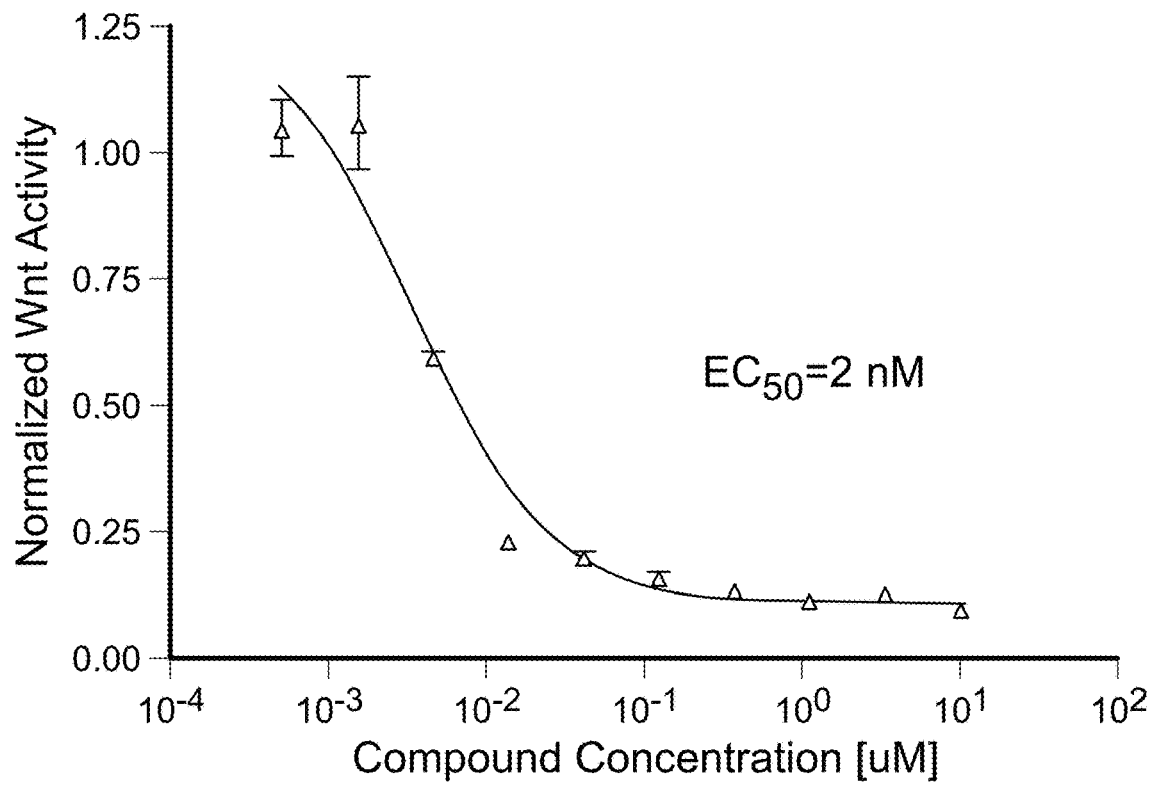
FIG. 14 is a line graph showing Wnt activity vs. concentration of the compound of Formula (I).

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistant gene were selected by treatment with 150 µg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%. For Sp5-Luc reporter gene assays, the cells were plated at 4,000 cells/well in 384-well plates with medium containing 1% fetal bovine serum and incubated overnight at 37° C. and 5% $CO_2$. Following incubation, 20 μL of BrightGlo luminescence reagent (Promega) was added to each well of the 384-well assay plates. The plates were placed on an orbital shaker for 2 min and then luminescence was quantified using the Envision (Perkin Elmer) plate reader. Readings were normalized to DMSO-only treated cells, and normalized activities were utilized for $EC_{50}$ calculations using the dose-response log (inhibitor) vs. response—variable slope (four parameters) nonlinear regression feature available in GraphPad Prism 5.0 (or Dotmatics). The results showed that there was a decrease in Wnt activity with an increase in the concentration of the compound of Formula (I), with an $EC_{50}$ of 2 nM (FIG. 14).

2. In vitro Wnt pathway inhibition

Figure 15:
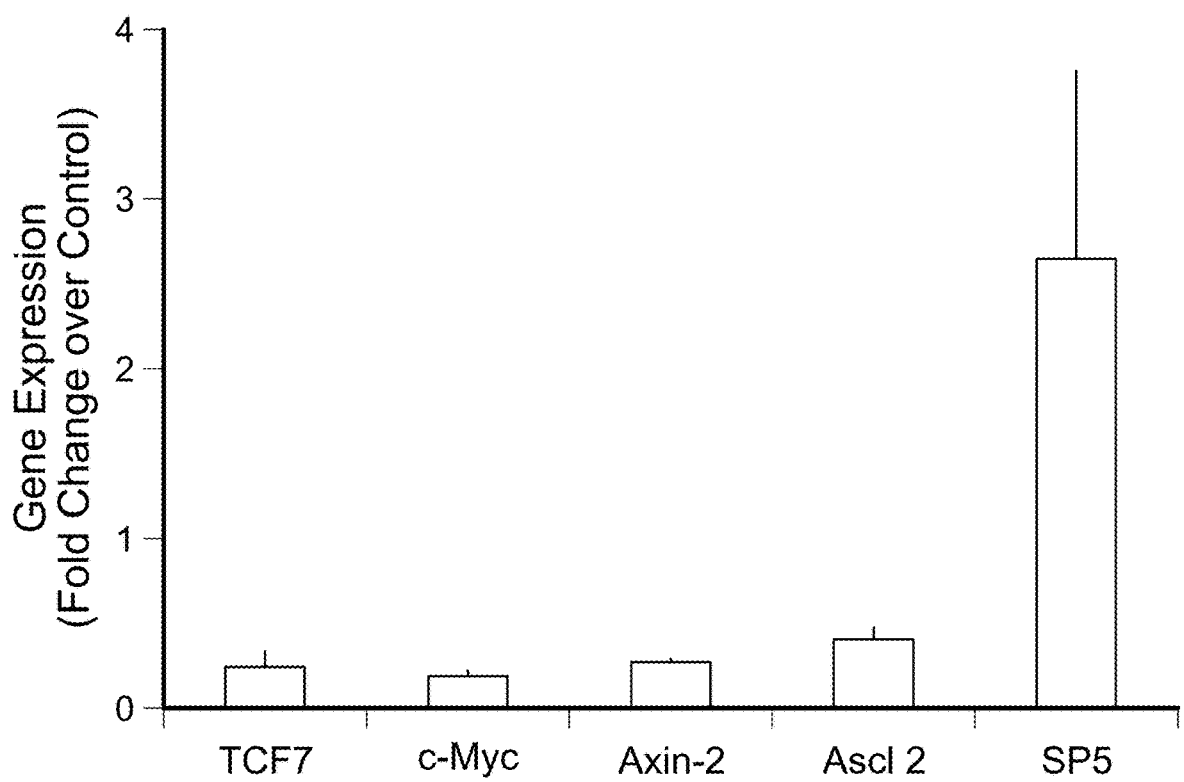
FIG. 15 is a bar graph showing expression of various Wnt genes as compared to control after treatment with the compound of Formula (I).

Human mesenchymal stem cells (MSCs) were plated in 6-well plates in chondrogenic induction medium (Lonza; DMEM, dexamethasone, ascorbate, insulin-transferrin-selenium [ITS supplement], gentamycin-amphotericin [GA-1000], sodium pyruvate, proline and L-glutamine) and treated with the compound of Formula (I) (30 nM) in DMSO or TGF-β3 (20 ng/mL) as a positive control. Cells were incubated at 37° C., 5% $CO_2$ for 48 hours. Cells were pelleted and washed, and total RNA was isolated and purified using RNeasy Plus Mini Kit (Qiagen). cDNA was synthesized from 1 μg of total RNA using QuantiTect Reverse Transcription kit (Qiagen). qRT-PCR was performed with QuantiTect SYBR Green PCR Kit (Qiagen) and gene-specific primers, using CFX384 thermal cycler (Biorad). Transcripts were quantitated by comparative Ct method and normalized to endogenous controls, β-actin and GAPDH. Fold changes were normalized to DMSO treated cells. The results showed downregulation of Wnt genes TCF7, c-Myc, Axin-2, Ascl 2, and SP5 at 48 hours (FIG. 15).

B. Chondrogenesis induction

1. Rhodamine B and Nile Red staining

Figure 16A:
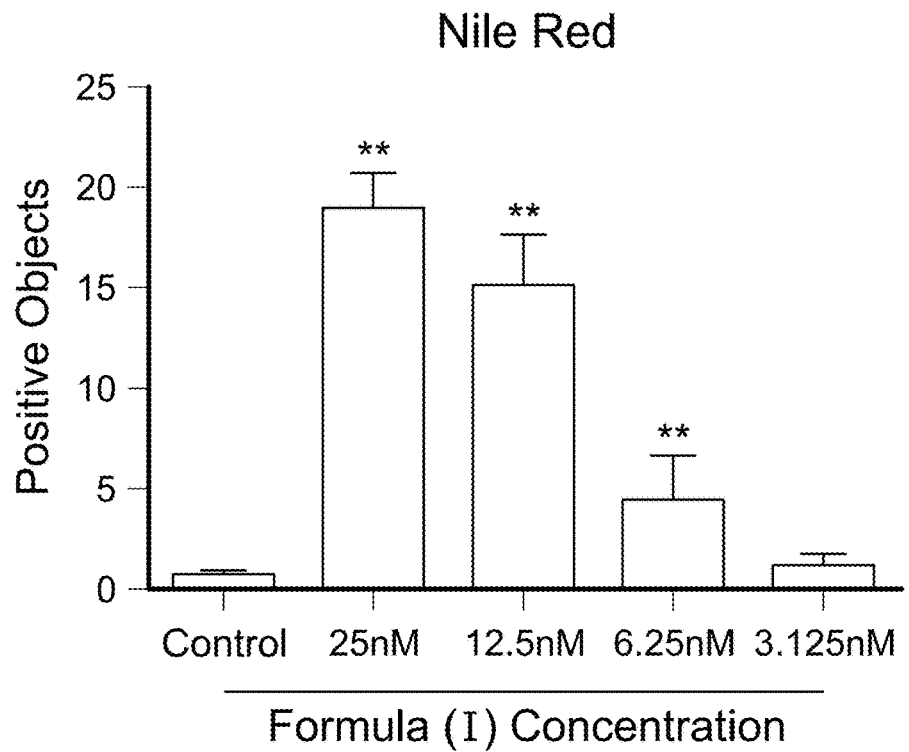
FIGS. 16A-B are bar graphs showing chondrogenesis.
Figure 16B:
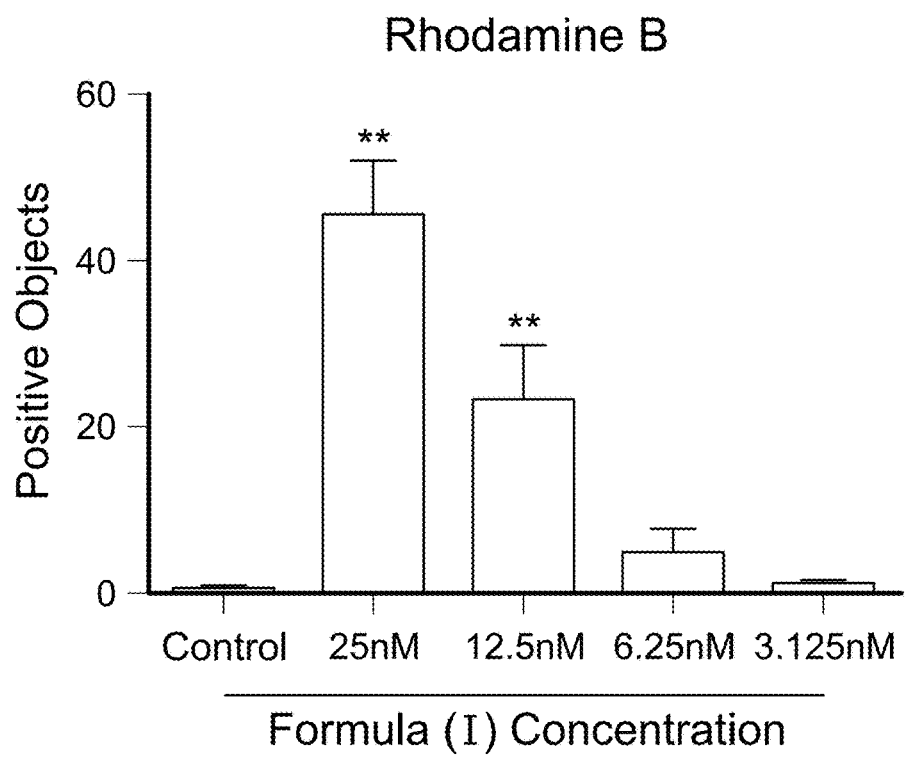

Human MSCs were plated in 96-well plates in chondrogenic induction medium (Lonza; DMEM, dexamethasone, ascorbate, insulin-transferrin-selenium [ITS supplement], gentamycin-amphotericin [GA-1000], sodium pyruvate, proline and L-glutamine) and treated with the compound of Formula (I) in DMSO or TGFβ3 (20 ng/mL) as a positive control. Cells were incubated at 37° C., 5% $CO_2$ for either 7 or 21 days, with media changes every 5 days. The cells were fixed using 4% formaldehyde (Electron Microscopy Sciences), and stained with 2 μg/mL Rhodamine B (Sigma-Aldrich) and 20 μM Nile Red (Sigma-Aldrich) (Johnson et al. (2012) Science 336(6082):717-721). The nodules were imaged (25 images per well for 96 well plates at 10× magnification) by excitation at 531 nm and emission at 625 nm and quantified using the CellInsight CX5 (Thermo Scientific). The number of nodules in each well was normalized to the average of 6 DMSO treated wells on the same plate using Excel (Microsoft Inc.). The normalized averages (fold change over DMSO) of 6 replicate wells for each compound concentration were calculated. The results showed a dose dependent increase in chondrogenesis in cells stained with Nile Red (FIG. 16A) and Rhodamine B (FIG. 16B).

Figure 17:
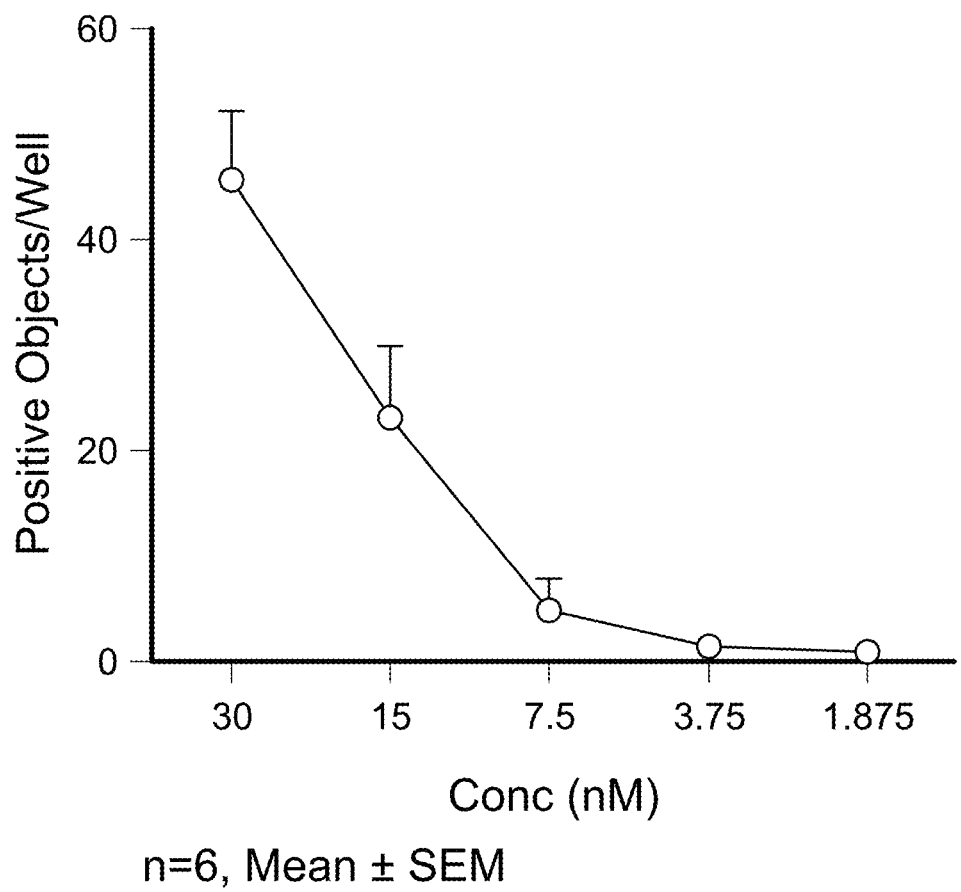
FIG. 17 is a line graph showing a dose-dependent increase in chondrogenesis in cells treated with the compound of Formula (I).

The results of the assay demonstrated dose-dependent chondrogenesis, with increased chondrocyte colonies/well as the concentration of the compound of Formula (I) increased from 1.88 nM to 30 nM (FIG. 17).

2. Alcian Blue staining

Figure 18A:
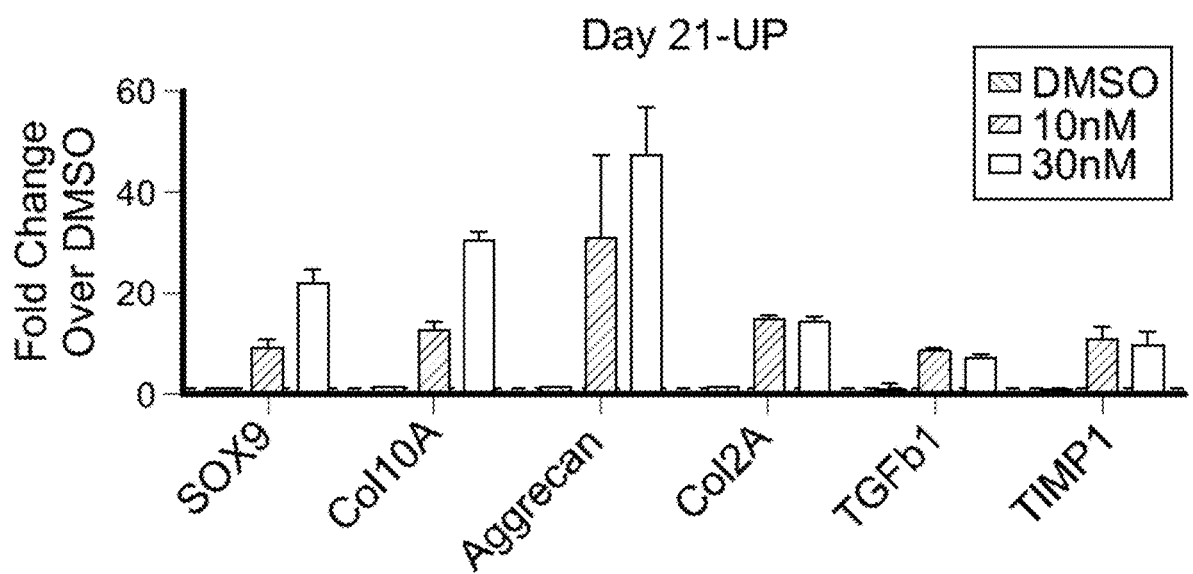
FIGS. 18A-B are bar graphs showing chondrogenesis in cells treated with the compound of Formula (I).
Figure 18B:
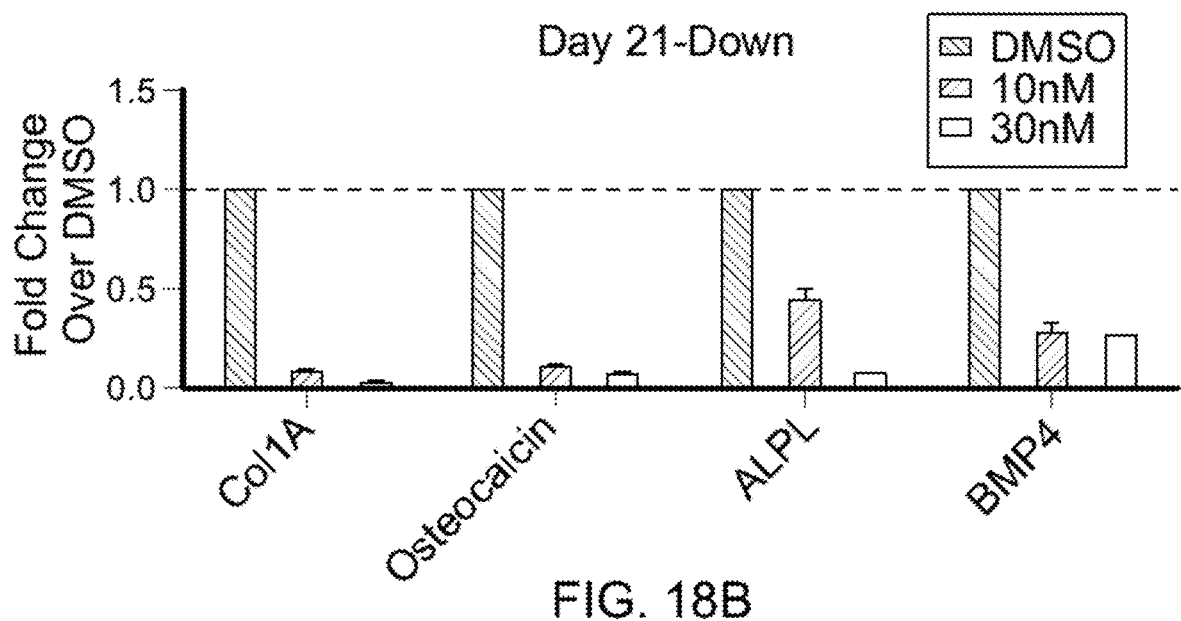

Human MSCs were plated in 10 cm dishes in chondrogenic induction medium (Lonza; DMEM, dexamethasone, ascorbate, insulin-transferrin-selenium [ITS supplement], gentamycin-amphotericin [GA-1000], sodium pyruvate, proline and L-glutamine) and treated with the compound of Formula (I) in DMSO (10 nM and 30 nM) or TGF-β3 (20 ng/mL) as a positive control. Cells were incubated at 37° C., 5% $CO_2$ for 21 days, with media changes every 5 days. Cells were pelleted and washed, and total RNA was isolated and purified using RNeasy Plus Mini Kit (Qiagen). cDNA was synthesized from 1 μg of total RNA using QuantiTect Reverse Transcription kit (Qiagen). qRT-PCR was performed with QuantiTect SYBR Green PCR Kit (Qiagen) and gene-specific primers, using CFX384 thermal cycler (Biorad). Transcripts were quantitated by comparative Ct method and normalized to endogenous controls, β-actin and GAPDH. Fold changes were normalized to DMSO treated cells. The results showed that the compound of Formula (I) upregulated chondrogenic gene expression (FIG. 18A) and downregulated osteogenic gene expression (FIG. 18B) at both concentrations of the compound of Formula (I) tested.

3. Alcian Blue, Safranin 0, and Type II Collagen Staining

Human MSCs were plated in 96-well plates in chondrogenic induction medium (Lonza; DMEM, dexamethasone, ascorbate, insulin-transferrin-selenium [ITS supplement], gentamycin-amphotericin [GA-1000], sodium pyruvate, proline and L-glutamine) and treated with the compound of Formula (I) in DMSO or TGFβ3 (20 ng/mL) as a positive control. Cells were incubated at 37° C., 5% $CO_2$ for either 14 or 21 days, with media changes every 5 days. The cells were fixed using 4% formaldehyde (Electron Microscopy Sciences). For Alcian Blue staining, cells were incubated with 10 mg/mL Alcian Blue (Sigma-Aldrich) in 3% acetic acid (Sigma-Aldrich), pH 2.5 for 30 minutes, washed with PBS, and imaged using a light microscope (Life Technologies) at 10× magnification. For Safranin 0 staining, cells were incubated with 0.1% Safranin 0 (Sigma-Aldrich) in distilled water for 5 minutes, washed with PBS and imaged using a light microscope (Life Technologies) at 10× magnification. For Type II collagen staining, cells were incubated with primary antibody in 3% BSA, 0.3% Triton X-100 in PBS with overnight incubation at 40° C. Cells were then washed and incubated with fluorophore-linked secondary antibody and DAPI (Life Technologies) for 1 hr at room temperature. Cells were washed and imaged using EVOS FL Microscope (Life Technologies). The results indicated an increased amount of chondrogenesis in the cells treated with the compound of Formula (I) as compared to control.

C. Inhibition of protease release

Figure 19A:
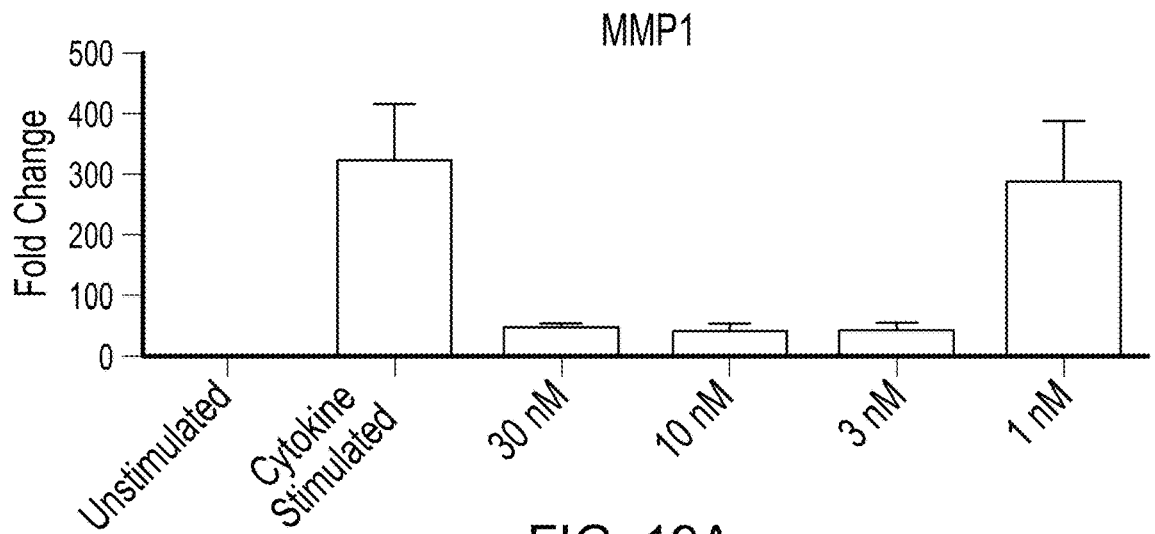
FIGS. 19A-C are bar graphs showing inhibition of protease release in cells treated with the compound of Formula (I).
Figure 19B:
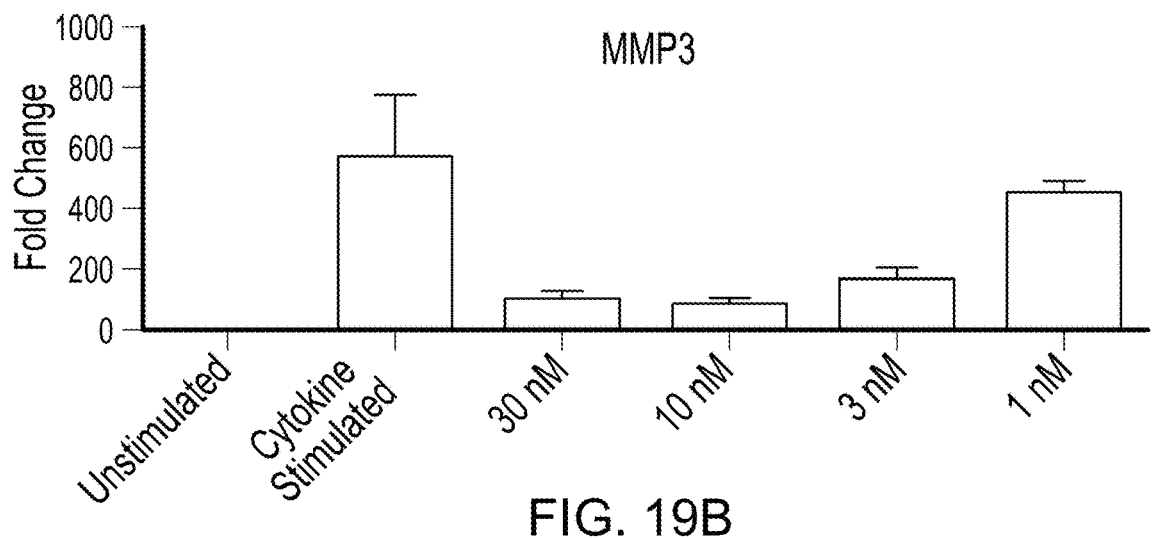
Figure 19C:
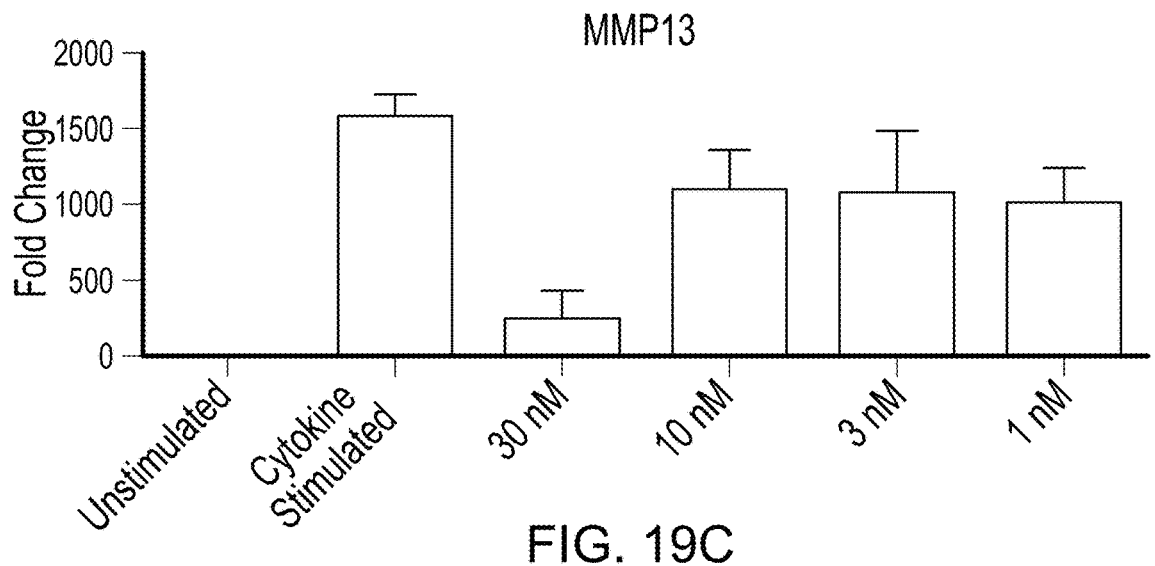

Human MSCs were plated in 10 cm dishes in chondrogenic induction medium (Lonza; DMEM, dexamethasone, ascorbate, insulin-transferrin-selenium [ITS supplement], gentamycin-amphotericin [GA-1000], sodium pyruvate, proline and L-glutamine) and treated with TGF-β3 (20 ng/mL) to induce chondrogenic differentiation. Cells from 4 dishes were pooled and re-plated in 24-well plates in Chondrogenic Induction Medium and treated with various concentrations of the compound of Formula (I). 4 hours later, MMP production was stimulated by adding TNF-α (20 ng/mL)+Oncostatin M (10 ng/mL) and cells were incubated at 37° C., 5% $CO_2$ for 72 hours. Cells were then pelleted and washed, and total RNA was isolated and purified using RNeasy Plus Mini Kit (Qiagen). cDNA was synthesized from 1 μg of total RNA using QuantiTect Reverse Transcription kit (Qiagen). qRT-PCR was performed with QuantiTect SYBR Green PCR Kit (Qiagen) and gene-specific primers, using CFX384 thermal cycler (Biorad). Transcripts were quantitated by comparative Ct method, and normalized to endogenous controls, β-actin and GAPDH. Fold changes were normalized to unstimulated cells. The results demonstrated a dose-dependent inhibition of protease expression. FIG. 19A depicts MMP1 production. FIG. 19B depicts MMP3 production. FIG. 19C depicts MMP13 production.

D. Immunosuppression

1. Primary synovial chondrocytes

Figure 20A:
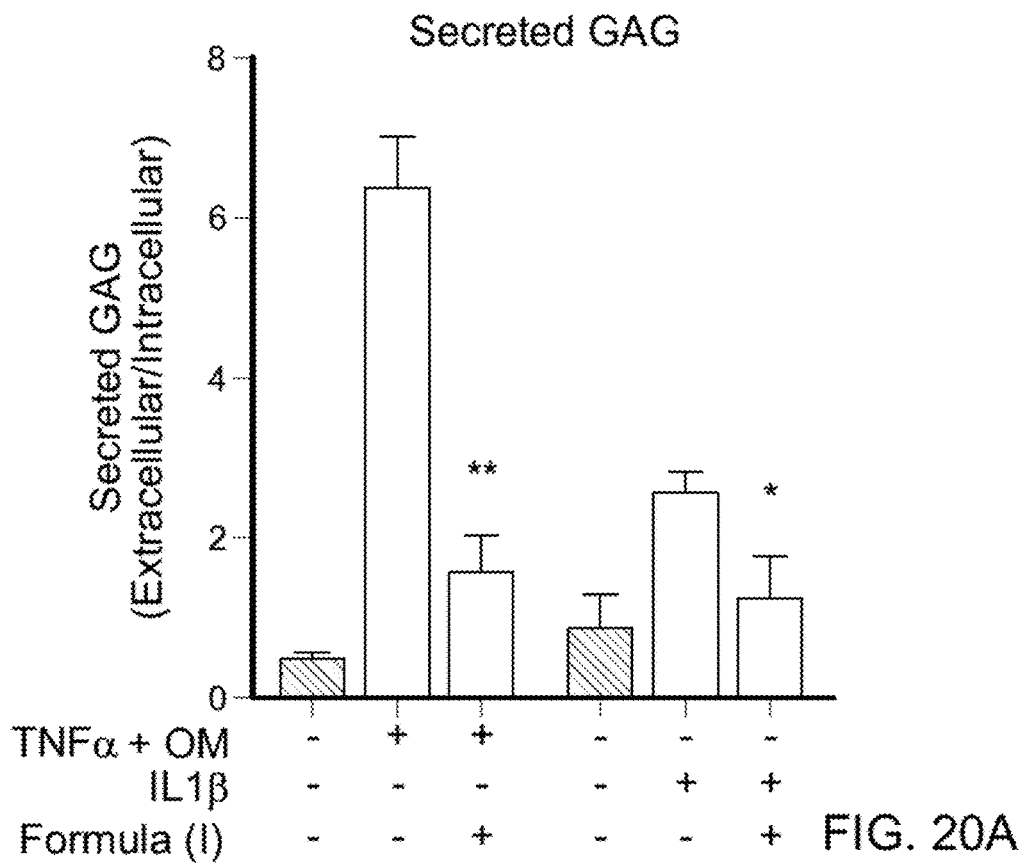
FIGS. 20A-B are bar graphs showing the immunosuppressive activity of the compound of Formula (I) in human mesenchymal stem cells stimulated with TNF-α and oncostatin M or IL-1β.
Figure 20B:
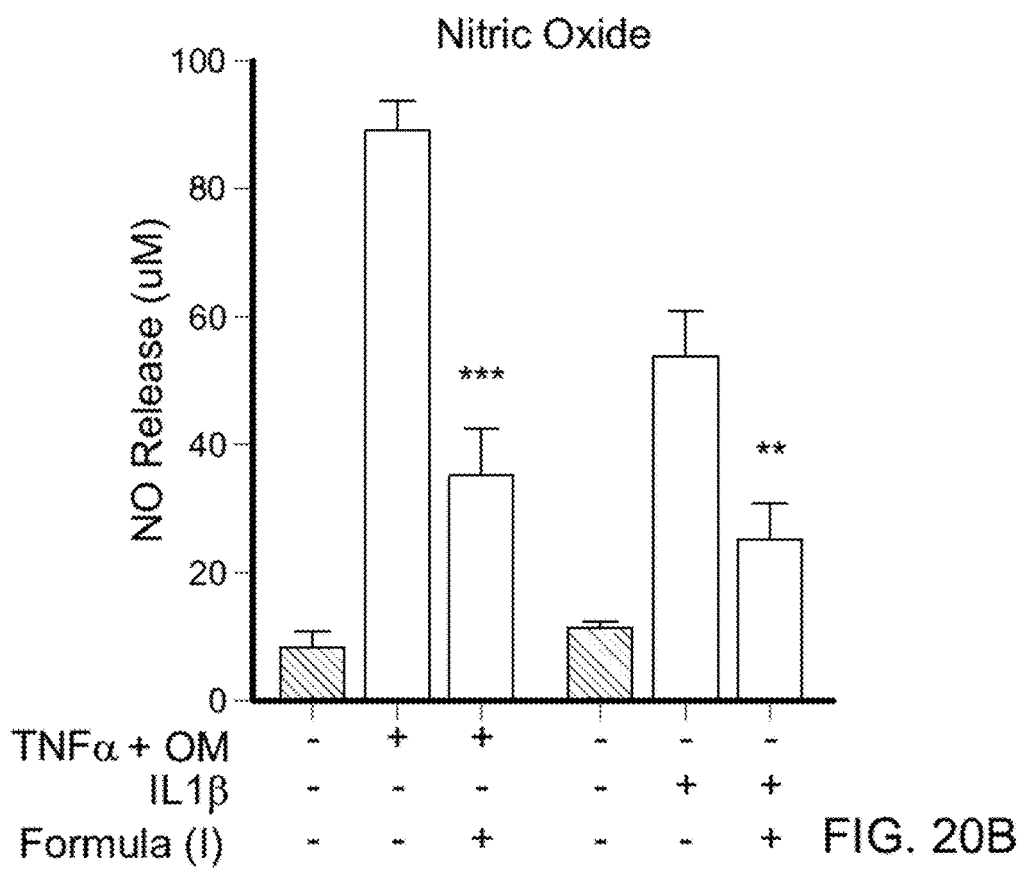

Human MSCs were plated in 10 cm dishes in chondrogenic induction medium (Lonza; DMEM, dexamethasone, ascorbate, insulin-transferrin-selenium [ITS supplement], gentamycin-amphotericin [GA-1000], sodium pyruvate, proline and L-glutamine) and treated with TGF-β3 (20 ng/mL) to induce chondrogenic differentiation. Cells from 4 dishes were pooled and re-plated in 24-well plates in Chondrogenic Induction Medium and treated with various concentrations of the compound of Formula (I). 4 hours later, cells were stimulated by adding TNF-α (20 ng/mL)+Oncostatin M (10 ng/mL) or IL-1β (10 ng/mL) and incubated at 37° C., 5% $CO_2$ for 72 hours. Chondrocytes were digested with papain (Sigma). GAG content was measured using the dimethylmethylene blue (DMMB) kit (Chondrex). Briefly, the digested chondrocytes were mixed with DMMB in formate buffer and absorbance at 535 nm was measured using Cytation 3 (Biotek). Nitric oxide was measured using Greiss reagent (Promega) according to manufacturer's protocol. The results showed that cells treated with the compound of Formula (I) reduced both secreted GAG (FIG. 20A) and the release of nitric oxide (FIG. 20B) in cells stimulated with TNF-α and oncostatin M and those stimulated with IL-1β.

2. Synovial fibroblasts

Figure 21A:
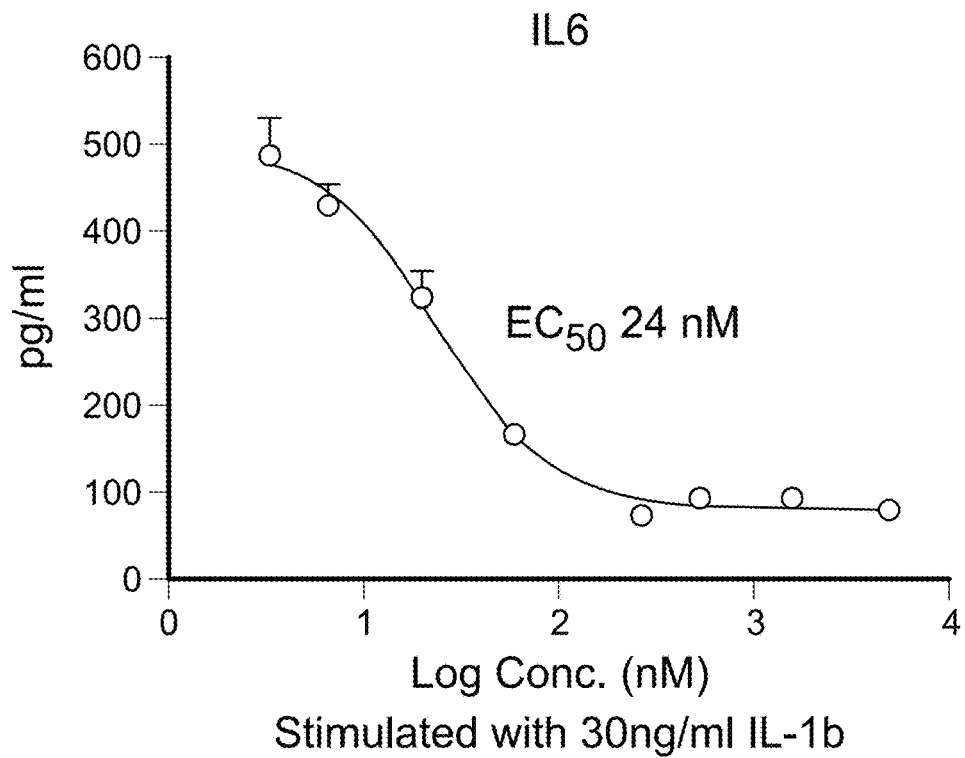
FIGS. 21A-B are line graphs showing the immunosuppressive activity of the compound of Formula (I) in synovial fibroblasts.
Figure 21B:
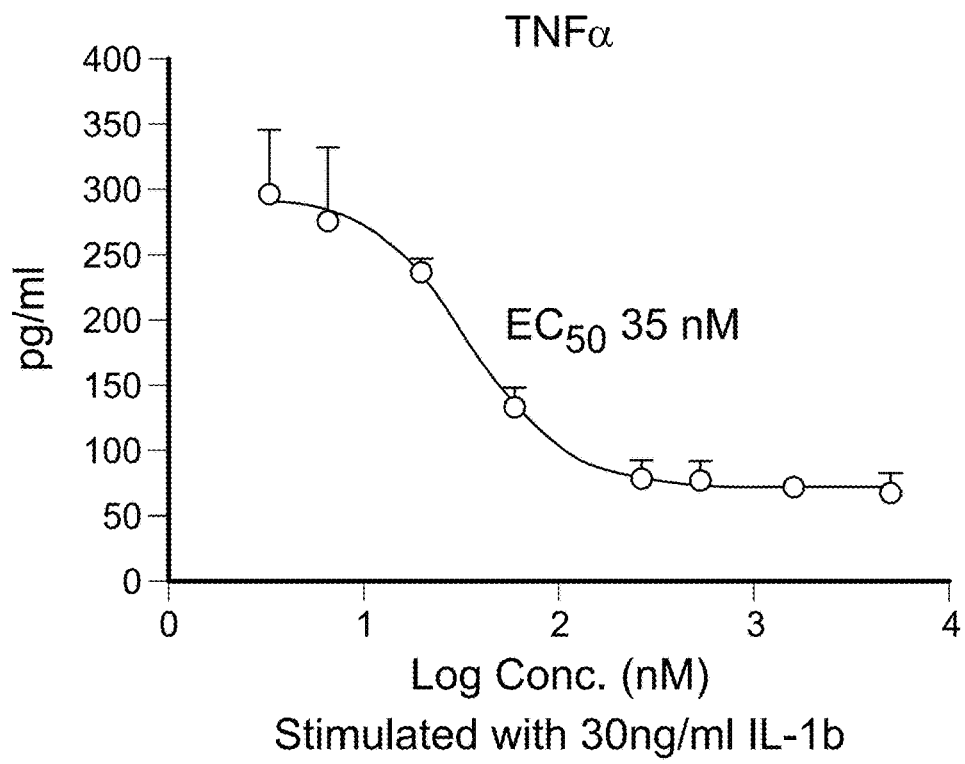

Synovial fibroblasts (SW982 cells; ATCC) were cultured in Leibovitz's L-15 Medium (ATCC) with 10% FBS at 37° C. and 0% $CO_2$. 24 hours before the start of the assay, the media was changed to Leibovitz's L-15 Medium with 1% FBS. The compound of Formula (I) was dissolved in DMSO as a 10 mM stock and used to prepare compound source plates. A serial dilution (8-point dose-response) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.05%. Synovial fibroblasts were plated at 2×10e4 cells/well and stimulated with IL-1β (20 ng/ml) and incubated at 37° C. for 48 hrs. Plates were spun in a centrifuge for 1 minute at 10,000 rpm and supernatants were collected for ELISA. Supernatants were diluted 1:1 for the TNF-α assay and 1:4 for the IL-6 assay using the assay medium. ELISA was performed using Human TNF-α ELISA MAX™ Deluxe (Catalog #430204, Biolegend, San Diego, Calif.) and Human IL-6 ELISA MAXIM Deluxe (Catalog #430504, Biolegend, San Diego, Calif.) kits. Briefly, 96-well plates were coated with the appropriate capture antibody overnight and washed to remove excess antibody. Blocking buffer was added and incubated for 1 hour to prevent non-specific binding. Diluted supernatants were incubated in the coated plates for 2 hours at room temperature. Following washes to remove unbound proteins, biotinylated detection antibody was added and incubated for 30 minutes at room temperature, followed by washes to remove unbound excess antibody. Avidin-HRP was then added and incubated for 30 minutes at room temperature. Following several washes to remove unbound avidin-HRP, the TMB substrate was added and the plates were read on the Cytation 3 plate reader (Biotek Inc., Winooski, Vt.) at an absorbance of 450 nm with correction at 570 nm. All samples were processed in triplicate. Inhibition profile and $EC_{50}$ was calculated using Prism 5 (GraphPad Software Inc, La Jolla, Calif., USA). The results showed a dose-dependent inhibition of both TNF-α (FIG. 21A) and IL-6 (FIG. 21B) production in synovial fibroblasts, with $EC_{50}$ values of ~35 nM and ~24 nM, respectively.

3. THP1 monocytes

Figure 22A:
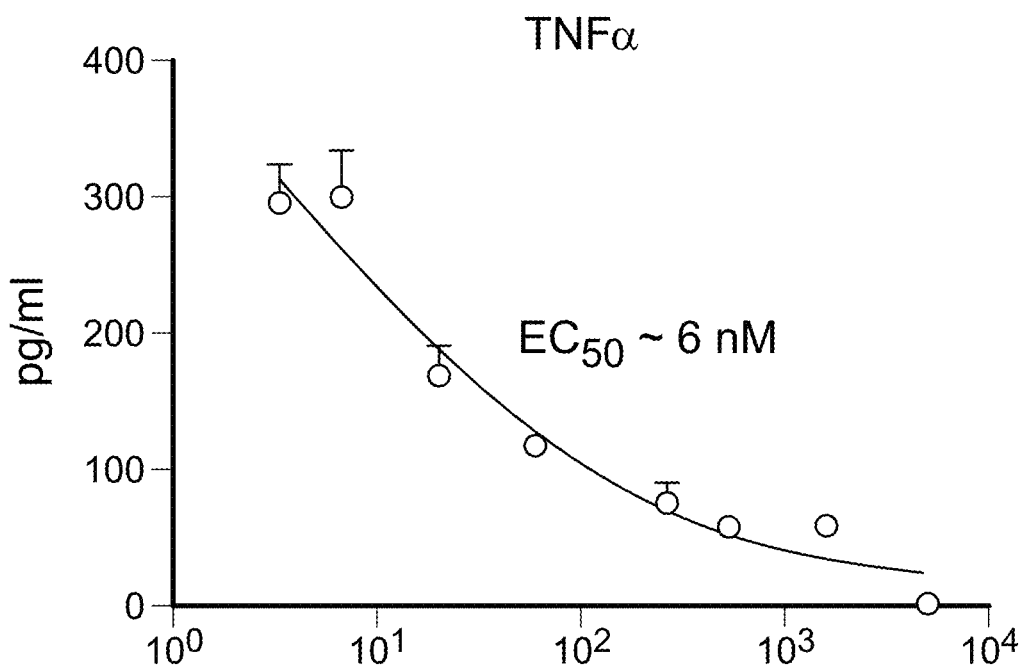
FIG. 22A-B are line graphs showing the immunosuppressive activity of the compound of Formula (I) in THP-1 monocytes.
Figure 22B:
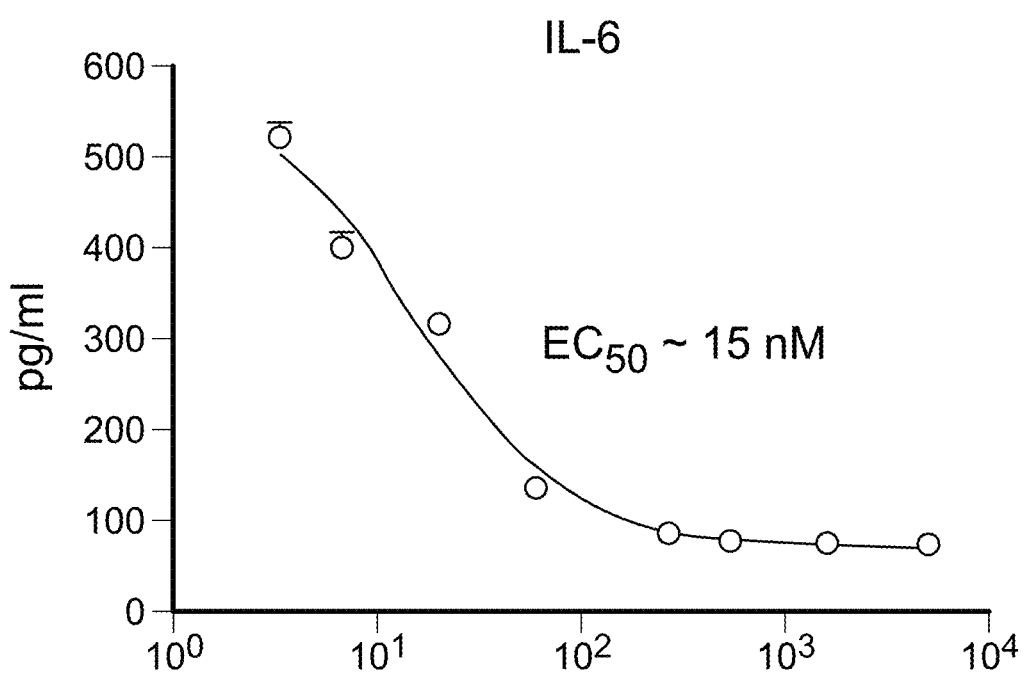

THP-1 cells (Catalog #TIB-202, ATCC, Manassas, Va.) were cultured and grown in Roswell Park Memorial Institute (RPMI) 1640 Medium (Catalog #21870-100, Buffalo, N.Y.) with 1% L-glutamine, 1% HEPES, 1% sodium pyruvate, 2% sodium bicarbonate supplemented with 100 units/mL penicillin, 50 μg/mL streptomycin, 2-mercaptoethanol (0.05 mM) [basal medium] and 10% fetal bovine serum (Catalog #16140089, Life Technologies, Carlsbad, Calif.) at 37° C. and 5% $CO_2$. THP-1 cells were cultured in basal medium with 1% FBS for 24 hours before the start of the assay. The compound of Formula (I) was dissolved in DMSO as a 10 mM stock and used to prepare compound source plates. A serial dilution (8-point dose-response) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.05%. THP-1 cells were plated at 6×10e4 cells/well. For the TNF-α assay, 50 ng/mL of LPS was added to the wells after 2 hours to induce cytokine production, and cells were incubated for 20 hours at 37° C. For the IL-6 assay, 500 ng/mL of LPS was added after 2 hours and cells were incubated for 6 hours at 37° C. Plates were spun in a centrifuge for 1 minute at 10,000 rpm and supernatants were collected for ELISA. Supernatants were diluted 1:1 for the TNF-α assay and 1:4 for the IL-6 assay using the assay medium. ELISA was performed using Human TNF-α ELISA MAX™ Deluxe (Catalog #430204, Biolegend, San Diego, Calif.) and Human IL-6 ELISA MAX™ Deluxe (Catalog #430504, Biolegend, San Diego, Calif.) kits. Briefly, 96-well plates were coated with the appropriate capture antibody overnight and washed to remove excess antibody. Blocking buffer was added and incubated for 1 hour to prevent non-specific binding. Diluted supernatants were incubated in the coated plates for 2 hours at room temperature. Following washes to remove unbound proteins, biotinylated detection antibody was added and incubated for 30 minutes at room temperature, followed by washes to remove unbound excess antibody. Avidin-HRP was then added and incubated for 30 minutes at room temperature. Following several washes to remove unbound avidin-HRP, the TMB substrate was added and the plates were read on the Cytation 3 plate reader (Biotek Inc., Winooski, Vt.) at an absorbance of 450 nm with correction at 570 nm. All samples were processed in triplicate. Inhibition profile and $EC_{50}$ was calculated using Prism 5 (GraphPad Software Inc, La Jolla, Calif., USA). The results showed a dose-dependent inhibition of both TNF-α (FIG. 22A) and IL-6 (FIG. 22B) production in THP-1 monocytes, with $EC_{50}$ values of ~6 nM and ~15 nM, respectively.

Example 5: Radiolabeled Studies

A. Plasma concentrations and terminal elimination half-lives in the blood

1. Plasma concentrations following a single intra-articular (IA) injection of radiolabeled compound of Formula (I) in rats Plasma concentration and distribution of the compound of Formula (I) following a single IA injection in Sprague Dawley (SD) rats were investigated in radiolabeled and mass balance studies with a tritium-labeled ($^3$H) compound of Formula (I). [$^3$H]-Formula (I) was formulated as a suspension in 0.5% carboxymethylcellulose/0.05% polysorbate 80 for intra-articular (IA) injection and diluted with unlabeled Formula (I) to the appropriate concentration and injected in the rat knee joint at a dose level equivalent to 1 μg/knee. Following the single IA injection, low circulating plasma levels (0.002 to 0.075 ng-equivalents/g) which declined over time (48 to 168 hours) were detected in the rat plasma by quantitative radiochemical analysis (QRA) with 50-fold higher sensitivity of 2 pg/g or pg/mL over that of the LCMS method (LLOQ of 0.1 ng/mL). Mean radioactivity exposures were low, ranging from 0.832 to 1.548 ng-equiv.h/g ($AUC_{(0-t)}$ and $AUC_{(0-inf.)}$) (males) and 1.040 to 1.818 ng-equiv.h/g ($AUC_{(0-t)}$ and $AUC_{(0-inf.)}$) (females), with $T_{max}$ values of 1 and 4 hours and apparent terminal elimination half-lives in the blood of 57 and 124 hours (in males and females, respectively).

2. Plasma concentration following two single IA injections

Two single IA injections of the 1 μg/knee of the suspension described above containing the compound of Formula (I) radiolabeled with tritium were made in both knee joints of SD rats. Low circulating plasma radioactivity (0.010 to 0.055 ng-equivalents/g) was detected with a dose-proportional increase following two (bilateral) IA injections compared to a single IA injection (see above) and a clear exponential decline from 48 to 168 hours.

B. Quantitative whole body autoradiography and excretion of radiolabeled compound of Formula (I) in rats 1. Quantitative Whole Body Autoradiography in Rats Following two IA injections at 1 μg/knee in SD rats, quantitative whole body autoradiography (QWBA) indicated ~75% total radioactivity was recovered from the whole carcass, feces, urine and cage wash, and autoradiographic images indicated that radioactivity was confined in the lymph nodes (inguinal and lumbar lymph nodes that drain the hind legs), small and large intestines, and fecal matter, and negligible/undetectable in major organs at 1 hour and up to 168 hours post-IA injection.

2. Excretion of Radiolabeled Compound

In terms of excretion, 95% of the excreted radioactivity was recovered in the feces and only 5% in the urine. QWBA radiographic images and quantitation of radioactivity in the feces with much less recovery in the urine, support the hypothesis that [$^3$H]-Formula (I) is being eliminated by drainage in the lumbar and inguinal lymph ducts and lymph nodes, and through the small and large intestines and cecum in a mechanism consistent with slow passive fecal excretion, a major route of elimination of slowly metabolized xenobiotics. During this process, the radiolabeled [$^3$H]-Formula (I) was degraded with only ~1.5% of parent detected in the fecal matter.

C. Persistence of radiolabeled compound of Formula (I) in the knee joints

1. Rabbit knee joints

In rabbits, following two single IA injections in two knees at 4 μg/knee (corresponding to the mid clinical dose of 70 μg/knee), 75% of administered radioactivity was recovered in the knee after 1 hour up to 168 hours, consistent with the recoveries in the SD rat knee joints. Rabbit knee joint microautoradiography indicated that radioactivity was confined in the fluid-filled synovial space and bursa, and surrounded the meniscus and femoral and tibial bone heads, following IA injection.

2. Rat knee joints

Following two IA injections at 1 μg/knee in the SD rats, hind legs were excised and solubilized for quantitation of radiolabeled [$^3$H]-Formula (I) in the whole knee joint at different time points post-IA injections: 1 h, 4 h, 12 h, 24 h, 48 h, 96 h and 168 h. These same animals were used for the QWBA experiments (above). Knee joint recoveries indicated that ~60-85% of the administered radioactivity was recovered in each knee joint immediately 1 h post-IA injection up to 168 h (1 week). The variable values obtained at 1 h to 168 h were due to the use of the same animals for QWBA and incomplete excision of the knees from the whole animal for solubilization, but it is generally consistent with the values recovered in the rabbit knee joint above (see above).

Further time points (Days 14-180) were collected from different animals not used for QWBA, resulting in more consistent recoveries between the hind legs A and B. Quantitation of [$^3$H]-Formula (I) in the solubilized knee joint indicated that there was a progressive decrease of [$^3$H]-Formula (I) in the knee joint, with mean values of 64%, 54%, 42% and 38% of administered dose per knee on Days 14, 30, 60 and 90, respectively. On Day 180, only about ~6.6% of administered dose was detected.

The stability and radiochemical purity (RCP) of the radiolabeled [$^3$H]-Formula (I) was established in a concurrent experiment where a formulation of radiolabeled [$^3$H]-Formula (I) was incubated at 37° C. and radiochemical purity (RCP) of aliquots were analyzed over time and determined to be ~95.5% (Days 0, 7, 14 and 30), 94.5% (Day 60), 93% (Day 90), and 83% (Day 180). Radiographic images were obtained and indicated that the compound of Formula (I) was still detectable in the knee joint space on Day 180.

D. Half-life in rat knee joints

The half-life ($T_{1/2}$) of [$^3$H]-Formula (I) in the knee joint of SD rats was calculated using the radioactivity values recovered in the rat hind legs (knee joints) on Days 14 to 180: $T_{1/2}$=51.64 days (including all time points, Days 14-180) with elimination rate constant, $K_e$, of 0.01342, and $T_{1/2}$=100.9 days (time points Days 14-90 only, but excluding Day 180) with elimination rate constant, $K_e$, of 0.00687.

Example 6: Preliminary In Vivo Animal Studies

In rats and dogs, the pharmacokinetic profile, safety profile, tissue distribution and cartilage regeneration following a single intra-articular (IA) injection of the compound of Formula (I) in the plasma and the knee joint (cartilage and bone) was determined. The compound of Formula (I) (Form 1) was formulated as a suspension composition in 0.5% CMC/0.05% Polysorbate 80 in PBS.

A. Dog pharmacokinetics

A 350 μL suspension of the compound of Formula (I) (Form 1), formulated as described above, and corresponding to 3 and 30 μg/knee, was injected intra-articularly (IA) into the right and left knees of twelve (12) naïve male beagle dogs. On Day 1, blood was collected at 15 minutes immediately after IA injection and on Days 45, 91 and 179, dogs were sacrificed and blood samples and the knee joints were collected. Plasma and tissue concentrations (bone, cartilage and synovial fluid) were determined using the HPLC-MS/MS bioanalytical method with a dynamic range of 2.00 to 1000 ng/mL in plasma or 5.00 to 5000 ng/g in tissue.

TABLE 39

Pharmacokinetics of the compound of Formula (I) in dogs

| Dose (μg/knee) | Day | Compound of Formula (I) Concentration | | Total Amount | |
|---|---|---|---|---|---|
| | | Cartilage ng/g [nM] | Bone ng/g [nM] | Recovered (ng) | % Recovered |
| 3 | 45 | 152 [301] | 11.2 [22] | 152 | 5.1 |
| | 91 | 37.0 [73] | BQL | 16.6 | 0.55 |
| | 179 | 63.7 [126] | 12.8 [25] | 79.0 | 2.6 |
| 30 | 45 | 4525 [8960] | 586 [1160] | 5057 | 16.9 |
| | 91 | 2328 [4609] | 118 [234] | 2175 | 7.4 |
| | 179 | 115 [228] | 1156 [2289] | 2109 | 7.0 |

All plasma samples had concentrations of the compound of Formula (I) below the quantitation limit (BQL<2.00 ng/mL) at 15 min post-dose in both the 3 or 30 μg/knee dose groups. The mean cartilage, bone, and synovial fluid tissue concentrations, as well as total amount recovered, were calculated and plotted against the time collected. The total amount of the compound of Formula (I) recovered from cartilage and bone tissues from the tibia were 152, 16.6 and 79.0 ng in the 3 μg/knee (Group 1, low dose) animals for Days 45, 91 and 179 respectively, representing 5.1, 0.55 and 2.5% of administered dose, while in the 30 μg/knee (Group 2, high dose) animals had a total amount of the compound of Formula (I) of 5057, 2248 and 2109 ng for Days 45, 91 and 179 respectively, representing 16.8, 7.25 and 7.03% of administered dose.

Acute intra-articular administration of the compound of Formula (I) at dosages up to 30 μg/knee in dogs resulted in no measurable systemic exposure as evidenced by lack of quantifiable plasma concentrations of the compound of Formula (I) 15 minutes post-dose collection period. At the end of 179 days, the compound of Formula (I) was still detectable in the cartilage and bones, at approximately 2.6% to 7.0% of the administered dose, indicating that the compound of Formula (I) can persist in the site of action for an extended period of time. There was no mortality in the study, all animals remained physically healthy, and no adverse effects from intra-articular administration of the compound of Formula (I) were noted in the dogs.

B. Rat pharmacokinetics

The pharmacokinetics of the compound of Formula (I) in rats was studied. Three Sprague Dawley rats were each injected with a single intra-articular (IA) injection (one IA injection per knee) of a suspension composition of the compound of Formula (I) (Form 1) at 0.3, 1, 3 and 9 μg/knee. Plasma was collected beginning at 15 minutes post-dose on Day 1 and the knee joint was collected at Days 30, 90, and 180 post-IA administration. The bone and cartilage tissues from the knee joint were segregated and concentrations analyzed. The compound was retained in the knee joint above the target concentration level (~30 nM, the intended clinical therapeutic dose) for greater than 180 days and was undetectable in the plasma at all time points. These results, shown in Table 40, show that the compound of Formula (I) had sustained local exposure and no systemic exposure.

TABLE 40

Pharmacokinetics of the compound of Formula (I) in rats

| Group and Dose Level | Tissue | Day 30 Formula (I) concentration (ng/g) [nM] | Day 90 Formula (I) concentration (ng/g) [nM] | Day 180 Formula (I) concentration (ng/g) [nM] |
|---|---|---|---|---|
| Group 1 - 0.3 μg/knee | Cartilage | 263 [521 nM] | 78 [154 nM] | 69.6 [138 nM] |
| | Bone | 25.8 [51 nM] | 6.56 [13 nM] | 19.0 [38 nM] |
| | Plasma | BQL | BQL | BQL |
| Group 2 - 1 μg/knee | Cartilage | 39 [774 nM] | 243 [481 nM] | 201 [398 nM] |
| | Bone | 196 [388 nM] | 44.4 [88 nM] | 46.4 [92 nM] |
| | Plasma | BQL | BQL | BQL |
| Group 3 - 3 μg/knee | Cartilage | 2574 [5097 nM] | 645 [1277 nM] | 717 [1420 nM] |
| | Bone | 738 [1461 nM] | 166 [329 nM] | 15 [313 nM] |
| | Plasma | BQL | BQL | BQL |
| Group 4 - 9 μg/knee | Cartilage | 3563 [7055 nM] | | 224 [4437 nM] |
| | Bone | 3293 [6520 nM] | | 67 [1335 nM] |
| | Plasma | BQL | BQL | BQL |

BQL = Below Quantitation Limit.
QL = Quantitation Limit = 5 ng/mL in plasma and tissues (cartilage or bone)

C. Toxicology (safety) studies in dogs

The local toxicology of Form 1 of the compound of Formula (I) in dogs was studied. The compound of Formula (I) (Form 1) was administered via single or multiple (9 times) intra-articular (IA) injections as a suspension composition in beagle dogs to evaluate local toxicity.

After IA injection, the right stifle joint was histologically evaluated for inflammation, cartilage health, bone density, etc. Toxicology was evaluated immediately after a single or multiple (3 or 9 once-monthly) IA injections. Following a single IA injection in the right femoral tibial (stifle) joint of dogs at 0.07, 1.75 and 35 mg of the compound of Formula (I), no adverse histopathological effects were observed in the bone and cartilage except local inflammatory response in the synovium and extra-articular tissues at the injection site of high-dose animals. The no observed adverse effect level (NOAEL) for the compound of Formula (I) in this study was the mid-dose of 1.75 mg/knee.

In the repeat-dose toxicology study in dogs, findings following once-monthly IA injection of the compound of Formula (I) at 12, 36 or 116 µg/knee per injection were limited to granulomatous inflammation in the synovium and/or periarticular tissue at the injection site (right stifle joint) at the end of the 3- and 9-month dosing intervals (with 3 and 9 repeat injections, respectively), with complete and partial recoveries in the 3 month- and 9 month-treated animals after a 4-week treatment-free period. The NOAEL for the compound of Formula (I) in this study was considered to be 116 µg/knee. In both the single and repeat-dose once-monthly IA toxicity studies, there was no measurable systemic exposure at all time points (all were below quantitation limit (BQL) with the lower limit of detection (LLOQ) of 0.1 ng/mL, and no systemic toxicity was observed, as evidenced by no effects on body weights, ECG and clinical pathology and no target organs.

D. Efficacy of a suspension composition of the compound of Formula (I)

The efficacy of the compound of Formula (I) on increasing cartilage thickness was determined in rats that underwent anterior cruciate ligament transection (ACLT) combined with medial meniscectomy (MMx).

Female rats (10-12 weeks old) were subjected to surgical severing of the anterior cruciate, medial collateral and medial meniscotibial ligaments (ACLT+pMMx). One-week post-surgery, after cartilage was allowed to degenerate, the rats were injected intra-articular (IA) with a single dose of a suspension of the compound of Formula (I) (0.1 µg or 0.3 µg or 1 µg). On Days 30, 60, and 90 after injection, joint cartilage, bone and plasma was isolated. Compound from these tissues was extracted using acetonitrile-methanol (70:30) and analyzed for concentrations using LC-MS.

Figure 23B:
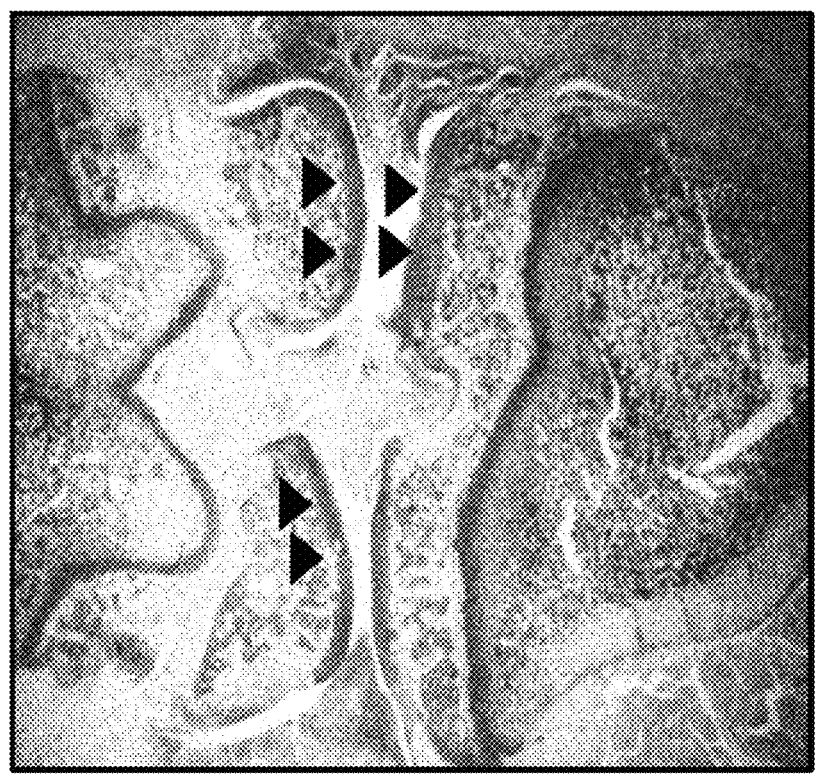
FIG. 23B shows a safranin O-stained section of a knee treated with 0.3 µg of Form 1 of the compound of Formula (I) after 12 weeks.
Figure 23A:
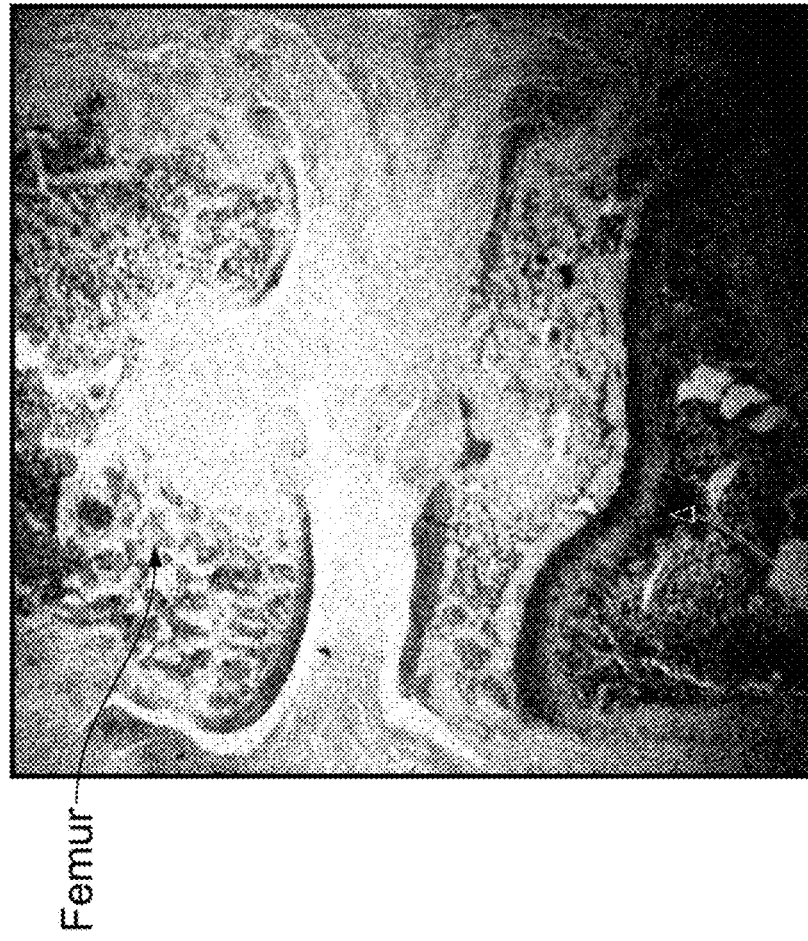
FIG. 23A shows a safranin O-stained section of a rat knee of a control knee after 12 weeks.

13 weeks after the surgery (12 weeks post-IA injection), knees were isolated, fixed in 10% formalin, decalcified, embedded in paraffin, and sectioned. Sections were stained with Safranin 0-Fast Green and histologically evaluated by two blinded observers based on OARSI scoring system (Pritzker et al. (2006) Osteoarthr. Cartil. 14:13-29). The OARSI score measures cartilage matrix loss, fissures, subchondral bone remodeling and bone cyst formation. Increased cartilage thickness, decreased fissures, and subchondral bone remodeling were observed after a single intra-articular injection of the compound of Formula (I). FIG. 23A shows a safranin O-stained section of a rat knee of a control knee after 12 weeks. FIG. 23B shows a safranin O-stained section of a knee treated with 0.3 µg of the compound of Formula (I) after 12 weeks that displays increased cartilage as compared to the control knee. A dose-dependent reduction in the total OARSI score (against vehicle) was demonstrated, indicating improved overall cartilage health. Results are shown in Table 41 below.

TABLE 41

OARSI score of safranin O-stained section from rat knee

| | OARSI score |
|---|---|
| Vehicle | 4.43 |
| 0.1 µg the compound of Formula (I) | 3.13 |
| 0.3 µg the compound of Formula (I) | 2.15 |

E. Efficacy of suspension compositions compared to a solution composition of the compound of Formula (I)

The efficacy of suspension compositions of the compound of Formula (I) (Form 1) as compared to a solution composition of the compound of Formula (I) in rat models of osteoarthritis (OA) was determined using a solution (final IA dose of 3 µg solution) and 0.1 µg and 0.3 µg suspension compositions of the compound of Formula (I) (Form 1).

Osteoarthritis was surgically induced in the right knee joint of 10 week-old male rats via ACLT and pMMx transection as described in previously published methods (Hayami et al. (2006) Bone 38:234-243). The rats were treated with final dose levels of either a 0.1 µg or 0.3 µg suspension or a 3 µg solution of the compound of Formula (I). Histology score of cartilage integrity in the knee was the readout. The results showed that the 0.3 µg suspension treatment showed significant difference at 3 months' time points; treatment with the 0.1 µg suspension showed a beneficial effect (vs. vehicle) at 3 months' time points, but did not reach the statistical significance; treatment with the 3 µg solution showed a beneficial effect (vs vehicle) at 2 months' time points, but did not reach the statistical significance.

Example 6: Clinical Studies

A. Initial clinical study

Twenty-one subjects were enrolled in the first cohort of a clinical trial for the treatment of osteoarthritis. All subjects completed a minimum of 12 weeks of follow-up after treatment. This study was a first-in-human, multicenter, placebo-controlled, single-dose, dose-escalation safety study in subjects suffering from moderately to severely symptomatic knee OA. Subjects were treated with a single ultrasound-guided intra-articular injection of a suspension of a non-stoichiometric hydrate of Form I having between 1% and about 20% by weight water or placebo.

A single-use injectable composition containing the compound of Formula (I) suspended in a 0.5% sodium carboxymethylcellulose and 0.05% polysorbate 80 in 10 mM phosphate buffered saline solution, pH 7.4, was prepared. For this study, a dosage of 0.03-0.230 mg of the compound of Formula (I) was administered per 2 mL injection.

Subjects were evaluated using the following primary and secondary assessments:

Primary:

1. Evaluation of the safety and tolerability of the therapeutic composition administered by intra-articular injection into the target knee joint of moderately to severely symptomatic osteoarthritis (OA) subjects. This included:

a) monitoring for treatment-emergent adverse events (AEs);

b) assessing bone loss by measuring bone biomarkers (cartilage oligomeric matrix protein [COMP], N-terminal propeptides of procollagen type I [PINP], and β-C-terminal telopeptide [β-CTX]) at Weeks 4 and 12 by computed tomography (CT) of both knee joints and at Week 12 after study medication injection compared to baseline; and c) assessing bone marrow edema by magnetic resonance imaging (Mill) at Week 12 compared to baseline.

2. Assessment of the pharmacokinetic (PK) behavior of the compound of Formula (I) under the conditions of this study at Days 1, 2, 4, and 12.

Secondary:

Estimation of clinical responses to treatment with the therapeutic composition, including:

a) change from baseline in pain visual analog scale (VAS) score assessed at Weeks 1, 2, 4, 8, and 12;

b) change from baseline in the Western Ontario and McMaster Universities Arthritis Index (WOMAC) assessed at Weeks 1, 2, 4, 8, and 12;

c) change from baseline OA pain as assessed by the WOMAC pain subscale at Weeks 1, 2, 4, 8, and 12;

d) change from baseline OA as assessed by the physician global assessment of disease activity at Weeks 1, 2, 4, 8, and 12;

e) change from baseline in total cartilage volume and thickness in the compartments of the target knee joint as documented by MM at Week 12;

f) changes from baseline in anabolic or catabolic biomarkers indicative of cartilage synthesis or degradation (cartilage oligomeric matrix protein [COMP], N-terminal propeptides of procollagen type I [PINP], and β-C-terminal telopeptide [β-CTX]) at Weeks 4 and 12;

g) change from baseline in plasma levels of cytokines related to inflammation (interleukin [IL] 1b, IL6, IL8, tumor necrosis factor (TNF), and interferon-alpha [IFNα]) at Weeks 4 and 12; and h) change from baseline in bone marrow edema as documented by Mill scan of the target knee at baseline and at Week 12.

Data from a representative set of patients is shown below in Table 42.

The data from this study provided an indication of the following correlations:

1) The correlation of total measured baseline cartilage width in the treatment group with change of total cartilage width at Week 12 was −0.20, a mild negative correlation (the higher cartilage width at baseline, the smaller the cartilage change at Week 12).

2) The correlation of total measured baseline cartilage width in the treatment group with Week 12 change in WOMAC was −0.31, a mild negative correlation (the higher cartilage width at baseline, the smaller the WOMAC change at Week 12).

3) The correlation of the change of total cartilage width at Week 12 in the treatment group with Week 12 change in WOMAC was −0.41, a moderate negative correlation (the more cartilage grew, the smaller the overall WOMAC score at Week 12).

B. Phase 1 clinical study

A Phase 1 study was conducted to evaluate the safety and tolerability of the compound of Formula (I) (Form 1) administered by intra-articular injection into a target knee joint of moderate-to-severe symptomatic OA subjects.

The study was a first-in-human, multicenter, 24-week, placebo-controlled, single-dose, dose-escalation safety study of a Wnt pathway inhibitor in subjects suffering from moderate to severe symptomatic knee OA. The sample size was 20 subjects (randomized 4:1, 16 active: 4 placebo) per dosing cohort. Inclusion criteria included: Age, 50-75 years; Western Ontario and McMaster Universities Arthritis Index (WOMAC) Total score, 36-72 (out of 96); Kellgren-Lawrence grade, 2 or 3; and a willingness to omit pain medication for 24 hours prior to pain assessments. Exclusion criteria included: BMI >40; and treatment with IA steroids within 2 months or HA derivatives within 6 months prior to injection. A full list of the inclusion and exclusion criteria for this study can be found on clinicaltrials.gov (NCT02095548).

The dosing sequence included suspension compositions of either 0.03 mg, 0.07 mg, or 0.23 mg of the compound of Formula (I) (Form 1) per 2 mL injection in a vehicle containing 0.5% carboxymethylcellulose sodium and 0.05% polysorbate 80 in pH 7.4 phosphate buffered saline. The placebo contained only the diluent of 0.5% carboxymethylcellulose sodium and 0.05% polysorbate 80 in pH 7.4 phosphate buffered saline. The subjects were given a single, intra-articular injection in the target knee on Treatment Day 1 and participated in a follow-up period of 24 weeks.

Safety, pharmacokinetics (PK), biomarker, and efficacy data were collected at baseline and during the 24-week follow-up period. Safety data included adverse events

TABLE 42

Representative results

| Subject | Baseline cartilage thickness (mm) | Week 12 cartilage thickness (mm) | Change in cartilage thickness | Baseline WOMAC score | Week 12 WOMAC score | Change in WOMAC score |
|---|---|---|---|---|---|---|
| Placebo 1 | 14.3 | 14.7 | 0.4 | 43 | 32 | −11 |
| Placebo 2 | 13.09 | 13.68 | 0.59 | 44 | 50 | 6 |
| Treatment 1 | 14.01 | 15.21 | 1.2 | 56 | 0 | −56 |
| Treatment 2 | 12.12 | 13.32 | 1.2 | 51 | 21 | −30 |
| Treatment 3 | 13.22 | 14.52 | 1.3 | 59 | 32 | −27 |
| Treatment 4 | 9.89 | 11.33 | 1.44 | 61 | 23 | −38 |

(AEs), concomitant medications, clinical laboratory sampling, medical history, vital signs, ECGs, hip bone density (DXA) analysis, qCT of the target knee, and evaluation of bone edema via MM. For PK data, samples were collected 0, 4, and 24 hours post dose, and at Weeks 4 and 12. Biomarker data included data for procollagen type 1 N-propeptide (P1NP), beta C-terminal telopeptide of type 1 collagen (βCTX), and cartilage oligomeric matrix protein (COMP). Efficacy data included measurements of WOMAC Total score, WOMAC Function and Pain subscores, pain VAS, Physician Global Assessment of Disease Activity, MM, and radiographs. Efficacy assessments were used to determine the percentage of OMERACT-OARSI "strict" responders. Exploratory analyses of efficacy outcomes were conducted using a baseline-adjusted repeated measures analysis of covariance (ANCOVA) in the Intention-to-Treat (ITT) population. The sponsor was unblinded after Week 12 for each cohort; site investigators remained blinded. All AEs reported in this study were considered related to study medication. Investigator opinion regarding whether AEs were related to the compound of Formula (I) was also collected for informational purposes.

Table 43 depicts subject characteristics for three dosing cohorts and a placebo group.

TABLE 43

Subject characteristics of clinical trial

|  | 0.03 mg | 0.07 mg | 0.23 mg | Placebo |
|---|---|---|---|---|
| N | 17 | 16 | 16 | 12 |
| Age at Consent (Years) [Mean (SD)] | 63.2 (6.6) | 60.6 (5.5) | 63.1 (4.9) | 63.7 (5.8) |
| BMI (kg/m$^2$) [Mean (SD)] | 31.4 (4.8) | 31.3 (4.1) | 28.7 (5.0) | 30.2 (4.6) |
| Female [N(%)] | 10 (59%) | 12 (75%) | 12 (75%) | 7 (58%) |
| Race [N(%)] |  |  |  |  |
| White | 14 (82%) | 13 (81%) | 14 (88%) | 10 (83%) |
| African-American | 2 (12%) | 3 (19%) | 1 (6%) | 2 (17%) |
| Asian | 1 (6%) | 0 | 1 (6%) | 0 |
| Kellgren-Lawrence Grade 3 [N(%)] | 7 (41%) | 8 (50%) | 11 (69%) | 5 (42%) |

Table 44 depicts safety data for three dosing cohorts and a placebo.

TABLE 44

Safety

|  | 0.03 mg | 0.07 mg | 0.23 mg | Placebo |
|---|---|---|---|---|
| SAE(s) Reported | 0 | 1* | 0 | 0 |
| DLT(s) Reported | 0 | 2* | 0 | 0 |
| AE(s) Reported - All | 15 | 11 | 25 | 19 |
| AE(s) Reported - Target knee |  |  |  |  |
| Arthralgia | 1 | 1 | 1 | 4 |
| Injection site bruising | 0 | 0 | 1 | 0 |
| Injection site pain | 0 | 2 | 1 | 0 |
| Joint injury | 1 | 0 | 0 | 0 |
| Joint stiffness | 0 | 0 | 1 | 0 |
| Joint swelling | 0 | 1 | 1 | 1 |
| Meniscus injury | 0 | 0 | 1 | 0 |

*Increased target knee pain (DLT) and paroxysmal tachycardia (DLT and SAE)

Table 45 depicts adverse effect reporting for three dosing cohorts and a placebo.

TABLE 45

Adverse effect reporting

|  | 0.03 mg | 0.07 mg | 0.23 mg | Placebo |
|---|---|---|---|---|
| Subjects Who Reported AE(s) [N(%)] | 9 (53%) | 6 (37%) | 7 (44%) | 6 (50%) |
| Subjects Who Reported No AE(s) [N(%)] | 8 (47%) | 10 (63%) | 9 (56%) | 6 (50%) |

Pharmacokinetics

PK samples were collected at 0, 4, and 24 hours post dose, and at Weeks 4 and 12. All subjects in cohorts 1, 2, and 3 had levels below limits of quantitation (BQL <0.100 ng/mL) at all recorded time points.

Biomarkers

Biomarker data showed significant reduction in cartilage oligomeric matrix protein (COMP) in the 0.07 mg cohort at Week 12 (130.13 ng/mL, P=0.001). There were no significant changes in COMP in the 0.03 mg cohort, 0.23 mg cohort, or the placebo group, or in βCTX or P1NP in any treatment or placebo group.

WOMAC Total [0-96]

Figure 24A:
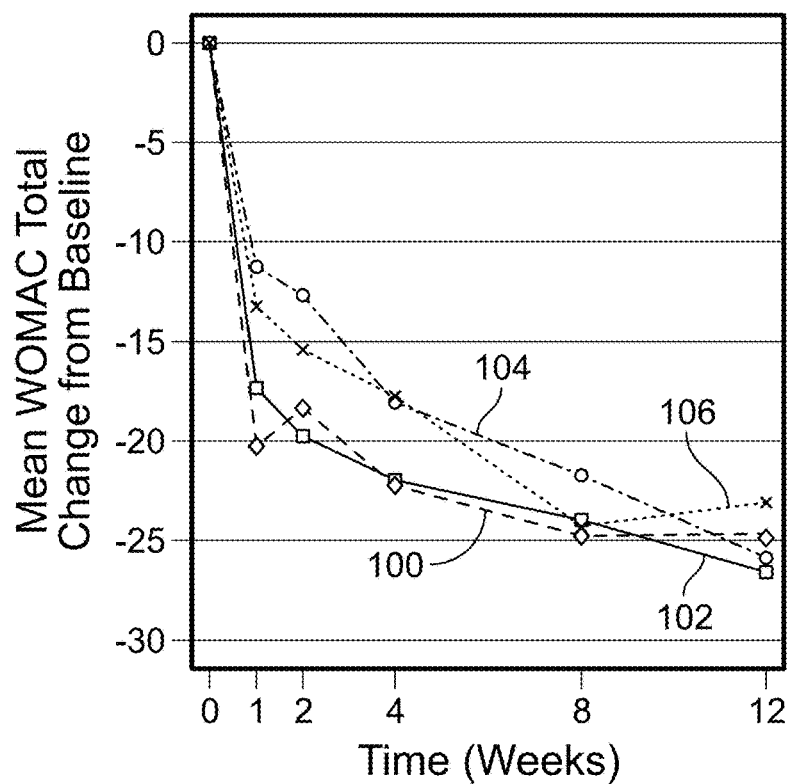
FIGS. 24A and 24B are line graphs depicting mean WOMAC total score vs. time and median WOMAC total score vs. time.
Figure 24B:
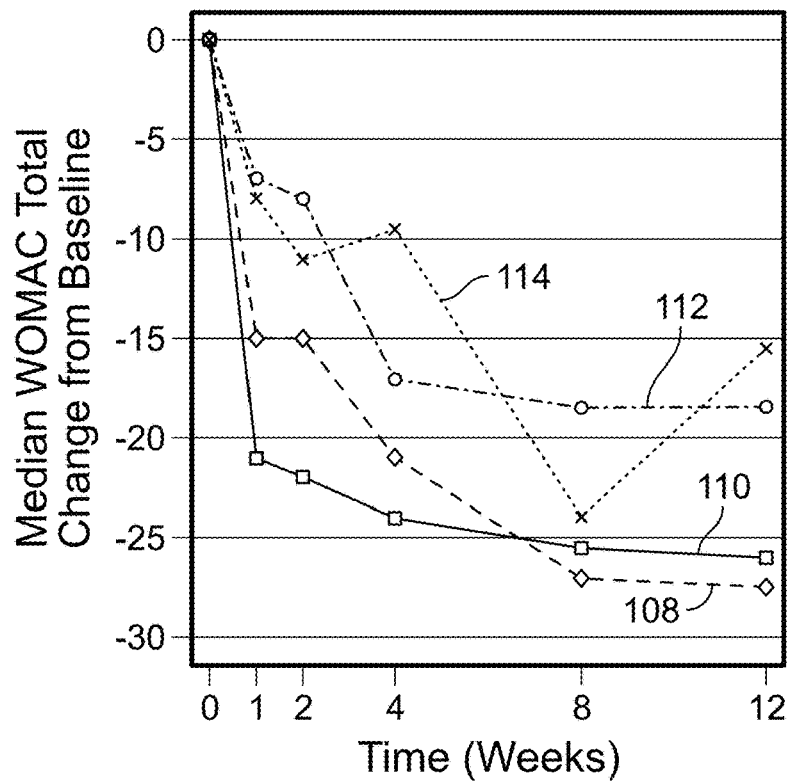

Mean WOMAC total score as a function of time in weeks and median WOMAC total score as a function of time in weeks, are depicted in FIGS. 24A and 24B, respectively. FIG. 24A depicts the mean WOMAC total score as a function of time for dosing cohorts of 0.03 mg (plot 100), 0.07 mg (plot 102), 0.23 mg (plot 104), and placebo (plot 106). All cohorts and the placebo group showed a decrease of about 23 or greater in WOMAC total score from baseline, with the 0.07 mg dosing cohort (plot 102) exhibiting the largest decrease at about 27.

FIG. 24B depicts the median WOMAC total as a function of time for dosing cohorts of 0.03 mg (plot 108), 0.07 mg (plot 110), 0.23 mg (plot 112), and placebo (plot 114). The 0.03 mg dosing cohort (plot 108) and the 0.07 mg dosing cohort (plot 110) each showed a decrease of greater than 25 in WOMAC total score from baseline, while the placebo group (plot 114) exhibited a modest decrease of about 15.

Table 46 depicts WOMAC function scores for three dosing cohorts and a placebo group.

TABLE 46

| | WOMAC function [0-68] | | | |
|---|---|---|---|---|
| | 0.03 mg | 0.07 mg | 0.23 mg | Placebo |
| N | 17 | 16 | 16 | 12 |
| Baseline [Mean (SD)] | 39.1 (7.2) | 37.6 (7.8) | 40.4 (8.6) | 34.5 (10.6) |
| Week 12 [Mean (SD)] | | | | |
| Actual | 20.3 (10.5) | 18.4 (15.9) | 22.6 (10.3) | 18.8 (11.8) |
| Change from baseline | −18.4 (13.5) | −19.2 (16.3) | −17.8 (15.1) | −15.8 (13.1) |

Table 47 depicts WOMAC pain scores for three dosing cohorts and a placebo group.

TABLE 47

| | WOMAC pain [0-20] | | | |
|---|---|---|---|---|
| | 0.03 mg | 0.07 mg | 0.23 mg | Placebo |
| N | 17 | 16 | 16 | 12 |
| Baseline [Mean (SD)] | 10.8 (2.0) | 10.8 (3.0) | 11.4 (2.7) | 9.9 (2.0) |
| Week 12 [Mean (SD)] | | | | |
| Actual | 6.3 (2.7) | 5.3 (4.5) | 5.8 (2.7) | 5.3 (3.9) |
| Change from baseline | −4.4 (3.0) | −5.6 (4.7) | −5.7 (4.4) | −4.6 (4.1) |

Physician Global Assessment of Disease Activity [0-100]

Figure 25A:
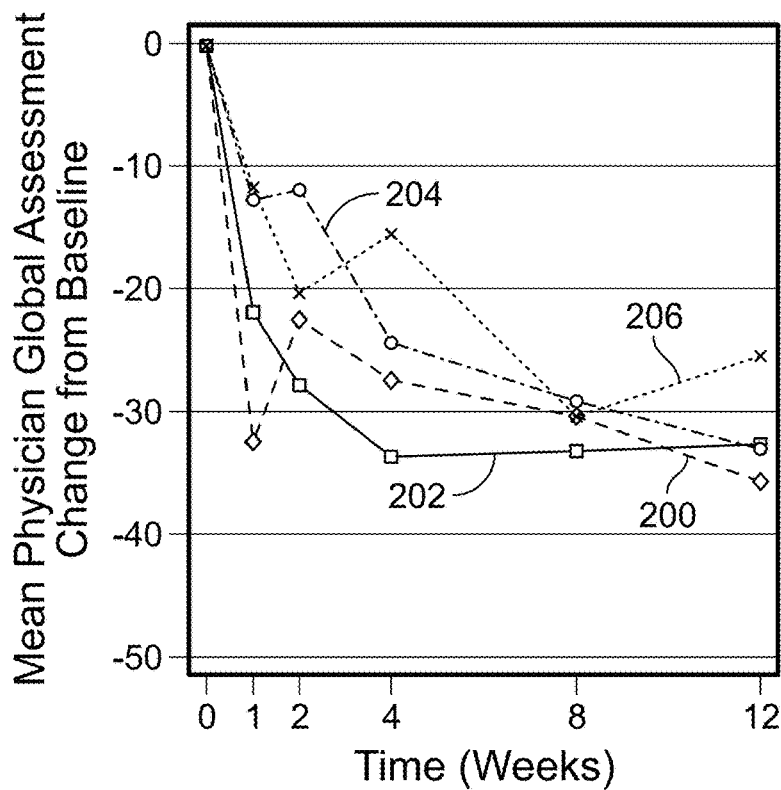
FIGS. 25A and 25B are line graphs depicting mean physician global assessment vs. time and median physician global assessment vs. time.
Figure 25B:
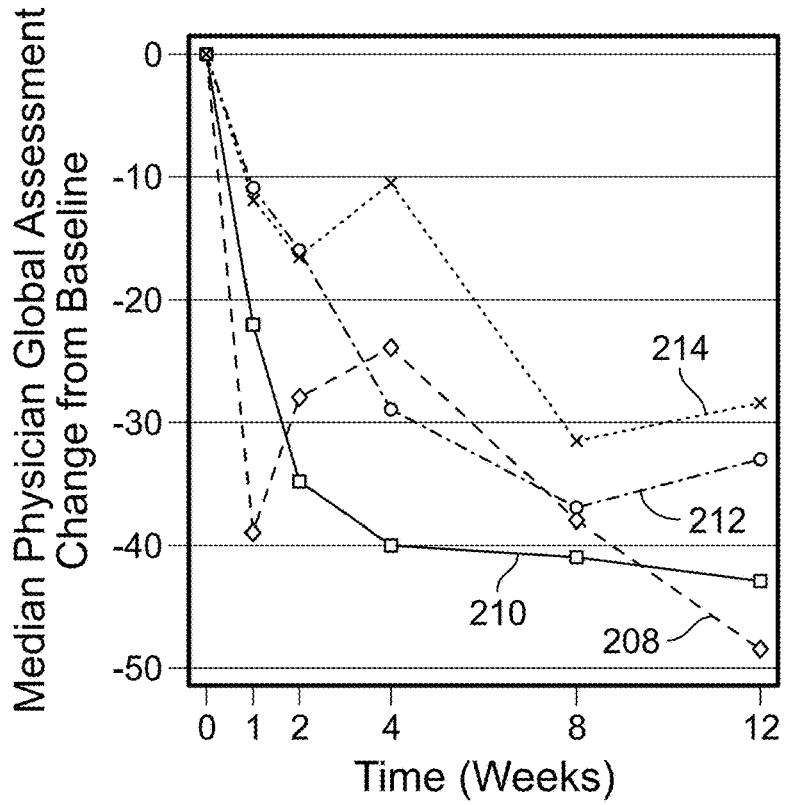

Mean physician global assessment scores as a function of time in weeks and median physician global assessment scores as a function of time in weeks is depicted in FIGS. 25A and 25B, respectively. FIG. 25A depicts the mean physician global assessment as a function of time for dosing cohorts of 0.03 mg (plot 200), 0.07 mg (plot 202), 0.23 mg (plot 204), and placebo (plot 206). All cohorts notwithstanding the placebo group showed a decrease of about 30 or greater in the mean physician global assessment score from baseline.

FIG. 25B depicts the median physician global assessment as a function of time for dosing cohorts of 0.03 mg (plot 208), 0.07 mg (plot 210), 0.23 mg (plot 212), and placebo (plot 214). The 0.03 mg cohort (plot 208) showed a median decrease of about 48 from baseline, while the placebo (plot 214) exhibited the lowest median decrease of about 29.

Percentage Strict OARSI Responders

Strict responders were classified by having either a WOMAC Function subscore improvement of ≥50% with a corresponding Function score improvement of ≥20 points (scaled to [0-100]), or a WOMAC Pain subscore improvement of ≥50% with a corresponding Pain score improvement of ≥20 points (scaled to [0-100]).

Figure 26:
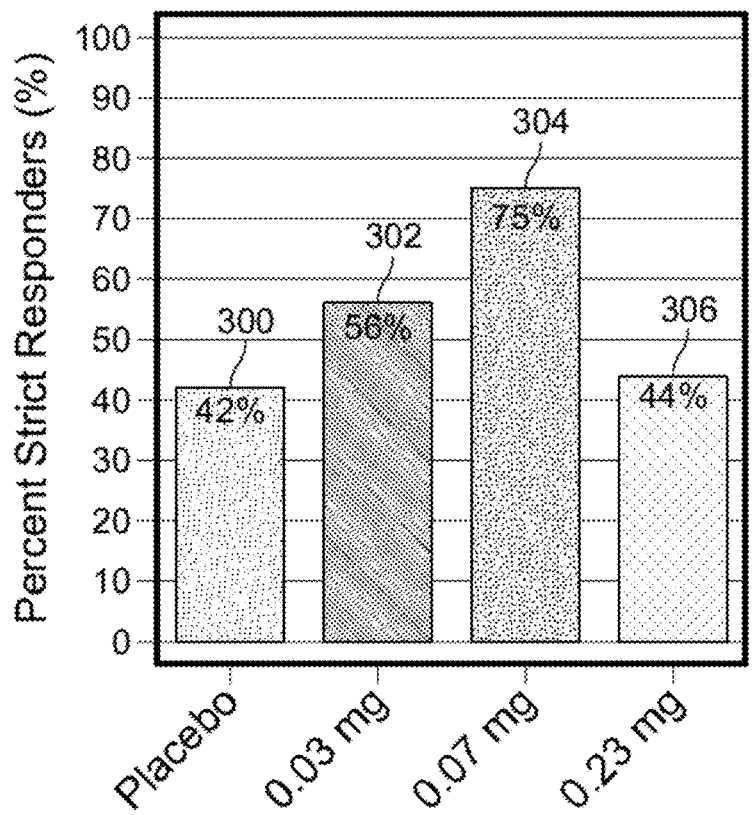
FIG. 26 is a bar graph of the percentage of strict responders for each dosing cohort and a placebo group.

FIG. 26 depicts a bar graph of percentage strict responders for the placebo cohort (300), the 0.03 mg cohort (302), the 0.07 mg cohort (304), and the 0.23 mg cohort (306) at week 12. The 0.07 mg cohort exhibited the highest percentage of strict responders at 75%, compared to the placebo group at 42%.

Discussion

The interim data from the phase 1 trial suggested that a single intra-articular injection into the knee of OA subjects of a suspension formulated from Form 1 of the compound of Formula (I) appears safe, well-tolerated, and potentially effective in reducing pain and improving function. All subjects had PK levels below the limit of quantitation at all recorded time points. 27 of 49 (55%) exposed subjects reported no AEs. All AEs reported in this study were deemed related to study medication. Only 16 of 77 (22%) AEs were considered related to study medication by the reporting investigator.

The phase 1 study was not powered to see any statistically significant differences between treatment groups and placebo. However, the data suggested that subjects treated with the compound of Formula (I) were more likely to have a strict OARSI response than placebo. At Week 12, 75% of 0.07 mg cohort achieved strict OARSI response compared to 42% of placebo (OR=4.2, P=0.081).

C. MRI and radiograph study

To assess the safety and efficacy of the compound of Formula (I) (Form 1), magnetic resonance imaging (MM) was used. Safety evaluations included assessment of bone marrow edema by Mill. MM was used to document changes from baseline in total cartilage volume and thickness in the compartments of the target knee joint. Imaging results (safety and exploratory outcomes) in the Phase 1 study are described above.

Knee MRIs were obtained with a 16 channel knee coil on a 3.0T MRI machine using a standard diagnostic protocol (resolution 0.1-0.4 mm). MM scans were collected at the baseline visit (which could occur ≤28 days prior to study injection) and again at Weeks 12 and 24. The sponsor was unblinded after Week 12 for each cohort; site investigators remained blinded.

An exploratory analysis of change in imaging outcomes was conducted using repeated measures analysis of covariance (ANCOVA) adjusting for baseline in the Intention-to-Treat (ITT) population.

Table 48 depicts subject characteristics of the MM and radiography study for three dosing cohorts and a placebo group.

TABLE 48

| Subject characteristics of MRI and radiography study | | | | |
|---|---|---|---|---|
| | 0.03 mg | 0.07 mg | 0.23 mg | Placebo |
| N | 17 | 16 | 16 | 12 |
| Age at Consent (Years) [Mean (SD)] | 63.2 (6.6) | 60.6 (5.5) | 63.1 (4.9) | 63.7 (5.8) |
| BMI (kg/m$^2$) [Mean (SD)] | 31.4 (4.8) | 31.3 (4.1) | 28.7 (5.0) | 30.2 (4.6) |
| Female [N(%)] | 10 (59%) | 12 (75%) | 12 (75%) | 7 (58%) |
| Race [N(%)] | | | | |
| White | 14 (82%) | 13 (81%) | 14 (88%) | 10 (83%) |
| African-American | 2 (12%) | 3 (19%) | 1 (6%) | 2 (17%) |
| Asian | 1 (6%) | 0 (0%) | 1 (6%) | 0 (0%) |
| Kellgren-Lawrence Grade 3 [N(%)] | 7 (41%) | 8 (50%) | 11 (69%) | 5 (42%) |

Bone Marrow Edema

As a safety assessment, MRI scans were used to monitor the presence of focal or diffuse bone marrow edema (BME) in all subjects. Table 49 depicts bone marrow edema data for three dosing cohorts and a placebo group.

TABLE 49

| Bone Marrow Edema (BME) | | | | | |
|---|---|---|---|---|---|
| Edema [N(%)] | | | | | |
| Baseline | Week 12 | 0.03 mg | 0.07 mg | 0.23 mg | Placebo |
| None | None | 9 (57%) | 11 (69%) | 4 (25%) | 5 (42%) |
| | Focal | 1 (6%) | 2 (13%) | 1 (6%) | 3 (25%) |
| | Diffuse | 0 | 0 | 0 | 0 |
| Focal | None | 0 | 1 (6%) | 1 (6%) | 0 |
| | Focal | 4 (25%) | 1 (6%) | 8 (50%) | 3 (25%) |
| | Diffuse | 0 | 0 | 0 | 0 |
| Diffuse | None | 0 | 0 | 0 | 0 |
| | Focal | 1 (6%) | 1 (6%) | 0 | 0 |
| | Diffuse | 1 (6%) | 0 | 2 (13%) | 1 (8%) |

Cartilage Thickness

Average cartilage thickness over covered subchondral bone was reported for the following four compartments: medial femoral condyles, lateral femoral condyles, medial tibial plateaus, and lateral tibial plateaus.

Figure 27:
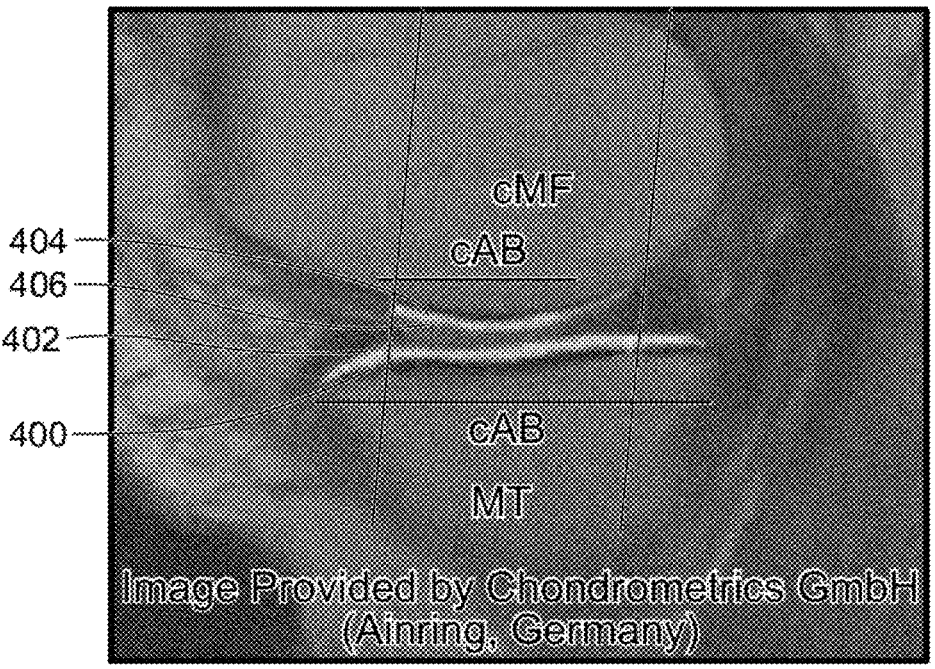
FIG. 27 is an MM of a human knee joint.

FIG. 27 depicts the MRI of a knee joint. To determine average cartilage thickness, the cartilage thickness between the subchondral bone area (400 and 404) and the articular cartilage surface (402 and 406) was measured at numerous (~400-2000) locations in both directions in the parts covered by cartilage (cAB) and averaged. Measurements were performed in three dimensions. Additionally, the average of the lowest 1% of cartilage thickness was also reported for all 4 compartments. The total for both average thickness and lowest thickness were derived by summing each of the 4 compartments' observations.

Table 50 depicts mean cartilage thickness as measured by MRI for three dosing cohorts and a placebo group.

TABLE 50

| Mean cartilage thickness by MRI at Week 12 | | | | |
|---|---|---|---|---|
| | 0.03 mg | 0.07 mg | 0.23 mg | Placebo |
| N | 16 | 16 | 15 | 12 |
| Baseline (mm) [Mean (SD)] | 5.43 (1.10) | 5.38 (0.70) | 5.36 (0.94) | 5.84 (0.65) |
| Week 12 (mm) [Mean (SD)] | | | | |
| Actual | 5.38 (1.19) | 5.37 (0.71) | 5.32 (1.03) | 5.84 (0.63) |
| Change from baseline | −0.06 (0.39) | −0.02 (0.25) | −0.04 (0.24) | 0.01 (0.20) |

Table 51 depicts mean thinnest cartilage as measured by MM for three dosing cohorts and a placebo group.

TABLE 51

| | Mean thinnest cartilage by MRI at Week 12 | | | |
|---|---|---|---|---|
| | 0.03 mg | 0.07 mg | 0.23 mg | Placebo |
| N | 16 | 16 | 15 | 12 |
| Baseline (mm) [Mean (SD)] | 3.75 (1.38) | 3.78 (1.37) | 3.14 (1.17) | 4.24 (1.45) |
| Week 12 (mm) [Mean (SD)] | | | | |
| Actual | 3.84 (1.57) | 3.88 (1.39) | 3.01 (1.27) | 4.18 (1.26) |
| Change from baseline | 0.11 (0.37) | 0.10 (0.55) | −0.13 (0.30) | −0.06 (0.43) |

Joint Space Width

Radiographs of the target knee were taken during the screening period and at Week 24 to document change from baseline in joint space width (JSW). Table 52 depicts joint space width as measured by radiography for three dosing cohorts and a placebo group.

TABLE 52

| | Joint space width by radiograph at Week 24 | | | |
|---|---|---|---|---|
| | 0.03 mg | 0.07 mg | 0.23 mg | Placebo |
| N | 15 | 14 | 16 | 12 |
| Baseline (mm) [Mean (SD)] | 4.50 (1.70) | 3.57 (1.63) | 3.62 (1.75) | 3.91 (1.62) |
| Week 24 (mm) [Mean (SD)] | | | | |
| Actual | 4.50 (1.72) | 4.16 (1.64) | 3.47 (1.68) | 3.53 (1.98) |
| Change from baseline | 0.00 (0.69) | 0.59 (0.66)* | −0.15 (1.07) | −0.38 (0.85) |

*p = 0.006 versus placebo

Discussion

MM was the primary method utilized to examine bone marrow edema (BME), which the FDA defined as a safety outcome in this phase 1 trial. BME stayed the same for most subjects from baseline to Week 12. For some subjects in both treatment (N=4) and Placebo (N=3) groups, BME worsened (none to focal). 4 subjects in the treatment groups showed improved BME results (focal to none and diffuse to focal). These interim BME imaging data suggest that a single intra-articular injection of the compound of Formula (I) into the knee of OA subjects appeared to have no appreciable effect compared to Placebo.

Although exploratory imaging results in this phase 1 trial suggested that the 0.23 mg dose was less effective than the 0.03 mg and 0.07 mg doses, it should be noted that the 0.23 mg cohort consisted of the highest percentage of K-L Grade 3 subjects.

Exploratory analyses of MRI outcomes suggested that treated subjects appeared to show no substantial degradation in mean cartilage thickness at Week 12. The measurement changes recorded likely reflect MRI signal noise only, as the mean values are at the limits of scan resolution. The area of mean thinnest cartilage showed a possible trend towards increase in the 0.03 mg and 0.07 mg cohorts at Week 12. Radiographs measuring the change from baseline at Week 24 in joint space width showed no change in the 0.03 mg cohort, an increase in the 0.07 mg cohort, and a decrease in the 0.23 mg cohort, with the Placebo group exhibiting a larger decrease. The MM safety outcomes from this interim analysis demonstrated no worsening of bone edema in knee OA subjects treated with Form 1 of the compound of Formula (I).

D. Phase II clinical study

A Phase II study was conducted to evaluate the safety and tolerability of the compound of Formula (I) (Form 1) administered by intra-articular injection into a target knee joint of moderate-to-severe symptomatic OA subjects.

The study was a multicenter, 52-week, single-dose, placebo-controlled study evaluating the safety, tolerability, and efficacy of a Wnt pathway inhibitor in subjects suffering from moderate to severe symptomatic knee OA. The sample size was 454 subjects (randomized 3:1, 338 active: 116 placebo) per dosing cohort. Clinic visits were scheduled at Screening, Treatment Visit Day 1 and Follow-up Weeks 4, 13, 26, 39 and 52. Inclusion criteria included: Age: males and females between 40 and 80 years; Western Ontario and McMaster Universities Arthritis Index (WOMAC) Total score: 72-192 (out of 240); Kellgren-Lawrence grade: 2 or 3; and a willingness to omit pain medication for 24 hours prior to pain assessments. Exclusion criteria included: BMI >40; and treatment with IA steroids within 2 months or HA derivatives within 6 months prior to injection. A full list of the inclusion and exclusion criteria for this study can be found on clinicaltrials.gov (NCT02536833).

The dosing sequence included suspension compositions of either 0.03 mg, 0.07 mg, or 0.23 mg of the compound of Formula (I) (Form 1) per 2 mL injection in a vehicle containing 0.5% carboxymethylcellulose sodium and 0.05% polysorbate 80 in pH 7.4 phosphate buffered saline. The placebo contained only 2 mL of phosphate buffered saline. The subjects were given a single, intra-articular injection in the target knee on Treatment Day 1 and participated in a follow-up at weeks 4, 13, 26, 39, and 52.

Safety and efficacy data were collected at baseline and during the 52-week follow-up period. Safety data included incidence, severity and relationship of adverse events (AEs), medical history, vital signs. Efficacy data included measurements of WOMAC Total score, WOMAC Function and Pain subscores, pain VAS, Physician Global Assessment of Disease Activity, and radiographs. Efficacy assessments were used to determine the percentage of OMERACT-OARSI "strict" responders. Exploratory analyses of efficacy outcomes were conducted using a baseline-adjusted repeated measures analysis of covariance (ANCOVA) in the Intention-to-Treat (ITT), Modified Intention-to-Treat (mITT), and Per-protocol (PP) population sets. Change in WOMAC total, WOMAC pain subscore, WOMAC function subscore, Patient Global Assessment, Physician Global Assessment, Joint Space Width (JSW) and Health-Related Quality of Life Research (HRQOL) from baseline. The sponsor was unblinded after Week 26 for each cohort; site investigators remained blinded. All AEs reported in this study were considered related to study medication. Investigator opinion regarding whether AEs were related to the compound of Formula (I) was also collected for informational purposes.

Table 53 depicts subject characteristics for three dosing cohorts and a placebo group.

What is claimed is:

1. A process for preparing a polymorph of a compound of Formula (I):

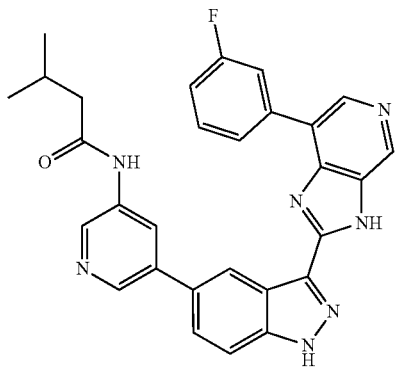

wherein the polymorph is Form 1 and has an X-ray powder diffraction pattern comprising peaks at ° 2θ values of 6.8±0.2, 12.4±0.2, and 18.5±0.2; wherein the process comprises drying a compound of Formula (I) to Form 1.

2. The process of claim 1, wherein the compound of Formula (I) comprises a mixture of a non-stoichiometric hydrate of Form 1 having between 1% and about 20% by weight water and Form 1.

3. The process of claim 1, wherein the process comprises reslurrying the compound of Formula (I) in a solvent to generate Form 1; wherein the solvent is selected from the group consisting of methanol, toluene, heptane, dichloromethane, water, and mixtures thereof.

4. The process of claim 2, wherein the process comprises reslurrying the compound of Formula (I) in a solvent to generate Form 1; wherein the solvent is selected from the group consisting of methanol, toluene, heptane, dichloromethane, water, and mixtures thereof.

5. The process of claim 1, wherein the process comprises reslurrying the compound of Formula (I) in water and a

TABLE 53

| | Subject characteristics of clinical trial | | | |
|---|---|---|---|---|
| | 0.03 mg | 0.07 mg | 0.23 mg | Placebo |
| N | 112 | 117 | 110 | 116 |
| Age at Consent (Years) [Mean (SD)] | 59.0 (9.0) | 60.0 (8.2) | 61.3 (8.7) | 60.3 (8.7) |
| BMI (kg/m$^2$) [Mean (SD)] | 29.80 (4.82) | 30.84 (4.75) | 29.68 (4.46) | 29.89 (4.64) |
| Female [N(%)] | 68 (60.7%) | 60 (51.3%) | 68 (61.8%) | 72 (62.1%) |
| Race [N(%)] | | | | |
| White | 92 (82.1%) | 102 (87.2%) | 96 (87.3%) | 102 (87.9%) |
| African-American | 18 (16.1%) | 14 (12%) | 12 (10.9%) | 10 (8.6%) |
| Asian | 1 (0.9%) | 0 | 2 (1.8%) | 0 |
| Kellgren-Lawrence Grade 3 [N(%)] | 74 (66.1%) | 74 (63.2%) | 71 (64.5%) | 74 (63.8%) |

OTHER EMBODIMENTS

It is to be understood that the foregoing description is intended to illustrate and not limit the scope of the disclosure, which is defined by the scope of the appended claims. Other aspects, advantages, and modifications are within the scope of the following claims.

solvent to generate Form 1; wherein the solvent is selected from the group consisting of acetonitrile, methanol, ethyl acetate, methyl tert-butyl ether, isopropyl alcohol, methyl acetate, methyl isobutyl ketone, dichloromethane, n-butyl acetate, heptane, and n-butanol.

6. The process of claim 2, wherein the process comprises reslurrying the compound of Formula (I) in water and a solvent to generate Form 1; wherein the solvent is selected from the group consisting of acetonitrile, methanol, ethyl acetate, methyl tert-butyl ether, isopropyl alcohol, methyl acetate, methyl isobutyl ketone, dichloromethane, n-butyl acetate, heptane, and n-butanol.

7. The process of claim 5, wherein the water is present in an amount of about 5% by weight of the total amount of water and solvent.

8. The process of claim 6, wherein the water is present in an amount of about 5% by weight of the total amount of water and solvent.

\* \* \* \* \*